US005762926A

United States Patent [19]
Gage et al.

[11] Patent Number: 5,762,926
[45] Date of Patent: *Jun. 9, 1998

[54] METHOD OF GRAFTING GENETICALLY MODIFIED CELLS TO TREAT DEFECTS, DISEASE OR DAMAGE OF THE CENTRAL NERVOUS SYSTEM

[75] Inventors: Fred H. Gage, La Jolla; Malcolm Schinstine; Jasodhara Ray, both of San Diego; Theodore Friedmann, La Jolla, all of Calif.; Michael D. Kawaja, Toronto, Canada; Michael B. Rosenberg, San Diego, Calif.; Jon A. Wolff, Madison, Wis.

[73] Assignee: The Regents of the University of California, Oakland, Calif.

[*] Notice: The term of this patent shall not extend beyond the expiration date of Pat. No. 5,082,670.

[21] Appl. No.: 464,397

[22] Filed: Jun. 5, 1995

Related U.S. Application Data

[62] Division of Ser. No. 209,609, Mar. 10, 1994, which is a continuation of Ser. No. 792,894, Nov. 15, 1991, abandoned, which is a continuation-in-part of Ser. No. 285,196, Dec. 15, 1988, Pat. No. 5,082,670.

[51] Int. Cl.$^6$ .............................. C12N 5/00; C12N 15/09; C12N 15/79; A61K 48/00
[52] U.S. Cl. ........................ 424/93.21; 435/320.1; 435/375; 435/69.1; 435/172.3; 935/62; 935/70; 514/44
[58] Field of Search ................. 424/93.21, 570; 435/172.3, 240.2, 948, 320.1, 375, 69.1; 935/62, 70; 514/44

[56] References Cited

U.S. PATENT DOCUMENTS

| | | | |
|---|---|---|---|
| 4,497,796 | 2/1985 | Salser et al. | 514/44 |
| 5,082,670 | 1/1992 | Gage et al. | 424/520 |
| 5,399,346 | 3/1995 | Anderson | 424/93.21 |

FOREIGN PATENT DOCUMENTS

| | | |
|---|---|---|
| 0289034 | 4/1988 | European Pat. Off. |
| 0334301 | 3/1989 | European Pat. Off. |
| 0474979 | 11/1991 | European Pat. Off. |
| WOA8902468 | 3/1989 | WIPO |
| WOA8911539 | 11/1989 | WIPO |
| WOA9006757 | 6/1990 | WIPO |
| WOA9209688 | 6/1992 | WIPO |

OTHER PUBLICATIONS

Khillan, J.S. (1986) Developmental and tissue–specific expression directed by the $\alpha_2$ type 1 collagen promoter in transgenic ice, *Proc. Natl. Acad. Sci.* 83:725–729.

Gage et al., *Neuroscience* S590 Suppl 22:1766.

Marion et al. (1990) *Brain Research*, 519:133–143.

Friedmann, T. (1989) Implantation of genetically modified cells into the rat brain an approach to restoration of CNA functions, *Gene Transfer and Gene Therapy*, pp. 409–416.

Rosenberg, K. et al. (1987) Introduction of new genes into adult rat brain via grafted cells, *Soc. Ns Abstracts* 13:515 141.15.

Eldrup–Jorgensen, J. et al., Antiplatelet therapy and vascular grafts, *Arch. Surg.*, 121:778–781.

Brems, J. et al. (1986) A five-year experience with the bovine heterograft for vascular access, *Arch. Surg.*, 121:941–944.

Kojima, Y. et al. (1987) Xenografts and artificial pancreas transplantation, *Transplantation Proceedings* 19:981–983.

Reach, G. (1984) Bioartificial pancreas, present state and future prospects, *Biomed. Biochem. Acta* 43:569–576.

Brynitz, S. et al. (1988) Post–mortem allogeneic vein for graft as vascular access in chronic haemodialysis, *The Lancet* 900–901.

Bjorklund and Stenevi, eds. (1985) Neural grafting in the mammalian CNS, Das, Freed Ch. 4, pp. 31–40 at pp. 35–36, Table III.

Lim and Sun (1985) *Science* 210:908–910.

R. Selden et al. *Science* 236:714.

R. Handschumacher, Drugs used for immunosuppression, Chapter 53 at pp. 1264–1276, at p. 1270.

Mathiesen (1989) Prolonged survival and vascularization of xenografted human glioblastoma cells in the central nervous system of cyclosporin a–treated rats, *Cancer Lett.* 44(2):151–156.

S. Boularand et al., Complete coding sequence of human tryptophan hydroxylase, *Nucleic Acids Research* 18(14):4257.

B. Koch et al. (1991) *PNAS* 88:8754.

Wan–I Li et al., Synthesis and secretion of immunoreactive methionine–enkephalin from rabbit reproductive tissues in vivo and in vitro, *Biology of Reproduction* 45:691.

G. Bruneau et al., Preparation of a human dopa decarboxylase cDNA probe by PCR and its assignment to chromosome 7, *Annales de Genetique* 33(4):208.

Negro et al. (1991) Cloning and expression of human ciliary neurotrophic factor, *Eur. J. Biochem.* 201:289.

P. Isackson et al., Comparison of mammalian, chicken, and Xenopus brain–derived neurotrophic factor coding sequences, *FEBS Letters* 285(2):260.

Maisonpierre et al. (1991) *Genomics* 10(3):558–568.

(List continued on next page.)

*Primary Examiner*—Jasemine C. Chambers
*Assistant Examiner*—Karen M. Hauda
*Attorney, Agent, or Firm*—Merchant, Gould, Smith, Edell, Welter & Schmidt

[57] ABSTRACT

Methods of genetically modifying donor cells by gene transfer for grafting into the central nervous system to treat defective, diseased or damaged cells are disclosed. The modified donor cells produce functional molecules that effect the recovery or improved function of cells in the CNS. Methods and vectors for carrying out gene transfer and grafting are described.

51 Claims, 70 Drawing Sheets

OTHER PUBLICATIONS

J. Hebert et al. (1990) Isolation of cDNAs encoding four mouse FGF family members and characterization of their expression patterns during embryogenesis, *Developmental Biology* 138:454.

Rosenstein, J.M. (1987) Neocortical transplants in the mammalian brain lack a blood–brain barrier to macromolecules, *Science* 235:772–774.

Bjorklund, et al. (1985) Neural grafting in the mammalian CNS, *Elsevier*, Amsterdam p. 709.

Sladek et al. (1984) Neural transplants: development and function, *Plenum Press*, New York.

Marsden (1986) Movement disorders and the basal ganglia, *Trends Neurosci.* 9:512–515.

Vinken et al., Eds. (1986) Drug–induced movement disorders (tardive dyskinesia and dopa–induced dyskinesia) Handbook of Clinical Neurology, *Elsevier*, Amsterdam (Tanner, author) 5:185–204.

Backlund et al. (1985) Transplantation of adrenal medullary tissue to striatum in parkinsonism, *J. Neurosurg.* 62:169–173.

Madrazo et al. (1987) Open microsurgical autograft of adrenal medulla to the right caudate nucleus in two patients with intractable Parkinson's Disease, *New Eng. J. Med.* 316:831–834.

Bjorklund et al. (1986) Neural grafting in animal models of neurodegenerative diseases, *Ann. N.Y. Acad. Sci.* 457:53–81.

Dunnett et al. (1983) Dopamine–rich transplants in experimental parkinsonism, *Trends Neurosci.* 6:266–270.

Gusella et al. (1983) A polymorphic DNA marker genetically linked to Huntington's disease, *Nature* 306:234–238.

Delabar et al. (1987) B amyloid gene duplication in alzheimer's disease and karyotypically normal down syndrome, *Science* New York 235:1390–1392.

Goldgaber et al. (1987) Characterization and chromosomal localization of a cDNA encoding brain amyloid of alzheimer's disease, *Science* N.Y. 235:877–880.

St. George–Hyslop et al. (1987) The genetic defect causing familia disease maps on chromosome 21, *Science* N.Y. 235:885–890.

Tanzi et al. (1987) Amyloid B protein gene: cDNA, mRNA distribution, and genetic linkage near the alzheimer locus, *Science* N.Y. 235:880–884.

Baron et al. (1987) Genetic linkage between x–chromosome markers and bipolar affective illness, *Nature* 326:289–292.

Sherrington et al. (1988) Localization of a susceptibility locus for schizophrenia on chromosome 5, *Nature* 336:164–167.

Anderson (1984) Prospects for human gene therapy, *Science* 226:401–409.

Freedman et al. (1972) Gene therapy for human genetic disease? *Science* 175:949–955.

Friedmann (1983) Gene therapy: fact and fiction in biology's new approaches to disease, *Cold Spring Harbor Laboratory*, New York.

Costantini et al. (1986) Correction of murine–b–thalassemia by gene transfer into the germ line, *Science* 233:1192–1194.

Mason et al. (1986) The hypogonadal mouse: reproductive functions restored by gene therapy, *Science* 234:1372–1378.

Readhead et al. (1987) Expression of a myelin basic protein gene in transgenic shiverer mice: correction of the dysmyelinating phenotype, *Cell* 48:701–712.

Gilboa et al. (1986) Transfer and expression of cloned genes using retroviral vectors, *Bio Techniques* 4:504–512.

Shimotohno et al. (1981) Formation of infectious progeny virus after insertion of herpes simplex thymidine kinase gene into DNA of an avian retrovirus, *Cell* 26:67–77.

Wei et al. (1981) Construction and isolation of a transmissible retrovirus containing the src gene of harvey murine sarcoma virus and the thymidine kinase gene of herpes simplex virus type I, *J. Virol.* 39:935–944.

Tabin et al. (1982) Adaptation of a retrovirus as a eucaryotic vector transmitting the herpes simplex virus thymidine kinase gene, *Cell Biol.* 2:426–436.

Willis et al. (1984) Partial phenotypic correction of human lesch–nyhan (hypoxanthine–guanine phosphoribosyltransferase–deficient) lymphoblasts with a transmissible retroviral vector, *J. Biol. Chem.* 259:7842–7849.

Kantoff et al. (1986) Correction of adenosine deaminase deficiency in cultured human T and B cells by retrovirus–mediated gene transfer, *Proc. Natl. Acad. Sci. USA* 83:6563–6567.

McIvor et al. (1987) Human purine nucleoside phosphorylase and adenosine deaminase: gene transfer into cultured cells and murine hematopoietic stem cells by using recombinant amphotropic Retroviruses, *Molec. Cell Biol.* 7:838–846.

Soriano et al. (1986) Tissue–specific and ectopic expression of genes introduced into transgenic mice by retroviruses, *Science* 234:1409–1413.

Wolff et al. (1987) Expression of retrovirally transduced genes in primary cultures of adult rat hepatocytes, *Proc. Natl. Acad. Sci. USA* 84:3344–3348.

Khoury et al. (1983) Enhancer Elements, *Cell* 33:313–314.

Serfling et al. (1985) Enhancers and eukaryotic gene transcription, *Trends Genet.* 1:224–230.

Wolff and Friedmann (1988) Approaches to gene therapy disorders of purine metabolism, *Rheumatic Dis. Clin. N. Amer.* 14(2):459–477.

Eglitis and Anderson (1988) Retroviral vectors for introduction of genes into mammalian cells, *BioTechniques*, 6:608–614.

Joyner et al. (1983) Retrovirus transfer of a bacterial gene into mouse haematopoietic progenitor cells, *Nature* 305:556–558.

Miller et al. (1984) Expression of a retrovirus encoding human hprt in mice, *Science* 225:630–632.

Williams et al. (1984) Introduction of new genetic material into pluripotent haematopoietic stem cells of the mouse, *Nature* 310:476–480.

Selden et al. (1982) Implantation of genetically engineered fibroblasts into mice: implications for gene therapy, *Science* 236:714–718.

Garver et al. (1987) Production of glycosylated physiologically normal human $\alpha_1$–antitrypsin by mouse fibroblasts modified by insertion of a human $\alpha_1$–antitrypsin cDNA using a retroviral vector, *Proc. Natl. Acad. Sci. USA* 84:1050–1054.

St. Louis et al. (1988) An alternative approach to somatic cell gene therapy, *Proc. Natl. Acad. Sci. USA* 85:3150–3154.

Morgan et al. (1987) Expression of an exogenous growth hormone gene by transplantable human epidermal cells, *Science* 237:1476–1479.

Geller et al. (1988) A defective HSV–1 vector expresses excherichia coli β–galactosidase in cultured peripheral neurons, *Science* 241:1667–1669.

Lowenstein (1979) Junctional intercellular communication and the control of growth, *Biochem. Biophys. Acta.* 560:1–65.

Gruber et al. (1985) Glial cells metabolically cooperate; A potential requirement for gene replacement therapy, *Proc. Natl. Acad. Sci. USA* 82:6662–6666.

Hefti (1986) Nerve growth factor promotes survival of septal cholinergic neurons after fimbrial transections, *J. Neuroscience* 6(8):2155–2162.

Williams et al. (1986) Continuous infusion of nerve growth factor prevents basal forebrain neuronal death after fimbria fornix transection, *Proc. Natl. Acad. Sci. USA* 83:9231–9235.

Gage et al. (1986) Retrograde cell changes in medial septum and diagonal band following fimbria–fornix transection; quantitative temporal analysis, *Neuroscience* 19:241–255.

Kershing and Thoenen (1983) Nerve growth factor in sympathetic ganglia and corresponding target organs of the rat: Correlation with density of sympathetic innervation, *Proc. Natl. Acad. Sci. USA* 80:3513–3516.

Whittemore et al. (1986) Developmental and regional expression of B nerve growth factor messenger RNA and protein in the rat central nervous system, *Proc. Natl. Acad. Sci. USA* 83:817–821.

Shelton and Reichardt (1986) Studies on the expression of the B nerve growth factor (NGF) gene in three central nervous system: Level and regional distribution of NGF mRNA suggest that NGF functions as a trophic factor for several distinct populations of neurons, *Proc. Natl. Acad. Sci. USA* 83:2714–2718.

Larkfors et al. (1987) Nerve Growth Factor Protein Level Increases in the Adult Rat Hippocampus After a Specific Cholinergic Lesion, *J. Neuroscience Res.* 18:525–531.

Seiler and Schwab (1984) Specific retrograde transport of nerve growth factor (NGF) from neocortex to nucleus basalis in the rat, *Brain Res.* 300:33–39.

Kromer (1987) Nerve growth factor treatment after brain injury prevents neuronal death, *Science* 235:214–216.

Silver et al. (1982) Axonal guidance during development of the great cerebral commissures: descriptive and experimental studies, in vivo, on the role of performed glial pathways, *J. Comp. Neurol.* 210:10–29.

David and Aguayo (1981) Axonal elongation into peripheral nervous system 'bridges' after central nervous system injury in adult rats, *Science* 214:931–933.

Wendt et al. (1983) Regeneration of rat hippocampal fimbria fibers after fimbria transection and peripheral nerve or fetal hippocampal implantation, *Exp. Neurol.* 79:452–461.

Kromer and Cornbrooks (1985) Transplants of schwann cell cultures promote axonal regeneration in the adult mammalian brain, *Proc. Natl. Acad. Sci.* 82:6330–6334.

Kromer et al. (1980) Innervation of embryonic hippocampal implants by regenerating axons of cholinergic septal neurons in the adult rat, *Brain Res.* 210:153–171.

Gage et al. (1988) Human amnion membrane matrix as a substratum for axonal regeneration in the central nervous system, *Exp. Brain Res.* 72:371–380.

Wendt (1985) Ache–positive fiber growth after hippocampal fimbria transection and peripheral nerve homogenate implantation, *Brain Res. Bull.* 15:13–18.

Yee et al. (1986) Gene expression from a transcriptionally disabled retroviral vector, *Cold Spring Harb. Symp. on Quant. Biol.* L1:1021–1026.

Jolly et al. (1987) High–efficiency gene transfer into cells, *Meth in Enzym.* 149:10–25.

Miller et al. (1987) Generation of helper–free amphotropic retroviruses that transduce a dominant–acting, methotrexate–resistant dihydrofolate reductase gene, *Mol. Cell Biol.* 5:431–437.

Palmer et al. (1991) Genetically modified skin fibroblasts persist long after transplantation but gradually inactive introduced genese, *Proc. Natl. Acad. Sci.* 88:1330–1334.

Banerji et al. (1981) Expression of a B–gloin gene is enhanced by remote SV40 DNA sequences, *Cell* 27:299–308.

Jolly et al. (1983) Elements in the long terminal repeat of murine retroviruses enhance stable transformation by thymidine kinase gene, *Nucleic Acids Res.* 11:85501872.

Schmidt et al. (1985) Regulation of a collagen gene promoter by the product of viral mos oncogene, *Nature* 314:286–289.

Rossi and de Crombugghe (1987) Identification of a cell––specific transcriptional enhancer in the first intron of the mouse $a_2$ (type I) collage gene, *Proc. Natl. Acad. Sci. USA* 84:5590–5594.

Prockop and Kivirikko (1984) Heritable diseases of collagen. *N. Eng. J. Med.* 311:376–386.

Smith and Niles (1980) Characterization of collagen synthesized by normal and chemically transformed rat liver epithelial cell lines, *Biochem.* 19:1820–1825.

de Wet et al. (1983) The mRNAs for the pro $\alpha 1(i)$ and pro $\alpha 2(i)$ chains of type i procollagen are translated at the same rate in normal human fibroblasts and in fibroblasts from two variants of osteogenesis imperfecta with altered steady state rations of the two mrnas, *J. of Biol. Chem.* 258:14385–14389.

Armelin (1973) Pituitary extracts and steroid hormones in the control of 3T3 cell growth, *Proc. Natl. Acad. Sci.* 70(9):2702–2706.

Gruss et al. (1981) Simian virus 40 tandem repeated sequences as an element of the early promoter, *Proc. Natl. Acad. Sci.* 78(2):943–947.

Benoist & Chambon (1981) In vivo sequence requirements of the sv40 early promoter region, *Nature* 290:304–310.

Fromm and Berg (1982) Deletion mapping of dna regions required for sv40 early region promoter function in vivo, *J. Mol. Appl. Fen.* 1(5):457–481.

Moreau et al. (1981) The Sv40 72 base repair repeat has a striking effect on gene expression both in sv40 and other chimeric recombinants, *Nucl. Acids Res.* 9(22):6047–6068.

Xu et al. (1983) Comparison of enhancer functions in simian virus 40 and rous sarcoma virus, enhancer and eukaryotic gene expression, *Cold Spring Harbor Labs*, Cold Spring Harbor, NY pp. 51–54.

Chua and Chua (1990) Tumor necrosis factor –αinduces mrna for collagenase and timp in human skin human skin fibroblasts, Conn. Tissue Res. 25:161–170.

Elias et al. (1990) Regulation of human lung fibroblast collagen production by recombinant interleukin–1, tumor necrosis factor, and interferon–, *Annals NY cad. Sci* 580:233–244.

Seliger et al. (1988) Tumor necrosis factor –α affects ltr–controlled oncogene expression in transformed mouse fibroblasts at the post transcriptional level, *J. Immunol.* 141.:2138–2144.

Seliger et al. (1988) Gamma interferon regulates long terminal repeat–controlled oncogene expression in transformed mouse fibroblasts at the level of mRNA transcription, *J. Virology* 62:619–921.

Cattaneo and McKay (1990) Proliferation and differentiation of neuronal stem cells regulated by nerve growth factor, *Nature* 347:762–765.

Das (1985) Intraparenchymal transplantation, neural grafting in the mammalian CNS, Bjorklund and Stenevi, eds. Ch.3, pp. 23–30.

Freed, Transplantion of tissues to the cerebral ventricles: methodological details and rate of graft survival, Neural Grafting in the Mammalian CNS, *Bjorklund and Steveni*, eds. Ch.4, pp. 31–40.

Brundin et al. (1985) Intracerebral grafts of neuronal cell suspensions, neural grafting in the mammalian CNS, *Bjorklund and Stenevi*, eds. Ch. 6, pp. 41–50.

David et al. (1985) Peripheral nerve transplantation techniques to study axonal regeneration from the cns of adult mammals, neural grafting in the mammalian CNS, *Bjorklund and Stenevi*, eds. Ch. 7 pp. 61–70.

Gage et al., Astrocytes are important for sprouting in the septohippocampal circuit, *Exp. Neurol.* 102:2–13.

Wolf et al. (1988) Retrovirus–mediated gene transfer of beta–nerve growth factor into mouse pituitary line at AtT–20, *Mol. Biol. Med.* 5:43–59.

Gage et al. (1983) Reinnervation of the partially deafferented hippocampus by compensatory collateral sprouting from spared cholineric and noradrenagic afferents, *Brain Res.* 268:27–37.

Robinson et al. (1986) Macrophage heterogeneity in the rat as delineated by two monoclonal antibodies mrc ox–41 and mrc ox–42, the latter recognizing complement receptor type 3, Immunol. 57:239–247.

Stenevi et al. (1976) Transplantation of central and peripheral monomaine neurons to the adult rat brain: techniques and conditions for survival, *Brain Res.* 114:1–20.

Rosenstein and Brightman (1986) Alterations of the blood–brain barrier after transplantation of autonomic ganglia into the mammalian central nervous system, *J. Comp. Neurol.* 250:339–351.

Gibbs et al., Transplantation of septal neurons maintained in long–term culture, *Brain Res.* 382:409–415.

Coyle and Schwarcz (1976) Lesion of striatal neurons with kainic acid provides a model for huntington's chores, *Nature* 263:244–246.

Dean et al. (1986) Regulation of c–myc transcription and mrna abundance by serum growth factors and cell contact, *J. Biol Chem.* 261:9161–9166.

Freed and Cannon–Spoor (1989) Cortical lesions interfere with behavioral recovery from unilateral substantial nigra lesions induced by brain grafts, *Behav. Brain Res.* 32:279:288.

Fonnum (1975) A rapid radiochemical method for the determination of choline acetyltransferase, *J. Neurochem.* 24:407–409.

Berrard et al., cDNA cloning and complete sequence of porceine choline acetyltransferase: in vitro translation of the corresponding rna yields in active protein, *Proc. Natl. Acad. Sci.* 84:9280–9284.

Horellou et al. (1990) In vivo release of dopa and dopamine from genetically engineered cells grafted top the denervated rat striatum, *Neuron* 5:393–402.

Fisher et al. (1991) Survival and function of intrastriatally grafted primary fibroblasts genetically modified to produce 1–dopa, *Neuron* 6:371–380.

Cohen and Wortman (1975) Brain acetylcholine: increase after systemic choline administration, *Life Sci.* 16:1095–1102.

Chen et al. (1991) Cellular replacement therapy for neurologic disorders: potential of genetically engineered cells, *J. Cell. Biochem.* 45:252–257.

Gorman et al. (1982) The Rous Sarcoma virus long terminal repeat is a strong promoter when introduced into a variety of eukaryotic cells by DNA–mediated transfection, *Proc. Natl. Acad. Sci.* 79:6777–6781.

de Crombrugghe and Schmidt (1987) Structure and expression of collagen genes, *Meth. in Enzymol.* 144:61–74.

Thompson et al. (1990) Methylation–dependent transcription repression of human pro–α1(1) Collagen Gene, *Annals. NY Acad. Sci.* 580:456–458.

Sleigh (1986) A nonchromatographic assay for expression of the cloramphenicol acetyltransferease gene In eukaryotic cells, *Anal. Biochem.* 156:251–256.

Kawaja and Gage (1986) Nerve growth factor receptor immunoreactivity in the rat septohioppocampal pathway: a light electron microscope investigation, *Brain Res.* 369:151–162.

Short et al. (1988) Autocrine differentiation of rat pheochromocytoms PC12 cells using a retroviral NGF vector, *Society of Neuroscience Abstracts*, Abstract No. 448.12 14:1115.

Friedman et al. (1988) Fate and gene expression in retrovirality–infected cells grafted to the rat brain; *J. Cell. Biochem.* Abstract No. H009; vol. Supp. 0 (12 Part B) p. 163.

Breakfield et al. (1988) Retroviral gene transfer of beta–nerve growth factor into cultured cells, *J. Cell Biochem.* Abstract No. H102; Vol. Suppl. 0 (Part B):170.

Gage et al. (1987) Grafting of genetically engineered cells to the adult rat brain, *Neurosci.* Abstract No. 1766P; 22:590.

Gage et al. (1987) Grafting of genetically modified cells to brain: possibilities for the future, *Neurosci.* 23(3):795–807.

Selden et al. (1987) Implantation of genetically engineered fibroblasts into mice: implications for gene therapy, *Science* 236:714–718.

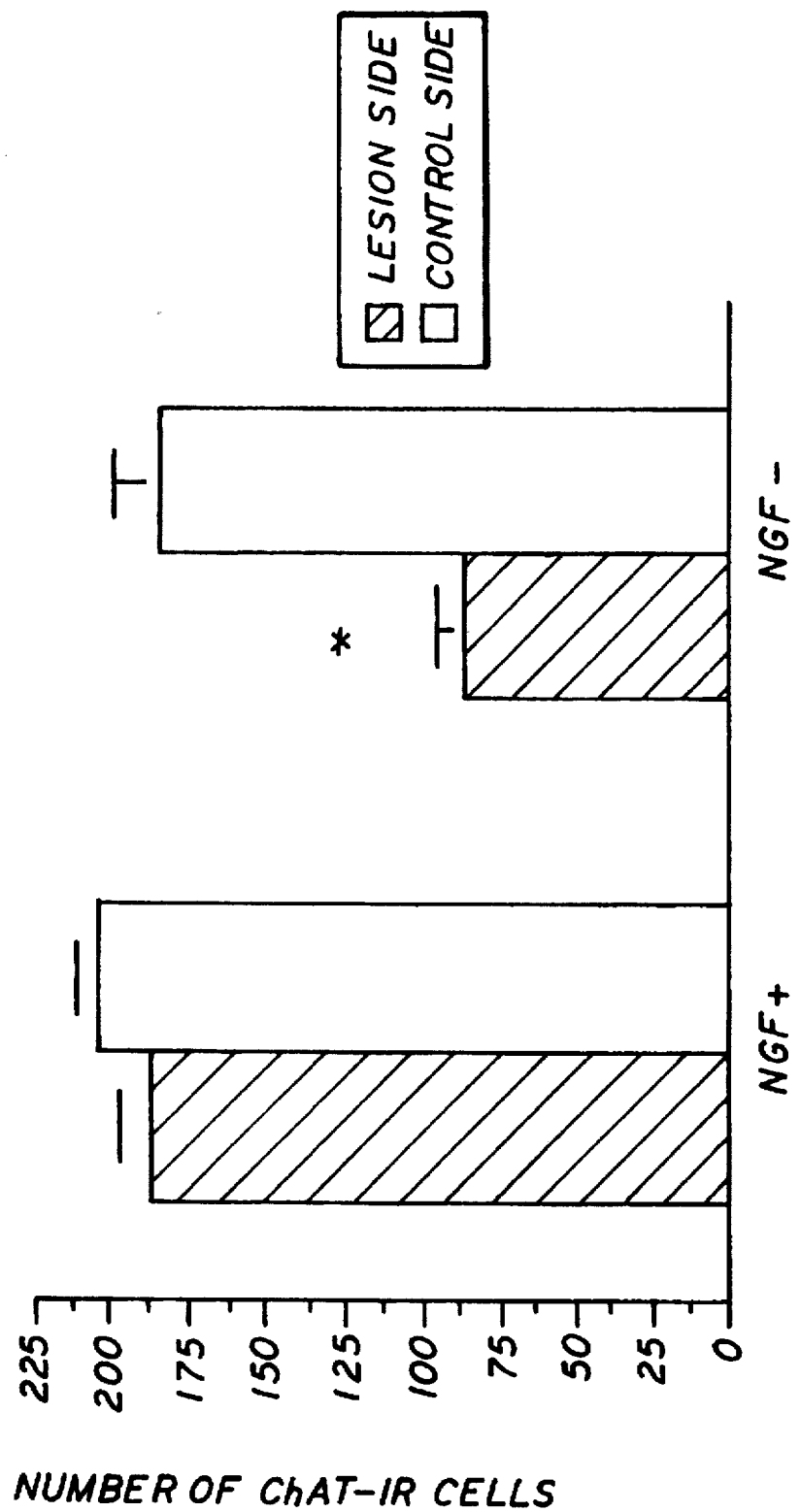

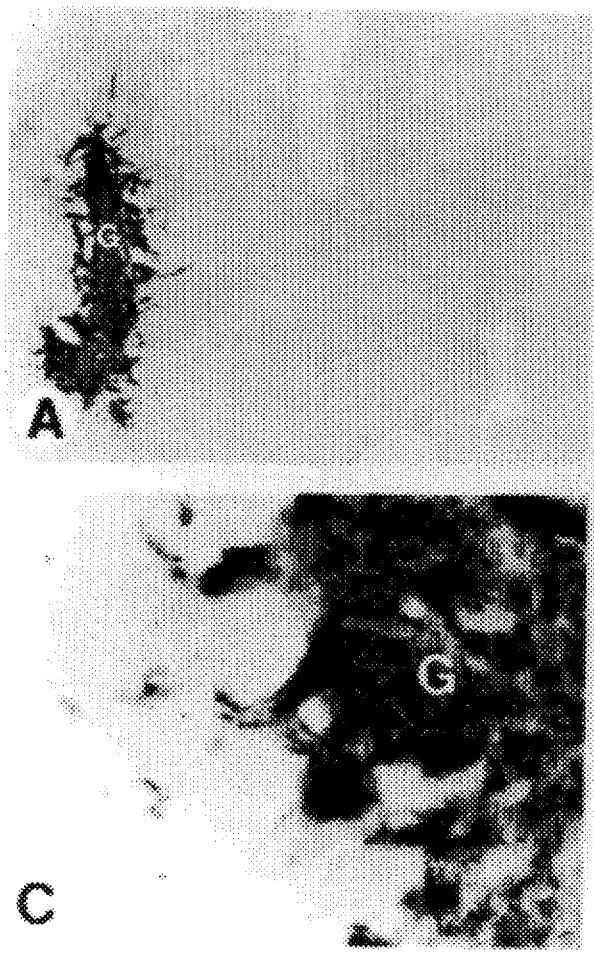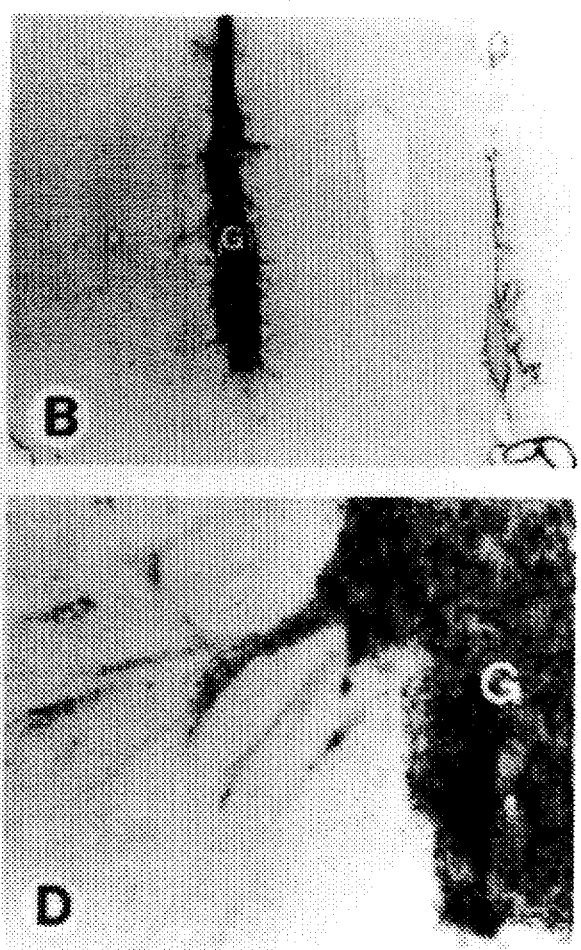
FIG. 23a  FIG. 23b
FIG. 23c  FIG. 23d

FIG. 25a
FIG. 25b
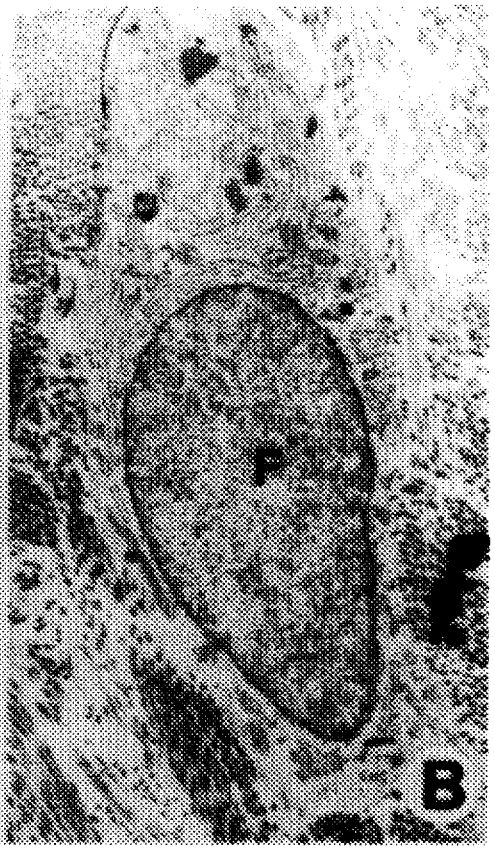
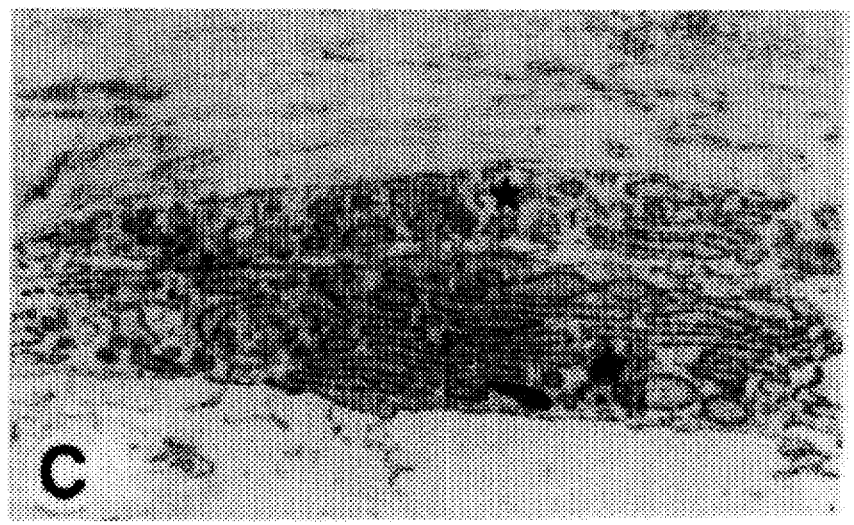
FIG. 25c

FIG. 26a
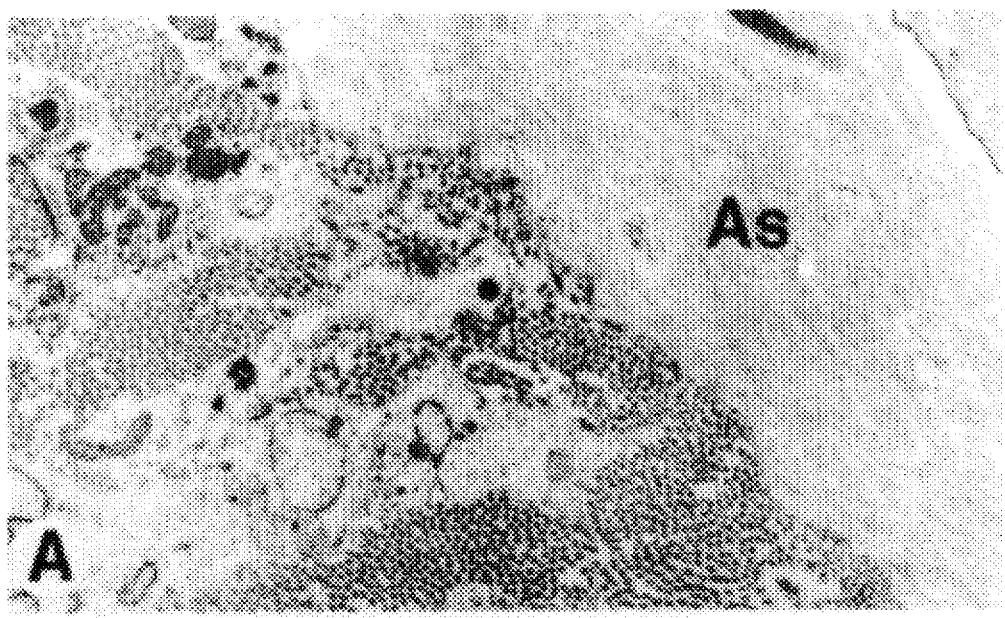
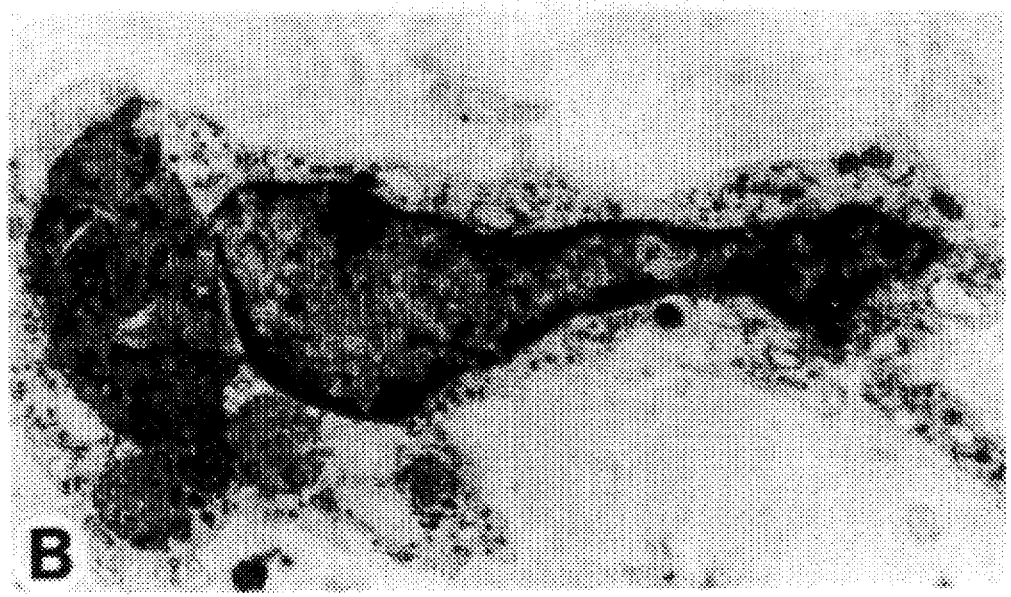
FIG. 26b

FIG. 27a
FIG. 27b
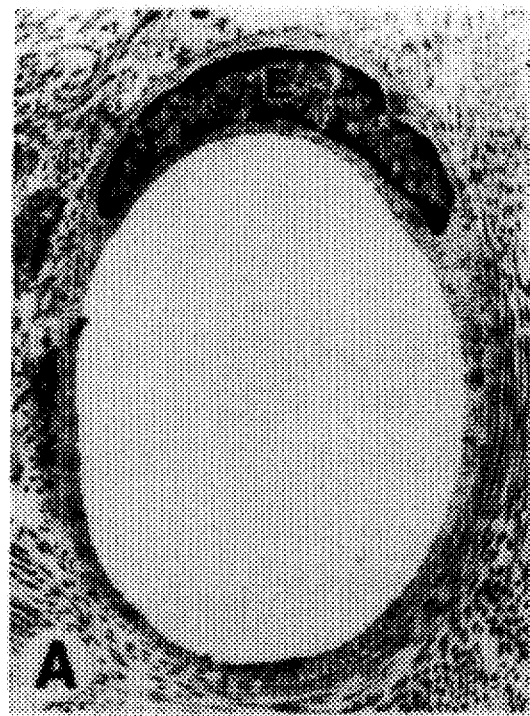
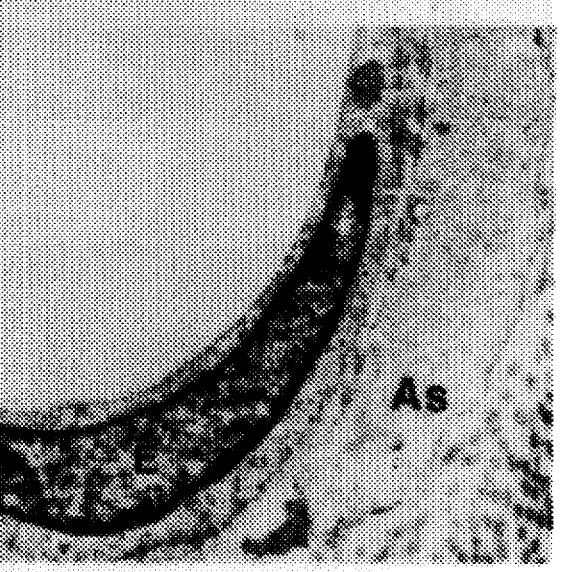
FIG. 27c
FIG. 27d

TOP

MIDDLE

BOTTOM

FIG. 31a
FIG. 31b
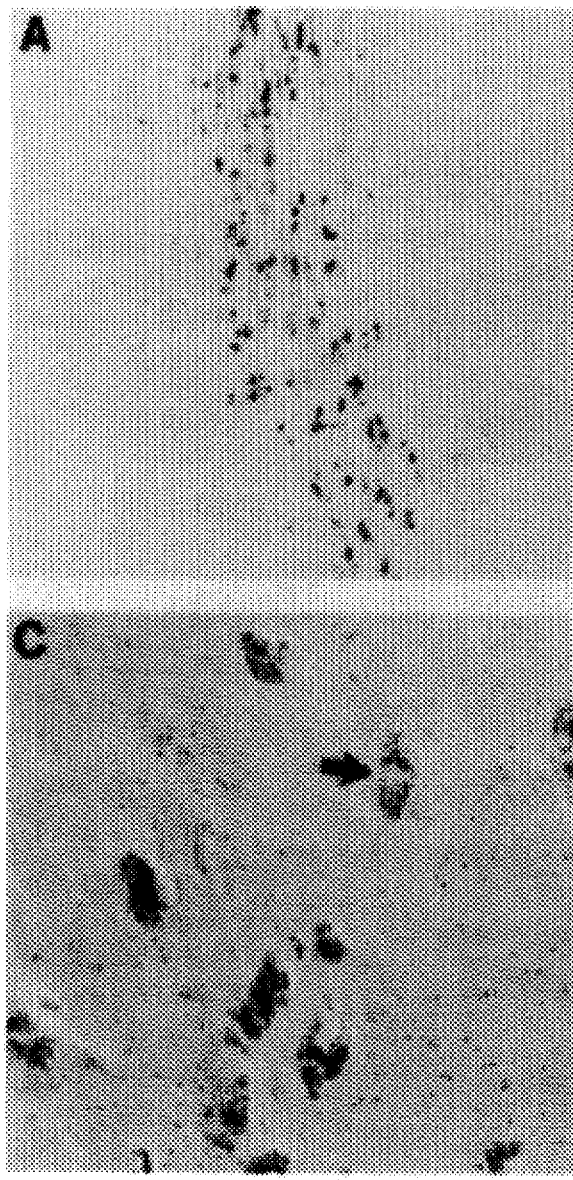
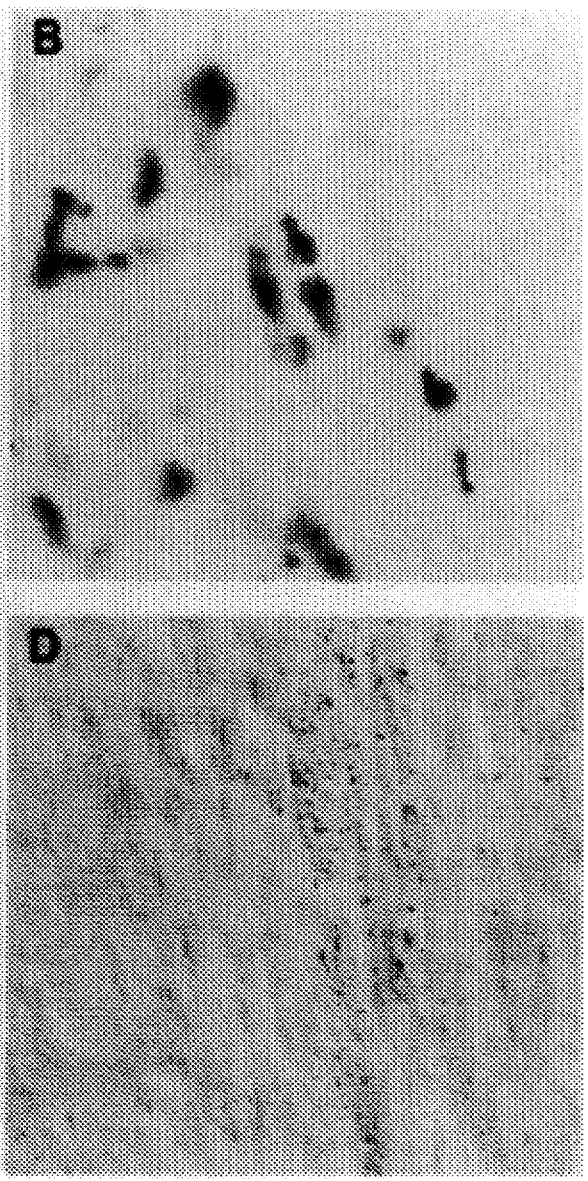
FIG. 31c
FIG. 31d

FIG. 32a
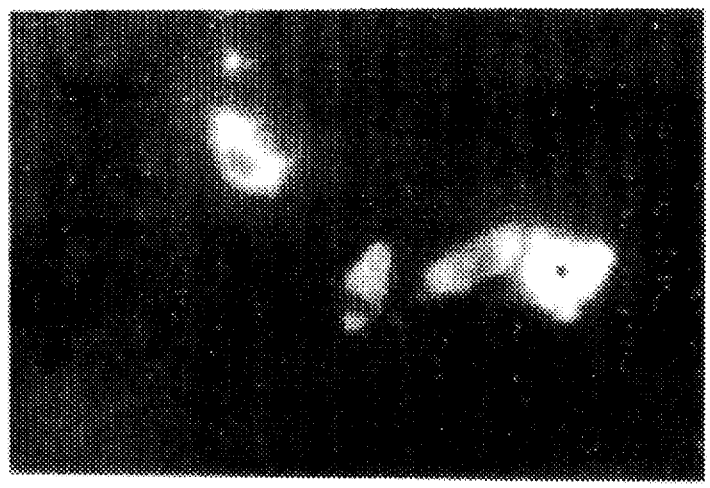
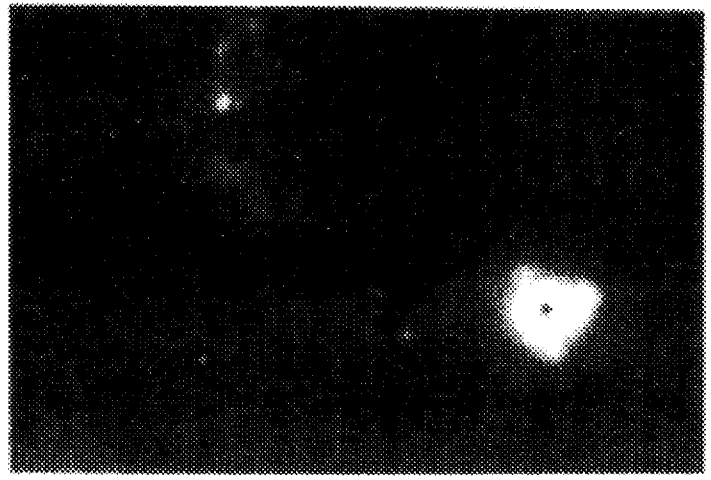
FIG. 32b

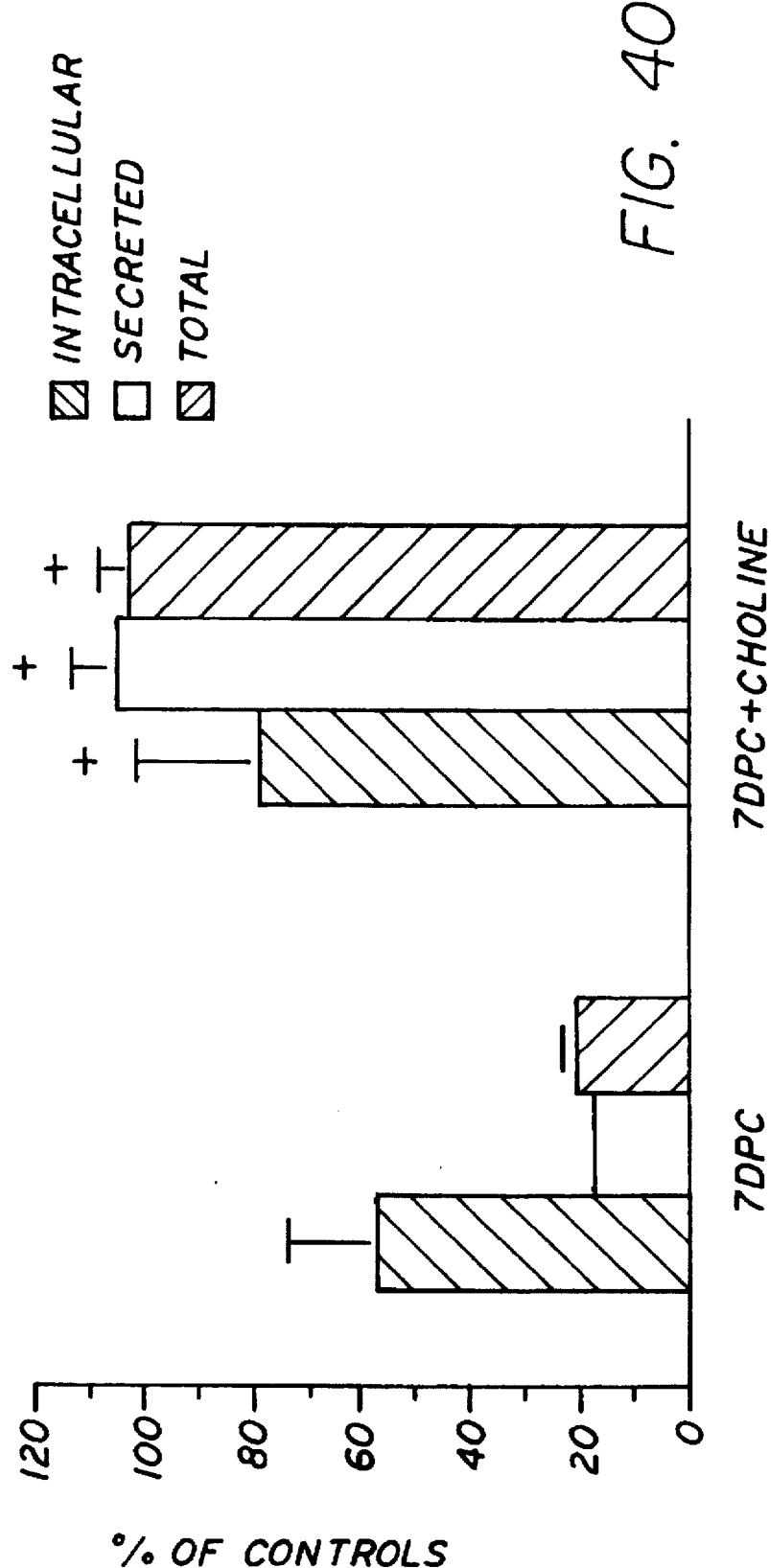

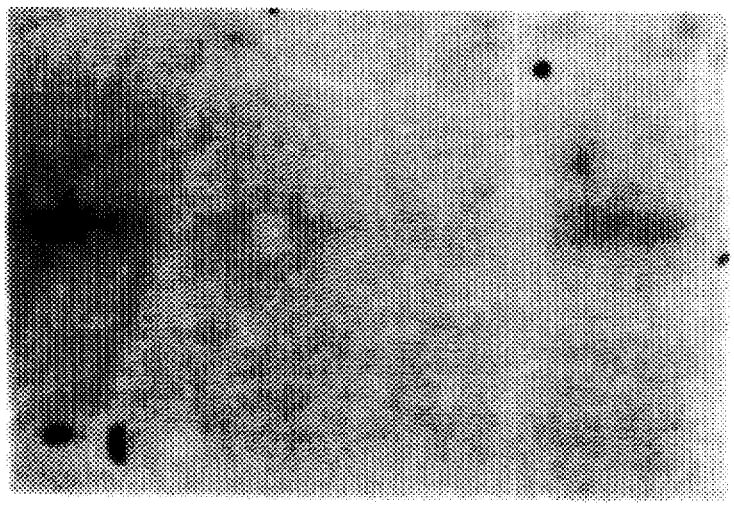
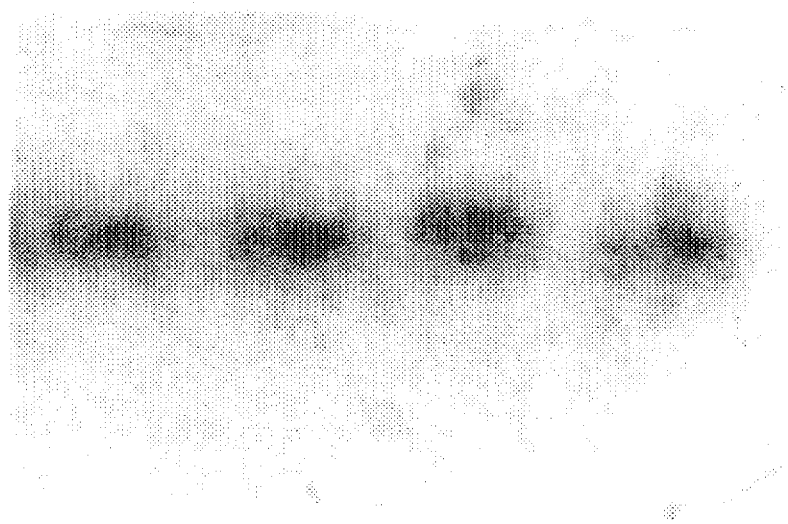
FIG. 45a

FIG. 49a
FIG. 49b
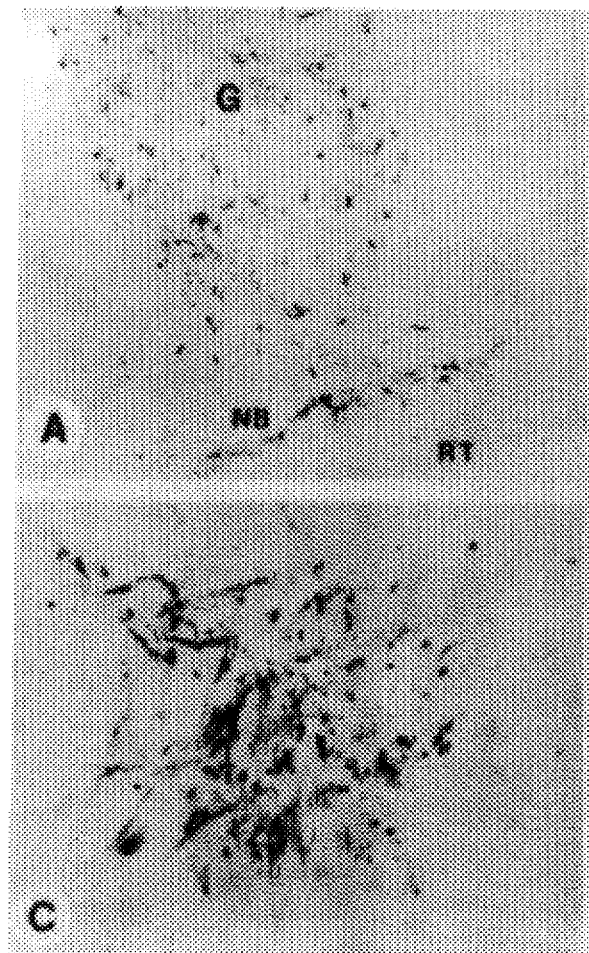
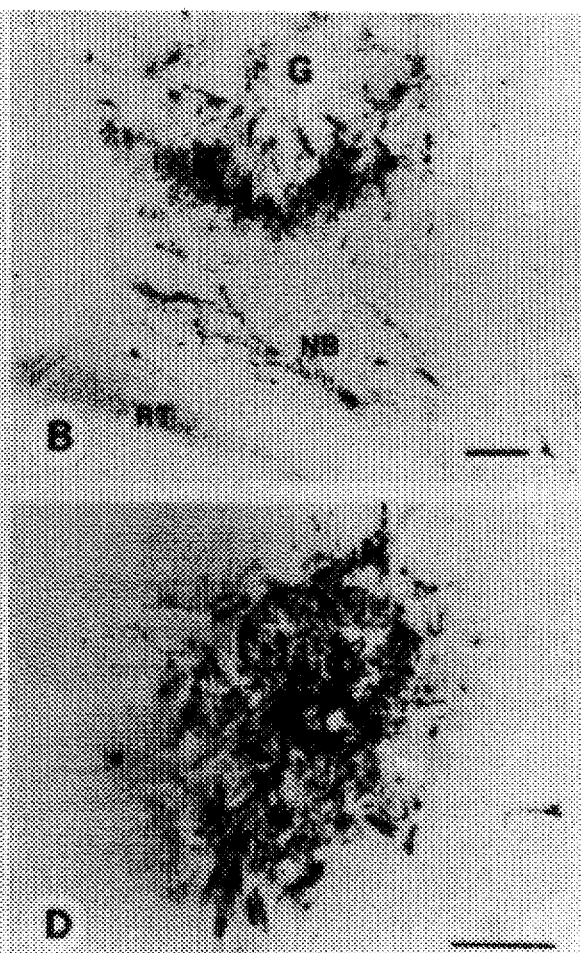
FIG. 49c
FIG. 49d

METHOD OF GRAFTING GENETICALLY MODIFIED CELLS TO TREAT DEFECTS, DISEASE OR DAMAGE OF THE CENTRAL NERVOUS SYSTEM

CROSS-REFERENCE TO RELATED APPLICATIONS

This application is a divisional application of U.S. Ser. No. 08/209,609, filed Mar. 10, 1994, which is a file wrapper continuation of U.S. Ser. No. 07/792,894, filed Nov. 15, 1991, now abandoned, which is continuation-in-part of U.S. Ser. No. 07/285,196 filed Dec. 15, 1988, now U.S. Pat. No. 5,082,670, the entire disclosure of which is expressly incorporated by reference herein.

ACKNOWLEDGEMENT OF GOVERNMENT SUPPORT

This invention was made with Government support under Grant Contract No. N00014-86-K-0347 awarded by the Office of Naval Research, and Grant Contract Nos. HD-20034, NIA-06088, HD-00669, awarded by NIH and NIA R01 AG08514, awarded by the Department of Health and Human Services. The Government has certain rights in this invention.

TECHNICAL FIELD OF THE INVENTION

The present invention relates to the use of recombinant technology for genetic modification of donor cells for grafting into the central nervous system (CNS) of a subject to treat defects, disease or damage of the CNS. More specifically, the invention relates to the insertion of genes into donor cells, encoding molecules having ameliorative effects on cells in the CNS, including neurons into donor cells such that when the donor cells are grafted into,the CNS the molecules are expressed and exert their effects on diseased or damaged cells.

BACKGROUND OF THE INVENTION

Attempts to repair the mammalian brain or replace CNS functions resulting from defects or following disease or damage to the CNS are hampered by an incomplete understanding of the complex structure-function relationships in the CNS. Although knowledge of some basic principles of cell function in the brain has advanced greatly in recent years, understanding of interactions between clusters of cells or systems and cell circuits in different regions of the brain and their relationship to the outward manifestations of behavior and neurological function lags far behind. Difficulties in approaching these problems have been caused, in part, by the large number of different cell types in the mammalian CNS and the number and complexity of their connections. In addition, the blood-brain barrier makes access to the brain for diagnosis, treatment and the design of new therapies more difficult.

In spite of the absence of sophisticated knowledge of the pathophysiology of most normal or abnormal brain functions, some attempts at pharmacological therapy for CNS dysfunction have already become useful and effective. These include the use of psycho-active drugs for psychiatric disorders such as schizophrenia, and specific replacement therapy in the rare cases in which the biochemical and cellular bases of the CNS disorder are relatively better understood, as in Parkinson's disease. At the core of most therapeutic approaches is the objective of replacing or reactivating a specific chemical function in the brain that has been lost as a consequence of disease or damage.

Intracerebral neural grafting has emerged recently as an additional potential approach to CNS therapy. The replacement or addition of cells to the CNS which are able to produce and secrete therapeutically useful metabolites may offer the advantage of averting repeated drug administration while also avoiding the drug delivery complications posed by the blood-brain barrier. (Rosenstein, *Science* 235:772–774 (1987)). While the concepts and basic procedures of intracerebral grafting have been known for decades, most of the factors that optimize the survival of grafted cells have only recently come to be investigated and partially understood. (Bjorklund et al., in *Neural Grafting in the Mammalian CNS*, p. 709, Elsevier, Amsterdam (1985); Sladek et al., in *Neural Transplants: Development and Function*, Plenum Press, NY (1984)). Several factors critical for reliable and effective graft survival have been identified, including the following:

(1) Age of the donor: efficiency of grafting is reduced with increasing age of donor cells.

(2) Age of the host: young recipients accept grafts more readily than older ones.

(3) Availability of neurotrophic factors in the host and donor tissue: wound-induced neurotrophic factors enhance graft survival.

(4) Immunological response: the brain is not totally an immunologically privileged site.

(5) The importance of target-donor matching: neurons survive better when they are grafted to a site which they would normally innervate.

(6) Vascularization: it is critical that the grafts be vascularized rapidly or otherwise sufficiently well nourished from the environment.

As these critical factors have become recognized and optimized, intracerebral grafting has become a valid and reliable tool for neurobiologists in the study of CNS function and potentially for clinicians for the design of therapies of CNS disease. This approach has reached a level of experimental clinical application in Parkinson's disease.

Parkinson's disease is an age-related disorder characterized by a loss of dopamine neurons in the substantia nigra of the midbrain, which have the basal ganglia as their major target organ. The symptoms include tremor, rigidity and ataxia. The disease is progressive but can be treated by replacement of dopamine through the administration of pharmacological doses of the precursor for dopamine, L-dopa, (Marsden, *Trends Neurosci.* 9:512 (1986); Vinken et al., in *Handbook of Clinical Neurology* p. 185, Elsevier, Amsterdam (1986)), although with chronic use of pharmacotherapy the patients often become refractory to the continued effect of L-dopa. There are many suggested mechanisms for the development of the refractory state, but the simplest is that the patients reach a threshold of cell loss, wherein the remaining cells cannot synthesize sufficient dopamine from the precursor.

Parkinson's disease is the first disease of the brain for which therapeutic intracerebral grafting has been used in humans. Several attempts have been made to provide the neurotransmitter dopamine to cells of the diseased basal ganglia of Parkinson's patients by homografting adrenal medullary cells to the brain of affected patients. (Backlund et al., *J. Neurosurg.* 62:169–173 (1985); Madrazo et al., *New Eng. J. Med.* 316:831–836 (1987)). The transplantation of other donor cells such as fetal brain cells from the substantia nigra, an area of the brain rich in dopamine-containing cell bodies and also the area of the brain most affected in Parkinson's disease, has been shown to be effective in reversing the behavioral deficits induced by selective dopaminergic neurotoxins. (Bjorklund et al., *Ann. N.Y. Acad. Sci.* 457:53–81 (1986); Dunnett et al., *Trends Neurosci.* 6:266–270 (1983)). These experiments suggest that synaptic connectivity may not be a requisite for a functional graft and that it may be sufficient to have cells constitutively producing and secreting dopamine in the vicinity of the defective cells.

With this background, it seems likely that Parkinson's disease is a candidate disease for the transplantation of genetically engineered cells, because (1) the chemical deficit is well known (dopamine), (2) the human and rat genes for the rate-limiting enzyme in the production of dopamine have been cloned (tyrosine hydroxylase), (3) the anatomical localization of the affected region has been identified (basal ganglia), and (4) synaptic connectivity does not appear to be required for complete functional restoration.

The recent demonstration of genetic components in a rapidly growing list of other CNS diseases, including Huntington's disease, (Gusella et al., *Nature* 306:234–238 (1983)) Alzheimer's disease, (Delabar et al., *Science*, N.Y. 235, 1390–1392 (1987); Goldgaber et al., *Science*, N.Y. 235:877–880 (1987); St. George-Hyslop et al., *Science*, N.Y. 235:885–890 (1987); Tanzi et al., *Science*, N.Y. 235:880–884 (1987)); bipolar disease (Baron et al., *Nature* 326:289–292 (1987)); schizophrenia (Sherrington et al., *Nature* 336:164–167 (1988) and many other major human diseases, suggests that gene therapy is an useful approach to treat these CNS diseases.

In parallel to the progress in neurobiology during the past several decades, advances in an understanding of molecular biology and the development of sophisticated molecular genetic tools have provided new insights into human disease in general. As a result, medical scientists and geneticists have developed a profound understanding of many human diseases at the biochemical and genetic levels. The normal and abnormal biochemical features of many human genetic diseases have become understood, the relevant genes have been isolated and characterized, and early model systems have been developed for the introduction of functional wild-type genes into mutant cells to correct a disease phenotype. (Anderson, *Science* 226:401–409 (1984)). The extension of this approach to whole animals, that is, the correction of a disease phenotype in vivo through the use of the functional gene as a pharmacologic agent, has come to be called "gene therapy". (Friedmann et al., *Science* 175:949–955 (1972); Friedmann, *Gene Therapy Fact and Fiction*, Cold Spring Harbor Laboratory, New York (1983)). Gene therapy is based on the assumption that the correction of a disease phenotype can be accomplished either by modification of the expression of a resident mutant gene or the introduction of new genetic information into defective or damaged cells or organs in vivo.

At present, techniques for the ideal versions of gene therapy, that is through site-specific gene sequence correction or replacement in vivo are just beginning to be conceived but are not yet well developed. Therefore, most present models of gene therapy are actually genetic augmentation rather than replacement models and rely on the development of efficient gene-transfer systems to introduce functional, wild-type genetic information into genetically defective cells in vitro and in vivo. To be clinically useful, the availability of efficient delivery vectors for functional DNA sequences (transgenes) must be combined with easy accessibility of suitable disease-related target cells or organs and with the development of techniques to introduce the vector stably and safely into those target cells.

Model systems for the genetic and phenotypic correction of simple enzymatic deficits are now being developed and studied, as is the identification of the appropriate potential recipient cells and organs associated with specific metabolic and genetic diseases. Evidence has recently been obtained to show that foreign genes introduced into fertilized mouse eggs can correct disease phenotype. (Constantini et al., *Science* 233:1192–1394 (1986); Mason et al., *Science* 234:1372–1378 (1986); and Readhead et al.; *Cell* 48:703–712 (1987)).

A great deal of attention has recently been paid to the use of gene delivery vectors derived from murine retroviruses (Anderson, *Science* 226:401–409 (1984); Gilboa et al, *Biotechniques* 4:504–512 (1986)) for gene transfer. Gene transfer in vitro using such retroviral vectors is extremely efficient for a broad range of recipient cells, the vectors have a suitably large capacity for added genes, and infection with them does little metabolic or genetic damage to recipient cells. (Shimotohno et al., *Cell* 26:67–77 (1981); Wei et al., *J. Virol*. 39:935–944 (1981); Tabin et al., *Molec. Cell. Biol.* 2:426–436 (1982)). Several useful systems have demonstrated that the expression of genes introduced into cells by means of retroviral vectors can correct metabolic aberrations in vitro in several human genetic diseases associated with single-gene enzyme deficiencies. (Willis et al., *J. Biol. Chem.* 259:7842–7849 (1984); Kantoff et al., *Proc. Natl. Acad. Sci. USA* 83:6563–6567 (1986)). There has been particular interest in bone marrow as a potential target organ for this approach to gene therapy because of the prevalence and importance of disorders of bone marrow-derived cell lineages in a variety of major human diseases, including the thalassemias and sickle-cell anemia, Gaucher's disease, chronic granulomatous disease (CGD) and immunodeficiency disease resulting from deficiencies of the purine pathway enzymes, adenosine deaminase (ADA) and purine nucleoside phosphorylase (PNP) (Kantoff, supra; McIvor et al., *Molec. Cell. Biol.* 7:838–846 (1987); Soriano et al., *Science* 234:1409–1413 (1986); Willis et al., supra)). Other metabolically important target organs, such as the liver, have also recently become theoretically susceptible for genetic manipulation through the demonstration of infection of cells from such organs with viral vectors (Wolff et al., *Proc. Natl. Acad. Sci. USA* 84:3344–3348 (1987)). Furthermore, the discovery of numerous cell-specific regulatory signals such as cis-acting enhancers, tissue-specific promoters and other sequences may provide tissue specific gene expression in many other organs even after general, non-specific infections and gene transfer in vivo (Khoury et al., *Cell* 33:313–314 (1983); Serflin et al., *Trends Genet.* 1:224–230 (1985)).

A recently developed model of gene therapy uses target cells removed from a subject, placed in culture, genetically modified in vitro, and then re-implanted into the subject (Wolff et al., *Rheumatic Dis. Clin. N. Amer.* 14(2) 459–477 (1988); Eglitis et al. *Biotechniques* 6:608–614 (1988)). Target cells have included bone marrow stem cells (Joyner et al., *Nature* 305:556–558 (1983); Miller et al., *Science* 225:630–632 (1984); Williams et al., *Nature* 310:476–480 (1984)); fibroblasts (Selden et al., *Science* 236:714–718 (1982); Garver et al., *Proc. Natl . Acad. Sci. USA* 84:1050–1054 (1987) and St. Louis et al., *Proc. Natl. Acad. Sci. USA* 85:3150–3154 (1988)), keratinocytes (Morgan et al., *Science* 237:1476–1479 (1987)) and hepatocytes (Wolff et al., *Proc. Natl. Acad. Sci. USA* 84:3344–3348 (1987)). This indirect approach of in vivo gene transfer is necessitated by the inability to transfer genes efficiently directly into cells in vivo. Although there has been some recent progress towards genetically modifying neurons in culture (Geller et al., *Science* 241:1667–1669 (1988)), this indirect approach of in vivo gene transfer has not yet been applied to the CNS.

There are several ways to introduce a new function into target cells in the CNS in a phenotypically useful way i.e. to treat defects, disease or dysfunction (FIG. 1). The most direct approach, which bypasses the need for cellular grafting entirely, is the introduction of a transgene directly into the cells in which that function is aberrant as a consequence of a developmental or genetic defect, i.e. neuronal cells in the case of Tay-Sachs disease, possibly Lesch-Nyhan disease, and Parkinson's disease (1, in FIG. 1). Alternatively, a new function is expressed in defective target cells by introducing a genetically modified donor cell that could establish gap junction or other contacts with the target cell (2, in FIG. 1). Some such contacts are known to permit the efficient diffusion of metabolically important small molecules from one cell to another, leading to phenotypic changes in the recipient cell (Lowenstein, *Biochim. Biophys. Acta.* 560:1–66 (1979)). This process has been called "metabolic cooperation" and is known to occur between fibroblasts and glial cells (Gruber et al., *Proc. Natl. Acad. Sci. USA* 82:6662–6666 (1985)), although it has not yet been demonstrated conclusively in neurons. Still other donor cells could express and secrete a diffusible gene product that can be taken up and used by nearby defective target cells (3, in FIG. 1). The donor cells may be genetically modified in vitro or alternatively they may be directly infected in vivo (4, in FIG. 1). This type of "co-operativity" has been demonstrated with CNS cells, as in the case of NGF-mediated protection of cholinergic neuronal death following CNS damage (Hefti, *J. Neurosci.* 6:2155 (1986); Williams et al., *Proc. Natl. Acad. Sci. USA* 83:9231–9235 (1986)). Finally, an introduced donor cell infected with not only replication-defective vector but also replication-competent helper virus, could produce locally high titers of progeny virus that might in turn infect nearby target cells to provide a functional new transgene (5, in FIG. 1).

There are several types of neurons in the mammalian brain. Cholinergic neurons are found within the mammalian brain and project from the medial septum and vertical limb of the diagonal band of Broca to the hippocampal formation in the basal forebrain. The short, nerve-like portion of the brain connecting the medial septum and vertical limb of the diagonal band with the hippocampal formation is termed the "fimbria fornix". The fimbria fornix contains the axons of the neurons located in the medial septum and diagonal band. An accepted model of neuron survival in vivo is the survival of septal cholinergic neurons after fimbria fornix transection or lesion (also termed "axotomy"). Axotomy severs the cholinergic neurons in the septum and diagonal band and results in the death of up to one-half of the cholinergic neurons (Gage et al., *Neuroscience* 19:241–256 (1986)). This degenerative response is attributed to the loss of trophic support from nerve growth factor (NGF), which is normally transported retrogradely in the intact brain from the hippocampus to the septal cholinergic cell bodies (Korsching et al., *Proc. Natl. Acad. Sci. USA* 80:3513 (1983); Whittemore et al., *Proc. Natl. Acad. Sci. USA* 83:817 (1986); Shelton et al., *Proc. Natl. Acad. Sci. USA* 83:2714 (1986); Larkfors et al., *J. Neurosci. Res.* 18:525 (1987); and Seilor et al., *Brain Res.* 300:33 (1984)).

Studies have shown that chronic intra-ventricular administration of NGF before axotomy will prevent cholinergic neuron death in the septum (Hefti, *J. Neurosci.* 8:2155–2162 (1986); Williams et al., *Proc. Natl. Acad. Sci. USA* 83:9231 (1986); Kromer, *Science* 235:214 (1987); Gage et al. *J. Comp. Neurol.* 269:147 (1988)). Axotomy thus provides an in vivo model for determining at various points in time the ability of various therapies to prevent retrograde neuronal death.

One of the characteristics of the adult mammalian CNS is that new axons generated following perturbation can only grow a relatively short distance within the brain (Cajal, in Degeneration and Regeneration of the Nervous System, Oxford University Press, London, England, (1928)). This inability of adult neurons to regenerate in response to damage may be due to the following: 1) Activation of astrocytes, which are support and nutritive cells found throughout the CNS, following injury results in the formation of scar tissue which acts as a physical barrier to regenerating axons such that fibers are unable to traverse the scar tissue; thus astrocytic scars are unable to provide a conducive substrate for axon elongation (Cajal, supra; Brown, *J. Comp. Neurol.* 87:131 (1947); Clemente, in Regeneration in the Central Nervous System, ed. Windle, pp. 147–161, Thomas, Springfield, (1955); Windle, *Physiol. Rev.* 36:426 (1956); and Reier et al., in Spinal Cord Reconstruction, eds. Kao et al., pp. 163–195, Raven, N.Y. (1983)). Astrocytes in the immature CNS, on the other hand, play an important role in the guidance of elongating axons (Silver et al., *J. Comp. Neurol.* 210:10–29 (1982)); 2) Myelin-associated substances released following damage to the brain have been shown to inhibit axon growth in vitro (Schwab and Croni, *J. Neurosci.* 8:2381–2393 (1988)) ; 3) The lack of axonal regeneration in the adult CNS may be due, in part, to inadequate levels of trophic or tropic molecules which induce neuronal regeneration and promote axon growth, respectively (Reier et al., in Neural Regeneration and Transplantation, pp. 183–209, Alan R. Liss, New York, (1989) and Schwartz et al., *FASEB J.* 3:2371–2378 (1989)).

Despite many factors which may impede axon regrowth within the adult brain, certain neurons in the rat CNS, especially retinal ganglion neurons and septal cholinergic neurons, exhibit a remarkable potential to extend new axons into substrates of various types, so-called "neural bridges", including segments of autologous peripheral nerve (David and Aguayo, *Science* 214:931 (1981); Benfry and Aguayo, *Nature* 296:150 (1982); Wendt et al., *Exp. Neurol.* 79:452 (1983); and Hagg et al., *Exp. Neurol.* 109:153 (1990)), cultured Schwann cells within a collagen matrix (Kromer and Cornbrooks, *Proc. Natl. Acad. Sci. USA* 82:6330 (1985) ), embryonic rat hippocampus (Kromer et al., *Brain Res.* 210:153 (1981)), and human amnionic membrane (Gage et al., *Exo. Brain Res.* 72:371 (1988)). Connectivity between the septum and hippocampus of the brain has also been demonstrated using implants of peripheral homogenates of neurons (Wendt, *Brain Res. Bull.* 15:13–18 (1985)).

It would be advantageous, therefore, to develop procedures for gene transfer via efficient vectors followed by intracerebral grafting of the genetically modified cells in vivo so as to ameliorate nerve cell disease, defect or dysfunction, and to promote axonal regeneration, to treat disorders of the CNS, such as Alzheimer's disease, Parkinson's disease and Huntington's disease.

SUMMARY OF THE INVENTION

The present invention provides methods for treating defective, diseased or damaged cells in the mammalian central nervous system by grafting genetically modified donor cells into the central nervous system to produce functional molecules in a sufficient amount to ameliorate the defective, diseased or damaged cells in the central nervous system. The cells may be modified using viral or retroviral vectors, including pLN.8RNL and pLThRNL, containing an inserted therapeutic transgene or transgenes encoding a product or products which directly or indirectly affect the cells, or by other methods of introducing functional DNA into a cell. The cells may be cultured and injected in suspension into the central nervous system and may be co-administered with a therapeutic agent for treating defective, diseased or damaged cells in the central nervous system. The methods of the invention include selection, preparation and transfection of donor cells, and grafting.

The donor cells may be a mixture of cell types from different anatomical regions and may be primary or immortalized cells.

Grafting of the donor cells may be accomplished by multiple grafting of the donor cells into several different sites within the mammalian CNS. For multiple grafting the cells may be a mixture of different types of donor cells, or may be the same or different types of cells containing the same or different transgenes.

Grafting may be accompanied by implanting the cells in a substrate material such as a collagen matrix to promote transplant survival and/or by the use of such material to facilitate reconnection between or ameliorative interactions of injured neurons.

Vectors for use in the invention include those carrying a promoter such as a collagen promoter to enhance expression of the transgene or transgenes. The vectors may also carry enhancer sequences to increase the activity of the promoter.

The secretion of the functional molecules may be regulated using a precursor for said molecules. A method of the invention is the grafting of fibroblasts modified to express acetylcholine into the CNS and the administration of choline chloride orally to maintain and enhance the secretion of acetylcholine from the grafted fibroblasts.

The invention includes a method for enhancing the expression of a therapeutic transgene product from quiescent donor cells grafted into a mammalian central nervous system, by inserting a quiescent promoter into a vector used to genetically modify the donor cells. The promoter may be a non-viral promoter such as a collagen promoter. Additional enhancer sequences may be inserted with the promoter. Cytokines may be administered to regulate promoter activity to enhance transgene expression.

Immunosuppression agents may be used to reduce the production of Interferon-γ to enhance transgene expression. Alternatively, an anti-inflammatory agent may be used to reduce the production of cytokines to enhance the expression of therapeutic transgenes. Growth factors may also be used to maintain the survival of the grafted donor cells in the CNS.

BRIEF DESCRIPTION OF THE DRAWINGS

FIG. 6b, FIG. 6e=cresyl violet; FIG. 6c, FIG. 6f=GFAP; magnification: FIG. 6a–FIG. 6c=88X; FIG. 6d FIG. 6f=440X).

FIG. 13c–FIG. 13f=coronal sections taken through the medial septum of tissue stained for ChAT; FIG. 13a, FIG. 13c, FIG. 13e=animal with graft of retrovirus-infected cells; FIG. 13b, FIG. 13d, FIG. 13f=animal with graft of control cells; Magnification (Mag.): FIG. 13a and 13b=20X; FIG. 13c and FIG. 13d=70 X; FIG. 13e and FIG. 13f=220X).

FIG. 14 is a graph showing survival of ChAT-immunoreactive cells in the septum of a rat in the presence and absence of NGF as described in Example II, infra.

FIG. 15c=higher power magnification of FIG. 15a through the medial septum; FIG. 15e=high power magnification of FIG. 15a through the dorsal lateral quadrant of the septum; FIG. 15b, FIG. 15d, FIG. 15f=animal grafted with control cells as described for FIG. 15a, FIG. 15c, FIG. 15e; Mag.: FIG. 15a, FIG. 15b= 20X; FIG. 15c–FIG. 15f=220X).

FIG. 18a, FIG. 18c=10X; FIG. 18b, FIG. 18d=20X).

FIG. 23a–FIG. 23d are photographs showing primary fibroblast grafts (G) in the striatum stained immunohistochemically for fibronectin at three (FIG. 23a, FIG. 23c) and eight (FIG. 23b, FIG. 23d) weeks after implantation as described in Example IV, infra (Mag. FIG. 23a, FIG. 23b=12X; FIG. 23c, FIG. 23d=120X).

FIG. 25a–FIG. 25c are photographs showing the ultrastructure of autologous grafts at eight weeks post implantation (F=fibroblast cell bodies; solid stars=fibroblast processes), as described in Example IV, infra (Mag. FIG. 25a=6,600X; FIG. 25b=9,100X; FIG. 25c=16,600X).

FIG. 26a–FIG. 26b are photographs showing astrocytic processes and phagocytic cells present in the grafts (As=astrocytic processes) as described in Example IV, infra (Mag. FIG. 26a=16,600X; FIG. 26b=15,000X).

FIG. 27a–FIG. 27d are photographs showing graft vasculature as described in Example IV, infra (FIG. 27a, E=non-fenestrated endothelial cells; FIG. 27b, arrowheads=invaginations; FIG. 27c, arrows=intercellular junctions; FIG. 27d, As=astrocytic processes; Mag. FIG. 27a=13,200X; FIG. 27b=25,400X; FIG. 27c=25,000X; FIG. 27d=16,600X).

FIG. 31a–FIG. 31d are photographs showing the results of in vivo labelling of grafted cells for either βGal histochemistry or in situ hybridization to TH mRNA as described in Example V, infra (FIG. 31a FF2/βGal graft stained for βGal histochemistry; FIG. 31b higher magnification of FF2/βGal graft; FIG. 31c in situ hybridization for TH mRNA in FF2/TH graft, arrow=fibroblasts; FIG. 31d in situ hybridization to TH mRNA in FF2/βGal graft; Mag. FIG. 31a=10X; FIG. 31b, FIG. 31c and FIG. 31d=40X).

FIG. 32a–FIG. 32b are photographs showing the TH-immunoreactivity of FF2/TH fibroblasts in vivo as described in Example V, infra (asterisks=rhodamine fluorescence; Mag.=20X).

FIG. 37b=effects on ChAT activity).

(FIG. 39c), as described in Example VII, infra.

FIG. 40 is a bar graph showing the effect of choline on the release of ACh from confluent fibroblasts as described in Example VII, infra.

FIG. 45a–FIG. 45b are photographs of Northern blots showing the effects of TGFβ, IL-1β and TNFα on dChAT-expressing fibroblasts, as described in Example IX, infra (FIG. 45a: effect of TGF-β (lane 2) and IL-1β (lane 3); FIG. 45b: effect of Infγ, lane 1=control; cyclophilin (Cyc)=internal control; lane 2=effects after 24 hrs; lane 3=effects after 48 hrs; dChAT=dChAT proviral MRNA).

FIG. 49a–FIG. 49d are photomicrographs showing horizontal sections through the left and right striatum at one (FIG. 49a, FIG. 49b) and eight (FIG. 49c, FIG. 49d) weeks after implants (genetically modified cells injected into the right striatum and non-infected controls injected into the left striatum) as described in Example X, infra (G=grafts; NG=nucleus basalis of Meynert; RT=reticular thalamic nucleus; scale bars: FIG. 49a, FIG. 49b, 0.45 mm; FIG. 49c, FIG. 49d, 0.22 mm).

FIG. 52c, FIG. 52d=coronal sections through grafts of either NGF-producing (FIG. 52c) or control, non-infected (FIG. 52d) fibroblasts stained for AChE (dotted line represents approximate boundary of the graft, scale bars in FIG. 52b and 52c=100 μm; scale bar in FIG. 52d=200 μm); FIG. 52e, FIG. 52f, FIG. 52g=coronal sections through the hippocampal dentate gyrus stained for AChE (G=granular layer;, IM=inner molecular layer; OM=outer molecular layer, and P=polymorphic layer)).

FIG. 53b=contralateral diagonal band; FIG. 53c=septal midline; and FIG. 53d=ipsilateral diagonal band; scale bar=50μm).

FIG. 55b=granular layer; FIG. 55c=molecular layer; FIG. 55 d,e,f, arrowheads=synaptic contacts, Sh=dendritic shafts; Sp=spines, As=astrocytic processes, scale bars: in FIG. 55a=25 μm; in FIG. 55b=0.5 μm, in FIG. 55c and representative for FIG. 55d–FIG. 55f=0.25 μm).

DETAILED DESCRIPTION OF THE INVENTION

In order that the invention herein described may be more fully understood, the following detailed description is set forth.

The present invention relates to a process for grafting genetically modified donor cells into the mammalian central nervous system (CNS) to treat disease or trauma of the CNS. More particularly, the invention relates to the use of vectors carrying functional gene inserts (transgenes) to modify donor cells to produce molecules that are capable of directly or indirectly affecting cells in the CNS to repair damage sustained by the cells from defects, disease or trauma. Preferably, for treating defects, disease or damage of cells in the CNS, donor cells such as fibroblasts are modified by introduction of a retroviral vector containing a transgene or transgenes, for example a gene encoding nerve growth factor (NGF) protein. The genetically modified fibroblasts are grafted into the central nervous system, for example the brain, to treat defects, disease such as Alzheimer's or Parkinson's, or injury from physical trauma, by restoration or recovery of function in the injured neurons as a result of production of the expressed transgene product(s) from the genetically modified donor cells. The donor cells may also be used to introduce a transgene product or products into the CNS that enhance the production of endogenous molecules that have ameliorative effects in vivo.

As used herein the term "transgene" or "therapeutic transgene" means DNA inserted into a donor cell encoding an amino acid sequence corresponding to a functional protein capable of exerting a therapeutic effect on cells of the CNS or having a regulatory effect on the expression of a function in the cells of the CNS.

Gene Transfer Into Donor Cells In Vitro

Figure 1:
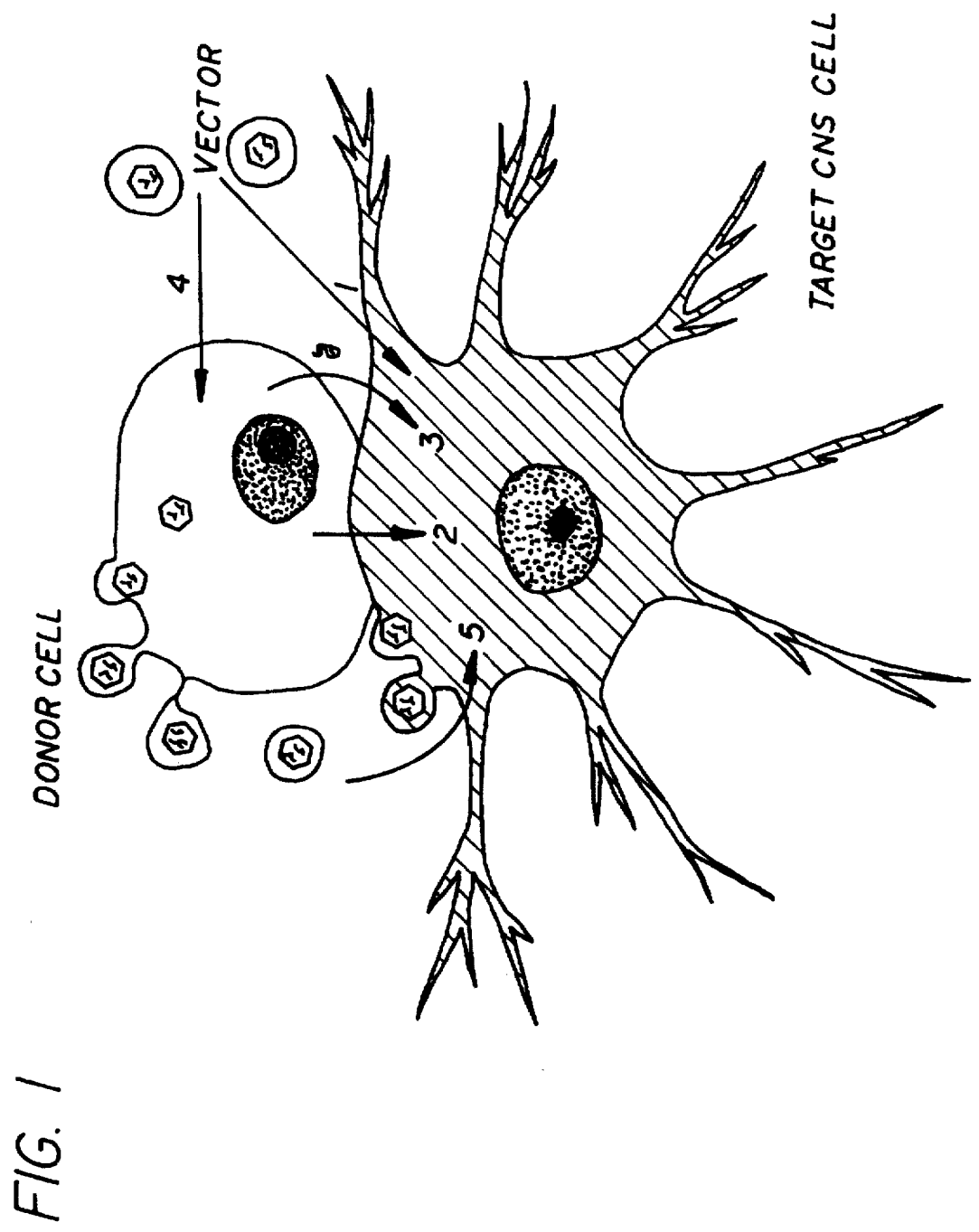
FIG. 1 is a diagrammatic representation of methods for introducing and analyzing the effect of a new function in target cells.
Figure 2:
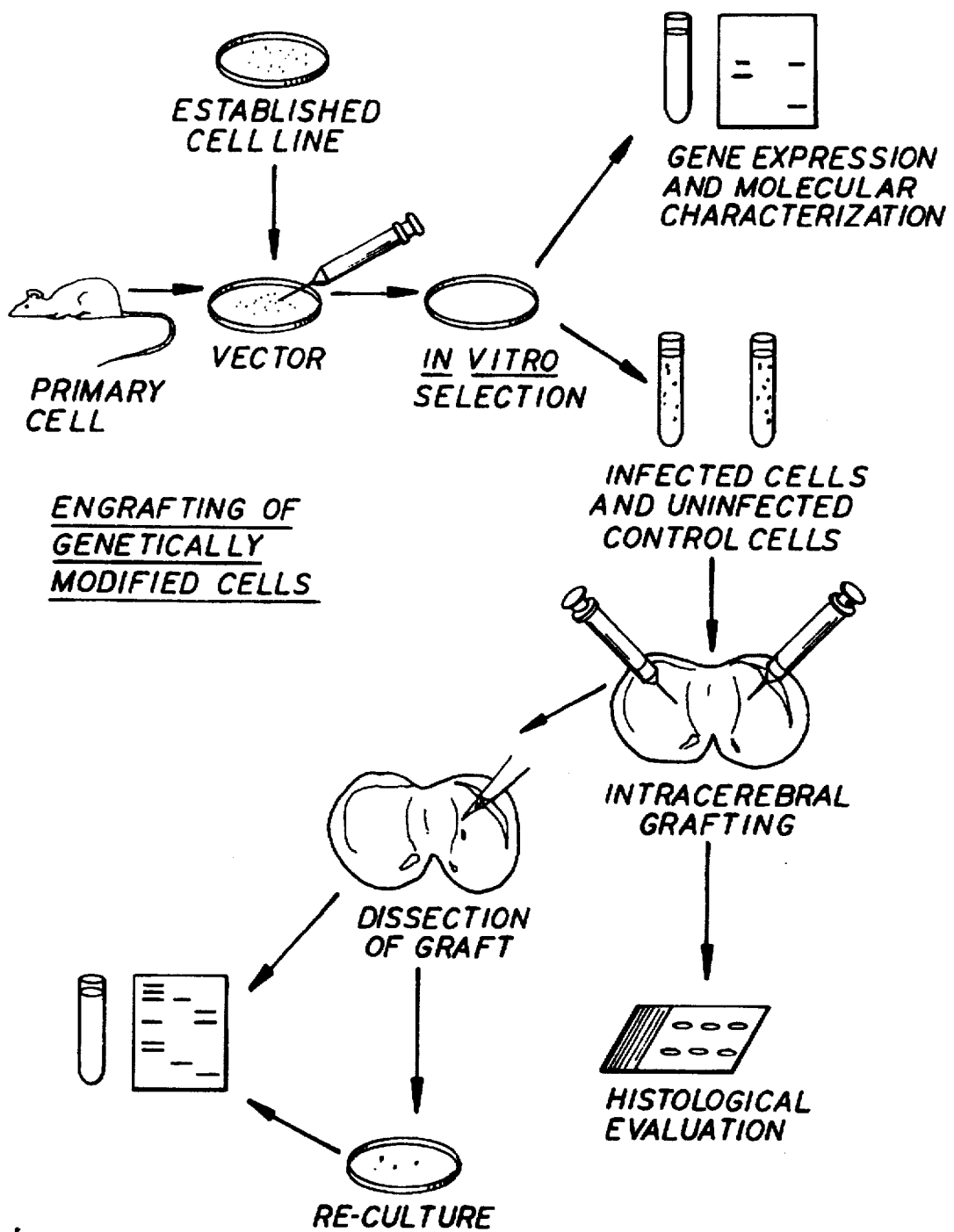
FIG. 2 is a diagrammatic representation of strategies for introducing a new function into target cells in the CNS using genetically modified donor cells.

The strategy for transferring genes into donor cells in vitro is outlined in FIG. 2 and includes the following basic steps: (1) selection of an appropriate transgene or transgenes whose expression is correlated with CNS disease or dysfunction; (2) selection and development of suitable and efficient vectors for gene transfer; (3) preparation of donor cells from primary cultures or from established cell lines; (4) demonstration that the donor implanted cells expressing the new function are viable and can express the transgene product(s) stably and efficiently; (5) demonstration that the transplantation causes no serious deleterious effects; and (6) demonstration of a desired phenotypic effect in the host animal.

The functional molecules produced by transgenes for use in the invention include, but are not limited to, growth factors, enzymes, gangliosides, antibiotics, neurotransmitters, neurohormones, toxins, neurite promoting molecules, antimetabolites and precursors of these molecules. In particular, transgenes for insertion into donor cells include, but are not limited to, tyrosine hydroxylase, tryptophan hydroxylase, NGF, ChAT, GABA-decarboxylase, Dopa decarboxylase (AADC), enkephlin, ciliary neuronal trophic factor (CNTF), brain derived neurotrophic factor (BDNF), neurotrophin (NT)-3, NT-4, and basic fibroblast growth factor (bFGF).

Genetic Modification of Donor Cells

The methods described below to modify donor cells using retroviral vectors and grafting into the CNS are merely for purposes of illustration and are typical of those that might be used. However, other procedures may also be employed, as is understood in the art.

Most of the techniques used to transform cells, construct vectors and the like are widely practiced in the art, and most practitioners are familiar with the standard resource materials which describe specific conditions and procedures. However, for convenience, the following paragraphs may serve as a guideline.

Choice of donor cells

The choice of donor cells for implantation depends heavily on the nature of the expressed gene, characteristics of the vector and the desired phenotypic result. Because retroviral vectors require cell division and DNA synthesis for efficient infection, integration and gene expression (Weiss et al., *RNA Tumor viruses*, 2nd Ed., Weiss et al., eds., Cold Spring Harbor Press, New York (1985)), if such vectors are used, the donor cells are preferably actively growing cells such as primary fibroblast culture or established cell lines, replicating embryonic neuronal cells or replicating adult neuronal cells from selected areas such as the olfactory mucosa and possibly developing or reactive glia. Primary cells, i.e. cells that have been freshly obtained from a subject, such as fibroblasts, that are not in the transformed state are preferred for use in the present invention. Other suitable donor cells include immortalized (transformed cells that continue to divide) fibroblasts, glial cells, adrenal cells, hippocampal cells, keratinocytes, hepatocytes, connective tissue cells, ependymal cells, bone marrow cells, stem cells, leukocytes, chromaffin cells and other mammalian cells susceptible to genetic manipulation and grafting using the methods of the present invention.

The application of methods to induce a state of susceptibility in stationary, non-replicating target cells may make many other cell types suitable targets for viral transduction. For instance, methods have been developed that permit the successful retroviral vector infection of primary cultures of adult rat hepatocytes, ordinarily refractory to infection with such vectors, and similar methods may be helpful for a number of other cells (Wolff et al., *Proc. Natl. Acad. Sci. USA* 84:3344–3348 (1987)). In addition, the development of many other kinds of vectors derived from herpes, vaccinia, adenovirus, or other viruses, as well as the use of efficient non-viral methods for introducing DNA into donor cells such as electroporation (Toneguzzo et al., *Molec. Cell. Biol.* 6:703–706 (1986)), lipofection or direct gene insertion may be used for gene transfer into many other cells presently not susceptible to retroviral vector infection.

Additional characteristics of donor cells which are relevant to successful grafting include the age of the donor cells. The results presented herein demonstrate that aged human cells may be used for transfection with transgenes for grafting.

Choice of Vector

Although other vectors may be used, preferred vectors for use in the methods of the present invention are viral, including retroviral, vectors. The viral vector selected should meet the following criteria: 1) the vector must be able to infect the donor cells and thus viral vectors having an appropriate host range must be selected; 2) the transferred gene should be capable of persisting and being expressed in a cell for an extended period of time without causing cell death for stable maintenance and expression in the cell; and 3) the vector should do little, if any, damage to target cells. Murine retroviral vectors offer an efficient, useful, and presently the best-characterized means of introducing and expressing foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

General Methods for Vector Construction

Construction of suitable vectors containing the desired therapeutic gene coding and control sequences employs standard ligation and restriction techniques, which are well understood in the art (see Maniatis et al., in *Molecular Cloning*: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog.) In general, about 1 μg of plasmid or DNA sequences is cleaved by one unit of enzyme in about 20 μl of buffer solution. Typically, an excess of restriction enzyme is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris (pH 7.6) 50 mM NaCl, 6 mM Mgcl$_2$, 6 mM DTT and 5–10 μM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 μl volumes under the following standard conditions and temperatures: 20 mM Tris-Cl pH 7.5, 10 mM MgCl$_2$, 10 mM DTT, 33 mg/ml BSA, 10 mM-50 mM NaCl, and either 40 µM ATP, 0.01–0.02 (Weiss) units T4 DNA ligase at 15° C. (for "sticky end" ligation) or 1 mM ATP, 0.3–0.6 (Weiss) units T4 DNA ligase at 25° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na+ and Mg+2 using about 1 unit of BAP or CIP per mg of vector at 37° C. for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

Methods of preparation of retroviral vectors have been described (Yee et al., Cold Spring Harbor Symp. on Ouant. Biol. Vol. LI, pp. 1021–1026 (1986); Wolff et al., Proc. Natl. Acad. Sci. USA 84:3344–3348 (1987); Jolly et al., Meth. in Enzymol. 149:10–25 (1987); Miller et al., Mol. Cell. Biol. 5:431–437 (1985); and Miller, et al., Mol. Cell. Biol. 6:2895–2902 (1986) and Eglitis et al., Biotechniques 6:608–614 (1988)) and are now in common use in many laboratories. Retroviral vectors contain retroviral long terminal repeats (LTRs) and packaging (psi, Ψ) sequences, as well as plasmid sequences for replication in bacteria and may include other sequences such as the SV40 early promoter and enhancer for potential replication in eukaryotic cells. Much of the rest of the viral genome is removed and replaced with other promoters and genes. Vectors are packaged as RNA in virus particles following transfection of DNA constructs into packaging cell lines. These include psi (Ψ) 2 which produce viral particles that can infect rodent cells and ΨAM and PA 12 which produce particles that can infect a broad range of species.

Figure 3:
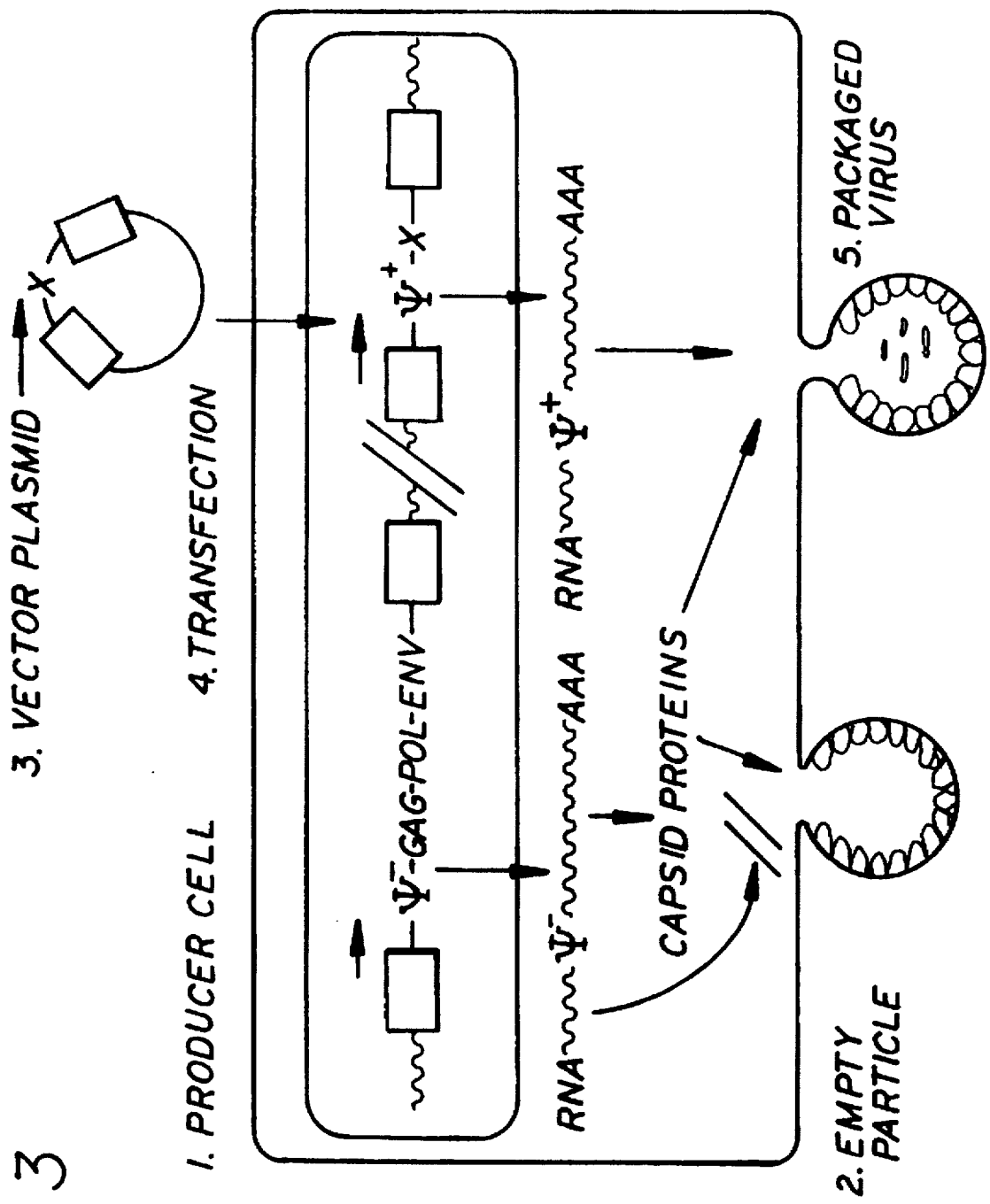
FIG. 3 is a diagrammatic depiction of the preparation of transmissible retrovirus vectors containing a transgene. (GAG=group specific antigen; Env=envelope; POL=reverse transcriptase).

In a preferred viral vector the transgene is brought under the control of either the viral LTR promoter-enhancer signals or of an internal promoter, and retained signals within the retroviral LTR can still bring about efficient integration of the vector into the host cell genome. To prepare transmissible virus (FIG. 3), recombinant DNA molecules of such defective vectors are transfected into "producer" cell lines that contain a provirus expressing all of the retroviral functions required for packaging of viral transcripts into transmissible virus particles, but lacking the crucial packaging signal for encapsidation of RNA transcripts of the provirus into mature virus particles. These include the group specific antigen (GAG) and envelope (ENV) genes which encode caps id proteins and reverse transcriptase (POL). Because of this deletion, transcripts from the helper cannot be packaged into viral particles and the producer cells, therefore, generate only empty virus particles. However, an integrated defective retroviral vector introduced into the same cell by means of calcium phosphate-mediated transfection (Graham and Vander Eb, Virol. 52:456–467 (1973)) in which the GAG, ENV and POL genes have been replaced by the transgene (x) with the intact psi sequence, produces transcripts that can be packaged in trans since they do contain the packaging sequence. The cells contain two provirus sequences integrated into different sites of the host cell genome. Because RNA transcripts from the newly introduced provirus contain the packaging sequence they are efficiently encapsidated into virus particles by means of viral functions produced in trans. Ideally, the result is the production by the cells of infectious particles carrying the transgene free of replication-competent wild-type helper virus. In most, but not necessarily all models of gene therapy, the production of helper virus is probably undesirable since it may lead to spreading infection and possibly proliferative disease in lymphoid or other tissue in the host animal.

Because herpes viruses are capable of establishing a latent infection and an apparently non-pathogenic relationship with some neural cells, herpes based vectors, e.g. HSV-1, may be used. Similarly, it should be possible to take advantage of an eventual improved understanding of other human and animal viruses that infect cells of the CNS efficiently, such as rabies virus, measles, and other paramyxoviruses and the human immunodeficiency retrovirus (HIV), to develop useful delivery and expression vectors. In most cases, with the exception of rabies virus, these viruses are not truly neurotropic for infection, but rather have a much more general susceptible host cell range. They seem, rather, to appear to be neurotropic because the metabolic and physiological effects of infection are most pronounced in cells of the CNS. It is, therefore, likely that many vectors derived from these viruses will be similarly promiscuous in their cell range, and that CNS specificity for expression must be conferred by the use of appropriate cell-specific enhancer, promoter and other sequences, such as those that regulate the oligodendroglial-specific expression of JC virus, glial-specific expression of the proteolipid protein and glial fibrillary acidic protein (GFAP) genes, and other possible CNS specific functions in the mouse.

Other virus vectors that may be used for gene transfer into cells for correction of CNS disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

A possible problem posed by the use of defective viral vectors is the potential for the eventual emergence or "rescue" of pathogenic, replication-competent, wild-type virus by recombination with endogenous virus-like or other cellular sequences. This possibility can be reduced through the elimination of all viral regulatory sequences not needed for the infection, stabilization or expression of the vector.

In addition to the above-described methods for inserting functional DNA transgenes into donor cells other methods may be used. For example, non-vector methods include nonviral physical transfection of DNA into cells; for example, microinjection (DePamphilis et al., Biotechnique 6:662–680 (1988)); electroporation (Toneguzzo et al., Molec. Cell. Biol. 6:703–706 (1986), Potter, Anal. Biochem. 174::361–373 (1988)); chemically mediated transfection such as calcium phosphate transfection (Graham and van der EB, supra, Chen and Okayama, Mol. Cell. Biol. 7:2745–2752 (1987), Chen and Okayama, Biotechnique, 6:632–638 (1988)) and DEAE-dextran mediated transfer (McCutchan and Pagano, J. Natl. Cancer Inst. 41:351–357 (1968)); cationic liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc.,32: 115–121 (1989)) and other methods known in the art.

Mechanisms of Phenotypic Correction by Donor Cells

Preparation of Donor Cells

The donor cells must be properly prepared for grafting. For example, for injection of genetically modified donor cells according to the present invention, cells such as fibroblasts obtained from skin samples are placed in a suitable culture medium for growth and maintenance of the cells, for example a solution containing fetal calf serum (FCS) and allowed to grow to confluency. The cells are loosened from the culture substrate for example using a buffered solution such as phosphate buffered saline (PBS) containing 0.05% trypsin and placed in a buffered solution such as PBS supplemented with 1 mg/ml of glucose; 0.1 mg/ml of $MgCl_2$; 0.1 mg/ml $CaCl_2$ (complete PBS) plus 5% serum to inactivate trypsin. The cells may be washed with PBS using centrifugation and are then resuspended in the complete PBS without trypsin and at a selected density for injection. In addition to PBS, any osmotically balanced solution which is physiologically compatible with the host subject may be used to suspend and inject the donor cells into the host.

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the introduced gene product. The mammalian brain has traditionally been considered to be an immunologically privileged organ, but recent work has shown conclusively that immune responses can be demonstrated to foreign antigens in the rat brain. It is important to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life.

The most effective mode and timing of grafting of the transgene donor cells of the invention to treat defects, disease or trauma in the CNS of a patient will depend on the severity of the defect and on the severity and course of disease or injury to cells such as neurons in the CNS, the patient's health and response to treatment and the judgment of the treating health professional.

Of course, as in all other gene-transfer systems, the important issues of appropriate or faithful gene expression must be resolved to ensure that the level of gene expression is sufficient to achieve the desired phenotypic effect and not so high as to be toxic to the cell.

A problem associated with the use of genetically engineered cells as transplants for gene therapy is that as cells become quiescent (non-dividing) the expression of genes, including transgenes, has been observed to decrease ("down regulate") (Palmer et al., *Proc. Natl. Acad. Sci. USA* 88:1330–1334 (1991)). Primary fibroblasts grafted into the brain do not continue to divide when implanted unless they are transformed and tumorigenic. They thus exist in a quiescent state in the brain. It is thus useful to provide means for maintaining and/or increasing expression of the transgene in the absence of cell division to promote long term stable expression of therapeutic genes used in fibroblasts for gene therapy.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., *Cell* 27:299 (1981); Corden et al., *Science* 209:1406 (1980); and Breathnach and Chambon, *Ann. Rev. Biochem.* 50:349 (1981)). For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, New York (1982)). Moloney murine leukemia virus (MLV) and Rous sarcoma virus (RSV) LTRs contain promoter and enhancer sequences (Jolly et al., *Nucleic Acids Res.* 11:1855 (1983); Capecchi et al., In: Enhancer and eukaryotic gene expression, Gulzman and Shenk, eds., pp. 101–102, Cold Spring Harbor Laboratories, Cold Spring Harbor, New York). Promoter and enhancer regions of a number of non-viral promoters have also been described (Schmidt et al., *Nature* 314:285 (1985); Rossi and de Crombrugghe, *Proc. Natl. Acad. Sci. USA* 84:5590–5594 (1987)).

The present invention provides methods for maintaining and increasing expression of transgenes in quiescent cells using promoters including collagen type I ($\alpha 1$ and $\alpha 2$) (Prockop and Kivirikko, *N. Eng. J. Med.* 311:376 (1984); Smith and Niles, *Biochem.* 19:1820 (1980); de Wet et al., *J. Biol. Chem.* 258:14385 (1983)), SV40 and LTR promoters.

In addition to using viral and non-viral promoters to drive transgene expression in donor cells such as primary fibroblasts, an enhancer sequence may be used to increase the level of transgene expression. Enhancers can increase the transcriptional activity not only of their native gene but also of some foreign genes (Armelor, *Proc. Natl. Acad. Sci. USA* 70:2702 (1973)). For example, in the present invention, collagen enhancer sequences are used with the collagen promoter $\alpha 2(I)$ to increase transgene expression. In addition, the enhancer element found in SV40 viruses may be used to increase transgene expression. This enhancer sequence consists of a 72 basepair repeat as described by Gruss et al., *Proc. Natl. Acad. Sci. USA* 78:943 (1981); Benoist and Chambon, *Nature* 290:304 (1981), and Fromm and Berg, *J. Mol. Appl. Genetics*, 1:457 (1982), all of which are incorporated by reference herein. This repeat sequence can increase the transcription of many different viral and cellular genes when it is present in series with various promoters (Moreau et al., *Nucleic Acids Res.* 9:6047 (1891)). In most cases, the SV40 enhancer element is fully functional when it is present in either orientation and/or at a variety of positions in the plasmid DNA (Fromm and Berg, supra). The ability of the SV40 enhancer to upregulate the transcription from the $\alpha 2(I)$ collagen promoter (ColI) has been previously demonstrated in embryonic chicken fibroblasts (CEF) and monkey kidney CV-1 cells (Xu et al., In Enhancer and Eukaryotic Gene Expression, Gulzman and Shenk, eds., Cold Spring Harbor Laboratories, Cold Spring Harbor, N.Y., pp. 51–54 (1983)). In these cells, vectors containing the SV40 enhancer region downstream from the $\alpha 2(I)$ collagen promoter increased chloramphenical acetyltransferase activity, the reporter gene used, by 64-fold and 18-fold in CV-1 and CEF cells, respectively.

Transgene expression may also be increased for long term stable expression after grafting using cytokines to modulate promoter activity. Several cytokines have been reported to modulate the expression of transgene from collagen $\alpha 2(I)$ and LTR promoters (Chua et al., *Connective Tissue Res.* 25:161–170 (1990); Elias et al., *Annals N.Y. Acad. Sci.* 580:233–244 (1990)); Seliger et al., *J. Immunol.*

141:2138–2144 (1988) and Seliger et al., *J. Virology* 62:619–621 (1988)). For example, transforming growth factor (TGF)βe, interleukin (IL)-1β, and interferon (Inf)α or γ down regulate the expression of transgenes driven by various promoters such as LTR. Tumor necrosis factor (TNF)α and TGFβ1 up regulate and IL-1β up regulates the expression of transgenes driven by the α2(I) collagen promoter (ColI). The results presented herein demonstrate that some cytokines such as TNFα, TGFβ and IL-1β, may be used to control expression of transgenes driven by a promoter in donor cells such as fibroblasts. Other cytokines that may prove useful include basic fibroblast growth factor (bFGF) and epidermal growth factor (EGF).

Collagen promoter with the collagen enhancer sequence (ColI(E)) can also be used to take advantage of the high level of cytokines present in the brain following grafting of the modified donor cells to increase transgene expression. In addition, anti-inflammatory agents including steroids, for example dexamethasone, may be administered to the graft recipient immediately after implantation of the fibroblasts and continued, preferably, until the cytokine-mediated inflammatory response subsides. In certain cases, an immunosuppression agent such as cyclosporin may be administered to reduce the production of interferon-γ which down-regulates LTR promoter and ColI(E) promoter-enhancer, and reduces transgene expression.

For in vivo use, transgenes driven by collagen promoter are introduced into cells and then directly implanted into the brain without requiring further intervention. The cytokines released after grafting as part of the recipient's natural response will stimulate the collagen promoter driven transcription of the selected transgene.

Cytokines including the growth factors bFGF and EGF, may also be administered before, during or after grafting, to promote survival of grafted donor cells in the CNS.

It is also useful to be able to regulate the secretion of the genetically engineered gene product after grafting. As shown in an embodiment presented herein, the release of a gene product such as acetylcholine (ACh), a transmitter, greatly decreased in Alzheimer's Disease, from cultured cells infected with a MLV vector expressing the choline acetyltransferase cDNA can be augmented using choline, a precursor for acetylcholine. This suggests a means for dietary regulation of intracerebral gene therapy.

The genetic correction of some, or many, CNS disorders may require the establishment or re-establishment of faithful intercellular synaptic connections. Model systems to study these possibilities have not yet been developed and exploited because of the paucity of replicating non-transformed cell-culture systems and the refractoriness of non-replicating neuronal cells to retroviral infection. However, recent studies, including those involving the immortalization of embryonic hippocampal neuronal cells, suggest that replicating neuronal cell culture systems may soon become available for in vitro gene transfer and then for in vivo implantation (Caettano and MacKay, *Nature* 347:762–765 (1990)). Such neurons might be susceptible to efficient transduction by retroviral or other viral vectors, and if they are also able to retain other neuronal characteristics, they may be able to establish synaptic connections with other cells after grafting into the brain. Alternatively, there are cells within the CNS that are late to develop, such as the ventral leaf of the dentate gyrus of the hippocampus, or continue to divide through adulthood, such as those in the olfactory mucosa and in the dentate gyrus. Such cells may be suitable targets for retroviral infection.

The use of non-neuronal cells for grafting may preclude the development of specific neural connections to resident target cells of the host. Therefore, the phenotypic effects of fibroblast or other non-neuronal donor cells or target cells in vivo would be through the diffusion of a required gene product or metabolite, through gap junctions ("metabolic co-operation") or through uptake by target cells of secreted donor cell gene products or metabolites. The donor cell may also act as a toxin "sink" by expressing a new gene product and metabolizing and clearing a neurotoxin.

Alternatively, neural bridges may be provided which facilitate reconnection between neurons in damaged CNS tissues. As noted above, grafted donor cells suspended in substrate material such as collagen matrices can serve as neural bridges to facilitate axonal regeneration and reconnection of injured neurons, or may be used in conjunction with neural bridges formed from synthetic or biological materials, for example homogenates of neurons or placenta, or neurite promoting extracellular matrices.

Grafting

The methods of the invention contemplate intracerebral grafting of donor cells containing a transgene insert to the region of the CNS having sustained defect, disease or trauma.

Neural transplantation or "grafting" involves transplantation of cells into the central nervous system or into the ventricular cavities or subdurally onto the surface of a host brain. Conditions for successful transplantation include: 1) viability of the implant; 2) retention of the graft at the site of transplantation; and 3) minimum amount of pathological reaction at the site of transplantation.

Methods for transplanting various nerve tissues, for example embryonic brain tissue, into host brains have been described in *Neural Grafting in the Mammalian CNS*, Bjorklund and Stenevi, eds., (1985) Das, Ch. 3 pp. 23–30; Freed, Ch. 4, pp. 31–40; Stenevi et al., Ch. 5, pp. 41–50; Brundin et al., Ch. 6, pp. 51–60; David et al., Ch. 7, pp. 61–70; Seiger, Ch. 8, pp. 71–77 (1985), incorporated by reference herein. These procedures include intraparenchymal transplantation, i.e. within the host brain (as compared to outside the brain or extraparenchymal transplantation) achieved by injection or deposition of tissue within the host brain so as to be opposed to the brain parenchyma at the time of transplantation (Das, supra).

The two main procedures for intraparenchymal transplantation are: 1) injecting the donor cells within the host brain parenchyma or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The donor cells may also be introduced into the putamen, nucleus basalis, hippocampus cortex, striatum or caudate regions of the brain, as well as the spinal cord.

Preferably, for passaged donor cells, cells are passaged from approximately 2 to approximately 20 passages.

For grafting, the cell suspension is drawn up into the syringe and administered to anesthetized graft recipients. Multiple injections may be made using this procedure. The age of the donor tissue, i.e. the developmental stage may affect, the success of cell survival after grafting.

The cellular suspension procedure thus permits grafting of genetically modified donor cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the CNS to form a transplantation cavity, for example as described by Stenevi et al., supra, by removing bone overlying the brain and stopping bleeding with a material such a gelfoam. Suction may be used to create the cavity. The graft is then placed in the cavity. More than one transplant may be placed in the same cavity using injection of cells or solid tissue implants.

Grafting of donor cells into a traumatized brain will require different procedures, for example, the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

The present invention therefore provides methods for genetically modifying donor cells for grafting CNS to treat defective, diseased and/or injured cells of the CNS.

The methods of the invention also contemplate the use of grafting of transgenic donor cells in combination with other therapeutic procedures to treat disease or trauma in the CNS. Thus, genetically modified donor cells of the invention may be co-grafted with other cells, both genetically modified and non-genetically modified cells which exert beneficial effects on cells in the CNS, such as chromaffin cells from the adrenal gland, fetal brain tissue cells and placental cells. The genetically modified donor cells may thus serve to support the survival and function of the co-grafted, non-genetically modified cells, for example fibroblasts modified to produce nerve growth factor (NGF) in vivo as described in the Examples, infra.

Moreover, the genetically modified donor cells of the invention may be co-administered with therapeutic agents useful in treating defects, trauma or diseases of the CNS, such as growth factors, e.g. nerve growth factor; gangliosides; antibiotics, neurotransmitters, neurohormones, toxins, neurite promoting molecules; and antimetabolites and precursors of these molecules such as the precursor of dopamine, L-dopa.

The methods of the invention are exemplified by preferred embodiments in which donor cells containing vectors carrying a therapeutic transgene are grafted intracerebrally into a subject. In a first preferred embodiment, the established HPRT-deficient rat fibroblast line 208F, primary rat fibroblasts, and day-1 postnatal primary rat astrocytes were used to demonstrate that cultured cells genetically modified using retroviral vectors can survive when implanted in the mammalian brain and can continue to express transgene products.

In a second preferred embodiment fibroblasts were genetically modified to secrete NGF by infection with a retroviral vector, and the modified fibroblasts were then implanted into the brains of rats with surgical lesions of the fimbria fornix region. The grafted cells survived and produced sufficient NGF to prevent the degeneration of cholinergic neurons that would die without treatment. In addition, the protected cholinergic cells sprouted axons that projected in the direction of the cellular source of NGF.

In a third preferred embodiment fibroblasts were genetically modified to express and secrete L-dopa by infection with a retroviral vector, and the modified fibroblasts were grafted into the caudate of rats modeling Parkinson's disease as a result of unilateral dopamine depletion. The cells survived and produced sufficient L-dopa to decrease the rotational movement caused by dopamine depletion.

In a fourth preferred embodiment primary skin fibroblasts isolated from skin biopsies and maintained in culture were employed as autologous cells for intracerebral grafting into the adult rat striatum. The fibroblasts ceased to proliferate once they reached confluency and were contact inhibited in vitro. The fibroblasts were able to survive for at least eight weeks following intracerebral implantation and continued to synthesize collagen and fibronectin in vivo. The grafts also maintained a constant volume between three and eight weeks, indicating that the primary skin fibroblasts did not tumor or die. Dynamic host-to-graft interactions, including phagocytic migration, astrocytic hypertrophy and infiltration into the grafts, and angiogenesis, were observed indicating the structural integration of grafts of primary skin fibroblasts in the adult rat CNS.

In a fifth preferred embodiment primary skin fibroblasts obtained from a skin biopsy from an inbred strain of rats were used as donor cells for genetic modification and grafting. When grafted into the brain of rats of the same genetic strain as the donor rats, the fibroblasts containing a transgene for either tyrosine hydroxylase (TH) or β-galactosidase survived for 10 weeks and continued to express the transgene. The TH synthesized by the implanted fibroblasts appeared to convert tyrosine to L-dopa, as observed in vitro, and to affect the host brain as assessed through a behavioral measurement. Supplying L-dopa locally to the striatum was shown to be sufficient to partially compensate for the loss of striatal dopaminergic input.

In a sixth preferred embodiment, the ability of aged human fibroblasts to serve as donor cells for human NGF was demonstrated.

In a seventh preferred embodiment rat fibroblasts were genetically modified to express and secrete choline acetyltransferase (dChAT). It was shown that intra- and extracellular levels of ACh could be increased by adding exogenous choline chloride. In addition, serum starvation or confluence-induced quiescence caused an 80% decrease in recombinant ChAT activity (as compared to actively growing cells). ACh release was also repressed in quiescent fibroblast cultures. Exogenous choline mitigated the decrease in ACh secretion. These results indicated that fibroblasts can be genetically modified to produce ACh and that ACh release can be regulated, for example increased, by introducing choline into the culture medium.

In an eighth preferred embodiment selected promoters including collagen promoters were demonstrated to increase expression of the transgene chloramphenicol acetyltransferase (CAT) in quiescent primary fibroblasts.

In a ninth preferred embodiment cytokines and an anti-inflammatory agent, dexamethasone, were evaluated for their effect on LTR promoter activity to enhance expression of the CAT and dChAT genes in primary skin fibroblasts. In addition, the collagen promoter α2(I) with the collagen enhancer (Coll(E)) was used to evaluate the effects of cytokines on the expression of CAT in quiescent fibroblasts.

In an tenth preferred embodiment primary skin fibroblasts were modified to express and secrete NGF and were grafted into the striatum of adult female rats. At one and three weeks following striatal implantations, NGF receptor-immunoreactive axons surrounded the grafts of NGF-producing fibroblasts. At three and eight weeks, NGF receptor-positive profiles were also found within the grafts. Control grafts of normal primary fibroblasts lacked immunoreactive axons. Ultrastructural examination showed that unmyelinated axons within the extracellular matrix of the grafts were enveloped within processes of reactive astrocytes and a distinct basal lamina surrounded the axo-glial bundles. Processes of reactive astrocytes were evident in both control and grafts containing genetically modified primary fibroblasts. This embodiment demonstrates an in vivo model showing that the release of NGF from the grafts induced directional growth of NGF receptor-positive axons and that mature reactive astrocytes provide a permissive substrate upon which axons migrated. In this embodiment, genetically modified fibroblasts were also placed in a collagen matrix graft to assess the regenerative capacity of the adult rat medial septum. The grafts produced NGF and promoted the regeneration of septal axons; the grafts possessed large numbers of unmyelinated axons compared to control fibroblast grafts. The regenerating septal axons provided a reinnervation to the deafferented hippocampus; the topographical and synaptic organization of the septal inputs within the hippocampal dentate gyrus was similar to that of the normal cholinergic innervation arising from septal nuclei.

In order that the invention described herein may be more fully understood, the following examples are set forth. It should be understood that these examples are for illustrative purposes only and are not to be construed as limiting the scope of this invention in any manner.

EXAMPLE I

Figure 4:
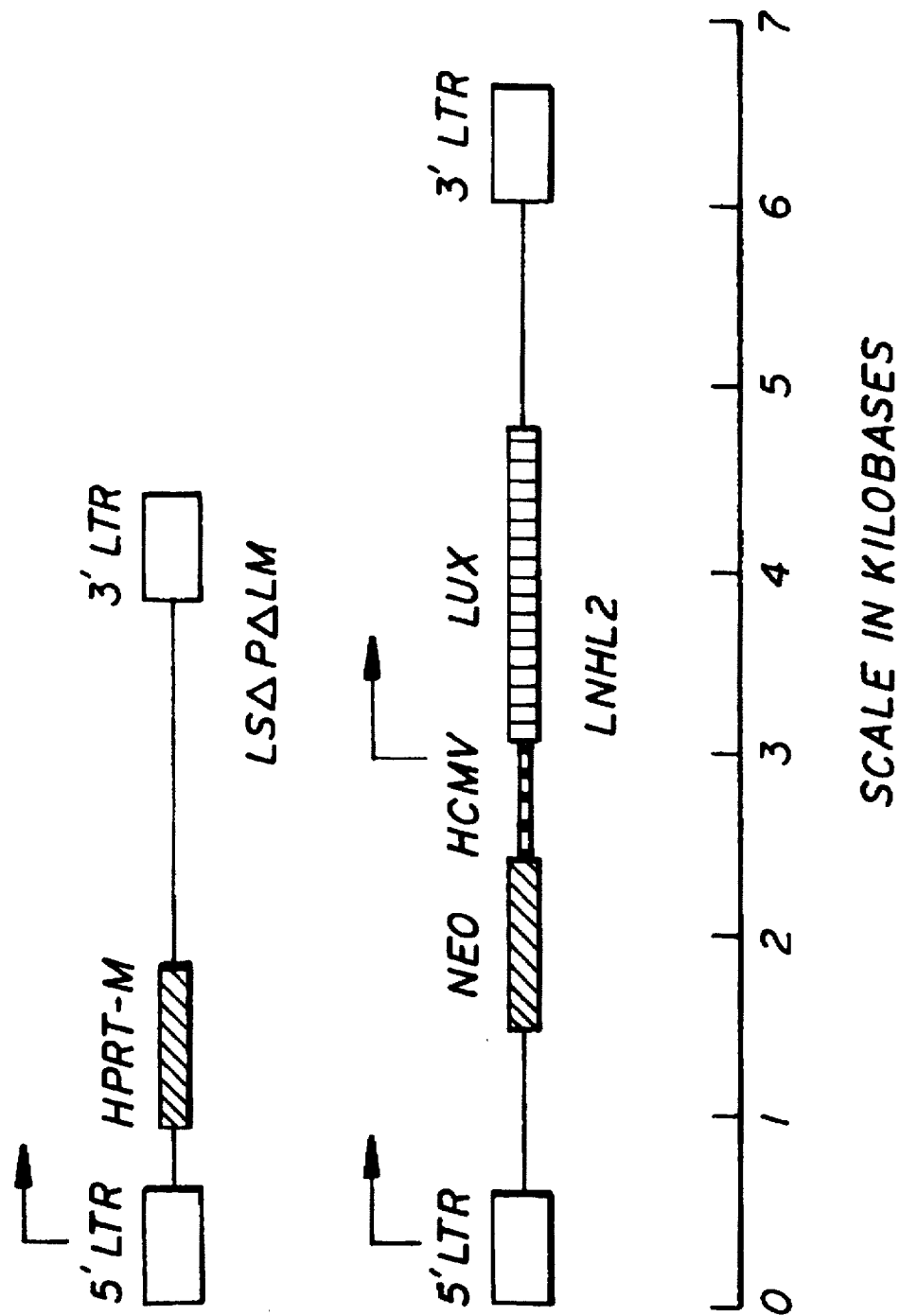
FIG. 4 is a diagrammatic representation of the linear restriction maps of the integrated vectors LSΔPΔLM and pLNHL$_2$ as described in Example I, infra (arrows indicate the location of the promoter and the direction of transcription. The diagonally hatched box of IS P LM represents the human HPRT cDNA encoding a protein with a novel terminal hexapeptide added by in vitro mutagenesis, LTR=long terminal repeat).

Intracerebral Grafting Of Genetically Modified Cells Expressing HPRT Transgene To The Brain Infection of Cells Donor hypoxanthine guanine phosphoribosyl transferase (HPRT)-deficient 208F rat fibroblast cells (Jolly et al., *Proc. Natl. Acad. Sci. USA* 80:477–481 (1983)) were infected with the prototype HPRT vector pLS P LM expressing HPRT cDNA (Miller et al., *Science* 225:630–632 (1984); Yee et al., *Gene* 53:97–104 (1987)) cDNA or with the neo$^R$-luciferase vector pLNHL2 (Eglitis et al., *Science* 230:1395–1398 (1985); Wolff et al., *Proc. Natl. Acad. Sci.* (*USA*) expressing both the Tn5 transposon neomycin-resistance gene (neo$^R$.) and the firefly luciferase cDNA (de Wet et al., *Molec. Cell. Biol.* 7:725–737 (1987)) (FIG. 4). The pLS P LM vector was derived from vector pLPL2 (Miller et al., *Molec. Cell. Biol.* 6:2895–2902 (1986)) and contains human HPRT cDNA encoding a protein with a novel C-terminal hexapeptide added by in vitro mutagenesis of the translational termination codon (Yee et al., *Gene* 53:97–104 (1987)). Vector pLS P LM was constructed as follows: Vector pLpLM (Yee et al., *Gene* 53:97–104 (1987)) was digested with XhoI and BamHI to yield a 1.3 Kb fragment which was then ligated into plasmid pLpL2 (Miller, supra) which had also been restricted using XhoI and BamHI. The resulting vector was pLS P LM.

Figure 5:
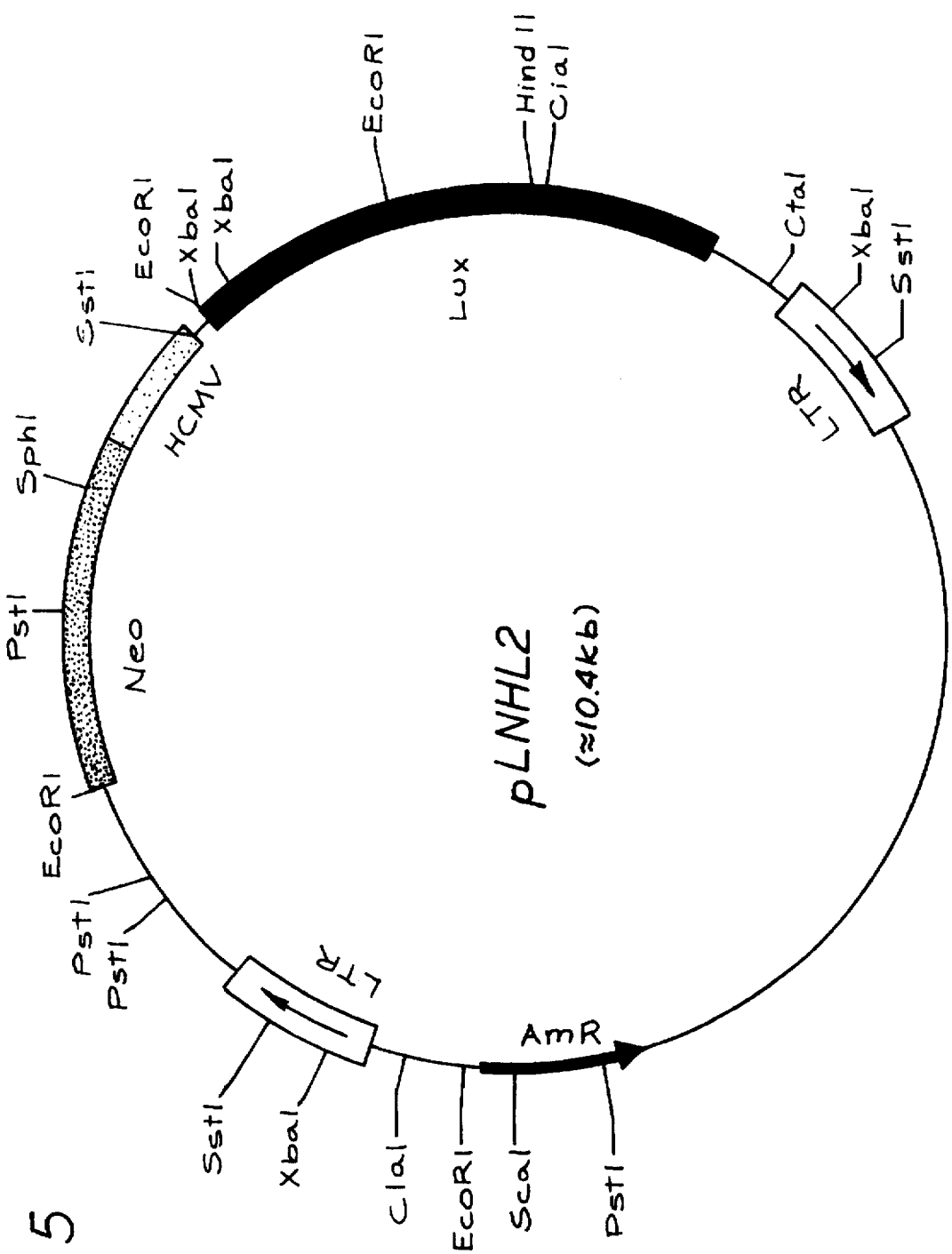
FIG. 5 is a depiction of the circular restriction map of vector pLNHL$_2$ as described in Example I, infra.
Figures 6A, 6B, 6C:
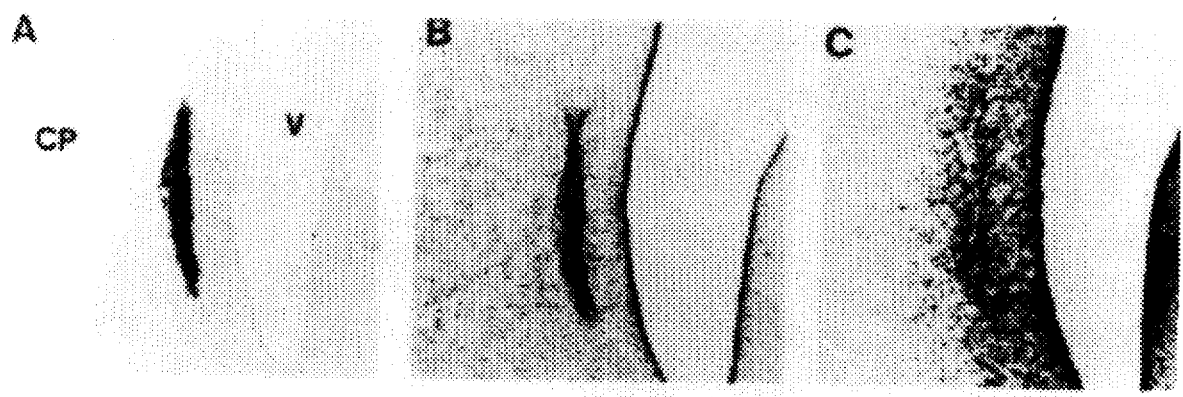
FIG. 6a–FIG. 6f are photomicrographs of primary rat fibroblasts previously infected with hypoxanthine-guanine phosphoribosyl transferase (HPRT) that have been implanted in rat basal ganglia as described in Example I, infra (FIG. 6a, FIG. 6d=anti-fibronectin.
Figure 6D:
Figure 6E:
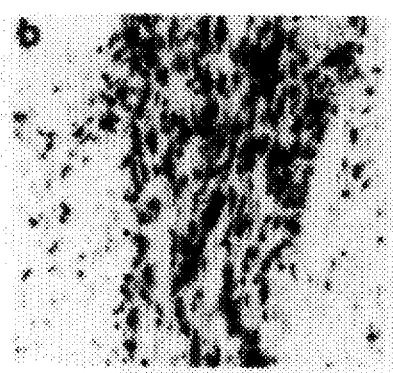
Figure 6F:
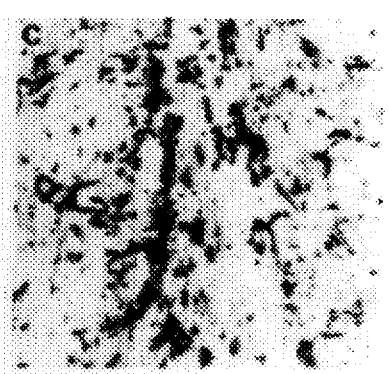

The vector pLNHL2 contained the cDNA encoding the firefly luciferase (LUX) and the Tn5 neomycin-resistance gene (neo$^R$) and the promoter and enhancer of the human cytomegalovirus immediate early gene (HCMV). The 5' and 3' LTRs were derived from cloned murine leukemia virus (MLV) as described by Mason et al., in *Science* 234:1372–1378 (1986). Vector pLNHL2 was constructed as follows: Plasmid pLNHPL2 (also known as PNHP-1, Yee et al., *Proc. Natl. Acad. Sci. USA* 84:5197–5209 (1987)) was restricted with BamHI to remove the HPRT DNA sequence. The ends were repaired using Klenow polymerase. Plasmid pSV2A (deWet et al., *Molec. Cell. Biol.*, supra, and supplied by) (Dr. Subramani, University of California, San Diego, Calif.) was restricted with HindIII and SspI to isolate the luciferase fragment. The ends were repaired as above. The BamHI restricted pLNHL2 and HindIII-SspI restricted pSV2A were ligated together forming vector pLNHL2 (FIG. 5).

The cells were grown in selective medium containing hypoxanthine, aminopterin and thymidine (HAT) for cells expressing HPRT and with the neomycin analog G418 for cells expressing neo$^R$, respectively, to ensure that only infected cells were used.

Primary fibroblasts and astrocytes were infected with the neo$^R$-luciferase vector only. HAT-resistant and G418-resistant cells were harvested following incubation overnight with serum-free medium or medium containing rat serum, to reduce the likelihood of immunological response in the rat brain.

Grafting

The cells were resuspended in a balanced glucose-saline solution and injected stereotaxically into several regions of the rat brain using a sterile syringe. Between 10,000 and 100,000 cells per microliter were injected at a rate of 1 µl/min for a total volume of 3–5 µl. After 1 week to 3 months the animals were killed and areas containing the implanted cells were identified, excised, and examined histologically and biochemically.

Histological Analyses

To evaluate the grafted cells histologically, the rats were perfused transcardially and their brains were sectioned and stained with Nissl stain and cresyl violet for general morphological characterization and with immunocytochemical methods to establish the presence of the specific cell antigenic markers fibronectin for the fibroblasts and glial fibrillary acidic protein (GFAP) for glial cells. Briefly, the sections were rinsed in Tris-buffered saline (TBS) solution (pH 7.4) containing 0.25% Triton-X. The sections were incubated for 24 hrs at 4° C. with rabbit polyclonal antibodies to fibronectin (1:2000 dilution; Baralle, University of Oxford, England) and GFAP (Gage et al., *Exp. Neurol.* 102:2–13 (1989); available from Dakopatts, Glostryp, Denmark) diluted 1:1000 in TBS containing 0.25% Triton-X and 3% goat serum or with the monoclonal antibody, mouse IgG2a, against a membrane polypeptide of rat macrophages, granulocytes and dendritic cells (MRC OX-42, Serotec) diluted 1:100 in TBS containing 0.25% Triton-X and 1% horse serum. After thorough rinsing, the sections were incubated for 1 hr with biotinylated goat anti-rabbit IgG (Vectastain) diluted 1:200 in 0.1M TBS containing 0.25% Triton-X and 15 horse serum, followed by several rinses in TBS containing 0.25% Triton-X and 1% goat serum or 1% horse serum. The sections were then incubated for 1 hr at room temperature with a complex of avidin and biotinylated horseradish peroxidase (Vectastain, ABC kit, Vector Labs, Burlingame, Calif.) diluted 1:100 in 0.1M TBS containing 0.25% Triton-X and 1% goat serum or 1% horse serum, followed by thorough rinses. The peroxidase was visualized by reacting with 0.05%, 3,3-diaminobenzidine tetrahydrochloride (DAB) (Sigma Chemical Co., St. Louis, Mo.) and 0.05% $NiCl_2$ and 0.01% $H_2O_2$ in TBS for 15 min at room temperature.

Primary rat fibroblasts grafted to the neostriatum of the rat seven weeks earlier are illustrated in FIG. 6. Serial 40 μm-thick sections were stained with antifibronectin (FIG. 6a, FIG. 6d), cresyl violet (Disbrey et al., Histological Laboratory Methods, E. & S. Livingstone, Edinburgh and London (1970)), (FIG. 6b, FIG. 6e) and anti-GFAP (FIG. 6c, FIG. 6f). The surviving cells appeared to be intact and to have clumped or aggregated around the area of the injection. The cells displayed an intense staining for fibronectin at the core of the graft, with a clear GFAP-staining derived from reactive gliosis at the edges of the grafts, similar to what one sees with the cannula tract alone. However, little GFAP-staining was observed in the graft itself. With cresyl violet, small, round, darkly stained cells were observed in the region of the graft which could either be microglia or lymphocytes that had infiltrated the area in response to injury. Macrophages could also be detected in many of the grafts. Many of the fibroblasts could be identified by cresyl violet staining by their long thin shape and by the pink pleated sheets of collagenous material surrounding them. The appearance of 208F fibroblasts was similar to the primary fibroblasts (not shown). Astrocyte grafts also had a similar appearance, except they were not fibronectin-positive, and stained for GFAP through the center of the grafts. For all three cell types, no differences were observed between retrovirus-infected cells and control cells. An important feature of these cell suspension grafts is that most of the cells remained aggregated near the site of injection and did not appear, under these circumstances, to migrate very far from the injection site into the host brain. This apparent lack of migration could certainly be different for other donor cell types and graft sites, and therefore the area of the brain into which the cells are to be implanted, the nature of the donor cells, and the phenotype of the target cells for the transgene may be important factors for the selection of donor cells.

Characterization of Implanted Cells

Figure 7:
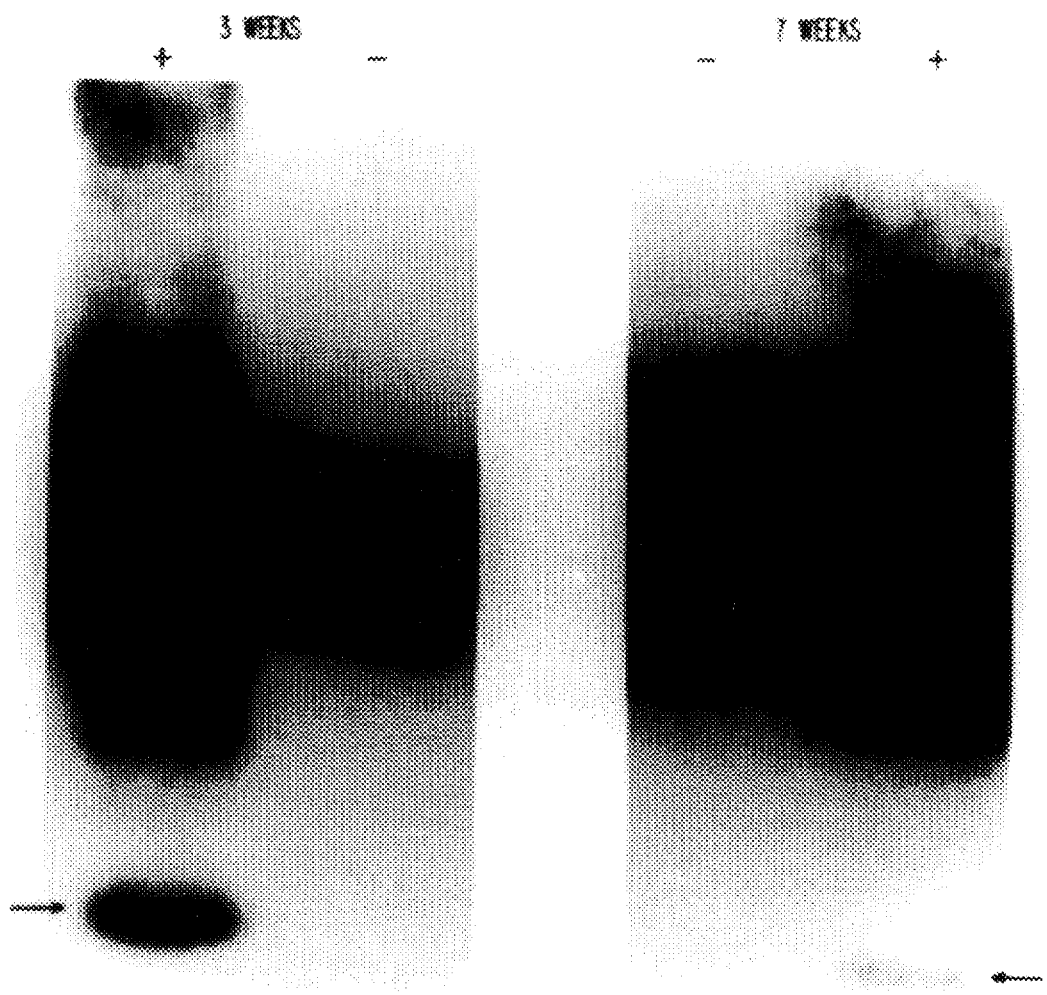
FIG. 7 is photographs of isoelectric focusing gels for HPRT enzymatic activity of brain extracts from basal ganglia as described in Example I, infra.

Implanted cells were dissected out and prepared for reculturing and for biochemical and molecular characterization by dissociating the cells with trypsin. For the detection of the human HPRT activity, cell extracts were prepared from the bulk of each sample as previously described and examined by a polyacrylamide gel isoelectric focusing HPRT assay (Jolly et al., Proc. Natl. Acad. Sci. USA) 80:477–481 (1983); Miller et al., Proc. Natl. Acad. Sci (USA) 80:4709–4713 (1983); Willis et al., J. Biol. Chem. 259:7842–7849 (1984); Miller et al., Science 225:630–632 (1984); Gruber et al., Science 230:1057–1061 (1985), and Yee et al., Gene 53:97–104 (1987)). The remainder of each sample was placed into culture. The results of an HPRT gel assay of rat 208F cells HAT resistance after infection with the HPRT vector implanted into one side of the rat basal ganglia 3 and 7 weeks after transplantation and prior to analysis are shown in FIG. 7.

The presence of human HPRT enzyme activity demonstrates that the infected, genetically modified rat 208F cells grafted into the brain survived and continued to express the HPRT transgene at easily detectable levels for at least 7 weeks. Furthermore, the implanted cells could be successfully recultured, producing cells morphologically identical to the starting cultures. Infection of these cells with helper virus resulted in the production of HPRT virus, confirming the identity of the cells and indicating that the provirus remained intact. Studies with the $neo^R$-luciferase vector confirm the survival and expression of luciferase-infected cells.

EXAMPLE II

Grafting of Genetically Modified Cells Expressing NGF to the Damaged Brain

The above example demonstrated that cultured cells genetically modified using retroviral vectors can survive when implanted into the mammalian brain and can continue to express transgene product. The present example was conducted to determine whether sufficient transgene product can be made by genetically modified cells in vivo to complement or repair an absent or previously damaged brain function.

Construction of NGF Vector pLN.8RNL

A retroviral vector, similar to one described previously (Wolf, et al., Mol. Biol. Med. 5:43–59 (1988)), was constructed from Moloney murine leukemia virus (MoMuLV) (Varmus et al., RNA Tumor Viruses; Weiss et al., Cold Spring Harbor Press, Cold Spring Harbor, N.Y., p. 233 (1982)). The pLN.8RNL vector contains the 777 base pair Hgal-Pstl fragment of mouse NGF cDNA (Scott et al., Nature 302; 538 (1983); Ullrich et al., Nature 303:821 (1983)), under control of the viral 5' LTR. This insert corresponds to the shorter NGF transcript that predominates in mouse tissue receiving sympathetic innervation (Edwards et al., Nature 319:784 (1986)) and is believed to encode the precursor to NGF that is secreted constitutively. The vector also included a dominant selectable marker encoding the neomycin-resistance function of transposon Tn5 (Southern et al., J. Mol. Appl. Genet. 1:327 (1982)), under control of an internal Rous sarcoma virus promoter.

Figure 8:
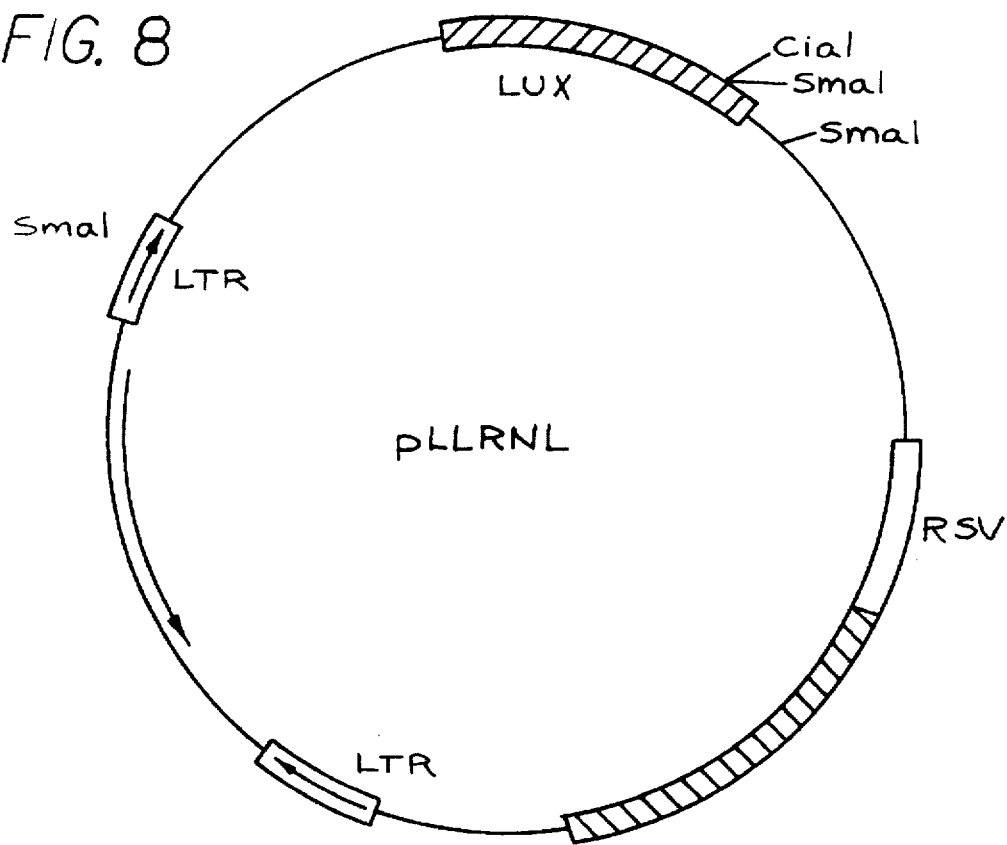
FIG. 8 is a depiction of the circular restriction map of vector pLLRNL as described in Example II, infra.

Plasmid pSPN15' (Wolf et al., Mol. Biol. Med. 5:43–59 (1988), supplied by Dr. Breakefield, Harvard Medical School, Boston, Mass.) was digested with restriction enzymes Pstl and Hgal using established methods (Maniatis et al., Cold Spring Harbor Press, Cold Spring Harbor, N.Y., (1982)) and the 777 base pair (bp) DNA fragment containing the NGF sequences was isolated by standard purification methods (Maniatis, et al., supra). The 777 bp fragment was then blunt-end ligated into plasmid pLMTPL as described by Yee et al., in Proc. Natl. Acad. Sci. (USA) 84:5197–5201 (1987), incorporated by reference herein. Plasmid pLMTPL was digested with Hind III to remove the metallothionein promoter and most of the HPRT cDNA, and the overhanging 5' ends were repaired using Klenow polymerase as described by Maniatis et al., supra. The overhanging ends of the 777 bp fragment isolated as above were similarly repaired. The 777 bp fragment was then blunt end ligated into the digested plasmid pLMTPL. The resulting plasmid was called PLN.8L and was transfected into E. coli strain DH1, grown and purified by established methods for plasmid purification including cesium chloride centrifugation (Maniatis et al., supra). The purified plasmid pLN.8L was then digested using restriction enzymes BamHI and Cla1 and the resulting 6.1 kilobase fragment was ligated to a 2.1 kilobase BamHI-Cla1 fragment isolated from plasmid pLLRNL. Plasmid pLLRNL was derived from plasmid JD204 described by de Wet et al., in Mol. Cell. Biol. 7:725–737 (1987) as follows: A 1717 bp HindIII-Ssp1 fragment from the firefly luciferase gene derived from plasmid JD204 and a 1321 bp HindIII-Smal fragment of the plasmid $pSV2Neo^R$ described by Southern and Berg in Mol. Appl. Genet. 1:327–341 (1982) were ligated with a fragment containing a mutated RSV promoter in a 300 bp BamHI-HindIII fragment from plasmid pUCRH. Plasmid pLLRNL is depicted in FIG. 8.

Figure 9:
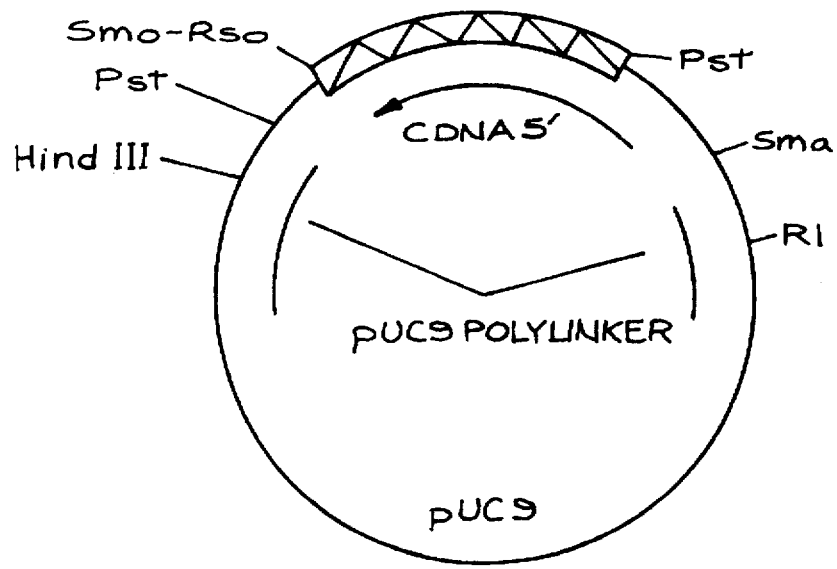
FIG. 9 is a depiction of the circular restriction map of vector pPRl as described in Example II, infra.

Plasmid pUCRH was produced as follows. Plasmid pRS-Vneo$^R$ was restricted using HindIII and the linearized plasmid was ligated with the remaining fragment from plasmid pPR1 (FIG. 9) (supplied by Dr. Friedmann, University of California, San Diego, Calif.) obtained by restriction using HindIII to remove HPRT sequences. Plasmid pPR1 was obtained from plasmid p4aA8 (Jolly et al., *Proc. Natl. Acad. Sci.* 80:477–481 (1983)) using Pst and Rsa. The resulting plasmid was called pRHN and was then restricted with PvuII and religated to form plasmids PN(+) and PAC(−). PN(+) was then restricted using BamHI. The resulting linearized plasmid was ligated with a fragment obtained from plasmid pSvori restricted with BamHI. Plasmid pSVori was obtained by restricting plasmid p4aA8 with SalI and PstI, and subcloning the resulting fragment into plasmid pUC18 (Bethesda Research Laboratories, Gaithersburg, Md.) that had been restricted with SalI and PstI. The resulting plasmid was termed pSVori.

The plasmid pRH+S+ that resulted from ligation of the BamHI restricted plasmid PN(+) and the BamHI restricted plasmid pSVori was then restricted with MstII and the overhanging 5' ends were repaired using Klenow polymerase as described above. This fragment was ligated with a M13mp18 (Bethesda Research Laboratories) linearized with SmaI and phosphatased with calf intestinal alkaline phosphatase (Boehringer Mannheim, Mannheim, W. Germany). The resulting plasmid was called pmpRH and contained the HPRT cDNA expressed from the RSV promoter.

Figure 10:
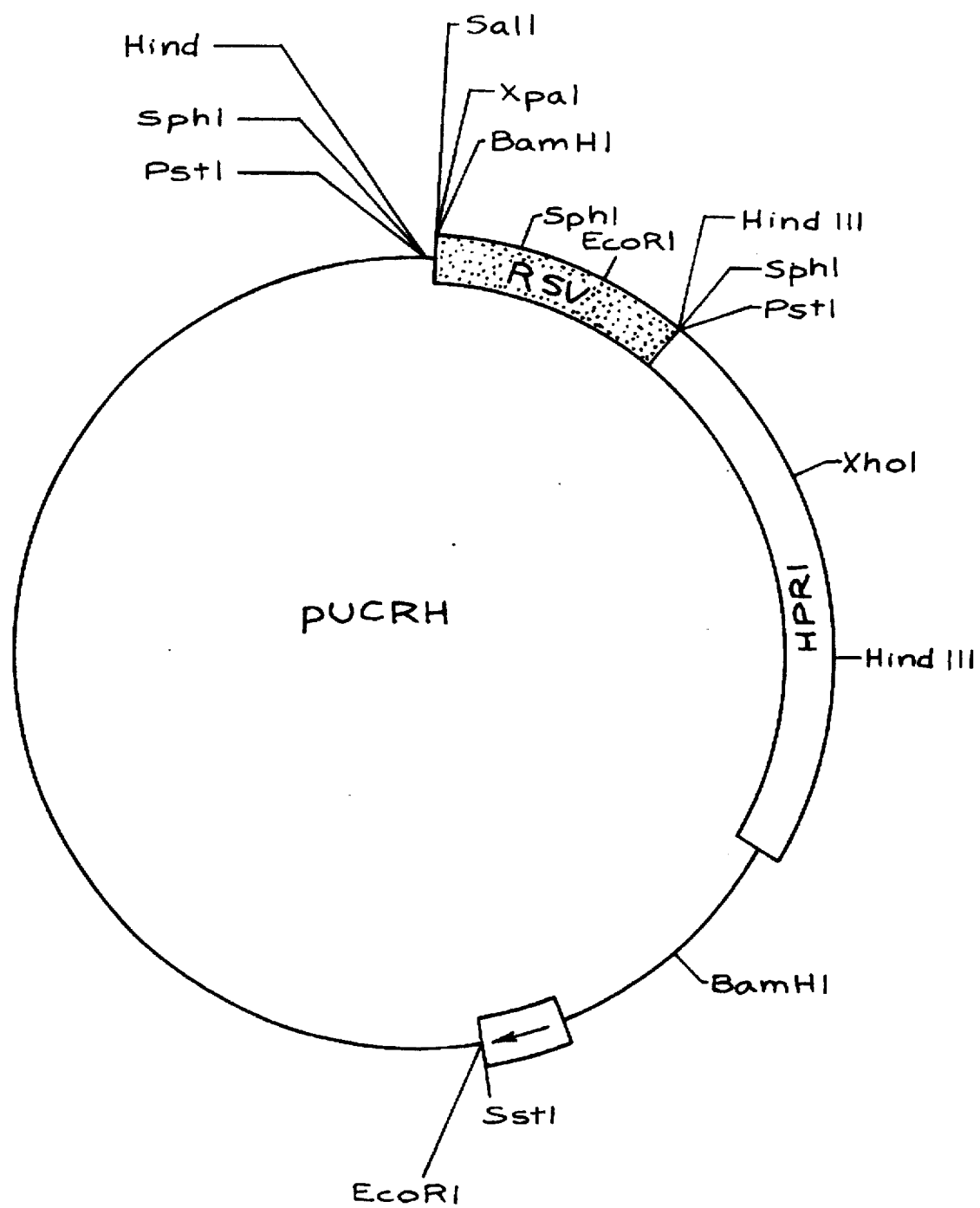
FIG. 10 is a depiction of the circular restriction map of vector pUCRH as described in Example II, infra.

Plasmid pmpRH was subject to site-directed mutagenesis as described by Kunkel et al., *Proc. Natl. Acad. Sci. USA* 82:488–492 (1985), incorporated by reference herein in order to alter the polyadenylation signal AATAAA to AGCAAA. After mutagenesis the resulting plasmid was restricted using HindIII and the resulting fragment was ligated to a HindIII fragment from restriction of plasmid pUC19 (Bethesda Research Laboratories) to produce plasmid pUCRSV. Plasmid PUCRSV was restricted using BamHI and PstI to produce a fragment containing the RSV promoter. This fragment was ligated to a PstI-SstI fragment containing the gene encoding HPRT obtained by restriction of the plasmid pLS P LM as described in Example I, supra and to a BamHI-SstI fragment obtained from plasmid pUC19, forming plasmid pUCRH (FIG. 10). The product of ligation between the BamHI-HindIII fragment from pUCRH, the 1717 bp HindIII-SspI fragment from pJD204 and the 1321 bp HindIII-SmaI fragment from pSV2NeOR was transfected and purified by established methods as described above and termed plasmid pLLRNL (FIG. 8).

Figure 11:
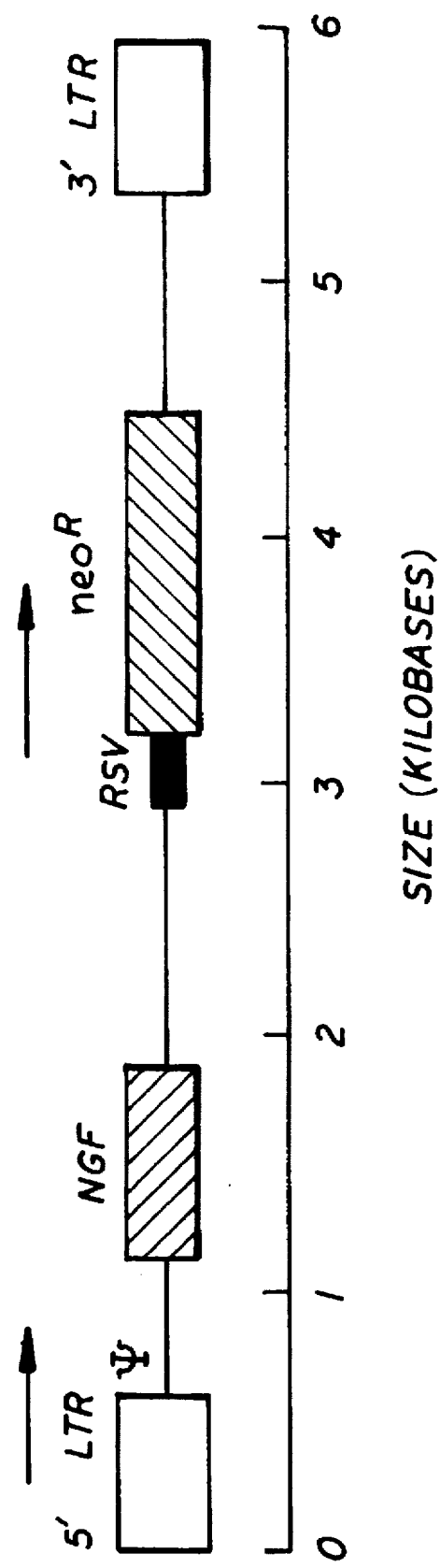
FIG. 11 is a diagrammatic depiction of the linear restriction map of the integrated NGF retroviral vector PLN.8RNL containing the 777 base pair Hgal-Pstl fragment of mouse nerve growth factor (NGF) cDNA under control of the viral 5' long terminal repeat (LTR) as described in Example II, infra (arrows indicate transcription initiation sites; psi (Ψ)= retroviral packaging signal; RSV=Rous sarcoma virus promoter; neo$^r$=neomycin-resistance gene marker.)
Figure 12:
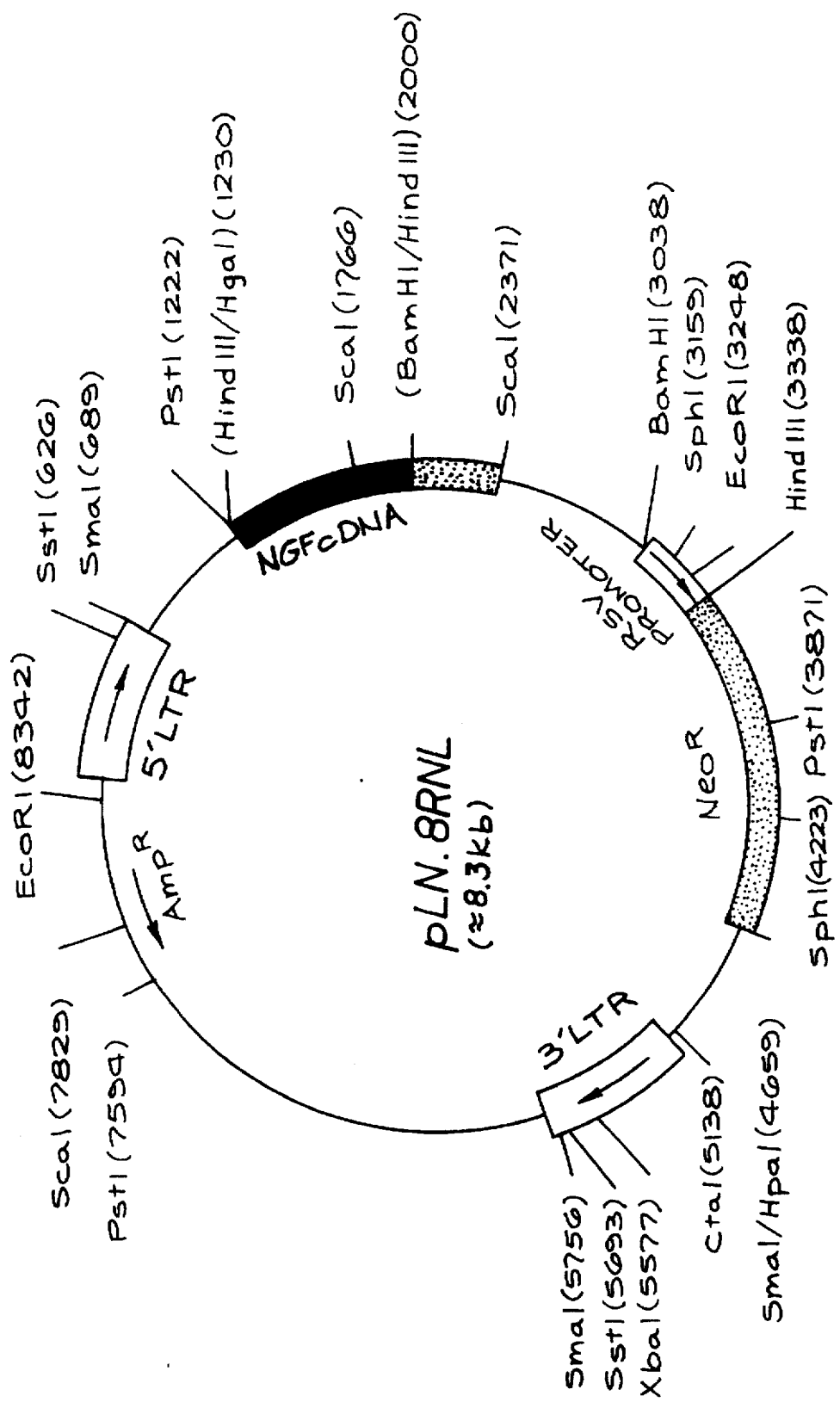
FIG. 12 is a depiction of the circular restriction map of vector pLN.8RNL as shown in FIG. 11 and described in Example II, infra.

After transfection and purification, the plasmid resulting from ligation of the 6.1 BamHI-ClaI kilobase fragment from plasmid PLN.8L and the 2.1 kilobase BamHI-ClaI fragment from plasmid pLLRNL was termed pLN.8RNL. (FIGS. 11 and 12).

Preparation of Transmissible Retrovirus

Transmissible retrovirus was produced by transfecting pLN.8RNL into PA317 amphotropic producer cells (Miller et al., *Mol. Cell. Biol.* 6:2895 (1986)), supplied by Dr. Miller, Fred Hutchinson Cancer Research Center, Seattle, Wash.), by the calcium phosphate co-precipitation method (Graham et al., *Virology* 52:456 (1973)), and using medium from these cells to infect Ψ-2 ecotropic producer cells (Mann et al., *Cell* 33:153 (1983)) in the presence of 4 µg/ml Polybrene (Sigma Chemical, St. Louis, Mo.). Virus from the *2 clone producing the highest titer, 4×10$^5$ colony forming units/ml, was used to infect the established rat fibroblast cell line 208F (Quade, *Virology* 98:461 (1979) as described by Miyanohara et al., in *Proc. Natl. Acad. Sci. USA* (1988)).
Assay for NGF Production and Secretion Individual neomycin-resistant 208F colonies, selected in medium containing the neomycin analog G418, were expanded and tested for NGF production and secretion by a two site (ELISA) enzyme immunoassay (Korsching et al., *Proc. Natl. Acad. Sci. (USA)* 80:3513–3516 (1983)), using commercially available reagents according to the manufacturer's protocol (Boehringer Mannheim). The clone producing the highest levels of NGF contained 1.7 ng NGF/mg total cellular protein and secreted NGF into the medium at a rate of 50 pg/hr 10$^5$ cells. The NGF secreted by this clone was biologically active, as determined by its ability to induce neurite outgrowth from PC12 rat pheochromocytoma cells (Greene, et al., *Proc. Natl. Acad. Sci. USA* 73:2424 (1976)). Uninfected 208F cells, in contrast, did not produce detectable levels of NGF in either assay.

Fimbria Fornix Transection

Fimbria fornix transection (axotomy) was performed as described by Gage et al., *Brain Res.* 268:27–37 (1983) and in *Neuroscience* 19(1) 241–255 (1986), both of which are incorporated by reference herein. Briefly, adult female Sprague-Dawley rats (Bantin and Kingman, San Francisco, Calif.) weighing between 200 g and 225 g at the beginning of the experiment were used. The animals were anesthetized with intraperitoneal injections of a ketamine-xylazine mixture (10 µg/kg Ketalar, Parke-Davis Ann Arbor, Mich., and 5 µg/kg Rompun, Hoechst, Frankfurt, W. Germany). Unilateral aspirative lesions were made by suction through the cingulate cortex, completely transecting the fimbria fornix unilaterally, and removing the dorsal tip of the hippocampus as well as the overlying cingulate cortex to inflict a partial denervation on the hippocampus target, as described in Gage et al., *Brain Res.* 268:27–37 (1983). All animals in each of the experimental groups received the same complete unilateral aspirative lesion. Fimbria fornix lesions as described above were made in 16 rats; 8 rats received grafts of infected cells while the remaining 8 received uninfected control cells.

Figure 13A:
FIG. 13a–FIG. 13f are photomicrographs of immunohistochemical staining for fibronectin and ChAT as described in Example II, infra (FIG. 13a, FIG. 13b=fibronectin staining in fibroblasts grafted into the fimbria fornix cavity.
Figure 13B:
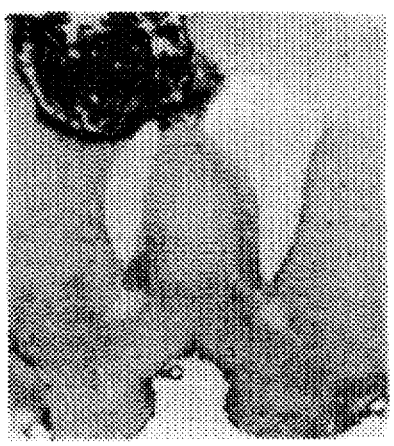
Figure 13C:
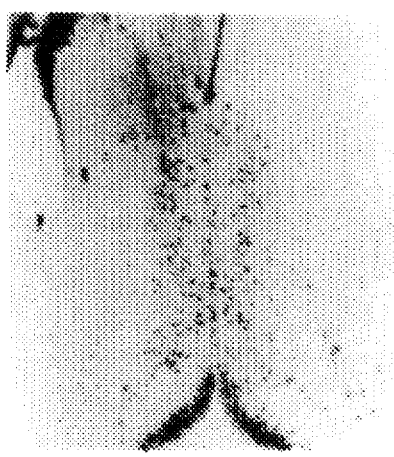
Figure 13D:
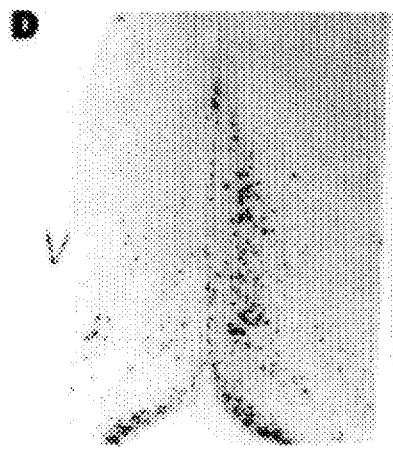
Figure 13E:
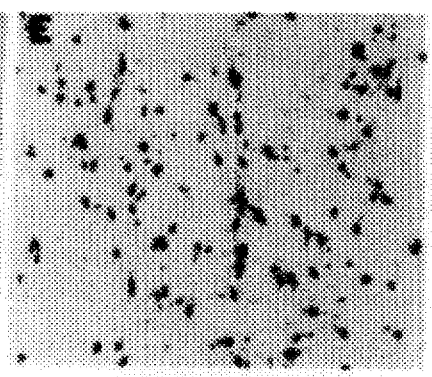
Figure 13F:
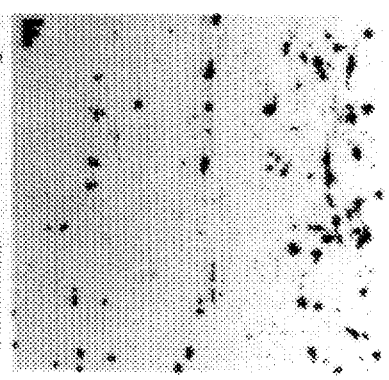
Figure 15A:
FIG. 15a–FIG. 15f are photomicrographs of acetylcholinesterase histochemistry as described in Example II, infra (FIG. 15a=low power magnification of an animal grafted with NGF-infected donor cells.
Figure 15B:
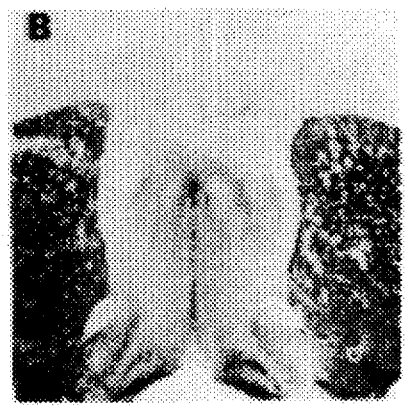
Figure 15C:
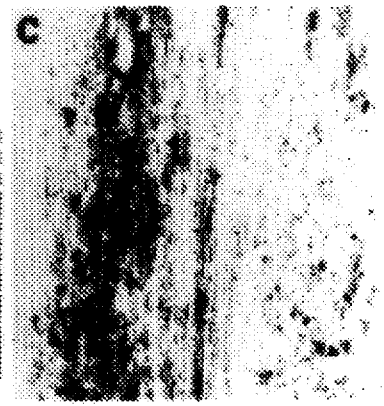
Figure 15D:
Figure 15E:
Figure 15F:
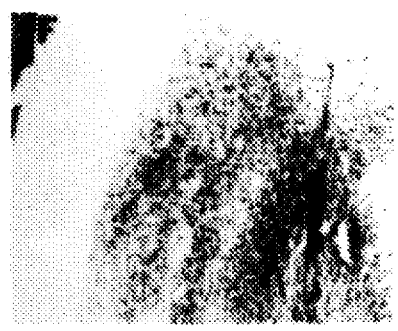

Sections stained for fibronectin, a fibroblast specific marker, revealed robust graft survival that was comparable in both groups (FIG. 13a, FIG. 13b). Sections stained for choline acetyltransferase (ChAT) to evaluate the survival of cholinergic cells bodies indicated a greater number of remaining neurons on the lesioned side of the medial septum in animals that had received grafts of infected cells than in animals that had received control grafts (FIG. 13c–FIG. 13f).

Retrovirus-infected (NGF secreting) and control 208F cells were removed from confluent plates with Dulbecco's phosphate buffered saline (PBS) containing 0.05% trypsin and 1 mM EDTA and taken up by trituration with PBS supplemented with 1 mg/ml glucose, 0.1 mg/ml each MgCl$_2$ and CaCl$_2$ (complete PBS) and 5% rat serum to inactivate the trypsin. Cells were pelleted by centrifugation at 1000×g for 4 min. at 4° C., washed twice with complete PBS, and resuspended in complete PBS at 10$^5$ cells/µl. Four µl of suspended cells were injected free-hand using a Hamilton syringe into the cavity and lateral ventricle ipsilateral to the cavity in the animals. A piece of Gelfoam was gently placed on the surface of the cavity and the animals were sutured.
Immunohistochemistry At 2 weeks following surgery the rats were perfused and their brains were removed, fixed overnight and placed in phosphate-buffered 30% sucrose for 24 hr at 4° C. Sections 40 µm thick were cut on a freezing sliding microtome and stored in cryoprotectant (phosphate-buffered glycerol and ethylene glycol) at −20° C. Every fifth section was labelled immunohistochemically by standard procedures using polyclonal antibodies to fibronectin to evaluate fibroblast survival. Polyclonal antibodies to choline acetyltransferase (anti-ChAT antiserum) were also generated to evaluate the survival of cholinergic cell bodies as described by Gage et al. in *J. of Comparative Neurol.* 269:147-155 (1988), incorporated by reference herein. Tissue sections were processed for immunohistology according to a modification of the avidin-biotin labeling procedure of Hsu et al., 29:1349–1353 (1981), incorporated by reference. This procedure consists of the following steps: 1) overnight incubation with antibody to ChAT or with control antibody (i.e. preimmune serum or absorbed antiserum). The ChAT antibody was diluted 1:1, 500 with 0.1M Tris-saline containing 1% goat serum and 0.25% Triton X-100; 2) incubation for 1 hr with biotinylated goat anti-rabbit IgG (Vector Laboratories, Burlingame, Calif.) diluted 1:200 with Tris-saline containing 1% goat serum: 3) 1 hr incubation with ABC complex (Vector Laboratories) diluted 1:100 with Tris-saline containing 1% goat serum; 4) treatment for 15 min with 0.05% 3,3'diaminobenzidine (DAB), 0.01% hydrogen peroxide and 0.04% nickel chloride in 0.1M Tris buffer. Immunolabeled tissue sections were mounted onto glass slides, air dried and covered with Permount and glass coverslips. Two sections stained for ChAT through the septum, 200 μm apart were used to evaluate the extent of cholinergic cell survival. All the ChAT-positive cells in the ipsilateral septum and in the contralateral septum were counted separately and sized for planar area using an Olympus Que-2 image analysis system. Tissues were also stained for acetylcholinesterase (AChE) as described by Hedreen et al., *J. Histochem. Cytochem.* 33:134–140 (1985), incorporated by reference herein, to evaluate the completeness of the fimbria fornix transection.

Neuronal survival was quantitated (FIG. 14) and, when expressed as a percentage of the remaining cholinergic cells in the septum ipsilateral to the lesion relative to the intact contralateral septum, was shown to be 92% in animals grafted with NGF-secreting cells but only 49% in animals grafted with control cells. The results from the control group are comparable to previous observations in lesioned animals that had received no grafts (Gage et al., *Neuroscience* 19:241 (1986); Hefti, *J. Neurosci.* 8:2155 (1986); Williams et al., *Proc. Natl. Acad. Sci. USA* 83:9231 (1986); Kromer, *Science* 235:214 (1987); Gage et al., *J. Comp. Neurol.* 369:147 (1988)).

In addition to the significant increase in the percentage of ChAT-positive cells in the NGF group, these animals also showed an increase in AChE-positive fiber and cell staining (FIG. 15). Most striking was the observation of a robust sprouting response in the dorsal lateral quadrant of the septum, with the most intense staining abutting the cavity containing the graft. This intense increase in AChE staining was not observed in the group receiving control grafts (FIG. 15).

The above results demonstrate the feasibility of continued transgene expression by cells grafted to the CNS and also present the first demonstration of a phenotypic correction in whole animals brought about by grafted, genetically modified cells.

EXAMPLE III

Grafting of Genetically Modified Fibroblasts Expressing L-dopa Into The CNS of A Rat Model of Parkinson's Disease This example was undertaken to demonstrate that the methods of the present invention for genetic modification of donor cells and grafting of the cells into the CNS can significantly ameliorate the signs of disease in an animal model, such as a rat model of Parkinson's disease.

The strategy for enabling fibroblasts to produce L-dopa used in this example is based upon the ability of the enzyme tyrosine hydroxylase (TH) to catalyze the conversion of tyrosine to L-dopa; the rate-limiting step in catecholamine synthesis. Tetrahydrobiopterine ($H_4$—B), the co-factor for TH is required for TH enzymic activity. Since the brain contains significant levels of biopterin, and fibroblasts can reduce biopterin to $H_2$-biopterin, TH should be active in fibroblasts situated within the brain.

Construction of Retroviral Vector pLThRNL

Figure 16:
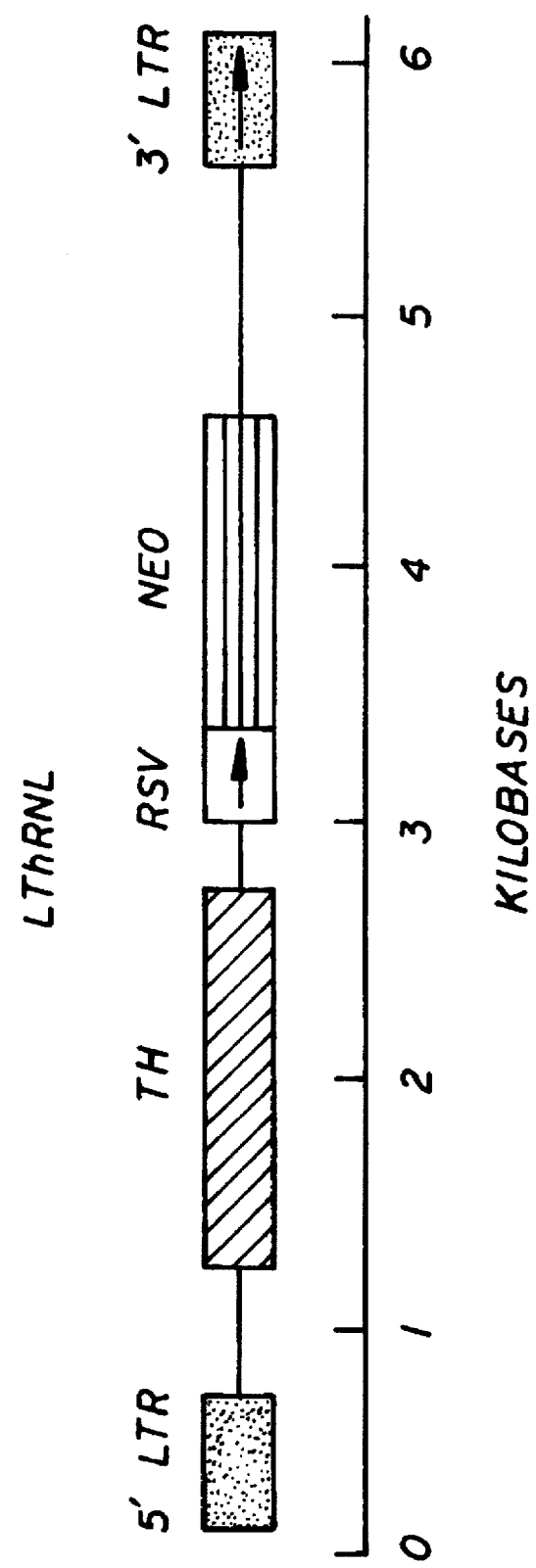
FIG. 16 is a diagrammatic depiction of the linear restriction map of pLThRNL retroviral integrated vector as described in Example III, infra (arrows indicate the location of the promoters and the direction of transcription; LTR= long terminal repeat; RSV=modified RSV promoter; neo$^R$= neomycin-resistance gene).

The vector pLThRNL, a Moloney leukemia virus (MoMLV) derived retroviral vector, was constructed expressing the rat cDNA for tyrosine hydroxylase (TH) from the 5' LTR sequence and contained a neomycin-resistant gene transcribed from an internal RSV promoter (FIG. 16). Fragments from three plasmids: pLRbL, pTH54 and pLHRNL were ligated together to form pLThRNL. Plasmid pLRbL was obtained by digesting plasmid pLMTPL (obtained as described above in Example II) with the enzymes HindIII and HpaI, and removing the fragment containing the HPRT gene. The remaining plasmid DNA was ligated with the 3.5 kb fragment obtained after restriction of plasmid pGEMl-4.5Rb old (pGEMl-4.5Rb old was constructed by inserting DNA encoding the retinoblastoma gene (Rb) into plasmid pGEMl, available from Promega, Madison, Wis., and was supplied by Dr. Lee, University of California, San Diego, Calif.) using HindIII and Sca2. The resulting plasmid was named pLRbL.

A 1688 bp fragment containing rat TH cDNA was obtained from the plasmid pTH54 (O'Malley, *J. Neurosci. Res.* 60:3–10 (1986), supplied by Dr. O'Malley, Washington University, St. Louis, Mo.) by digestion with BamIII and SphI.

Figure 17:
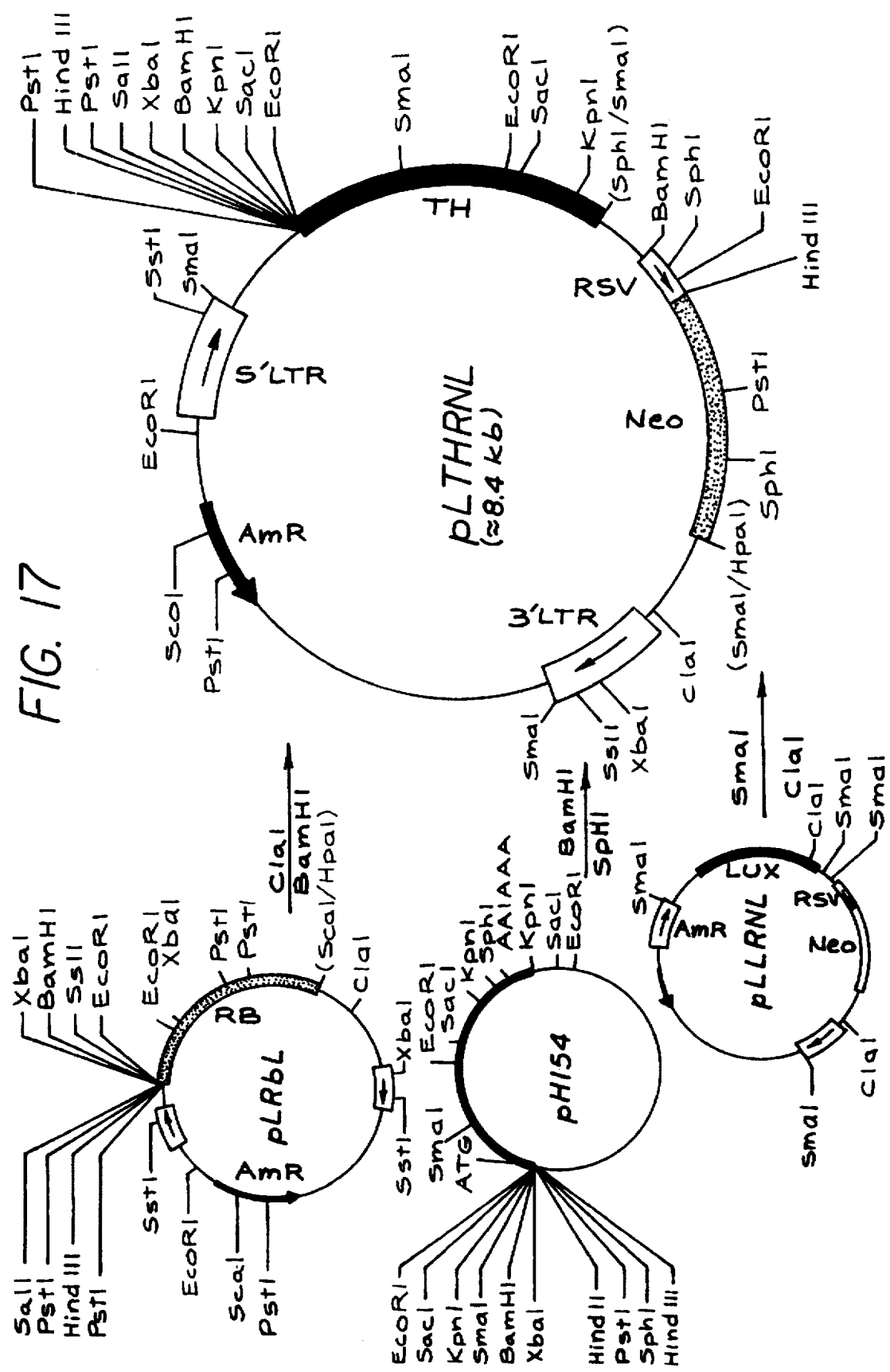
FIG. 17 is a depiction of the derivation of vector pLTh-RNL as shown in FIG. 16 and described in Example II, infra.

The fragments from plasmid pTH54 and plasmid pLRbL were ligated with a ClaI and SmaI fragment obtained from plasmid pL2RNL (described above in Example I) to obtain the vector pLThRNL containing the retroviral provirus for transfection into producer cells to produce virus carrying the gene encoding the enzyme tyrosine hydroxylase. The derivation of and circular restriction map for pLThRNL is shown in FIG. 17.

Helper-free retrovirus was produced and retroviral infections were done as described in Example II, supra Plasmid DNA containing the LThRNL provirus was $CaPO_4$ transfected as described by Wigler et al., *Cell* 11:223–232 (1977), incorporated by reference herein, into the amphotropic PA317 helper line supplied by Dr. Miller, Fred Hutchinson Cancer Research Center, Seattle, Wash. Two days post-transfection, media from these cells were filtered and used to infect the ecotropic Ψ2 helper line (Miller et al., *Mol. Cell. Biol.* 6:2895–2902 (1986), supplied by Dr. Miller). A G418-resistant Ψ2 clone (Ψ2/TH) that contained the highest level of TN activity and produced the highest titre of virus ($5 \times 10^5$/ml) was selected. Immortalized, rat fibroblasts (208F) (Quade, *Virology* 98:461–465 (1979)) were infected at a multiplicity of infection (MOI) of less than $10^{-4}$ with LThRNL virus produced by the Ψ2/TH producer cells. G418 resistant clones were established for further study. All retroviral infections were done in the presence of 4 μg of Polybrene (Sigma) per ml. Cells were selected for expression of the neomycin-resistance gene by growth in 400 μg/ml of G-418.

Assay of Tyrosine Hydroxylase Activity

Confluent 10 cm plates of cells were washed two times with Dulbecco's phosphate buffered saline (PBS) not containing calcium or magnesium chloride and the cells were scraped off the plates. The cells were homogenized in 0.15 ml of ice cold 50 mM Tris/50 mM sodium pyrophosphate/ 0.2% Triton X-100, adjusted to pH 8.4 with acetic acid, and were centrifuged at 32,000×g for 15 min at 2°–40° C. The supernatant fraction was used for both TH and protein measurements. TH activity was measured with a decarboxylase-coupled assay essentially as described previously (Iuvone et al., *J. Neurochem*, 43:1359–1368 (1986)), but with $^{14}$C-labelled 20 µM tyrosine, 1 mM 6-methyl-5,6,7,8-tetrahydropterin (6MPH4) (Calbiochem, La Jolla, Calif.), and potassium phosphate buffer (pH 6). Protein was determined by the method of Lowry et al. (*J. Biol. Chem.* 193:265 (1951)) using bovine serum albumin as standard.

Assays of Catecholamines and their Metabolites

Cultured cells were scraped off plates as in the assay of tyrosine hydroxylase activity except ascorbic acid (final concentration of 50 nM) was added to the cell pellets prior to freezing. Cells were grown in DME plus 10% fetal calf serum. Some cultures were supplemented with 0.1 mM 6MPH$_4$, 16 hours prior to harvesting. Cells were homogenized in 250 µl of ice cold 0.1N HCl/0.1% sodium metabisulfite/0.2% Na$_2$EDTA containing 5 ng/ml of 3,4-dihydroxybenzylamine (DHBA) as internal standard. Dopamine, DOPA, 3,4-dihydroxyphenylacetic acid (DOPAC), DHBA and 3-methoxy-4-hydroxyphenylglycol (MHPG), were extracted from the supernatant fraction by alumina absorption (Anton et al., *J. Pharmacol. Exp. Ther.* 138:360–375 (1962)) and eluted with 150 µl of 0.1N H$_3$PO$_4$. They were analyzed by HPLC with electrochemical detection as described by Iovone et al., *Brain Res.* 418:314–324 (1987), with the mobile phase modified to contain a higher concentration of sodium octylsulfate (0.45 mM) and lower pH (2.8). Hiomovanillic acid (HVA) was analyzed by HPLC. The concentration of catecholamines and metabolites in the media was also determined using a different method, HPLC-EC. The alumina extraction procedure described above was omitted and the media was adjusted to 0.1 perchloric acid/0.01M EDTA was centrifuged 10,000 g×10 min to remove precipitated material and used directly for HPLC-EC. In this system, the whole phase consisted of 0.137% SDS in 0.1M phosphate buffer, pH 3.2 (Buffer A) or 40% methanol in 0.1M phosphate buffer, pH 3.35 (Buffer B). Compounds in sample were eluted for 12 minutes in 100% Buffer A, followed by a gradient increasing linearly over 30 minutes to 100% Buffer B. The eluant was then passed through a series of 16 coulometric electrodes set at 60 mV increments.

Rat Model of Parkinson's

Female Sprague-Dawley rats received a unilateral injection of 12 µg in 2 µl saline-ascorbate 6-hydroxy-dopamine (6-OHDA) into the medial forebrain bundle (coordinates: AP=-4.4; ML=1.1; DV=7.5). Completeness of the lesion produced was assessed 10 to 20 days postinjection by either apomorphine (0.1 mg/kg, subcutaneously (s.c.)) or amphetamine (5 mg/kg, s.c.) induced rotational behavior (Ungerstedt and Arbuthnott, *Brain Res.* 24:485–493 (1970)). Prior to transplantation, each animal was tested at least twice on separate days to establish the baseline rotational response to apomorphine or amphetamine for each animal. Animals turning at a rate of more than 7 turns per minute (Schmidt et al., *J. Neurochem.* 38:737–748 (1982)) were included in the study (at least 7 contralateral rotations/min following apomorphine administration and at least 7 ipsilateral rotations/min towards the side of the lesion following amphetamine administration; 19 apomorphine tested, 14 amphetamine tested). The average percent change in the number of rotations from baseline to post-transplantation was compared in the 4 experimental groups of animals.

Grafting of Fibroblasts

Confluent 10 cm plates of cultured TH-infected or non-infected fibroblasts were loosened from the plates in PBS containing 0.05% trypsin and pipetted up in PBS supplemented with 1 mg/ml glucose, 0.1 mg/ml MgCl$_2$ and 0.1 mg/ml CaCd$_2$ (complete PBS) plus 5% rat serum to inactivate the trypsin. The cells were washed twice with complete PBS using centrifugation at 1000×g and were resuspended in complete PBS at a density of 80,000 cells per µl. Since graft placement has been shown to be crucial for recovery from rotational asymmetry (Herrera et al., *Brain Res.* 297:53–61 (1984); Dunnett et al., *Scand. Suppl.* 522:29–37 (1983)), suspended cells were injected stereotaxically into 2 to 3 separate locations within the rostral (coordinates: AP=1.4; ML=2.0; DV=3.5–5.5 to AP=2.5; ML=1.5; DV=3.5/4.5) and caudal areas (AP=0.4; ML=3.0; DV=3.5/4.5) of the denervated caudate. A total of 4 µl were delivered in two equal deposits over a 1 to 2 mm area at each site. Control lesioned animals received injections of noninfected fibroblasts.

Post-Grafting Behavioral Testing

Grafted rats were tested for rotational asymmetry 1 and 2 weeks following fibroblast grafting.

Histological Methods

Following the final behavioral test, rats were deeply anesthetized and perfused with 10% formalin. Brains were postfixed overnight, placed in 30% sucrose for 48 hrs and then sectioned (40 µm) on a freezing microtome. Alternate sections were stained for cresyl violet, fibronectin (FB) or TH using a polyclonal anti-tyrosine hydroxylase antibody (Eugenetech, N.J). Briefly, the sections were rinsed in Tris-buffered saline (TBS) solution (pH 7.4) containing 0.25% Triton-X. The sections were incubated for 24 hrs at 4° C. with rabbit polyclonal antibodies to tyrosine hydroxylase diluted 1:600 or polyclonal anti-fibronectin diluted 1:2000 in TBS containing 0.25% Triton-X and 3% goat serum. After thorough rinsing, the sections were incubated for 1 hr with biotinylated goat anti-rabbit IgG (Vectastain) diluted 1:200 in 0.1M TBS containing 0.25% Triton-X and 1% goat serum, followed by several rinses in TBS containing 0.25% Triton-X and 1% goat serum. The sections were then incubated for 1 hr at room temperature with a complex of avidin and biotinylated horseradish peroxidase (Vectastain, ABC kit, Vector Labs, Burlingame, Calif.) diluted 1:100 in 0.1M TBS containing 0.25% Triton-X and 1% goat serum, followed by thorough rinses. The peroxidase was visualized by reacting with 0.05%, 3,3-diaminobenzidine tetrahydrochloride (DAB) (Sigma Chemical Co., St. Louis, Mo.) and 0.05% NiCl$_2$ and 0.01% H$_2$O$_2$ in TBS for 15 min at room temperature. Mounted sections were assessed for size and placement of fibroblast positive grafts.

Establishment of a Fibroblast Clone Expressing High Levels of TH

Immortalized, rat fibroblasts (208F) were infected with LThRNL virus produced by the Ψ2/TH producer cells and 12 G418-resistant clones were established. Table 1 shows the TH activity of 3 of these 12 G418 resistant clones with the highest TH activity and the TH activity of the Ψ2 producer line. The TH activity of the clones with the highest activity (clones 208F/TH-8 and 208F/TH-11) contained approximately a quarter of the TH activity of rat striatum. The 208F/TH-8 clone that contained the highest TH activity, was chosen for further study.

TABLE 1

TH Activity of Cell and Tissue Extracts

| Cell Line | TH Activity* |
|---|---|
| Ψ2/TH | 1.7 |
| 208F/TN-8 | 2.9 |
| 208F/TH-11 | 2.6 |
| 208F/TH-9 | 0.4 |
| 208F/CONTROL | 0.0 |
| Rat Striatum | 9.8 |

*TH activity is expressed in units of pmoles DOPA/min/mg protein

Fibroblasts Expressing TH Produce and Secrete L-dopa.

Cell extracts from the 208/TH-8 fibroblasts expressing TH and control 208F fibroblasts were assayed for L-dopa (Table 2). Only 208F/TH-8 cells cultured in media supplemented with 6MPH$_4$ produced L-dopa. Control cells did not contain any detectable amounts of L-dopa. Dopamine and its metabolites DOPAC and HVA were below detectable levels in both 208F/TH-8 and 208F control cells.

TABLE 2

L-dopa Concentration of Cell Extracts and Media

| | L-dopa Concentration[1] | | | |
|---|---|---|---|---|
| | Cell Extract | | Cell Media | |
| Cell Clone | no 6MPH$_4$[2] | +6MPH$_4$[3] | no 6MPH$_4$[2] | +6MPH$_4$[3] |
| 208F/CONTROL | <0.25 | <0.25 | N.D.[4] | 63 |
| 208F/TH-8 | <0.25 | 1.38 | N.D. | 239 |

[1]L-dopa concentration is expressed in units of nanograms (ng)/mg protein for cell extracts and in units of ng/hr/10⁶ cells for cell media.
[2]Cell incubated in normal media.
[3]Cells incubated overnight in normal media supplemented with 0.1 mM DL-6-Methyl-5,6,7,8-tetrahydropterin.
[4]N.D. not determined As shown in Table 2, L-dopa was also detected in the media of the 208F/TH-8 cells: 63 ng/hr per 10⁶ cells in control 208F media and 239 ng/hr per 10⁶ cells in TH-infected media. There was no detectable levels of L-dopa metabolites contained or released in 208F/TH8 or control fibroblasts.

Histologic Examination of Grafts

Figure 18A:
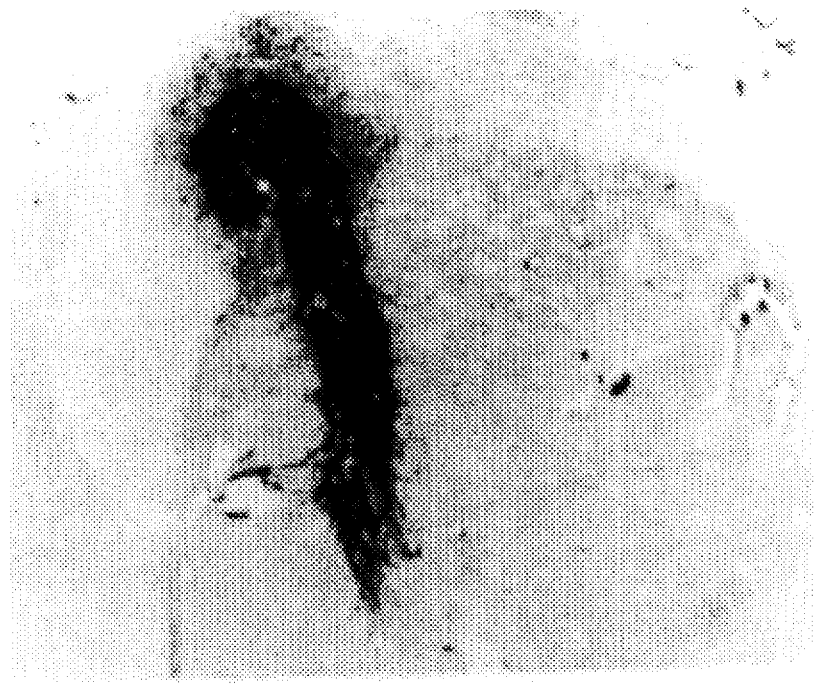
FIG. 18a–FIG. 18d are photomicrographs of fibroblast grafts to the caudate showing fibronectin immunoreactivity as described in Example III, infra (Mag.
Figure 18B:
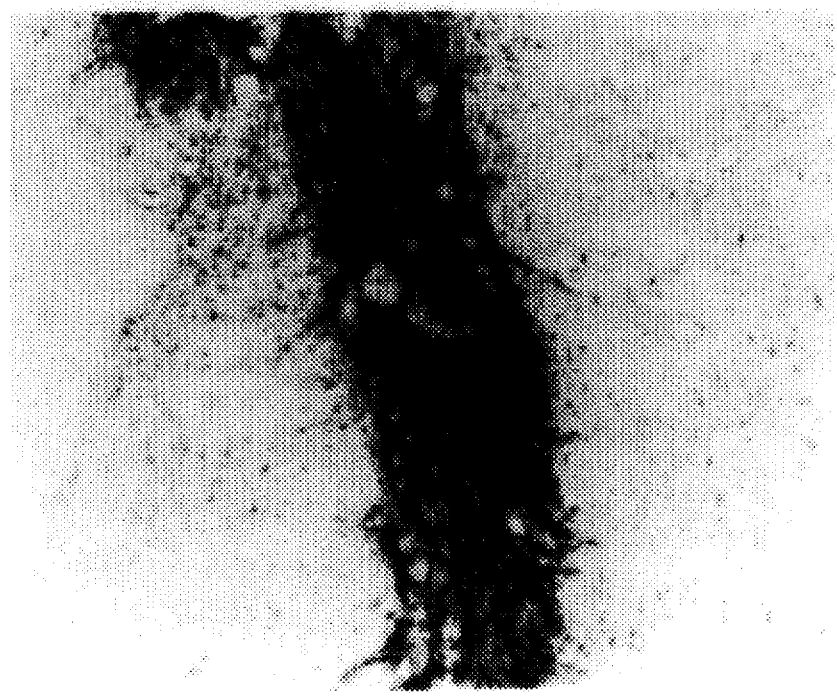
Figure 18C:
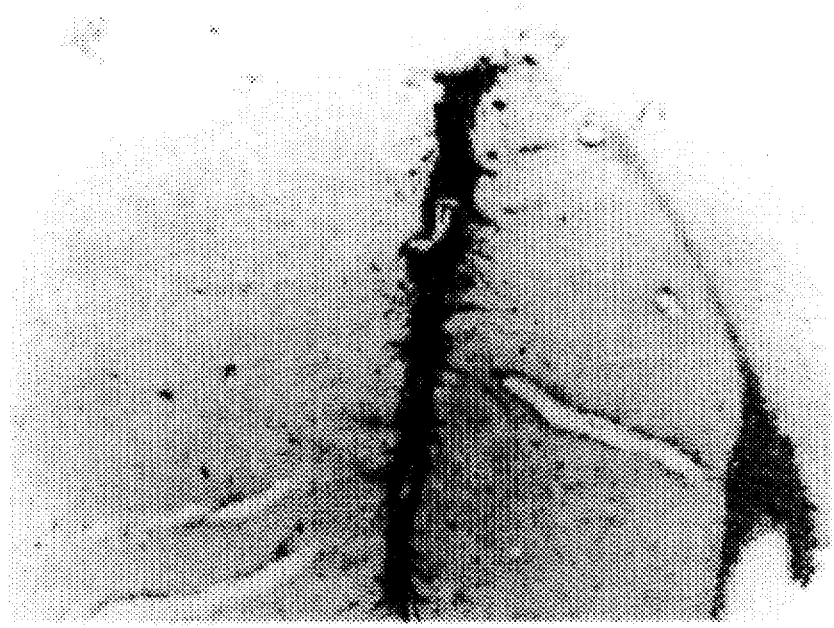
Figure 18D:
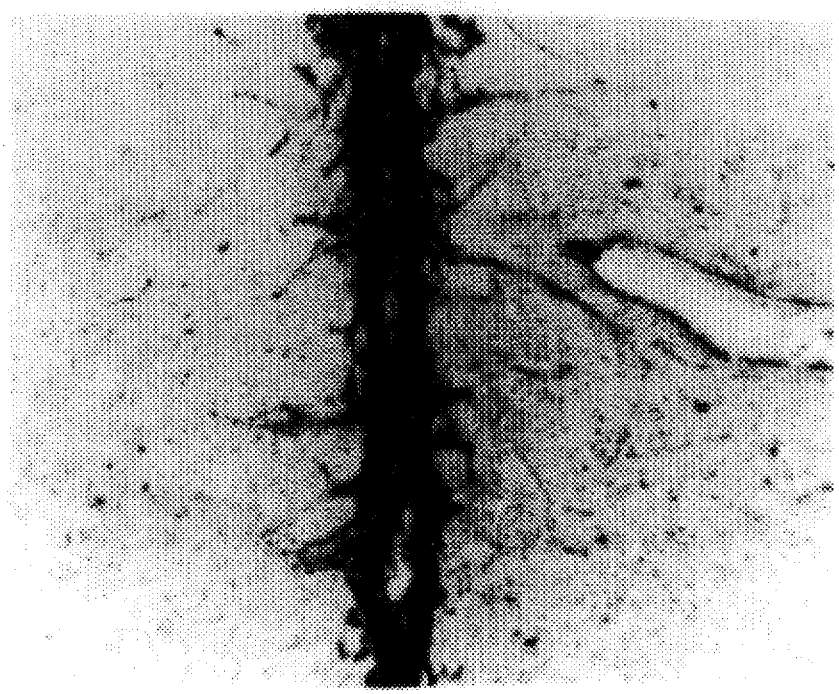

Fibroblast grafts survived intraparenchymal transplantation to many areas within denervated caudate. Surviving fibronectin positive grafts were typically moderate to large in size regardless of placement (FIG. 18a and b). Only 4 out of 31 grafts were classified as non-surviving based on the confinement of fibronectin staining to the syringe tract (FIG. 18c and d). Behavioral data from the rats with nonsurviving grafts were excluded from statistical analyses. TH immunoreactivity was not observed in the fibroblasts either in vitro or in vivo.

Effect of Grafts on Rotational Asymmetry

The number of drug-induced rotations for each individual animal were compared before and 2 weeks after transplantation. Rotational scores from rats tested with apomorphine were pooled with those from rats tested with amphetamine since no difference was seen between these groups.

Figure 19:
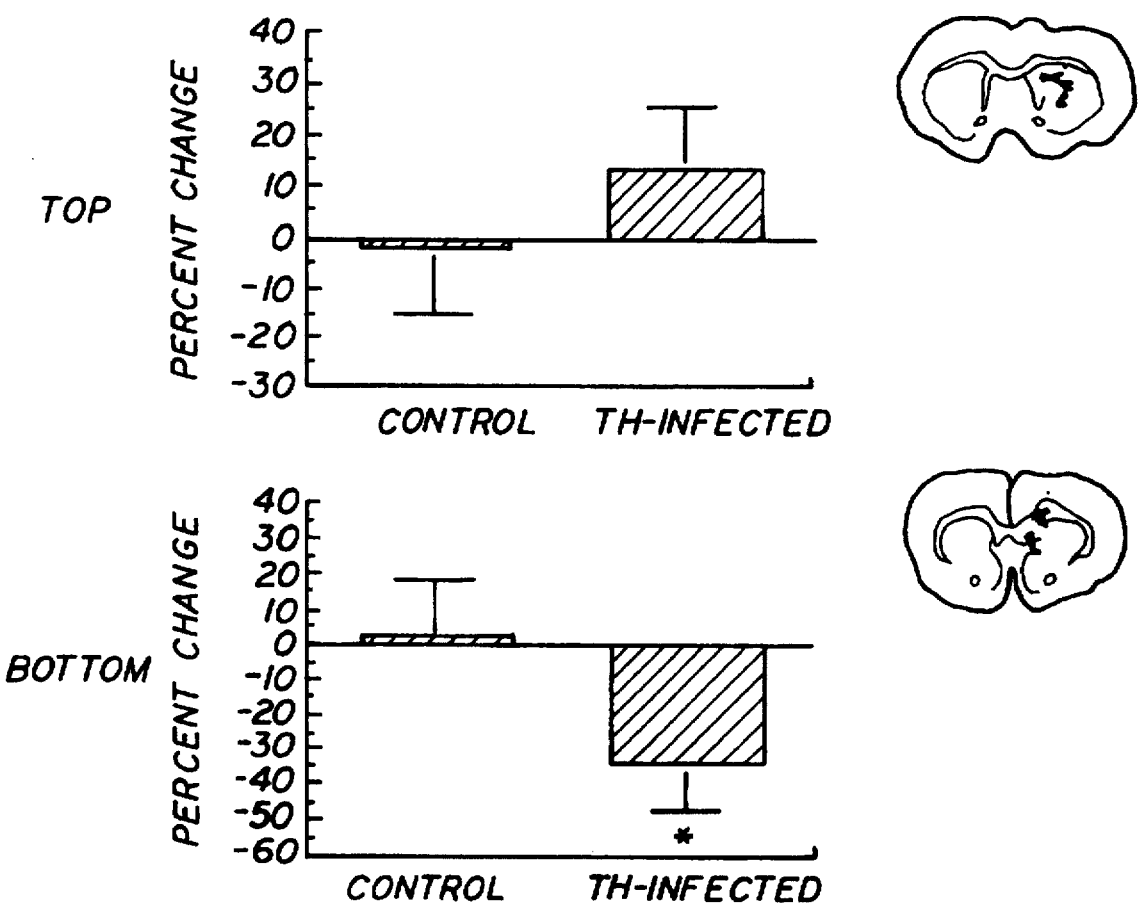
FIG. 19 is a graph showing the average percent change in the number of rotations from baseline to post-transplantation in 4 experimental groups of animals as described in Example III, infra (Top of figure: placement of control and TH-infected grafts in caudal striatum; Bottom: placement of control and TH-infected grafts in rostral striatum; bars indicate standard deviation).

Amelioration of rotational asymmetry was dependent on graft placement. Rats with fibroblast grafts confined to caudal areas of the caudate (FIG. 19 Top) (AP=0 to 0.4) had no significant changes in rotational behavior. Rats which had surviving TH-infected fibroblasts in rostral caudate striatum (AP=1.4 to 2.2) showed an average 33% reduction in drug-induced rotations 2 weeks following transplantation (FIG. 19 Bottom).

These results demonstrate that the rat cDNA coding for the TH gene can express functional TH enzymic activity when stably transduced into fibroblasts. Fibroblasts expressing the TH gene can produce and secrete L-dopa in vitro. When these DOPA-producing fibroblasts were implanted into the rostral caudate region, they substantially and significantly reduce the rotational asymmetry in the rat model of Parkinson's. Since control fibroblasts do not produce significant levels of L-dopa in vitro and do not attenuate the rotational asymmetry of these rats, the ability of these DOPA-producing cells to attenuate these rat's rotational symmetry must be due solely to the presence of the TH gene within the cells. These data demonstrated an effect on rotational behavior for at least two weeks.

The effect of the DOPA-producing fibroblasts on rotational behavior were dependent on placement in the rostral caudate. Previous data utilizing fetal neuronal grafts into rats have shown that attenuation of rotational asymmetry is best achieved when the grafts are placed into the rostral caudate, (Dunnett, supra). Since the fibroblasts used cannot sprout axons, the location of the graft is even more critically dependent upon proper graft placement.

The exact mechanism by which the DOPA-producing fibroblasts reduce rotational asymmetry remains to be determined. Presumably, once L-dopa is secreted, there remains enough caudate DOPA decarboxylase activity, even within these totally denervated animals (Lloyd et al., Science 170:1212–1213 (1970); Hornykiewicz, British Med. J. 29:172–178 (1973)), to convert L-dopa to dopamine that then modifies drug-induced rotational behavior. This postulated mechanism of action of these DOPA-producing cells would be consistent with the well established efficacy of systemic L-dopa therapy for Parkinson's disease (Calne, N. Eng. J. Med. 310:523–524 (1984)). These DOPA-producing fibroblasts are in effect small localized pumps of L-dopa.

The ability, demonstrated in this example, to modify cells to produce L-dopa broadens the search for the ideal type of cell for transplantation therapy of Parkinson's. Any cell that can be genetically modified to express the TH gene and that can survive long-term in the brain without forming a tumor or causing other damage, may be used. Although these particular immortalized rat fibroblasts have not formed tumors for up to three months, primary cells such as primary fibroblasts or primary glial cells may offer the theoretical advantage of decreased propensity for tumor formation and may be preferred for grafting in certain applications. In addition, the use of the patients own primary cells for an autologous graft would decrease the chance of graft rejection. However, the use of immortalized cells such as the 208F cells used in this example, does offer the advantage of having large amounts of well-characterized cells readily available.

These results demonstrate that a fibroblast can be genetically modified to supply a function normally supplied by a neuron, therefore not requiring the use of fetal tissue for neuronal transplantation. The ability to combine transplantation modalities with gene-transfer presents a powerful method for the treatment of CNS dysfunction. The methods of the present invention may thus be used for treatment of other models of animal and human brain disease.

EXAMPLE IV

Grafting of Cultured Autologous Primary Skin Fibroblasts

As noted above, it may be desirable in certain circumstances to minimize rejection of intracerebral grafts and avoid tumor formation using autologous cells such as primary skin fibroblasts. In this example, primary skin fibroblasts were used to evaluate this cellular population for intracerebral grafting by assessing the growth and survival of the cells in vitro and in vivo and the integration of the grafted cells into the donor's striatum.

In these experiments, the growth rate of primary skin fibroblasts in culture was measured. This growth pattern was compared with that of immortalized Rat-1 fibroblasts in vitro, to determine whether growth-and cellular characteristics in culture would predict those following implantation. Variables that might influence the survival of primary fibroblast grafts were also examined, including the number of passages the cells can be taken through in culture before implantation and the density of cells implanted. Introduction of new genetic material into cultured cells requires several passes to select and expand the modified populations, making assessment of the former parameter important. The density of cells implanted was varied to determine an optimal graft size. The morphological and neurochemical characteristics of the grafts were also examined, and the cellular interactions between the autologous fibroblast grafts and host striatum were revealed.

Skin biopsies were taken from the ventral abdominal wall of twenty-three female Sprague-Dawley rats (200–250 g). Pure fibroblast cultures from each biopsy were maintained under standard conditions and fed DMEM containing 10% fetal bovine serum three times a week. The fibroblasts were grown to confluency and then split 1:2. The growth rate of primary skin fibroblasts was determined with the aid of a Coulter Counter (Coulter Electronics Inc). Triplicate samples of these cells were counted each day, and the growth rate of primary fibroblasts was compared to that of immortalized Rat-1 fibroblasts grown and sampled under the same conditions.

For intracerebral grafting, primary skin fibroblasts from each animal were taken to either one or four passages (there were approximately five cell divisions between passage one and four). These cells were then grown to confluency and harvested at a resting state. The cultured fibroblasts were suspended in a solution of grafting phosphate buffered saline supplemented with 1 mg/ml of $MgCl_2$ and $CaCl_2$, and 0.1% glucose. The density of the suspensions ranged from $10^4$ to $10^5$ cells/μl. The animals were anesthetized with intramuscular injections of ketamine-xylazine (10 mg/kg Ketarar, Parke-Davis, Ann Arbor, Mich.; 5 mg/kg Rumpun, Hoechst, Frankfurt, Germany; and 6 mg/kg acepromazine maleate, TechAmerica) and placed in a stereotaxic frame. Each animal received implants of cultured skin fibroblasts taken from its own skin biopsies. A total of four cell suspensions (3 μl/site) were injected stereotaxically into the striatum with a Hamilton syringe, two rostrally and two caudally. Following implantation, the animals survived for periods of three or eight weeks.

To assess parameters that may influence the survival of intracerebral primary skin fibroblast grafts, two experiments were designed to address the issues of cell passage (n=12) and cell density (n=9). First, groups of three rats received injections of their own primary skin fibroblasts ($10^5$ cells/μl) that were taken through one or four passages; these animals were sacrificed and perfused three or eight weeks following surgery. Second, groups of three animals received suspensions at $10^4$, $2.5\times10^4$, $5.0\times10^4$ or $10^5$ cells/μl; the number of passages (four) and the survival period (eight weeks) were constant.

Tissue Preparation and Histology

For light microscopy, the animals were perfused transcardially with a solution of 4% paraformaldehyde in phosphate buffer (pH 7.3). The brains were removed, postfixed overnight, and stored in 30% sucrose for three days. Coronal sections through the striatum were cut on a freezing microtome at a thickness of 40 μm and collected in cryoprotectant. One series of sections was stained with cresyl violet. The remaining sections were divided into three groups for the immunohistochemical detection of fibronectin, glial fibrillary acidic protein (GFAP) and reactive microglia and/or macrophages. The sections were treated initially with 0.6% hydrogen peroxide in Tris buffer (pH 7.4) for thirty minutes to block endogenous peroxidase activity. Sections were rinsed in buffer and then incubated in rabbit anti-human fibronectin immunoglobulin (IgG) (1:2000 dilution) or rabbit anti-human GFAP IgG, 1:1000 dilution) with 3% normal goat serum and 0.25% Triton-X in Tris buffer overnight at room temperature. Next they were rinsed in buffer and incubated in biotinylated goat anti-rabbit IgG (1:250 dilution) for one hour. After another rinse, they were incubated in avidin-biotin complex (Vector Laboratories) for one hour and rinsed. They were then treated with a solution of 0.025% diaminobenzidine (DAB) tetrahydrochloride, 0.5% nickel chloride and 0.03% hydrogen peroxide in Tris buffer for five minutes.

Immunohistochemical localization of reactive microglia and/or macrophages was achieved using the mouse monoclonal antibody MRC OX-42 (Serotec). Sections were rinsed in buffer, and then incubated with MRC OX-42 (at a concentration of 10 μg/ml) with 3% normal horse serum and 0.25% Triton-X in Tris buffer overnight at room temperature. They were rinsed and incubated in biotinylated horse anti-mouse IgG (1:160 dilution) for one hour. The sections were then rinsed, incubated in avidin-biotin-complex, rinsed again, and reacted in a DAB solution (as above). Following the immunoperoxidase reaction, all sections were rinsed in Tris buffer and then in phosphate buffer. They were mounted on chrome alum-gelatin coated slides, dehydrated through a graded series of ethanols, and coverslipped.

For electron microscopy, animals (n=2, from the cell density study) were perfused transcardially with a solution of 4% paraformaldehyde and a 0.1% glutaraldehyde in Tris buffer (pH 7.4). The brains were removed and post-fixed for three hours, after which coronal sections through the striatum were cut on an Oxford vibratome at a thickness of 50 μm and collected in Tris buffer. Sections were then either stained immunohistochemically for fibronectin or fixed in 1% buffered osmium tetroxide for one hour. The latter sections were rinsed, dehydrated through a graded series of methanols, cleared in propylene oxide, and embedded in a mixture of Poly/Bed and Araldite. Semithin sections (1–2 μm) were collected and stained with 1% toluidine blue to assess the graft. Ultrathin sections were then cut on a Reichert Om U3 ultramicrotome, collected on copper grids and stained with uranyl acetate and lead citrate. The sections were viewed with a JEOL 100 CXII transmission electron microscope.

Graft Analysis

Since fibronectin is not normally detected in the rat brain, fibroblast grafts were defined by the area stained immunohistochemically for fibronectin. Sections possessing immunoreactivity were analyzed with a Cue-2 Image Analysis System (Olympus Corp). Immunostaining was traced manually (mag.=4×) and the area of the graft was computed for each section in a given series. Graft volume ($mm^3$) was calculated from this series according to Uylings et al. (*J. Neurosci. Meth.* 18:19–37 (1986)), incorporated by reference herein. Sections stained for cresyl violet, GFAP and MRC OX-42, as well as sections viewed with the electron microscope, were evaluated qualitatively.

Growth Curves for Rat-1 Fibroblasts and Primary Fibroblasts

Figure 20:
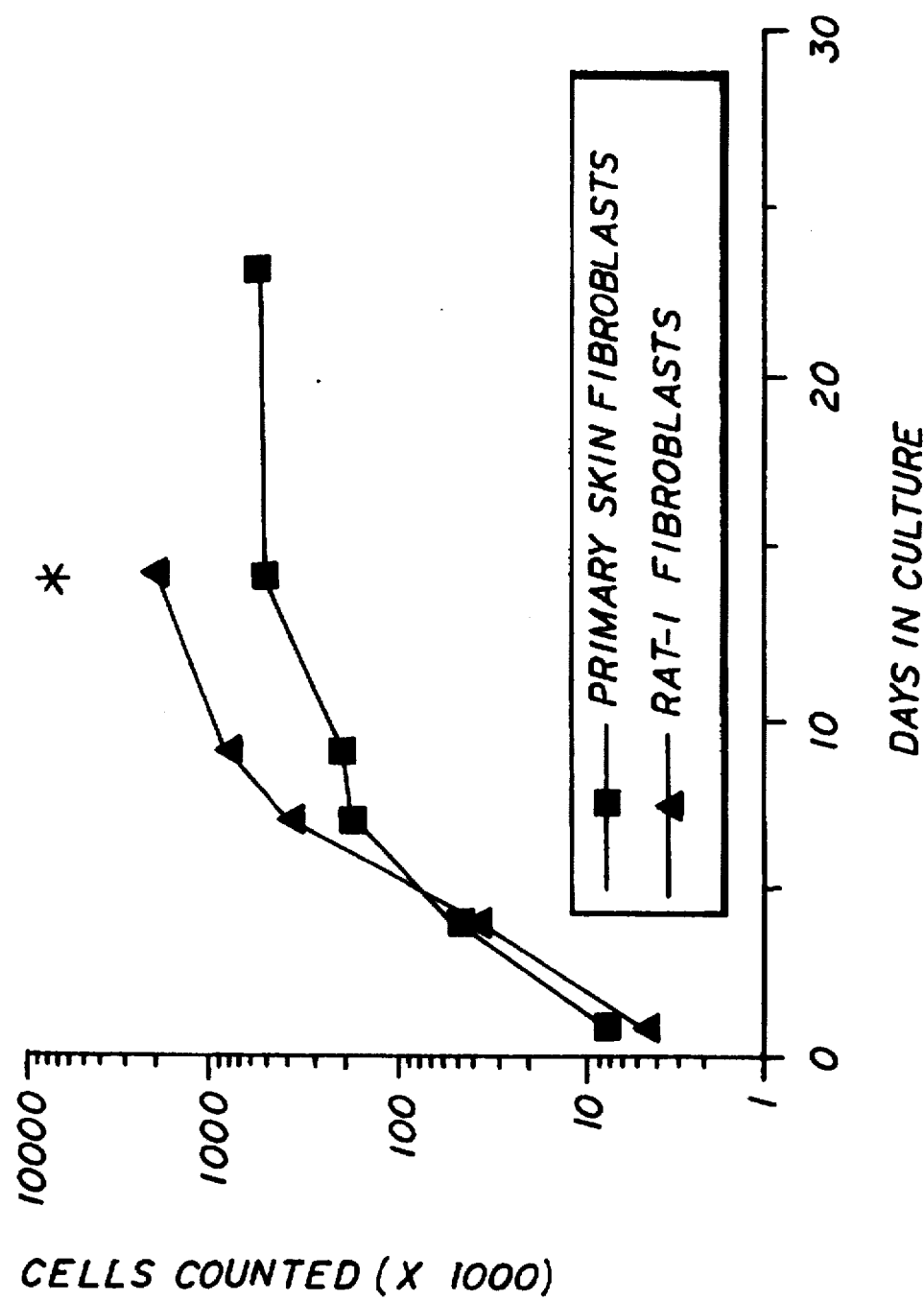
FIG. 20 is a graft of growth curves of primary skin fibroblasts and Rat-1 fibroblasts in vitro as described in Example IV, infra.

The growth rate of Rat-1 cells, which are immortalized fibroblasts that are putatively contact inhibited, was compared to that of primary skin fibroblasts cultured under similar conditions. Although the growth curves of both cell types were similar for the first week, dramatically different growth patterns were observed after ten days (FIG. 20). Rat-1 cells continued to grow once confluency was reached, and therefore did not appear to be contact inhibited. The growth of primary skin fibroblasts, on the other hand, stabilized once the cells reached confluency. These patterns of continued growth (Rat-1 fibroblasts) versus quiescence (primary skin fibroblasts) persisted for up to three weeks.

Cell Passage

Figure 21:
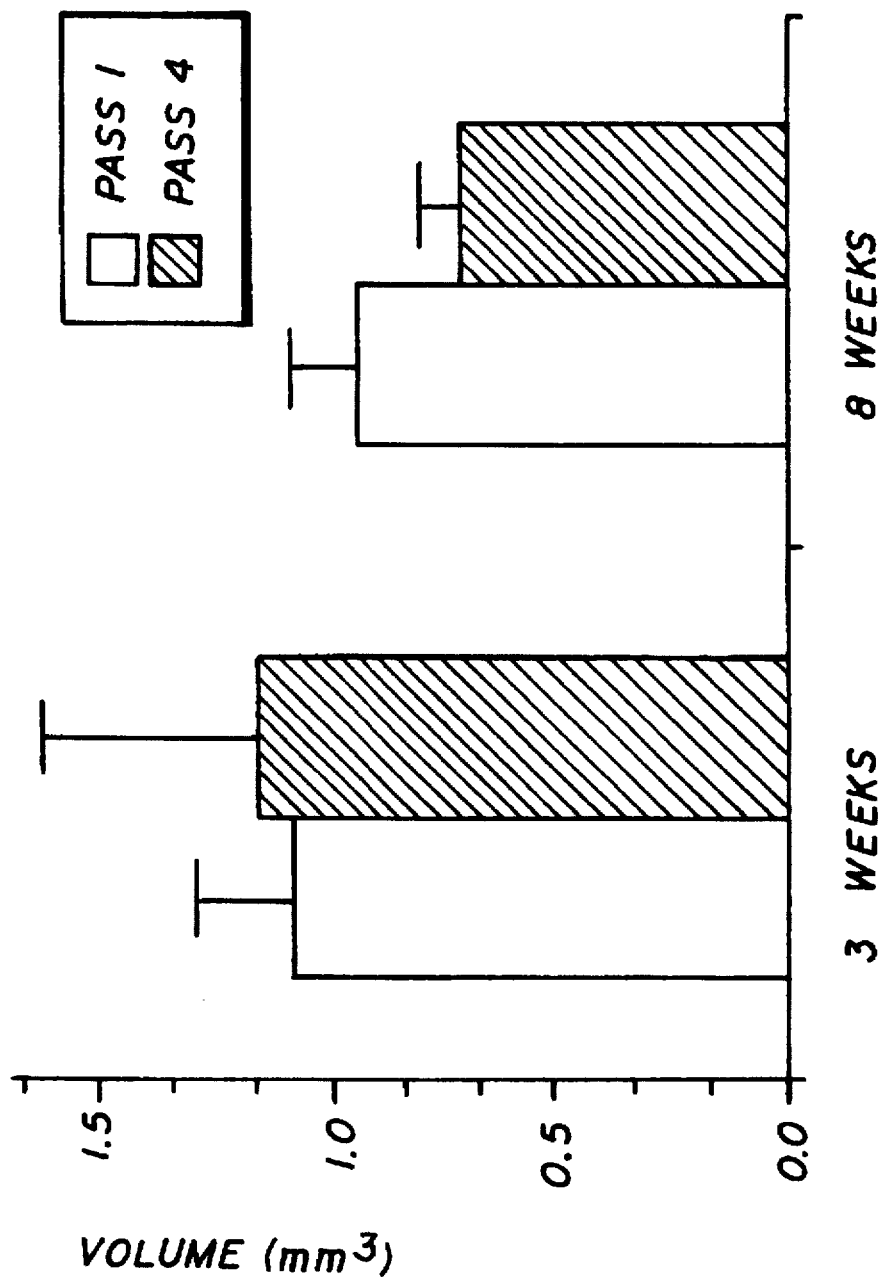
FIG. 21 are histograms showing the volume ($mm^3$) of autologous fibroblast grafts after one and four passages in culture prior to grafting and after three and eight weeks post-operative survival, as described in Example IV, infra.

A parameter that may influence the size of primary fibroblast grafts in the striatum was the number of in vitro passages the cells were taken through prior to implantation. For this study, the cell density of grafts was constant at $10^5$ cells/µl. Six animals received cell suspensions of fibroblasts taken through one passage in culture, and another six received fibroblasts taken through four passages. Three animals from each group were sacrificed and perfused three or eight weeks after implantation. A 2-factor ANOVA was employed to assess the difference in volume of grafts at passage one and four, and after postoperative periods of three and eight weeks (FIG. 21). Graft volume, determined with fibronectin immunostaining, did not differ as a function of the number of passages in culture prior to implantation (one versus four). It was also evident that cultured autologous fibroblasts implanted into the brain did not create tumors, nor did these grafts atrophy and die. In fact, the size of the grafts did not differ significantly after three and eight weeks survival in vivo.

Cell Density

Figure 22:
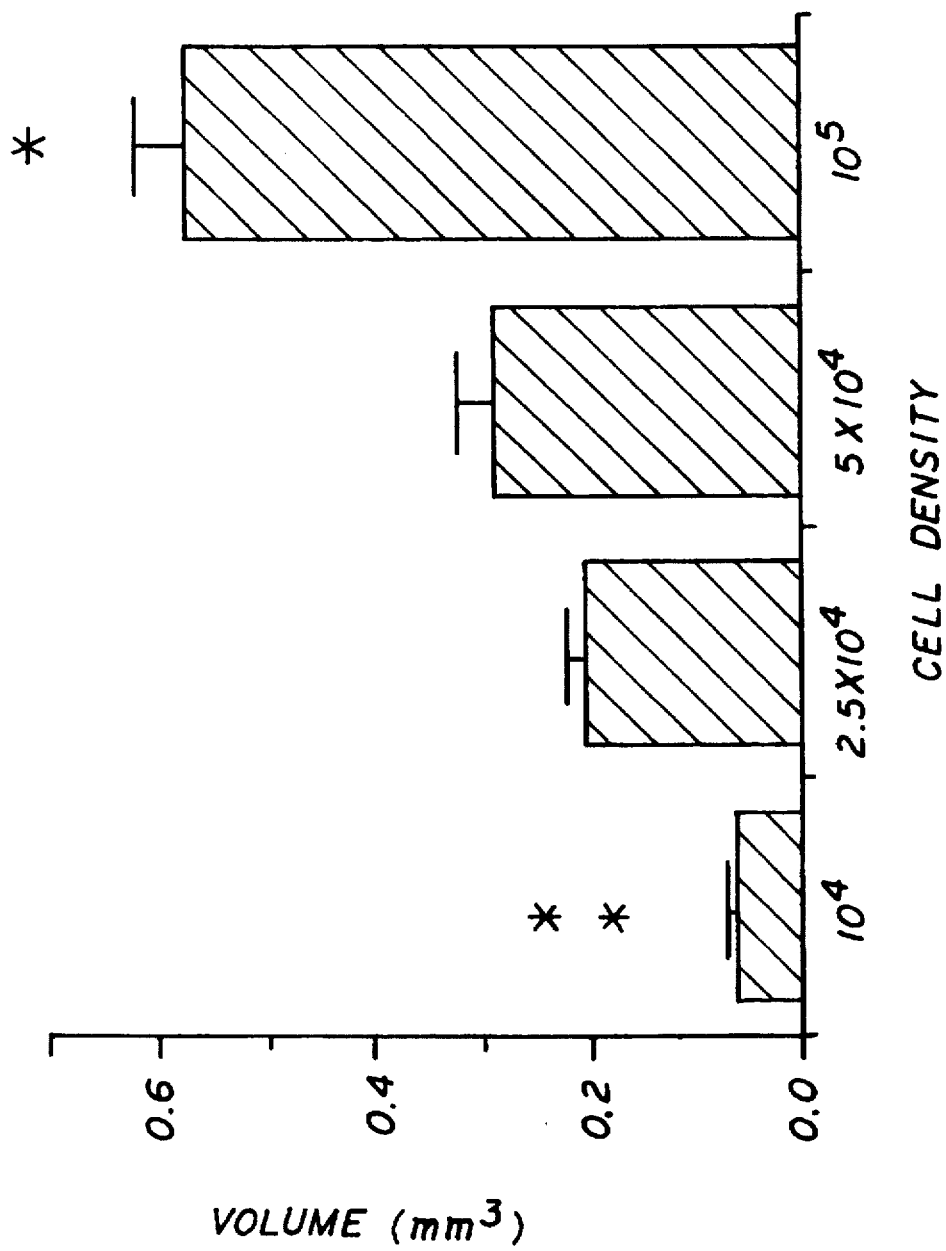
FIG. 22 are histograms showing the volume ($mm^3$) of autologous fibroblast grafts resulting from implantations of $10^4$, $2.5 \times 10^4$, $5 \times 10^4$ and $10^5$ cells/$\mu$l as described in Example IV, infra.

Another parameter of graft size examined was the density of cells implanted into the striatum. Four densities ($10^4$, $2.5 \times 10^4$ and $10^5$ cells/µl) were assessed, and the volume of the grafts was determined immunohistochemically for fibronectin. The fibroblasts for intracerebral grafting were harvested following the fourth passage in culture and the animals were sacrificed after a post-operative period of eight weeks. With a 2-factor ANOVA, significant differences in graft volume were observed among the fours groups; suspension grafts of high cell density produced larger grafts than grafts of low cell density (FIG. 22). Thus, a relationship between the volume of the graft and the density of cells implanted was evident.

Histology

Figure 24A:
FIG. 24a–FIG. 24f are photographs of primary fibroblast grafts (G) in the striatum stained with cresyl violet (FIG. 24a, FIG. 24b) and stained immunohistochemically for GFAP (FIG. 24c, FIG. 24d) and OX-42 (FIG. 24e, FIG. 24f), at three weeks (FIG. 24a, FIG. 24c, FIG. 24e) and eight weeks (FIG. 24b, FIG. 24d, FIG. 24f) as described in Example IV, infra (Mag.=120X).
Figure 24B:
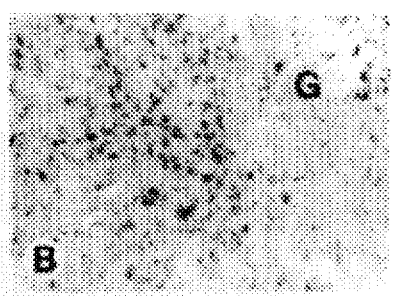
Figure 24C:
Figure 24D:
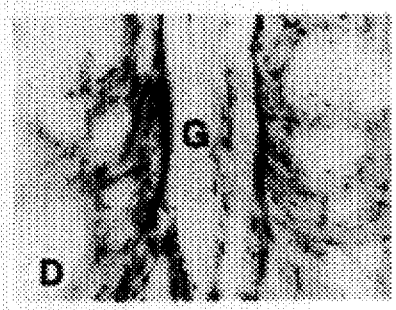
Figure 24E:
Figure 24F:
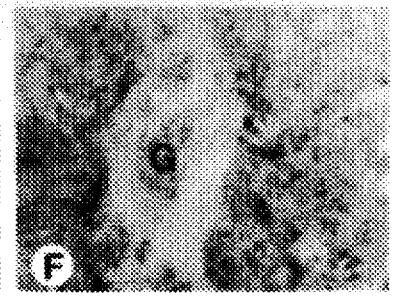

Immunostaining for fibronectin, a group of structurally related glycoproteins, revealed the size and limits of the intracerebral grafts. At three weeks, the grafts possessed several small extensions into the neuropil of the striatum, whereas those examined at eight weeks appeared more compact and possessed fewer projections (FIG. 23). Fibronectin immunostaining, however, did not allow for the resolution of individual fibroblasts or other cellular components in or near grafts. From cresyl violet staining, elongated nuclei that are typical of fibroblasts were observed in the grafts (FIGS. 24a, b). Blood vessels were also found through the grafts, and debris-filled cells were located predominantly at the center. Astrocytes stained immunohistochemically for GFAP were prominent in the host striatum surrounding the grafts at three weeks, yet immunostaining within the grafts was sparse. GFAP-immunoreactive processes were observed both within and around the grafts at eight weeks (FIGS. 24c, d). Reactive microglia and/or macrophages visualized with MRC OX-42 immunoreactivity surrounded the grafts at three weeks, but were less prevalent and more variable at eight weeks (FIGS. 24e, f).

Ultrastructure

The structural organization of primary fibroblast autografts at eight weeks after implantation was examined at the electron microscope level. The most striking feature of the grafts was the abundance of fibroblasts and collagen. The fibroblasts possessed an elliptical nucleus that was often condensed; a distinct nucleolus was rarely observed (FIG. 25a, b). The cytoplasm of these cells contained rough endoplasmic reticulum, elongated mitochondria, and secretory vesicles, a paucity of Golgi apparatus was evident. Slender fibroblast processes found throughout the grafts also contained rough endoplasmic reticulum and secretory vesicles (FIG. 25c). Dense bundles of collagen surrounded fibroblast cell bodies and their processes. Neither fibroblasts nor collagen were observed in the striatal neuropil. Other cellular components of the grafts included reactive astrocytic processes and phagocytes. Hypertrophied astrocytic extensions were observed in the extracellular matrix of the grafts passing among collagen bundles; the cell bodies of astrocytes were not found within the fibroblast implants (FIG. 26a). The morphology of phagocytic cells of the grafts was variable; the cytoplasm possessed few organelles and was usually filled with electron-dense debris (FIG. 26b). The nucleus of these cells was irregular and chromatin was often clumped beneath the nuclear envelope. A small number of lymphocytes was also observed around and within the grafts at eight weeks after grafting.

Another prominent feature of the primary fibroblast grafts was the presence of continuous-type capillaries; the endothelial lining of the lumen was uninterrupted, and fenestrations were not evident (FIG. 27a). A basal lamina enveloping these vessels was present. Endothelial cells surrounding the lumen possessed few organelles and a nucleus with condensed chromatin under the nuclear envelope. Numerous vesicular invaginations of both the luminal and abluminal plasma membranes of endothelial cells were evident, as well as clear vesicles within the cytoplasm (FIG. 27b). Intercellular junctions were observed at sites of close apposition between endothelial cells (FIG. 27c). Collagen and/or reactive astrocytes were closely associated with the graft capillaries. These reactive astrocytic profiles adjacent to capillaries were filled with filaments, and did not resemble those endfeet astrocytes that envelope normal cerebral vessels (FIG. 27d). Certain capillaries also possessed several reactive astrocytic processes completely surrounding the vessel; the perivascular space between the endothelium and astrocytes usually possessed collagen and was variable in size.

Primary skin fibroblasts cease to proliferate once they are confluent, thereby exhibiting contact inhibition in vitro. As shown herein, following implantation in the striatum, the graft volume of primary skin fibroblast grafts remains constant between three and eight weeks; thus a propensity for either tumor formation or death is not a characteristic of primary skin fibroblasts in vivo. Features of primary fibroblasts in culture, e.g., contact inhibition, may reflect the growth and survival of the grafts following implantation into the CNS. Data from the present investigation also reveal that the density of the cell suspension is another factor that determines the size of primary skin fibroblast grafts: cell suspensions of a high density produce larger grafts than those of a low density. The number of cell passages in culture prior to implantation and the post-operative period, on the other hand, do not appear to be parameters that influence graft size.

Another advantage of employing primary skin fibroblasts for grafting is that the likelihood of immune rejection of autologous cells is lessened. An immunological response against allografts, especially 208F fibroblasts, may be one factor that leads to cell death following implantation. In this example, fibroblasts from skin biopsies were grown under cultured conditions and implanted into the donor's striatum. Following stereotaxic placements of fibroblasts in the striatum, the blood-brain barrier is damaged, and several cell populations, including lymphocytes, enter the wound area. Despite the presence of lymphocytes near the graft, the immunological reaction against these autologous cells appears to be minimal. Therefore, the histocompatibility of primary fibroblasts may also enhance graft survival in vivo.

This example provides direct evidence for the sustained survival of primary skin fibroblasts grafted in the adult rat CNS. Ultrastructural analysis reveals that these grafts are composed primarily of fibroblasts and collagen, in addition to possessing other cellular populations (e.g., phagocytes, lymphocytes). It is noteworthy that the morphological features of grafted fibroblasts after eight weeks in the striatum are similar to those normally found in the skin, including an elliptical nucleus with condensed chromatin, elongated mitochondria, and a few Golgi apparatus. The presence of rough endoplasmic reticulum and secretory vesicles within the cytoplasm and processes of the fibroblasts strongly indicates active protein production. Further, the abundance of fibronectin immunostaining and collagen provide evidence for the synthesis of two distinct cellular products of fibroblasts within the grafts. Despite collagen production, the size of the grafts remains relatively constant between three and eight weeks after implantation. One plausible explanation for this observation is that cultured fibroblasts are known to produce collagenase (Millis et al., *Exp. Geront.* 24:559–575 (1989)); fibroblasts may therefore regulate the levels of collagen production and degradation within the grafts. From the light and electron microscopic date, it is concluded that primary skin-fibroblasts grafted in the rat striatum maintain their morphological characteristics, produce and secrete collagen and fibronectin, and survive up to eight weeks. Although the total number of surviving cells or the percentage of cells that survive was not determined, a higher percentage of cells within the grafts at eight weeks following implantation is unlikely. Trophic substances such as fibroblast growth factor (FGF) may augment the survival of primary skin fibroblasts grafted into the rat CNS.

Host-to-graft Interactions

An important consideration of cultured autologous skin fibroblast implants is whether these grafts are integrated into the host nervous system. After implantation of cultured primary skin fibroblasts into the rat striatum three prominent cellular events were observed that constitute dynamic interactions between the host and graft. These may be temporal events and occur as follows: 1) activation and migration of microglia and/or macrophages to the graft; 2) neovascularization; and 3) hypertrophy and infiltration of astrocytic processes into the graft. Data from prior investigations of the initial response to the CNS to penetrating wounds that compromise the blood-brain barrier may be extrapolated to the model system described herein. It has been shown that mononuclear phagocytes are the first cells that respond to wounds within the CNS (Imamoto and Leblond, *J. Comp. Neurol.* 174:255–280 (1977)). Macrophages, microglia and granulocytes may be shown immunohistochemically using the MRC OX-42 antibody which recognizes the rat homologue of complement receptor type 3 of mouse and man (Robinson et al., *Immunol.* 57:239–247 (1986)). The results presented herein indicate that cells possessing OX-42 immunoreactivity are present at the periphery of the graft at three and eight weeks after implantation. Electron microscopic examination of tissue at eight weeks confirms the presence of phagocytic cells in the interface zone between the graft and the intact neuropil, and these cells may be those stained immunohistochemically for OX-42. Phagocytic cells were also present throughout the graft, yet OX-42 immunoreactivity was not evident within the graft itself. Therefore, non-immunoreactive phagocytes may constitute either another cellular population or macrophages, microglia and granulocytes that lack the complement receptor. The cells migrate to the wound site and infiltrate the graft.

An important host-to-graft cellular interaction that may determine the fate of fibroblasts following implantation is the establishment of a vascular system within the grafts. The establishment of a vascular system within the grafts may depend in part on angiogenic substances such as fibroblast growth factor. Production and release of fibroblast growth factor by grafted skin fibroblasts may promote angiogenesis. Neovascularization within the grafts may also be enhanced by reactive microglia and macrophages which produce and release interleukin-1.

Implants of avascular tissue into the CNS are completely dependent on the surrounding host tissue for the formation of new capillaries. Capillaries within the skin fibroblast grafts are composed of non-fenestrated endothelial cells that form a continuous lumen and possess intercellular junctions (not necessarily tight junctions) at sites of cellular apposition; these vessels are reminiscent of those found in both connective and nervous tissues; however several features distinguish graft capillaries from those in the adjacent striatum. First, endothelial cells within the grafts possess numerous intracellular vesicles and vesicular invaginations on the plasma membranes, whereas neural capillaries have few endothelial invaginations on the luminal and abluminal sides. Second, reactive astrocytes associated with graft vessels are unlike endfeet astrocytes surrounding neural capillaries, in that the former profiles are filled with filaments, hypertrophied and do not always envelope the graft capillaries. Third, the perivascular space between endothelium and reactive astrocytic profiles of graft capillaries is variable and often contains intervening elements, including collagen; neural vessels possess a narrow perivascular space containing basal lamina.

The third interaction observed between the striatal neuropil and grafts of primary fibroblasts was the responsiveness of astrocytes to the autografts. Intracerebral grafting usually results in a glial reaction that involves the migration of reactive astrocytic processes and/or the formation of a glia limitans. These studies show that GFAP-immunoreactive astrocyte perkarya are abundant around the graft at three and eight weeks, and immunoreactive processes are found within the graft at eight weeks. Ultrastructural data corroborate the latter observation, revealing that reactive astrocytic processes are present throughout the graft, but astrocytic cell bodies remain outside the graft itself. Astrocytic responses observed in the present study and others may be due, in part, to the presence of reactive microglia and macrophages near the wound site; these cells are known to produce and release interleukin-1 in vitro.

These results provide direct evidence for the survival of cultured primary skin fibroblasts grafted into the CNS of adult rats. These grafts do not form tumors within the striatum, and possible immunological responses appear minimal due to the autologous nature of these cells. Moreover, fibroblast grafts are structurally and functionally integrated into the host brain. Dynamic cellular interactions between the host striatum and fibroblast implants indicating the structural and functional integration of the fibroblasts into the adult rat CNS include the establishment of a vascular system within the graft, the migration of phagocytic cells, and the hypertrophy and infiltration into the grafts of reactive astrocytic processes. Collectively, these features indicate that primary skin fibroblasts are suitable donor cell candidates for cerebral grafting, and therefore may be employed as genetically modified cells for gene therapy in diseased or damaged CNS.

EXAMPLE V

Grafting of Primary Fibroblasts Producing L-dopa

This example examines the long term survival of genetically modified primary fibroblasts following grafting into the brain. Extending the above experiments, the rat TH gene was inserted into primary fibroblasts obtained from a skin biopsy from Fischer rats. The survival of TH-containing primary fibroblasts was then examined for a 2 month period following implantation into the brain of Fischer rats with a prior 6-OHDA lesion of the nigrostriatal pathway. In addition, both the presence of the TH transgene and transgene product within the implanted fibroblasts were examined. Finally, prolonged functioning of the genetically modified fibroblasts in vivo was explored through assessment of rotational behavior of the implanted rats every 2 weeks for an 8 week period after grafting.

Preparation of Retroviral Vector

Preparation of the vector used in the present experiments, pLThRNL, was as described above in Example III (see FIGS. 16 and 17).

Fibroblast preparation

Primary fibroblasts were obtained from abdominal skin biopsies of inbred Fischer 344 rats, according to the protocol of Sly and Grubb (in "Methods in Enzymology", Vol. LVIII, Colowick and Kaplan, Eds., Academic Press, New York, pp. 444–450 (1979)). Briefly, rats were anesthetized with a mixture of ketamine, aceptomazine and rompun. The abdomen was shaved and scrubbed thoroughly with alcohol. An area of approximately 1–2 cm$^2$ of skin was removed, rinsed briefly in alcohol and immediately placed in a vial containing sterile DMEM/S. Biopsies were typically transferred to coverslips within 2 hours of collection and grown in DMEM/S for 21 days. Cells were then infected with ecotropic LThRNL or BAG virus (Price et al. Proc,. Natl. Acad. Sci. USA 84:156–160 (1987)) at a multiplicity of infection of 10 in the presence of Polybrene (4 µg/ml). G418-resistant cells were grown to confluency and tested for expression of TH activity by a decarboxylase-coupled assay (Iuvone, J. Neurochem 43:1359–1368 (1984)). A subclone expressing TH activity and TH immunoreactivity in vitro was selected for implantation (FF2/TH). Fibroblasts infected with the BAG virus and expressing β-galactosidase (βGal) activity in vitro were used as control cells (FF2/βGal).

In vitro Biochemical Analyses

The production and release of L-dopa and its metabolites from the infected fibroblasts were assessed after growing cells for 24 hours in DMEM/S supplemented with 100 µm tetrahydrobiopterin, the active cofactor for TH. Conditioned media and cells were collected, adjusted to 0.1M perchloric acid (PCA) and 0.05M EDTA, and centrifuged at 10,000×g for 15 min at 4° C. to remove precipitated material. Samples were analyzed for the presence of catecholamines and catecholamine metabolites as described above in Example II by injecting the PCA extracts onto a coulometric electrode array, gradient liquid chromatography system (CEAS model 55-0650, ESA, Bedfore, Mass.) equipped with 16 electrochemical sensors (Matson et al., Clin. Chem. 30:1477–1488 (1984); Langlais et al., in "Monitoring Neurotransmitter Release During Behavior", Fillenz, et al., eds., Horwood, Chichester, U.K., pp. 224–232 (1986); and Matson et al., Life Sci. 41:905–908 (1987)).

Lesions

The dopaminergic nigrostriatal pathway was unilaterally destroyed with the neurotoxin 6-hydroxydopamine (6-OHDA). The 6-OHDA was dissolved in saline at a concentration of 6 µg/µl and supplemented with 0.1% ascorbic acid to retard oxidation. Female Fischer 344 rats (130–160 g) were anesthetized as above and placed in a stereotaxic frame. A 2 µl injection of 6-OHDA was delivered at 1 µl/min to the left medial forebrain bundle (AP=−4.4 mm, ML=1.1 mm, DV=7.5 mm; according to the atlas of Paxinos and Watson, 1986, "The Rat Brain in Stereotaxic Coordinates", San Diego, Academic Press, (1986)). Following the injection, the syringe was raised 2 mm and allowed to rest another 2 minutes to permit diffusion of the neurotoxin. After a 10 to 14 day recovery period, lesioned rats were tested with apomorphine to assess the extent of the lesion.

To assess the contribution of non-specific striatal damage to changes in rotational behavior the procedures described above in Example III were employed using 6-OHDA lesioned rats subjected to unilateral kainic acid (KA) lesion of the striatum. For this experiment, female Sprague-Dawley rats were anesthetized and lesioned as above with 6-OHDA. Rats which displayed greater than 7 rotations per minute to apomorphine (0.05 mg/kg) were selected for KA lesion. Kainic acid was dissolved in saline at a concentration of 5 µg/µl and injected into the striatum (AP=0.3 mm, ML=2 mm, DV=4 mm) of anesthetized rats at varying doses. Three rats received 1.0 µg, 3 rats received 2.0 µg, 3 rats received 4.0 µg and 2 rats received 5.0 µg. The KA was delivered at a rate of 0.1 µl/min, and the syringe was then slowly lifted 2 mm and left in place for an additional 2 minutes to allow diffusion of the neurotoxin. Rats were administered diazepam (2 mg/kg) immediately following the injection to block seizures which may have resulted from the use of the KA.

Behavioral Testing

The sensitivity of postsynaptic dopamine receptors within the denervated striatum was assessed 7–10 days after 6-OHDA lesion with apomorphine (0.1 mg/kg) administration as described above in Example III. Rats were placed in automated rotometer bowls and total rotations were collected every 10 minutes for a period of 60 minutes. After 2 apomorphine tests, rats which displayed at least 7 rotations/minute for 60 minutes were selected for further study. Rats were tested with apomorphine at least 3 times or until the number of rotations did not change from the previous testing session (Bevan, Neurosci. Letter 35:185–189 (1983); Castro et al., Castro et al., Psychopharm. 85:333–339 (1985)). A period of 4–10 days elapsed between each apomorphine test. After grafting, rats were tested with apomorphine (0.1 mg/kg) every 2 weeks for 8 weeks. Rats with KA lesions were tested with apomorphine (0.05 mg/kg) 2, 4 and 6 weeks after lesioning. For statistical comparisons, the net rotations/minute over a 60-minute time period were determined following grafting and compared to pre-transplantation values using the Least Squares Difference Test.

Grafting

Fibroblasts were prepared for grafting as described above in Example II. Briefly, cells were removed from tissue culture plates with 0.05% trypsin and 1 mM EDTA in Dulbecco's PBS, and suspended in PBS supplemented with MgCl$_2$, CaCl$_2$, 0.1% glucose (complete PBS) and 5% rat serum. Cells were collected by centrifugation, washed twice with complete PBS, and resuspended in complete PBS at a density of 100,000 cells/μl.

Fifteen anesthetized rats received a total of 10 μl of either FF2/TH (N=10) or FF2/μGal (N=5) fibroblasts injected into two sites within the striatum (AP=0.3 mm, ML=2.0 mm, DV=4.5 mm, AP=1.5 mm, ML=2.0 mm, DV=4.5 mm). At each site, 2.5 μl of cells were dispensed, the syringe was raised 1 mm, and an additional 2.5 μl of cells were ejected from the cannula. Cells were delivered at a rate of 1 μl/min. After the most dorsal injection, the syringe was left in place for 2 minutes to allow diffusion of the cells. An additional 5 lesioned rats, which were not grafted, served as untreated controls.

Anatomical Procedures

For in vitro immunohistochemical analyses, infected fibroblasts were fixed onto slides with 4% paraformaldehyde, permeabilized with 0.2% triton X-100 and incubated overnight with a monoclonal antibody to TH (Boehringer Mannehim Biochemicals). The stain was developed by the avidin-biotin method (Vector Laboratories, Elite Kit) with nickel-intensified 3,3'-diethylaminobenzidene (DAB) as the chromagen.

For in vivo analyses, implanted fibroblasts were examined for TH- and fibronectin-immunoreactivity 10 weeks after grafting. Rats were deeply anesthetized and perfused with 4% paraformaldehyde following a brief saline rinse. Brains were removed and placed in the same fixative overnight and then transferred to 30% sucrose until they equilibrated. Frozen sections were cut on a sliding microtome (40 μm) and collected in cryoprotectant for storage until processing. Free floating sections were incubated overnight with either an antibody to the fibroblast marker (Organon Technica), or with the monoclonal antibody to TH. Fibronectin staining was developed with avidin-biotin followed by nickle-intensified DAB. TH labeled sections were incubated with a secondary antibody to the mouse antigen conjugated to rhodamine for fluorescence microscopy (Jackson ImmunoResearch Labs., Inc., Bar Harbor, Md.). Some sections were also processed with antibodies OX-42 (Serotec) or ED-1 (Chemicon) for identification of microglia or monocyte/macrophages. Sections were incubated with the OX-42 antibody for 48 hours and the ED-1 antibody for 24 hours at 4° C. The following day, OX-42 was developed with avidin-biotin with nickle-intensified DAB while the ED-1 labeled sections were incubated with the rhodamine-labeled secondary antibody as described above.

In situ Hybridization

In situ hybridization for TH mRNA was performed using [$^{35}$S] labelled probes as described by Higgins et al., Proc. Natl. Acad. Sci. (USA) 85:1297–1301 (1988), incorporated by reference herein. A 63 base pair template for the TH probe was generated by digestion of the plasmid pSP65 containing a 311 nucleotide cDNA complementary to rat TH mRNA (provided by Dr. Dona Chikaraishi, Tufts Medical School, Boston, Mass.) with Ava II, and transcribed by the SP6 polymerase. Slide-mounted sections were fixed for 1 minute with 4% paraformaldehyde, digested with proteinase K for 5 minutes and then incubated in triethanolamine (0.1M, 0.9% NaCl and 0.1% acetic anhydride) for 10 minutes at room temperature. Sections were subsequently dehydrated in graded alcohols followed by chloroform for 5 minutes at room temperature, returned to 100% ethanol for 2 minutes and then 95% ethanol for another 2 minutes prior to air drying. Dehydrated sections were prehybridized for 1–3 hours in buffer containing 50% formamide, 0.75M NaCl, 20 mM Pipes (pH 6.8), 10 mM EDTA, 250 mM DTT, 5×Denhart's solution (0.02% BSA, 0.02% Ficoll, 0.02% polyvinylpyrrolidone), 0.2% SDS, 10% dextran sulfate, and 500 μg/ml denatured yeast tRNA. Following prehybridization, excess buffer was removed and sections were hybridized at 55° C. for 18 hours with 10–15 ng of labeled probe in a total volume of 75 μl of hybridization buffer. Slides were thoroughly rinsed following the hybridization in solutions containing 0.6M NaCl, 0.06M Na citrate with or without RNase. Following posthybridization rinsing, the sections were air-dried and exposed to X-ray film (Kodak XAR) for 24 hours. The sections were then dipped in Kodak NTB-2 emulsion, exposed for 4 days (at 4° C.), and developed.

Figure 28:
FIG. 28 is a photograph showing the results of in vitro labelling for tyrosine hydroxylase of primary fibroblasts containing a TH transgene as described in Example V, infra (Mag.=25X).

When the bulk population of TH-expressing fibroblasts was stained for TH-immunoreactivity, differing intensities of TH-labeling were observed. To try to isolate a clone that stably expressed high levels of TH, the bulk population of TH-expressing cells was subcloned. The clone selected, FF2/TH, exhibited a relatively homogeneous TH-immunoreactivity (FIG. 28). This clone was similar in gross morphological appearance to uninfected fibroblasts or fibroblasts infected with the vector carrying βGal. Cells were generally elongated with multiple processes extending from the soma. Cells expressing βGal did not display TH-immunoreactivity in vitro.

In Vitro Analyses

Primary fibroblasts infected with vectors carrying genes for TH or βGal (FF2/μGal) were examined for TH activity using a decarboxylase-coupled assay. TH activity was only found in FF2/TH cells, at a level of 1.1±0.4 pmole L-dopa/minute/mg protein. This level of TH within the FF2/TH primary fibroblasts was comparable to that seen previously for immortalized 208F fibroblasts infected with the same LThRNL vector (see Example III above).

Infected fibroblasts were assayed for the production and release of L-dopa and other catecholamines 24 hours after exposure to 100 μM BH$_4$, the natural cofactor for TH. Medium collected from cells containing the TH gene was found to contain 17.2 μg L-dopa/10$^6$ cells. Intracellular quantities of L-dopa, as assessed through analysis of the FF2/TH cell pellet, were 0.2 μg L-dopa/10$^6$ cells. Control FF2/βGal cells did not contain or release L-dopa. There were no detectable metabolites of L-dopa, such as dopamine, 3,4-dihydroxyphenylacetic acid or homovanillic acid, in samples collected from the media or cell pellet of either FF2/TH or FF2/βGal cells.

Behavioral Analyses-fibroblast implanted rats

All 6-OHDA lesioned rats implanted with FF2/TH or FF2/βGal cells were eating and drinking normally within 24 hours of the transplantation surgery and showed stable or slightly increasing body weight during the 2-month post-grafting test period. There was no obvious change in spontaneous behavior of the grafted rats; grooming and locomotor behaviors were comparable to those displayed by the lesioned control rats that were not grafted.

Figure 29A:
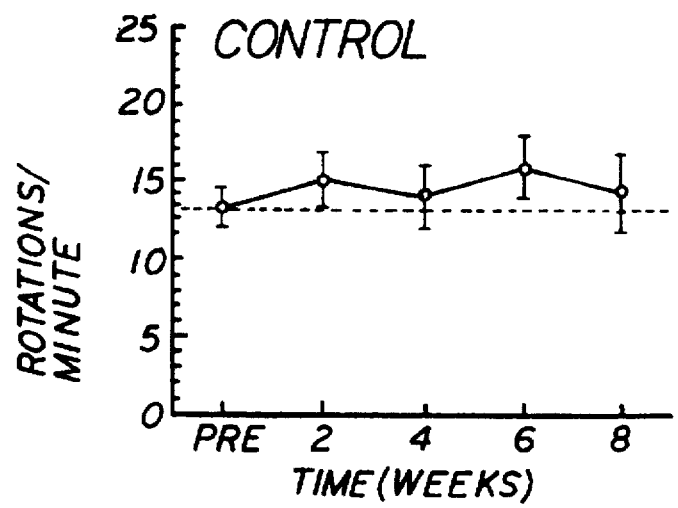
FIG. 29 are graphs showing the results of grafts on apomorphine-induced rotational behavior of 6-OHDA-lesioned rats as described in Example V, infra (Control, top; βGal fibroblast grafts, FF2/βGal, middle; TH fibroblasts, FF2/TH, bottom; PRE=prior to grafting, **=$p<0.01$, *=$p<0.05$).
Figure 29B:
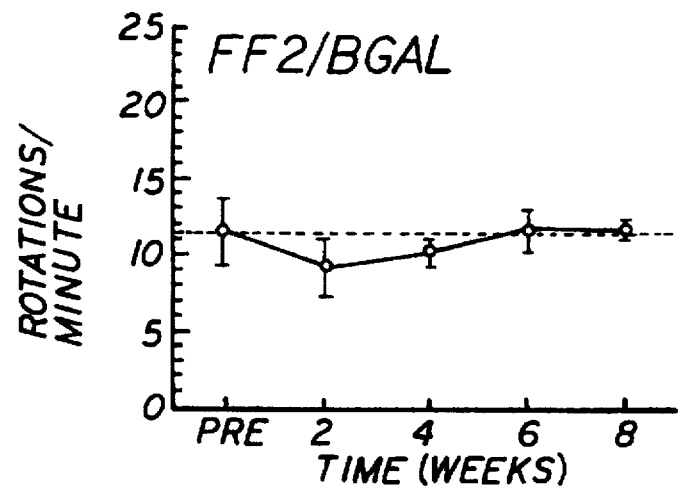
Figure 29C:
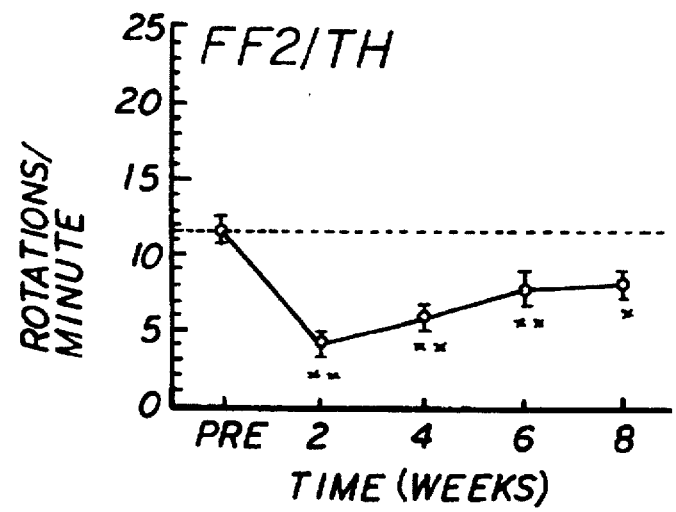

To assess the production and release of L-dopa from the implanted cells in vivo, a behavioral test was conducted. Rats were administered apomorphine, which results in activation of receptors in the dopamine-depleted striatum. This drug-induced stimulation causes the rats to walk in a circular or rotational pattern which can be quantified (Ungerstedt and Arbuthnott, Brain Res. 24:485–493 (1970)). Following grafting, average rotations per minute over a 60 minute period following apomorphine administration were determined for grafted and control non-grafted rats and compared to pretransplantation rotations for statistical analyses. Control animals showed a slightly increased level of rotations following grafting (FIG. 29, control) which was not statistically different from that observed prior to grafting (p>0.05). The apomorphine-induced rotations of rats implanted with βGal-containing cells were also not different from pregrafting rotations through the 2-month post-grafting time period (p>0.05; FIG. 29, FF2/βGal). In contrast, FF2/TH rats displayed a significant decrease in rotational behavior 2 weeks after grafting, which persisted through 8 weeks post-implantation (FIG. 29, FF2/TH). The initial 65% decrease in rotations of FF2/TH rats, from 11.7±3.0 to 4.1±2.9 (mean±standard error of the mean), narrowed to a plateau of approximately 30% below pre-grafting levels between 6 and 8 weeks post-grafting.

Anatomical Analyses

Fibroblast grafts were present within the brains of all of the implanted rats 10 weeks post-implantation. However, grafts from 2 animals were lost during processing. In general, the placement of FF2/TH and FF2/βGal grafts were found to be similar, both extended along comparable rostral-caudal and medio-lateral domains. Typically, however, FF2/TH grafts were larger than FF2/βGal grafts. Within the FF2/TH group, there was no correlation between the size of the grafts and reduction of rotational behavior.

All grafts contained elongated fibroblast-like cells interspersed among an abundance of collagen fibers. In addition to typical fibroblasts, large yellow cells, apparently filled with hemasiderin, were seen within the core of the grafts. As these cells were often filled with debris, sections through the graft were stained with OX-42, and ED-1, markers specific for microglia and monocyte/macrophages. However, while immunoreactive macrophages were found on the periphery of the grafts, the large debris-filled core cells did not label with OX-42 or ED-1.

Figure 30A:
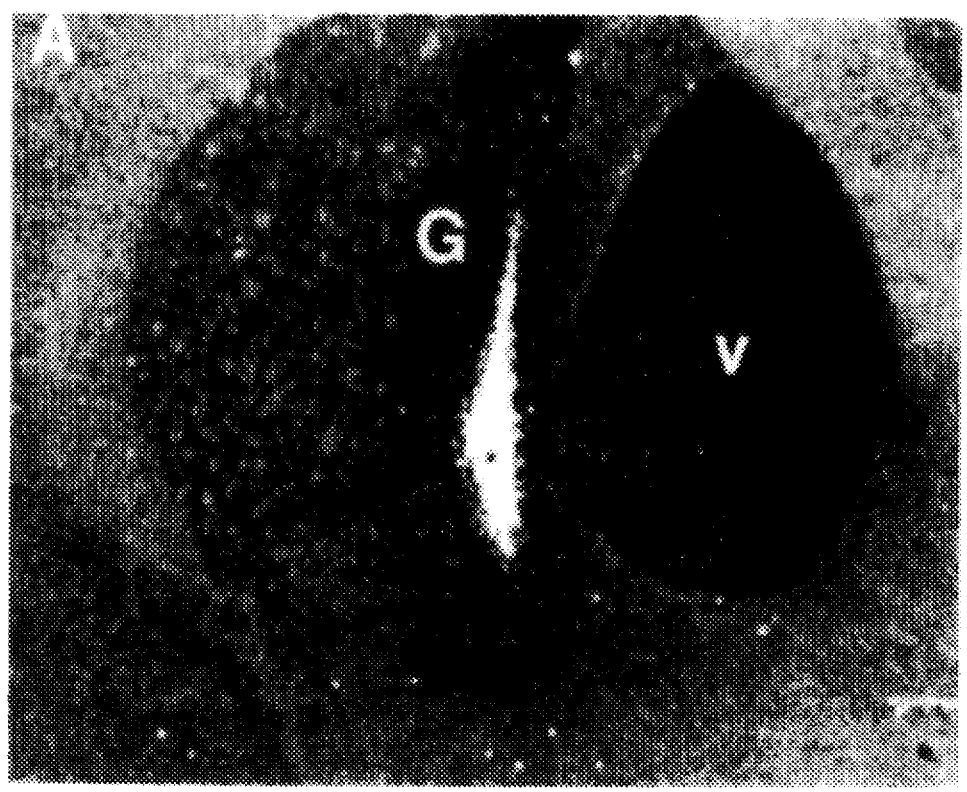
FIG. 30a–FIG. 30b are photomicrographs showing the results of in situ hybridization to TH primary fibroblasts grafted into the striatum of rats as described in Example V, infra (FIG. 30a graft of FF2/TH cells; 30b graft of FF2/βGal cells (control); G=graft; V=ventricle)).
Figure 30B:
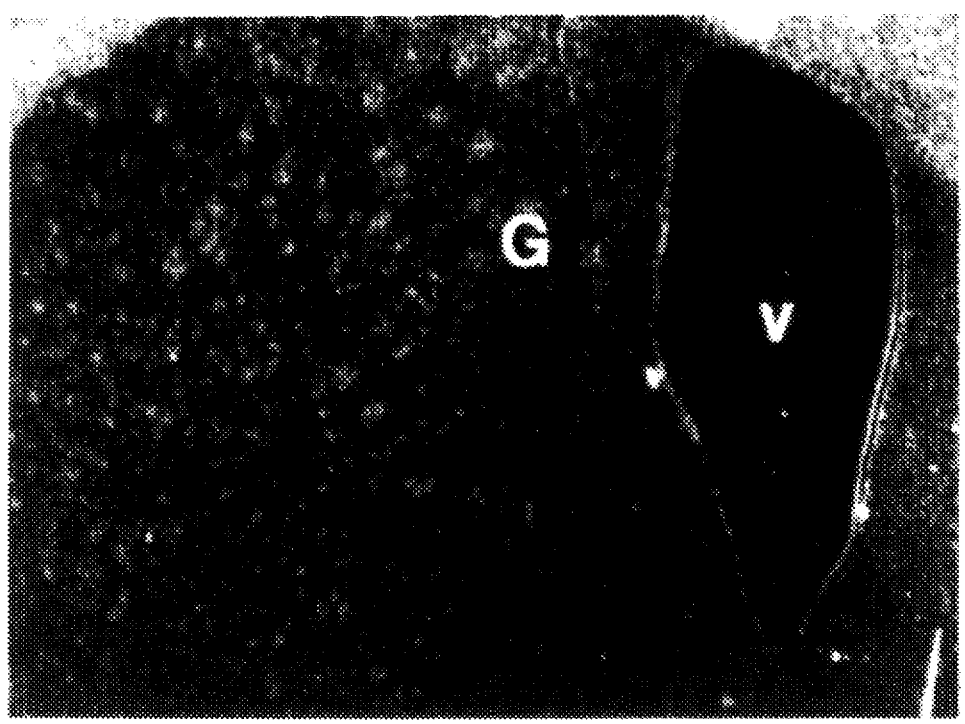

To assess whether the TH transgene continued to be expressed within the implanted fibroblasts, sections through the graft were processed for in situ hybridization to TH mRNA. Positive hybridization for TH MRNA was only found to be present over cells in the grafts containing FF2/TH fibroblasts (FIG. 30a). In both FF2/TH and FF2/βGal grafts (FIG. 30b, control), areas of the graft which were predominantly composed of collagen fibers showed a grain density which was significantly less than the surrounding background. The morphology of the cells displaying increased grain density was varied, with many exhibiting the elongated shape characteristic of fibroblasts (FIG. 31c). However, some cells with positive TH hybridization were observed to be large and rounded, often filled with hemasiderin and granulated particles. There were no cells present within βGal grafts which displayed specific hybridization to TH MRNA (FIG. 31d).

To determine if the transgene products were synthesized and present within the fibroblasts, grafts were examined for TH-immunoreactivity and βGal histochemistry. Within the FF2/TH grafts, TH-labeled cells with the elongated shape typical of fibroblasts were observed to be scattered among the collagen fibers (FIG. 32a). Autofluorescent material was present within the grafts but was readily discernible form the rhodamine-specific labeling (emission 582 nm) by the shape of the material and its broad fluorescence through 528 nm (FIG. 32a and 32b, asterisks). There was a heterogeneity in the intensity of the TH labeling, as observed in vitro. Autofluorescent cells, but no discernible TH-immunoreactive fibroblasts, were present within FF2/βGal grafts.

Sections stained for βGal histochemistry revealed diffuse cytoplasmic labelling of cells within the FF2/βGal grafts (FIG. 31a). FF2/βGal staining was observed in some of the large rounded cells within the core of the graft and in cells with the elongated shape typical of fibroblasts (FIG. 31b). βGal reactivity within FF2/TH grafts was confined to a small number of rounded cells with the blue granular staining previously described for endogenous macrophages (Shimohama et al., *Mol. Brain Res.* 5:271–278 (1989)).

These results confirm that primary fibroblasts obtained from a skin biopsy can be grown and genetically manipulated in culture to express a transgene. Evidence that the inserted TH gene product was synthesized and biologically active in vitro was provided by histological and biochemical measures. Cells containing the TH gene showed positive immunoreactivity for TH in vitro. And, in the presence of the pterin cofactor for TH, tyrosine present in the cell culture medium was converted to L-dopa through TH enzymatic activity.

The fundamental advantage of primary fibroblast cells for genetic manipulation is the potential for using these altered cells as donor material for autotransplantation and thus minimizing problems with immunological responses from the host. The primary fibroblasts used in the present study were not implanted within the same donor animal; rather, genetically inbred Fischer 344 rats were used as both donors of the fibroblasts and recipients of the altered cells. This isograft approach was selected as it simplified the maintenance of the cells in vitro, while still providing conditions which approximated those of autotransplantation. Following iso-implantation into the brain of rats with 6-OHDA lesions, it was found that primary fibroblasts containing genes for either βGal or TH survived for at least 10 weeks. Further, implanted fibroblasts continued to express the βGal and TH transgenes through the 2-monthly post-grafting survival period. Evidence that the TH-containing cells continued to produce and secrete L-dopa in vivo was provided by a behavioral measure: a significant decrease in rotational asymmetry was observed only for those rats with grafts of TH-containing fibroblasts.

Fibroblast survival within the brain

When examined at 2 months, FF2/TH grafts were observed to be larger than FF2/βGal grafts. The reason for this difference is not known. There are many factors which may contribute to the survival of primary fibroblasts within the brain, including the state of the cell prior to implantation and the time that cells remain in culture prior to grafting. The FF2/TH cells used in the present study were a subclone of a TH-expressing fibroblast, while the FF2/βGal cells were a bulk population of βGal-expressing fibroblasts. The subcloning procedure which caused the FF2/TH cells to undergo more doublings than the bulk FF2/βGal cells may have influenced the ability of the fibroblasts to survive in vivo. Through early passages there does not appear to be a correlation between the size of a fibroblast graft and the number of cell divisions in culture prior to grafting as revealed in Example IV. Fibroblasts carried longer in culture, as were the FF2 cells used in the present study, have been seen to survive well within the brain over 6 months with essentially no change in graft size or composition after 4–6 weeks.

Additional factors which may affect fibroblast survival within the brain include the accessibility of implanted cells to an adequate nutrient supply. Vascular processes were evident within FF2/TH grafts and less obvious within the smaller FF2/βGal grafts. The time course for the development of a vascular supply to the grafts may also affect the long-term survival of the fibroblasts. Grafts containing other cell types, such as fetal neurons, have been found to be dependent on rapid vascularization for survival post-implantation (Stenevi et al., *Brain Res.* 114:1–20 (1976)). Whether blood vessels within the grafts establish a barrier to macromolecules, as typical of brain vasculature, or remain leaky, as may be typical of grafts of peripheral origin (Rosenstein and Brightman, *J. Comp. Neurol* 250:339–351 (1986), may also influence the survival of implanted fibroblasts. A rupture in brain vasculature following grafting has been suggested to provide a "window" into the brain for factors which are not typically available to cells within the brain (Rosenstein and Brightman, supra; Sandberg et al., *Exp. Neurol.* 102:149–152 (1988)). Such factors may be beneficial to cells which have been maintained in a serum-enriched culture medium (Gibbs et al., *Brain Res.* 382:409–415 (1986); Ezerman, *Brain Res.* 469:253–261 (1988)). Conversely a vascular portal may place the grafted cells in a position vulnerable to attack from circulating macrophages.

Composition of the graft

Although implanted cells were found to survive through a 2-month period, all grafts were characterized by a core of large, hemasiderin and debris-filled cells which initially suggested a sustained macrophage infiltration. However, while a limited number of ED-1-positive macrophages were observed scattered around the periphery of some grafts, cells within the core of the graft were not immunoreactive with either ED-1 or OX-42, markers which are specific for microglia and monocytes/macrophages. Further, when grafts were stained for βGal, an enzyme which had previously been shown to exhibit a distinct granular appearance within endogenous macrophages (Shimohama et al., supra, 1989), none of the large core cells within either the FF2/TH or FF2/βGal grafts displayed granular staining. However, some of the core cells within the FF2/βGal grafts did display a diffuse and cytoplasmic βGal reactivity, labelling which has previously been shown to be characteristic of immortalized fibroblasts which contain the βGal transgene (Shimohama et al., supra, 1989). Finally, some of the large core cells within the FF2/TH grafts displayed positive hybridization to TH MRNA. These observations strongly suggested that the phagocytic cells within the core of the fibroblast grafts were derived from the original donor cell suspension.

Mechanisms of Graft Function

The possibility that the fibroblast implantation produced an artifactual "recovery" in behavior due to damage of striatal tissue and an associated loss of postsynaptic dopamine receptors was considered. However, there were two pieces of evidence which suggested that this was unlikely. First, FF2/βGal rats implanted with the same volume and number of cells as the FF2/TH rats did not show a significant change in rotational behavior following grafting. Second, destruction of intrinsic striatal neurons and receptors with kainic acid resulted in a post-damage rotational profile which was distinctly different from that observed for FF2/TH rats. Rats with the smallest KA lesions, or those which affected a much smaller area than that encompassed by the grafts, showed a steady decrease in rotations from 19% at 2 weeks to more than 50% by 6 weeks post-damage, consistent with the known degenerative changes which occur within the striatum following KA administration (Coyle and Schwarcz, *Nature* 263:244–246 (1976)). In contrast, the most pronounced decrease in rotations observed for FF2/TH grafted rats occurred 2 weeks after grafting (65%), followed by a gradual increase to a stable, but higher, number of rotations between 6–8 weeks (30% below baseline). This apparent decrease in graft efficacy between 2 and 8 weeks may result from several different mechanisms. First, some of the grafted cells may be lost during the initial weeks after grafting. In other studies, fibroblast grafts have been found to shrink in size within the brain through 3 weeks following implantation. After this time, a stable graft size is attained which persists for at least 6 months. A second reason for reduced graft efficacy at long post-grafting intervals may involve an alteration in the metabolic properties of the fibroblasts. Established fibroblasts may assume properties of quiescent cells with reduced metabolic activity (Dean et al., *J. Biol. Chem.* 261:9161–9166 (1986); Rao and Church *Exp. Cell Res.* 178:449–456 (1988)), and decreased production of L-dopa. Finally, graft effectiveness may be compromised by genetic events such as deletion or rearrangement of the TH cDNA inserted in the fibroblasts, or epigenetic shut-off of transcription from the LTR promoter driving transcription of the TH cDNA. Such occurrences have been documented in other retroviral vectors (Xu et al., supra, 1989).

One final possibility which could account for a reduction in apomorphine rotations of the FF2/TH-implanted rats is that the grafts may have disrupted cortico-striatal interactions through non-specific damage to cortical tissues. Such damage is reported to reduce rotational behavior of 6-OHDA-lesioned rats (Freed and Canon-Spoor, *Behav. Brain Res.* 32:279–288 (1989)). However, in our previous work with immortalized Rat-1 fibroblasts which exhibited uncontrolled growth within the brain, extensive damage restricted to cortical tissues was not associated with a drop in apomorphine-induced rotational behavior. As the grafts examined in the present study exhibited much more limited graft extension into cortical tissue than was seen for Rat-1 grafts, it seems unlikely that the decreased rotations of FF2/TH rats reflected non-specific damage to cortico-striatal pathways.

Currently, L-dopa is the most effective treatment of the symptoms of Parkinson's Disease (PD). However, prolonged systemic administration of L-dopa results in undesired side effects, such as dyskinesias and an "on-off" phenomena (Marsden and Parks, *Lancet* 7:292–296 (1976)). It has been suggested that some of these problems result from fluctuating levels of L-dopa in the plasma following oral ingestion of L-dopa, and may be alleviated by continuous infusion of L-dopa (Nutt et al., *New Eng. J. Med.* 310:483–488 (1984); Quinn et al., *Neurology* 34:1131–1136 (1984)). Intracerebral grafts of cells genetically modified to produce L-dopa or dopamine may provide an alternative for controlling the symptoms of PD, and minimizing untoward side effects of extended L-dopa administration, by providing a continuous, local infusion of dopamine directly to appropriate target areas within the brain.

These results demonstrate that primary fibroblasts genetically modified to express a transgene provide viable donor cells for intracerebral implantation and a useful strategy for the treatment of human neurological disease such as PD.

EXAMPLE VI

Ability of Aged Fibroblasts to Serve as Donor Cells

This example demonstrates that aged human fibroblasts may be useful as donor cells for intracerebral grafting.

Retroviral Construct for Human Nerve Growth Factor ((NGF)

A molony murine leukemia virus vector (MOMLV) containing the human NGF cDNA (obtained from Syntex Research, Palo Alto, Calif.), pLhNRNL was used. This vector was prepared by inserting the NGF cDNA into plasmid pLChRNL (see Example VII, FIG. 34) in place of the dChAT gene. The 5' long terminal repeat (LTR) drives the expression of the human NGF (hNGF) cDNA. Internal Rous sarcoma virus LTR promoter drives the expression of the selectable bacterial neomycin resistant gene (neo$^R$)).

Production of Viral Stock

Production of infectious virus stock was accomplished by first transfecting the amphotropic cell line PA317 as described by Miller and Buttimore, *Mol. Cell. Biol.* 6:2895–2902 (1986) (provided by Dr. Miller, Fred Hutchinson Cancer Research Center, Seattle, Wash.) with the plasmid DNA by calcium phosphate co-precipitation. Conditioned media from these cells were collected, filtered and used to infect ecotropic helper cell line psi ($\psi$)2 as described by Mann et al. *Cell* 33:153–159 (1983). The conditioned media from these cells were then used to infect amphotropic helper cell PA317. Producer cells from this line were selected for their expression of the neo$^R$ gene by growing the cells in culture medium containing 400 µg/ml of the neomycin analog G418 ((Gibco/BRL, Gaithersburg, Md.). Virus from the PA317 clones, producing the highest titer (approximately 4×10$^4$ c.f.u./ml) were used to infect various cell lines as described below.

Infection of Cells

Primary fibroblasts, obtained from skin biopsy and established as cell lines, were infected with amphotropic retrovirus. Young rat (approximately 3 months) primary fibroblasts were infected with ecotropic virus expressing mouse NGF or amphotropic virus expressing human NGF. Primary skin fibroblasts from aged humans (male 66 years of age with Alzheimer's and male 69 years of age without Alzheimer's) were obtained by skin biopsy from Dr. R. Katzman, University of California, San Diego, Calif. Young (neonatal) human skin fibroblasts were obtained from the Core Tissue Culture Facility, University of California, San Diego, Calif. Rhesus monkey skin fibroblasts (10 year old male and 11 year old female) were obtained by skin biopsy from the Primate Center, University of California, Davis, Calif.

Fibroblasts, grown to 70 to 80% confluency, were incubated overnight with 10 ml of medium containing the retroviruses and 4 µg/ml of polybrene. The infection was performed for 3 days in a row. Subsequently, the medium was aspirated and replaced with fresh medium containing 400 µg/ml of G418. After infection, the cells were continually maintained in G418 supplemented culture medium.

Assay of NGF Activity

Figure 33:
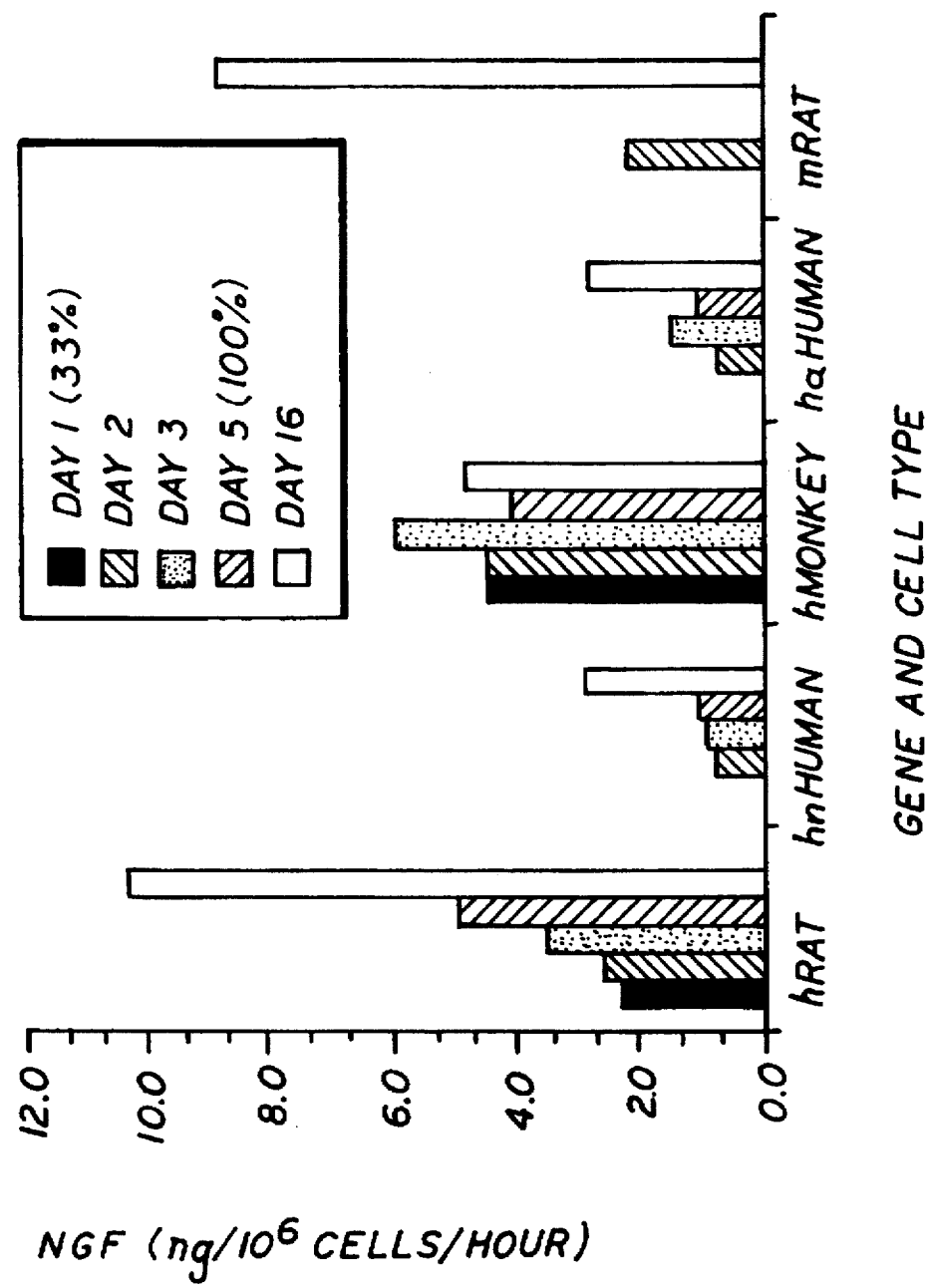
FIG. 33 is a graph depicting the secretion of human NGF from genes and cell types as indicated, as described in Example VI, infra.

NGF production and secretion by the infected fibroblasts were assayed by a two site ELISA assay using anti-β NGF antibody (Boehringer-Mannheim, Germany) as described above in Example II. NGF activity was measured in the medium on the days indicated in FIG. 33. FIG. 33 shows the amount of NGF secreted at different confluency from fibroblasts of different origin expressing either human NGF (hNGF) or mouse NGF (rat fibroblasts). In all cases the production of NGF increased or at least remained constant (for monkey cells) during confluency. There was almost no difference in production of NGF by young or aged human fibroblasts during log phase or confluency.

These results demonstrate that nonhuman primate (e.g. monkeys) models of human disease can be used to test the efficacy of grafting genetically modified transgenes. In addition, these results show that aged human fibroblasts may be successfully infected with vectors carrying transgenes, and suggest that aged human fibroblasts may be used as donor cells.

EXAMPLE VII

Regulation of the Release of Transgene Product from Donor Cells

This example illustrates the regulation of secretion of a transgene product, acetylcholine (ACh), from transfected cells using choline.

Cell Culture

Rat-1 fibroblasts were grown in DMEM supplemented with 0.1% glutamine and 10% FBS. Cultures were incubated in a 10% $CO_2$ atmosphere at 37° C.

Retroviral Construct

Figure 34:
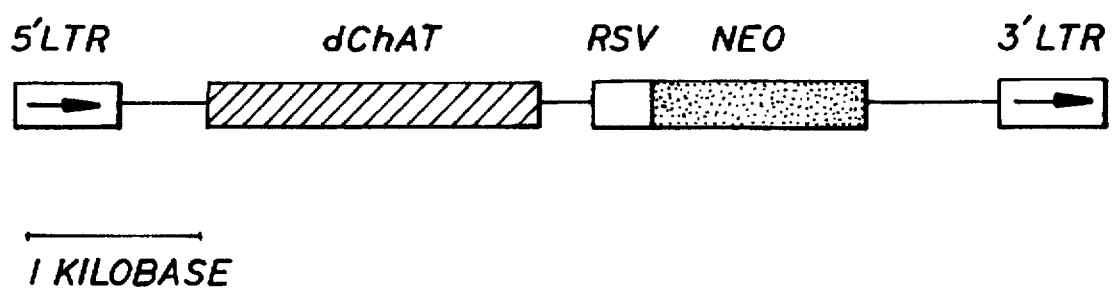
FIG. 34 is a schematic representation of the pLChRNL vector as described in Example VII, infra.

A Moloney murine leukemia viral vector (MOMLV) containing the *Drosophila* ChAT (dChAT) cDNA (obtained from Dr. P. Salvaterra, Duarte, Calif.), pLChRNL, was constructed as shown in FIG. 34. A 2519 basepair (bp) HindIII/EcoRI fragment, containing the dChAT cDNA from the plasmid pCha-2 (Itoh et al., *Proc. Natl. Acad. Sci. USA* 83:4081–4085 (1986)), a 377 bp EcoRI/BamHI fragment from pBR322, and a 6500 bp fragment of the retroviral construct PLLRNL (Xu et al, *Virology* 171:331–341 (1989)) were ligated by standard procedures (see Sambrook et al., In: Molecular Cloning, A Laboratory Manual, ed. C. Nolan, Cold Spring Harbor Laboratory Press, Cold Spring Harbor, N.Y. (1989)). A 5' LTR within pLLRNL drives the expression of the dChAT gene. Similarly, an internal RSV promoter drives the expression of the selectable bacterial neomycin resistance gene (neo$^R$).

Infection

Production of infectious vector stock was accomplished by first transfecting the amphotropic helper cell line PA317 (Miller and Buttimore, *Mol. Cell. Biol.* 6:2895–2902 (1986)) with the plasmid DNA. Medium conditioned by these cells was collected, filtered and used to infect the ecotropic helper cell line Ψ-2 (Mann et al., *Cell* 33:153–159 (1983)). Producer cells form this line were selected for their expression of neo$^R$ by growing the cells in culture medium containing 400 µg/ml of the neomycin analog G418 (Gibco). The two G418-resistant colonies, from a total of 16, that expressed the highest level of ChAT activity and the highest titer of virus (approximately 10$^4$ C. f.u./ml) were used to infect Rat-1 cells.

Rat-1 fibroblasts, grown to confluence on a 10 cm tissue culture plate, were split 1:5 and allowed to grow for one day before they were incubated with 5 ml of medium containing the retroviruses and 4 µg/ml of polybrene. Cells were incubated overnight in this medium. Subsequently, the medium was aspirated and replaced with fresh medium containing 400 µg/ml of G418. After infection, the cells were continually maintained in G418 supplemented culture medium.

Determination of ChAT Activity

The method used to determine ChAT activity is a modification of the procedure described by Fonnum, in the *J. Neurochem.* 24:407–409 (1975), incorporated by reference herein. Fibroblasts were seeded into 35 mm tissue culture dishes and allowed to reach 70–80% confluence. Cells were subsequently washed with PBS and collected by scraping the cells in 0.5 ml homogenization buffer (0.87 mM EDTA solution containing 0.1% Triton X-100). The resuspension was transferred into a 1.5 ml Eppendorf tube and sonicated (3×, for 10 sec). Ten microliters of the sonicated homogenate was placed into another Eppendorf tube. Ten microliters of radioactive solution (0.2 mM $^{14}$C acetyl Coenzyme A, 1 mg/ml BSA, 0.2 mM eserine salicylate, 4 mM choline chloride, 18 mM EDTA, 0.6 mM NaCl, and 0.1 mM $NaH_2PO_4$) was added. This mixture was incubated at 37° C.

for 5 min. The reaction was stopped by adding 100 µl of ice cold distilled water. Samples were extracted with 1.0 ml extraction buffer (15 g of sodium tetraphenylboron in 850 ml toluene and 150 ml acetonitrile) and centrifuged for 2 min in an Eppendorf microcentrifuge, after which 0.65 ml of the organic phase was collected and added to 5.0 ml scintillation cocktail (National Diagnostics, Manville, N.J.). Samples were counted in a scintillation counter for 10 min. The amount of protein per culture was determined by a Coomassie protein assay (Pierce Rockville, Ill.).

Northern Blot Analysis

Fibroblasts were seeded onto a 10 cm tissue culture plate and allowed to reach 70–80% confluence. After washing with PBS, total RNA from each culture was isolated by extracting the cells in 0.5 ml of a guanididium isothiocyanate solution as described by Chomczynski and Sachhi, *Anal. Biochem.* 162:156–159 (1987), incorporated by reference herein. The amount of RNA was quantified by measuring absorbance at 260 nm. Ten to 15 µg of total RNA was loaded onto a 1.2% formaldehyde-agarose gel. Separated RNA was blotted onto nylon membranes (MSI) as described by Sambrook et al., in "Molecular Cloning, A Laboratory Manual", (Ed. Nolan), Cold Spring Harbor Lab. Press, Cold Spring Harbor, N.Y. (1989), incorporated by reference herein. Blots were prehybridized (50% formamide, 5×Denhardt's solution, 5×SSPE, 0.5% SDS, 100 µg/ml denatured herring sperm DNA) for 1–4 hrs at 42° C. Probes were prepared by excising an approximately 2.5 Kb EcoR1 fragment from pLChRNL or a 953 bp BamHI fragment from pGCyc (provided by H. Jinnah, University of California, San Diego, Calif.) to identify dChAt or cyclophilin mRNA, respectively. The fragment was isolated on a 1.0% low-melt agarose gel, purified using Gene Clean (Bio 101, San Diego, Calif.) and labelled by random priming (Boerhinger Mannheim, Indianapolis, Ind.) using $^{32}$P-dCTP. Approximately $1\times10^6$ cpm/10 ml hybridization buffer was used per blot. The radiolabelled probe was directly applied to the prehybridization solution. Hybridization was performed for 12–20 hrs at 42° C. Afterwards, the blot was washed two times with 6×SSC, 0.1% SDS at ambient room temperature, two times with 1×SSC, 0.1% SDS at 42° C., and finally once with 0.1×SSC, 0.1% SDS at 65° C. All washes lasted for 10 min. The washed blot was wrapped in plastic film and autoradiographed (XAR film, Kodak, Rochester, N.Y.). The probe was removed for subsequent hybridizations by incubating the blot in 50% formamide, 10×SSPE at >65° C. for 1 hr. The blot was rinsed in 2×SSPE before the next prehybridization. Densimetric scans of autoradiographs were conducted on a LKB ultrascan XL laser densitometer.

Immunocytochemistry

Fibroblasts were seeded at a density of $1\times10^4$ cells onto two-welled tissue culture slides (Tissue Tek) and allowed to grow for two to three days before they were fixed with 4% PBS-buffered paraformaldehyde. Cultures were permeabilized with 0.25% Triton-PBS for 15 min, washed twice with PBS, and incubated with primary antibody at ambient room temperature overnight. The primary antibodies used were a rabbit-anti-dChAT (1:100, from Dr. P. Salvaterra, Duarte, Calif.), mouse-anti-vimentin (1:250, Vector Laboratories), or a rabbit-anti-rat ChAT (1:7500, Boehringer Mannheim). In most cases, cultures were simultaneously incubated with antibodies against vimentin and one or the other ChAT antibody. After the primary incubation, cultures were again washed with PBS (twice) and incubated for 1 hr at 37° C. with fluorescent labelled goat-anti-rabbit (1:100, Vector Laboratories) and goat-anti-mouse (1:100, Chemicon, Temecular, Calif.), secondary antibodies. Slides were mounted in Hydromount (National Diagnostics) and viewed with an Olympus fluorescent microscope.

Serum Starvation and Confluence-Induced Quiescence

Rat-1 cells were plated at a density of $2.5\times10^5$ cells per 60 mm plate. For serum starvation experiments, cells were allowed to reach 70–80% confluence before the culture medium was aspirated and replaced with fresh DMEM only. Control cells were fed normal serum-supplemented medium. Incubation lasted for 20 hr.

For confluence-induced quiescence, cells were plated as described. Cultures were then maintained for 3, 7, and 14 days after they reached confluence. To feed these cultures, half of the culture medium was aspirated and replaced with an equal volume of fresh medium. The last feeding was three days before the cells were to be assayed. Cultures containing actively growing cells served as controls. For Northern blot analysis, cells were plated in 10 cm plates and treated as described.

[Methyl]-$^3$H-thymidine incorporation

Incorporation of thymidine was used to monitor the proliferative rate of fibroblasts in logarithmic or quiescent growth state. Cells were plated onto a 10 cm culture dish and incubated with $^3$[H]-thymidine (25 Ci/mmol; 0.5 µCi/ml; Boehinger Mannheim) for 5 hr. Cultures were subsequently trypsinized, counted using a hemacytometer, pelleted, and resuspended in 1 ml of 0.3M NaOH. Incubation in the NaOH solution lasted for 30 min. The entire lysate was then pipetted into a scintillation vial containing 10 ml of scintillation fluid and counted on a Mark III liquid scintillation system, model 6881 (Tracor Analytic, Austin, Tex.).

Measurement of ACh by HPLC

ACh was measured by HPLC with electrochemical detection. ACh was separated from choline on a weak cation exchange column. This column was prepared by loading a reverse phase Chrompher Cartridge C18 column (100 mm×3 mm, Chompack) with laurylsulphate. An enzymatic post-column reactor (10×2.1 mm, Bioanalytical Systems, West Lafayette, Ind.) containing immobilized acetylcholinesterase (type VI-S) and choline oxidase (Sigma, St. Louis, Mo.) was used to convert ACh to hydrogen peroxide. The hydrogen peroxide was subsequently measured by electrochemical detection (Bioanalytical Systems) at a platinum electrode held at a potential of ±0.5 v against a Ag/AgCl reference electrode. Mobile phase containing 0.1M potassium phosphate and 0.1 mM tetramethylammonium hydroxide at pH 8.1 was delivered using a LKB 2248 isocratic pump (Pharmacia, Piscataway, N.J.) at a flow rate of 0.8 ml/min.

Medium conditioned by fibroblasts was filtered through a 0.22 µm Millipore filter and injected directly onto the analytical column without any further sample preparation. Intracellular ACh levels were measured by resuspending the pellet, sonicating the suspension, removing cellular debris by centrifugation, and then filtering the sample first through a 0.45 µm and then a 0.22 µm Millipore filter. The remaining filtrate was then injected onto the analytical column.

Effect of Choline Chloride and Acetyl-dl-Carnitine on ACh Production

Fibroblasts were plated at $1\times10^5$ cells per 35 mm plate and allowed to reach 70–80% confluency. The medium was subsequently aspirated and replaced with fresh medium containing the appropriate amount of choline chloride (Sigma) or acetyl-dl-carnitine (Sigma). Cells were incubated in this medium for 20 hr. Fibroblasts were harvested and prepared either for the ChAT assay or for measurement of ACh by HPLC. Cultures to be analyzed by HPLC had 0.1 mM eserine included in the medium.

Statistical Analysis

Student's t-test and a one way ANOVA statistical analysis (STATView, Palo Alto, Calif.) were used to determine differences between experiments. A post-hoc Dunnet t test was used to determine individual differences between groups.

Confirmation of dChAT Expression by Rat-1/dChAT Fibroblasts

Figure 35A:
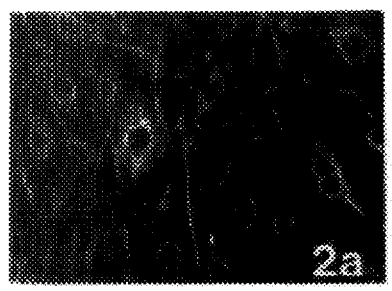
FIG. 35a–FIG. 35f are photographs of immunostained fibroblasts as described in Example VII, infra.
Figure 35B:
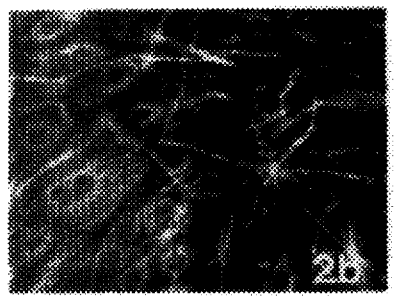
Figure 35C:

Rat-1 Fibroblasts were infected with retrovirus (FIG. 34) and selected in G418-containing medium. The presence of dChAT in infected cells was initially confirmed by immunocytochemistry. Uninfected Rat-1 (control) and Rat-1/dChAT fibroblasts were simultaneously stained with antibodies against vimentin and dChAT or vimentin and rat-ChAT (FIG. 35a–f). Vimentin immunoreactivity effectively revealed the morphology of the fibroblasts (FIG. 35a–c). Most Rat-1/dChAT cells were morphologically indistinguishable from controls, displaying a flat, epithelial-like phenotype. Some lines of Rat-1/dChAT fibroblasts were observed to be morphologically distinct from controls, exhibiting an elongated morphology.

Figure 35D:
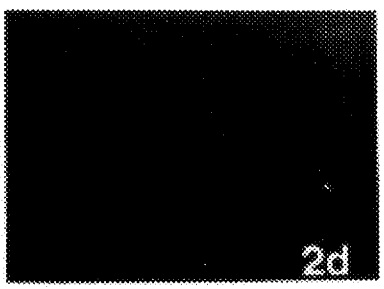
Figure 35E:
Figure 35F:
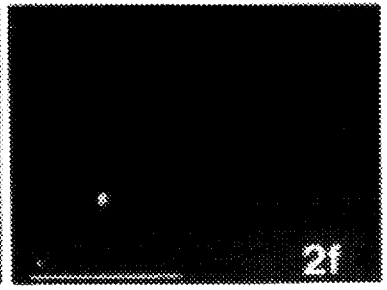

As expected, anti-dChAT antibodies labeled only Rat-1/dChAT fibroblasts (compare with FIG. 35d and 35e). Staining of dChAT was evenly distributed throughout the cytoplasm; however, there was an area of more intense immunoreactivity immediately around the nucleus. The nucleus itself was not stained. In addition to staining for the presence of recombinant dChAT, Rat-1 and Rat-1/dChAT cells were also stained for the presence of rat-ChAT. There was no indication of rat-ChAT immunostaining in either control or Rat-1/dChAT cells (FIG. 35f). The lack of rat-ChAT immunoreactivity indicates that there is very little, if any, endogenous ChAT activity in Rat-1 cells. Moreover, these observations demonstrate that the dChAT molecule is immunologically distinct from rat-ChAT. Previous biochemical and molecular studies have reported sequence differences between dChAT and the other mammalian ChATs that have been cloned (Berrard et al., Proc. Natl. Acad. Sci. USA 84:9280–9284 (1987); Itoh et al., Proc. Natl. Acad. Sci. USA 83:4081–4085 (1987)). These data show that dChAT, in addition to catalyzing the formation of ACh, may be used as a specific marker for dChAT-expressing fibroblasts that have been transplanted into the rat CNS.

Figure 36B:
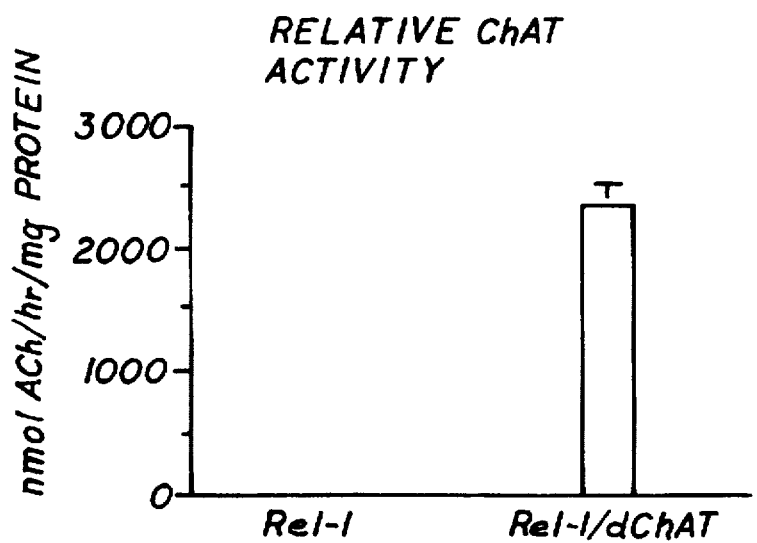
FIG. 36a–FIG. 36c illustrate the results of: Northern blot analysis of total RNA from fibroblasts (36a); assay of ChAT activity in fibroblasts (36b) and HPLC analysis of ACh secreted into the medium by fibroblasts (36c), as described in Example VII, infra.
Figure 36C:
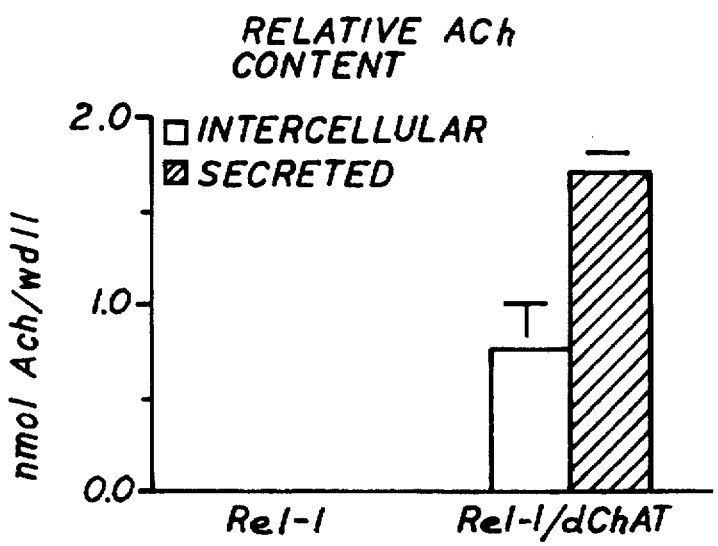
Figure 36A:
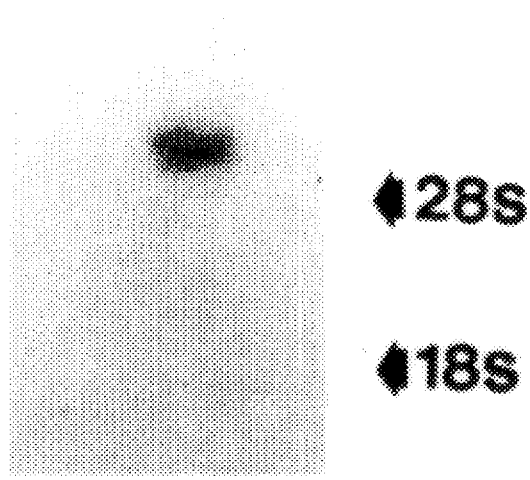

Total RNA from Rat-1 and Rat-1/dChAT fibroblasts was also compared by Northern blot analysis to determine specificity of expression of the transgene. The results from these studies clearly demonstrate that the mRNA encoding for dChAT is present only in Rat-1/dChAT fibroblasts (FIG. 36a). The size of the dChAT mRNA isolated from Rat-1/dChAT cells was approximately 6 kb. The size of the mRNA is due to the lack of a polyadenylation sequence between the dChAT cistron and RSV promoter. This allows unimpeded transcription to proceed from the 5' LTR to the 3' LTR.

Finally, control and Rat-1/dChAT fibroblasts were assayed for ChAT activity. The level of ChAT detected in Rat-1 cells was widely variable, ranging from no activity to approximately 6.4 nmoles ACh/hr/mg protein. The average activity displayed by control cells was approximately 1.9±1.1 nmoles ACh/hr/mg protein (FIG. 36b). In contrast to the low levels of ChAT detected in Rat-1 cells, ChAT activity in Rat-1/dChAT cells was >1200-fold higher. The average activity of Rat-1/dChAT cultures was 2397±149 nmoles ACh/hr/mg protein (FIG. 36b). Moreover, expression of dChAT by transduced fibroblasts was stable. The activity of ChAT in fibroblasts that were continuously passaged for one year after infection was similar to that in fibroblasts assayed one week after infection.

Rat-1/dChAT Cells Produce and Secrete ACh

The demonstration that transduced Rat-1 cells express an active recombinant enzyme capable of acetylating choline in an in vitro assay does not prove that the cells are capable of manufacturing and extruding ACh from the cytoplasm. Therefore, the level of ACh found in the culture medium and within the cells was analyzed by HPLC with electrochemical detection. No ACh was found either within the cells or in the nutrient medium of uninfected Rat-1 cells (FIG. 36c). This result suggests that the ChAT activity detected in Rat-1 cells is due to a contaminating enzyme which is capable of acetylating choline. Carnitine acetyltransferase, an enzyme found in most cells, is capable of transferring the acetyl moiety from acetyl-CoA to choline (White and Wu, Biochemistry 12:841–846 (1973)). In contrast to the absence of ACh in control cultures, significant levels of ACh, both intra- and extracellular, were measured in Rat-1/ChAT cultures (FIG. 36c). The average cellular content of ACh was approximately 0.78±0.23 nmol. Comparatively, approximately 1.7±0.10 nmol of ACh was found in the culture medium.

These results demonstrate that ACh is actively being manufactured by Rat-1/dChAT fibroblasts and that most of the ACh is released from the cells into the surrounding culture medium.

Effect of Choline Chloride and Acetyl-dl-Carnitine on ChAT and ACh Expression

Figure 37A:
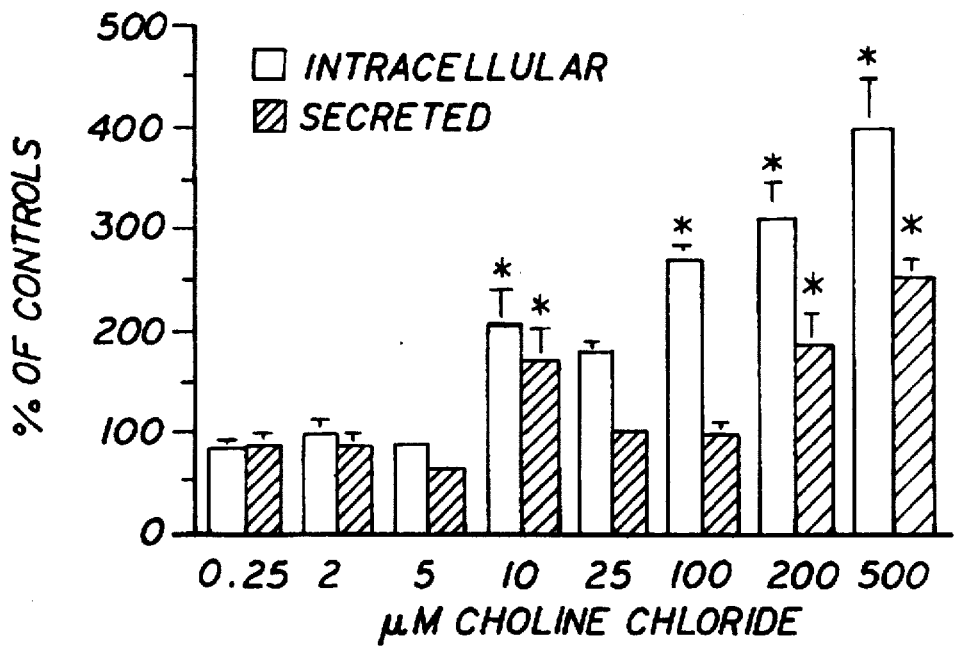
FIG. 37a–FIG. 37b are graphs depicting the results of adding choline chloride to cultures of Rat-1/dChAT cells as determined by HPLC and described in Example VII, infra (FIG. 37a=effects on intracellular and extracellular ACh.

Because choline chloride and acetylcarnitine have been reported to enhance ACh secretion from neurons or synaptosomes in various model systems (Gilson and Shimada, Biochem. Pharmacol. 29:167–174 (1980); Imperato, Neurosci. Lett. 107:251–255 (1989); Jenden et al., Science 19:635–637 (1976); Tucek, J. Neurochem. 44:1–24 (1985)), these drugs were tested for their ability to modulate ACh secretion and ChAT activity in Rat-1/dChAT fibroblasts. Choline chloride was used in concentrations ranging from 0.25–500 µM (FIG. 37a). These concentrations were in addition to that normally found in the medium (approximately 28 µM) and in the serum (<2 µM). Exogenous choline concentrations of 0.25–5.0 µM had no affect on ACh levels. At 10 µM, both intracellular and secreted ACh concentrations increased (FIG. 37a). Intracellular levels of choline increased by approximately 2-fold; the concentration of ACh found in the culture medium increased by approximately 1.8-fold. Intracellular levels of ACh continued to rise with increasing concentrations of choline (FIG. 37a). The addition of choline in amounts greater than 500 µM did not cause any further increase in ACh content.

In contrast to the consistent rise in intracellular ACh, secreted ACh declined back to baseline levels at 50 and 100 µM choline after increasing by 80% at 10 µM choline (FIG. 37a). At 200 µM choline, released levels of ACh increased by approximately 2.0-fold. ACh continued to increase at 500 µM choline, reaching 2.6 times the levels observed in control (no added choline) cultures. Concentrations above 500 µM choline did not elicit any further increase in ACh release. The addition of choline (up to 10 mM) to the medium of uninfected Rat-1 cells did not result in the detection of ACh as determined by HPLC.

Figure 37B:
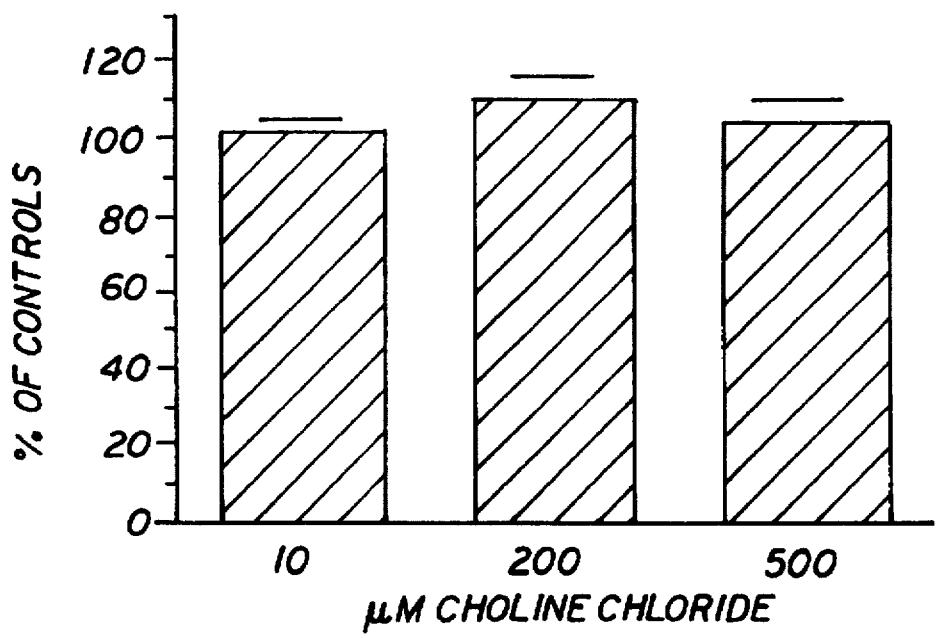

The effect of choline on ChAT activity was also determined (FIG. 37b). Concentrations of 10, 200 and 500 µM choline were tested. The addition of choline to the culture medium did not significantly affect the ChAT activity of Rat-1/dChAT fibroblasts.

The influence of acetyl-dl-carnitine on ACh was also tested. Acetyl-dl-carnitine had no effect on the amount of ACh produced or released from Rat-1/dChAT fibroblasts or on ChAT activity.

Effect of Serum Starvation and Confluency on the Expression of dChAT

Most of the characterization of Rat-1/dChAT cells has been conducted on cultures of proliferating fibroblasts. However, the ultimate goal is to use fibroblasts for grafting. Fibroblasts that have been transplanted into the brain are most likely not actively proliferating. Thus, the in vitro activity of quiescent fibroblasts, which may more accurately reflect the conditions found in vivo, should be assessed. This assessment provides predictive information about the activity of non-dividing fibroblasts that have been implanted into the brain. To induce quiescence in fibroblast cultures, Rat-1/dChAT fibroblasts were maintained in either a serum-free medium or at high density for several days. Although both methods significantly reduced thymidine incorporation, maintaining fibroblasts in a post-confluent state for a prolonged period resulted in much lower thymidine incorporation (Table 3).

TABLE 3

| | [$^3$H]-Thymidine Incorporation | | |
|---|---|---|---|
| Culture Condition | CPM/10$^5$ Cells | Cells/ml | % Control |
| Log, 10% serum (control) | $3.6 \times 10^4$ | $9.9 \times 10^5$ | — |
| No Serum | $3.7 \times 10^{3*}$ | $4.7 \times 10^5$ | 10.3 |
| 14 DPC, 10% Serum | $55.4 \pm 8.5*$ | $3.0 \times 10^6$ | <0.2 |

*Significance of p < 0.01
14 DPC = 14 days post confluence

Figure 38A:
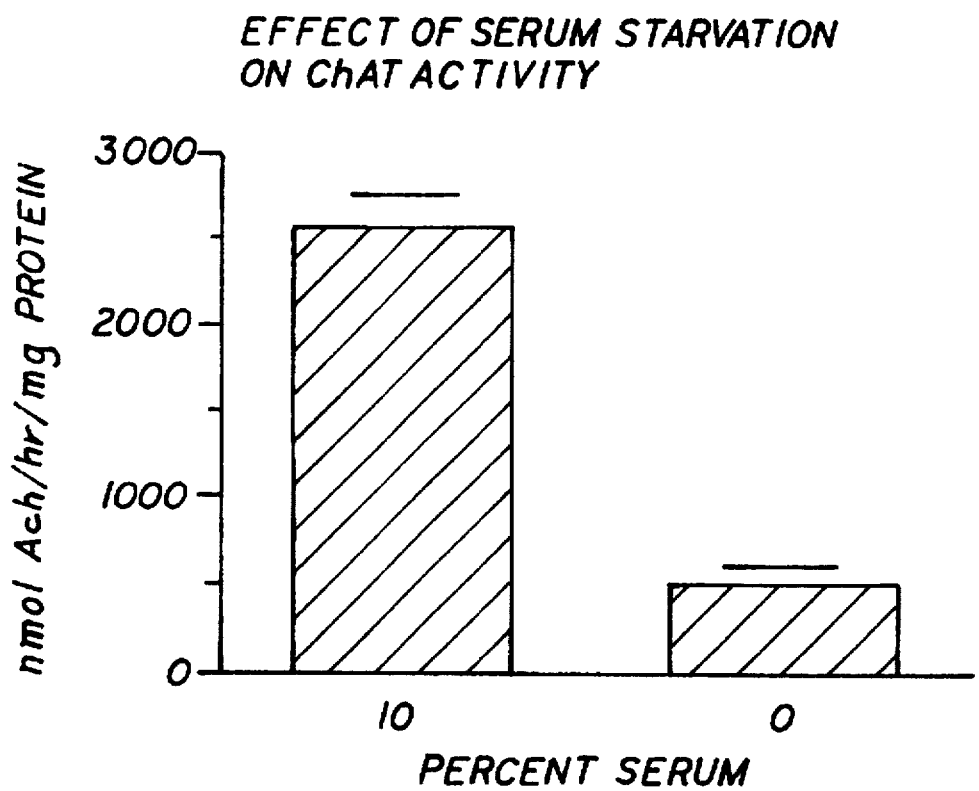
FIG. 38a–FIG. 38c illustrate the results of quiescence induced by serum starvation on the expression of dChAT as shown by the effects on: ChAT activity (FIG. 38a); steady state levels of dChAT mRNA (FIG. 38b) and on the ratio of dChAT/cyclophilin (cyc.) mRNA (FIG. 38c), as described in Example VII, infra.

FIG. 38a illustrates the effect of serum starvation on ChAT activity. This treatment did not noticeably affect the morphology or the health of the fibroblasts. In contrast, maintaining Rat-1/dChAT fibroblasts in serum-deficient medium caused a marked reduction in the expression of the transgene. The absence of serum caused an approximately 80% decrease in ChAT activity.

Figure 38C:
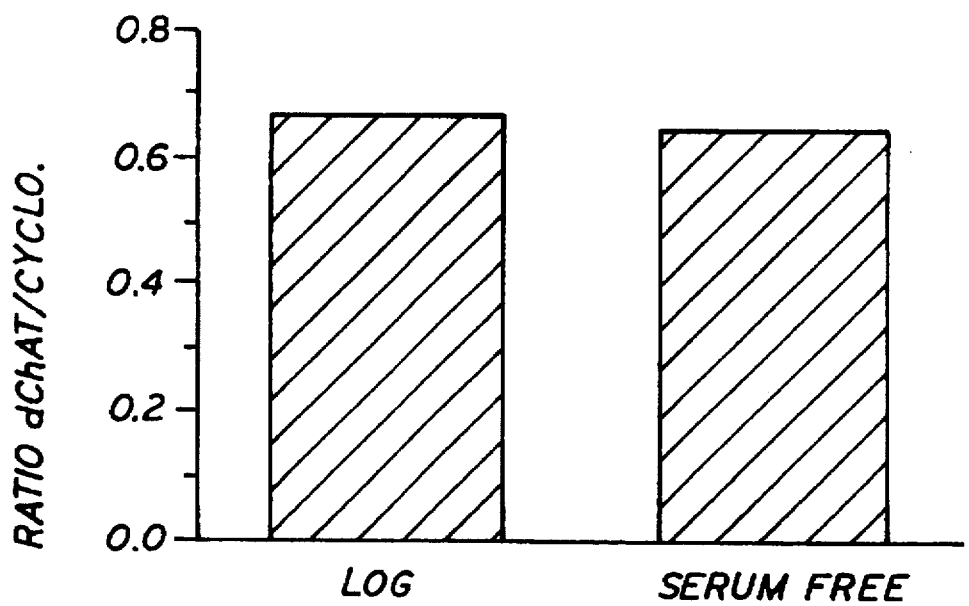
Figure 38B:
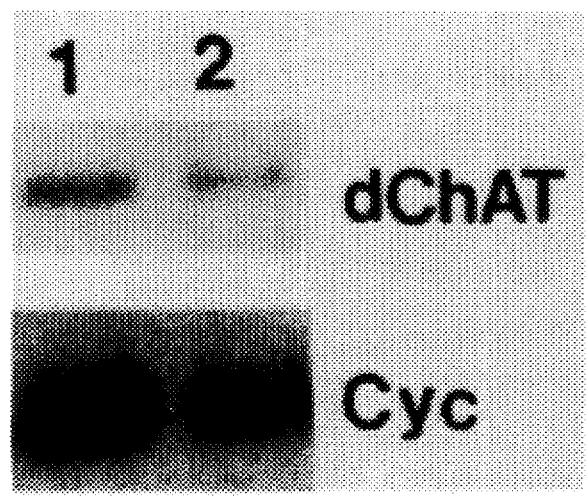

Northern blot analysis was conducted to determine if the steady state level of dChAT mRNA decreased with serum deprivation. There was a significant decrease (approximately 46%) in the level of dChAT mRNA when serum was withdrawn from the cultures (FIG. 38b). The same blots were also probed with a CDNA probe to cyclophilin which served as an internal control (McKinnon et al., Mol. Cell. Biol. 7:2148–2154 (1987)). Unexpectedly, the steady state levels of cyclophilin mRNA also appeared to decrease (approximately 43%) in serum-starved fibroblasts. The absorbance ratio of dChAT to cyclophilin was measured with a densitometer to confirm that the observed decreases in the steady state levels of dChAT and cyclophilin mRNA were proportional. Indeed, the ratio of the relative absorbance of dChAT to cyclophilin was similar in control and serum-starved cultures (FIG. 38c). The amount of actin and HPRT MRNA was also reduced in serum-starved fibroblasts.

Figure 39A:
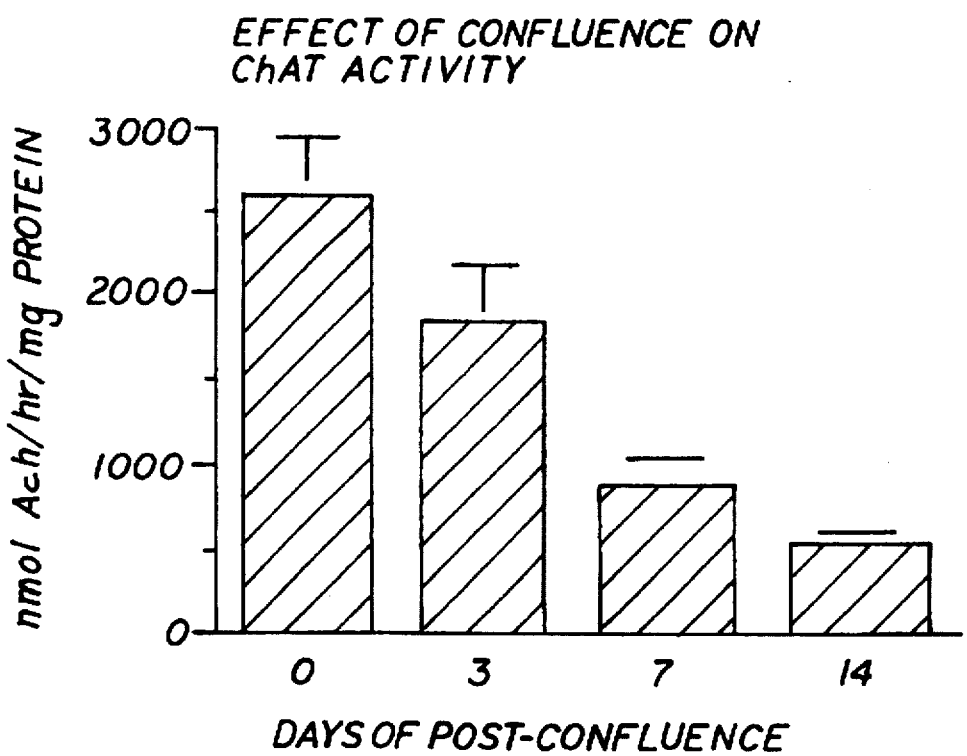
FIG. 39a–FIG. 39c illustrate the effects of quiescence induced by contact inhibition on the expression of dChAT as shown by the effects on: ChAT activity (FIG. 39a); levels of dChAT MRNA (FIG. 39b); and on the ratio of dChAT/cyc.

Since serum deprivation appeared to affect the general metabolism of fibroblasts, an alternative method was employed in which quiescence was induced by continuing to maintain fibroblasts for 3, 7 and 14 days after they reached confluency (days post confluence, DPC). At 3 DPC, the level of ChAT declined to 80% of the activity observed in control, growing cultures (FIG. 39a). The activity of ChAT continued to drop with increasing DPC, decreasing to 50% and 20% of control levels at 7 and 14 DPC, respectively (FIG. 39a). Maintaining the cells beyond 14 DPC did not result in a further decline in ChAT activity.

Figure 39C:
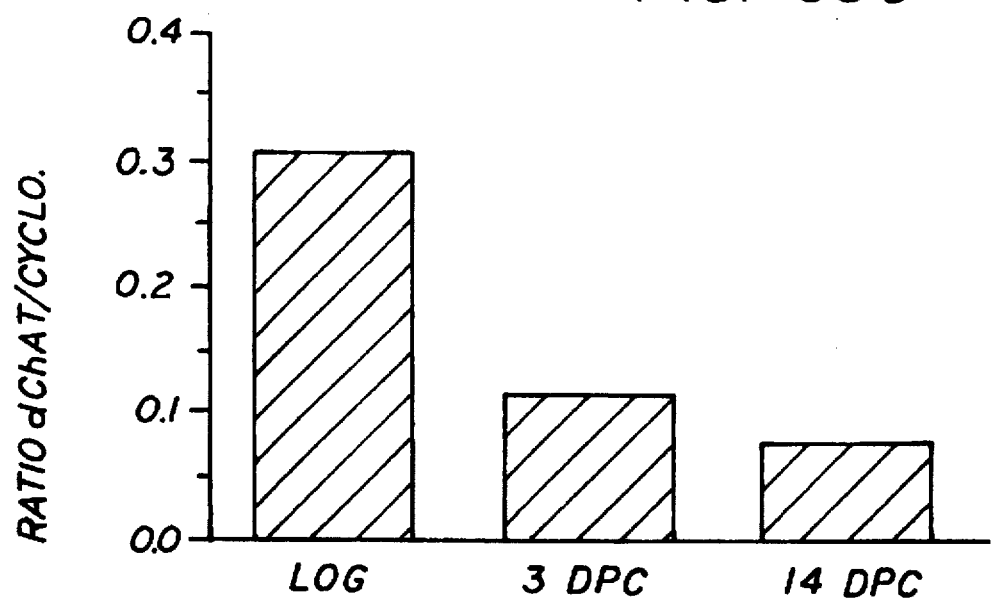
Figure 39B:
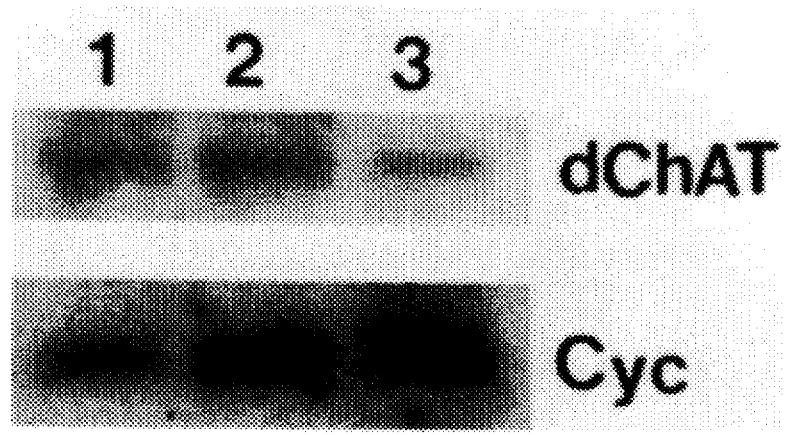

The amount of dChAT mRNA in confluent Rat-1/dChAT cultures was determined by Northern blot analysis (FIG. 39b). There was no obvious decrease in the level of dChAT mRNA isolated from growing (control) or confluent Rat-1 cultures, however, densitometric analysis revealed that the steady state level of dChAT mRNA decreased by approximately 29% and approximately 35% at 3 and 14 DPC, respectively. Interestingly, as the relative levels of dChAT mRNA decreased, the levels of cyclophilin mRNA increased. As compared to controls, the relative amount of cyclophilin mRNA isolated from 3 and 14 DPC cultures increased by approximately 84%. Determination of the dChAT to cyclophilin ratio indicated that a 60.5% decrease occurred at 3 DPC and a 64% decrease occurred at 14 DPC (FIG. 39c). All numbers are relative to the dChAT/cyclophilin ratio determined for growing cells.

Effect of Choline on the release of ACh from Confluent Fibroblasts

To assess whether choline could enhance the release of ACh from confluent fibroblasts, Rat-1/dChAT cells were maintained for 7 DPC in either control or choline-supplemented (500 μM) medium. FIG. 40 illustrates the effects of maintaining Rat-1/dChAT fibroblasts in a confluent state on ACh production and release. The overall content of ACh (intra- and extracellular) in 7 DPC Rat-1/dChAT cultures was 18.9% of that measured in cultures containing mitotic cells. The decrease in total ACh was manifested as a 50.1% and 82.1% decline in intracellular and released ACh, respectively. In contrast to confluent cultures maintained in normal medium, quiescent Rat-1/dChAT fibroblasts maintained in choline-supplemented medium demonstrated ACh levels that were comparable to the levels of ACh measured in proliferating Rat-1/dChAT cultures (FIG. 40). Intracellular ACh levels increased by 138%, as compared to confluent fibroblasts maintained in normal medium, when exogenous choline was added to the nutrient medium. Similarly, the amount of extracellular ACh increased by 473%.

The above results set forth in this example demonstrate that Rat-1 fibroblasts can be successfully infected with a retroviral vector containing the cDNA encoding dChAT. Moreover, these cells can manufacture and, more importantly, release the product of ChAT catalysis, ACh. The production and secretion of ACh from proliferating fibroblasts can be modulated if additional choline chloride is added to the culture medium. These data also show that the expression of the transgene is decreased in quiescent fibroblasts; however, choline can enhance the release of ACh from these cells.

Rat-1/dChAT cells were developed so that some of the factors which may affect ACh production could be studied in vitro. Rat-1 fibroblasts were chosen because they can be continuously maintained in culture with little, if any, change in their genotype or phenotype. The stability in the expression of the transgene in these cells is reflected by the observation that ChAT activity was similar in cells assayed one week or one year after retroviral infection. A short-term goal for developing ACh-secreting fibroblasts is to assess the function of these cells following implantation into the CNS. However, Rat-1 and other fibroblast cell lines implanted into the rat CNS often form tumors (see Horellou et al., Neuron 5:393–402 (1990); Wolff et al., Proc. Natl. Acad. Sci. USA 86:9011–9014 (1989)). By contrast, primary dermal fibroblasts can survive for extended periods in the brain (6 mos.) without any indication of tumor development (see Fisher et al., Neuron 6:371–380 (1991); Kajawa et al., J. Comp. Neurol. 308:2–13 (1991)). Thus, if ACh-secreting fibroblasts are to be used in brain transplant paradigms, primary cells should be used. Primary dermal fibroblasts appear to react in a similar manner to Rat-1/dChAT cells with regards to choline and quiescence (i.e., increased ACh secretion and decreased ChAT activity, respectively). Therefore, the Rat-1 fibroblasts used in this Example serve as an accurate in vitro model for the reaction of primary fibroblasts grown under similar culture conditions.

To enhance the ability of cells transplanted into the CNS to produce a functional effect, it would be useful if the secretion of the molecule of interest could be modulated by manipulating the humoral environment within the CNS. In the in vitro experiments described herein, choline increased the production and secretion of ACh by Rat-1/dChAT fibroblasts. Importantly, choline also elicited an increase in ACh production and release from quiescent (confluent) fibroblasts. This latter observation may provide a means to modulate ACh production by ChAT-producing cells transplanted into the CNS. At present, the mechanism behind the increase in intra- and extracellular ACh caused by exogenous choline is not known. However, the amount of enzyme, as assessed by measuring ChAT activity, is not affected by increasing the extracellular concentration of choline. These results indicate that the rate of the forward reaction, i.e. towards the formation of ACh and not the amount of enzyme, is responsible for the increased level of ACh observed in choline-supplemented fibroblast cultures.

These results suggest that the release of ACh may be increased in dChAT-expressing fibroblasts that have been implanted into the brain by administering choline, for example as a dietary supplement. Choline has been reported to pass through the blood-brain barrier (Cohen and Wurtman, *Life Sci.* 16:1095–1102 (1975); Cohen and Wurtman, *Science* 191:561–562 (1976); Wecker and Schmidt, *Brain Res.* 184:234–238 (1980)).

In addition to the possible modulation of the secretion of transgenic products, another desirable quality of genetically modified cells is stable, long term expression of the recombinant gene after the modified cells have been transplanted. Fibroblasts implanted into the brain surround themselves with copious amounts of collagen and apparently cease to proliferate (Kawaja et al., supra, 1991). Current work strongly suggests that the expression of transgenes from the MOMLV LTR is dramatically decreased in serum starved and contact-inhibited quiescent fibroblasts. The mechanisms of action behind serum-starved and confluence-induced quiescence are not clear, but they do appear to be different. This is evidenced by the observation that dChAT mRNA and ChAT activity decreases more rapidly in serum starved fibroblasts than in cultures containing contact inhibited cells.

Current data suggests that once primary fibroblasts are implanted into the brain, the expression from a proviral transgene in these cells is reduced. This hypothesis is supported by previous studies that have shown that TH-expressing 208F fibroblasts, which can be immunolabeled for TH in vitro, are not effectively stained once implanted into the brain (Wolff et al., supra, 1989). Primary fibroblasts that express the gene for GAD also demonstrate a marked decrease in GAD activity when they are transplanted into the brain (Chen et al., *J. Cell. Biochem.*, 45–252–257 (1991)). More recent in situ hybridization and immunocytochemical studies have indicated that a residual amount of TH mRNA and protein are present in late post-transplantation (ten weeks) primary fibroblasts (Fisher et al., supra, 1991)). These results, coupled with those presented in this example, demonstrate that although the amount of recombinant product decreases in quiescent fibroblasts, there is a residual amount still present in the cells. Results show that a baseline level of dChAT activity (approximately 20% of that found in proliferating cells) exists in quiescent Rat-1/dChAT fibroblasts. This amount of activity does not decrease by maintaining the fibroblasts in a confluent state for periods longer than 14 DPC. Thus, if the activity of the transgene is high enough (as measured in confluent cells in vitro), the amount of activity remaining once the cells have been transplanted may be enough to elicit a functional effect. This hypothesis is supported by the observation that increased amounts of substrate (choline) enhance the release of ACh from quiescent Rat-1/dChAT fibroblasts. Therefore, the drop in the expression of some transgenes may be compensated for by defined epigenetic factors.

In conclusion, these results demonstrate that fibroblasts can be genetically altered to produce and secrete ACh. ACh release can be increased by manipulating the extracellular concentration of choline, possibly by administering dietary choline. These data also demonstrate that transgene expression markedly decreased with the cessation of proliferation in vitro.

EXAMPLE VIII

Use of Promoters In Quiescent Fibroblasts

This example provides a comparison of promoters in growing (Log) and confluent (quiescent) fibroblast cultures. The reporter transgene used in this study was chloramphenicol acetyltransferase (CAT).

Expression Vectors

Figure 41:
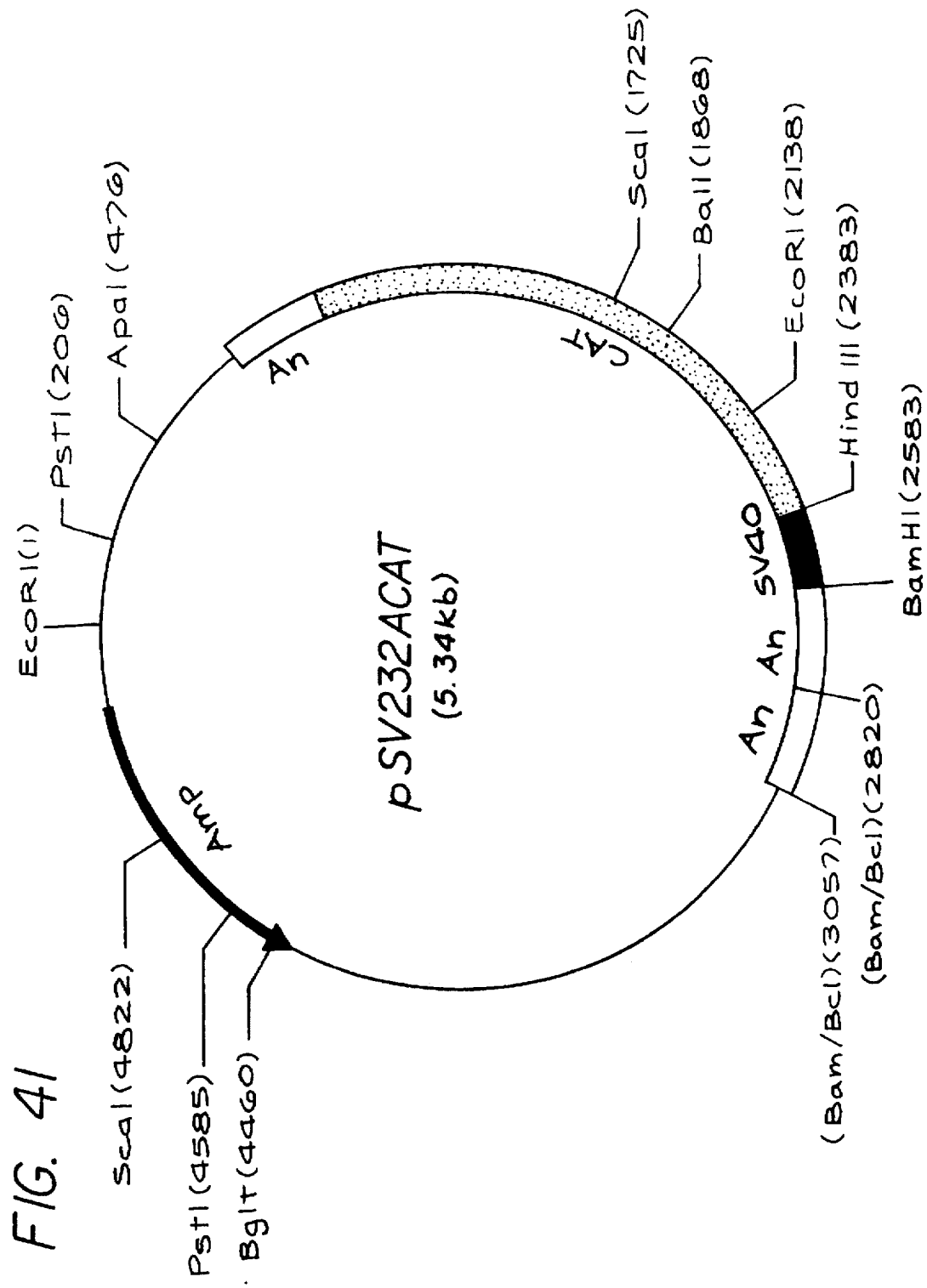
FIG. 41 is a depiction of the circular restriction map of vector pSVS32ACAT, as described in Example VIII, infra.
Figure 42:
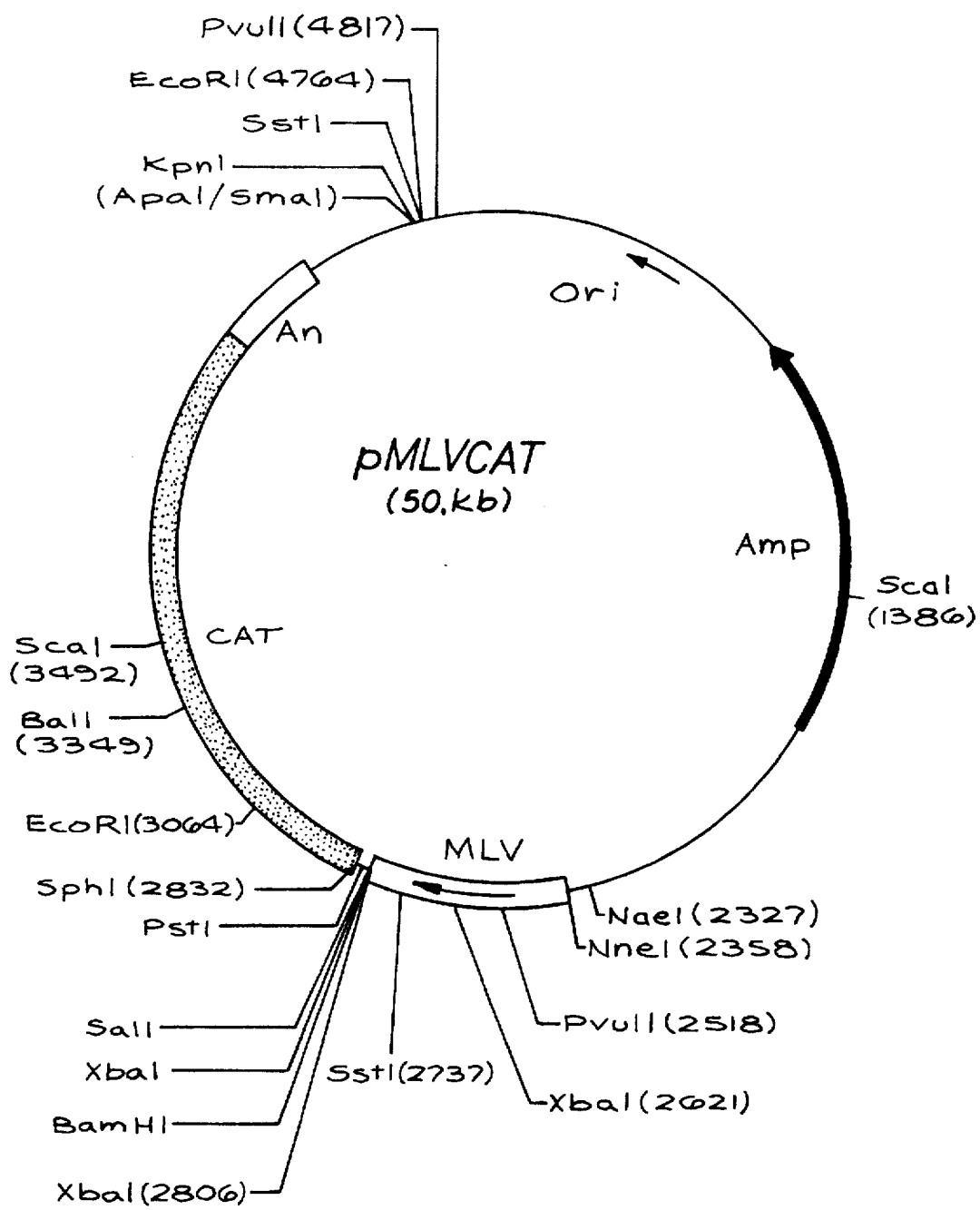
FIG. 42 is a depiction of the circular restriction map of vector pMLVCAT, as described in Example VIII, infra.
Figure 43:
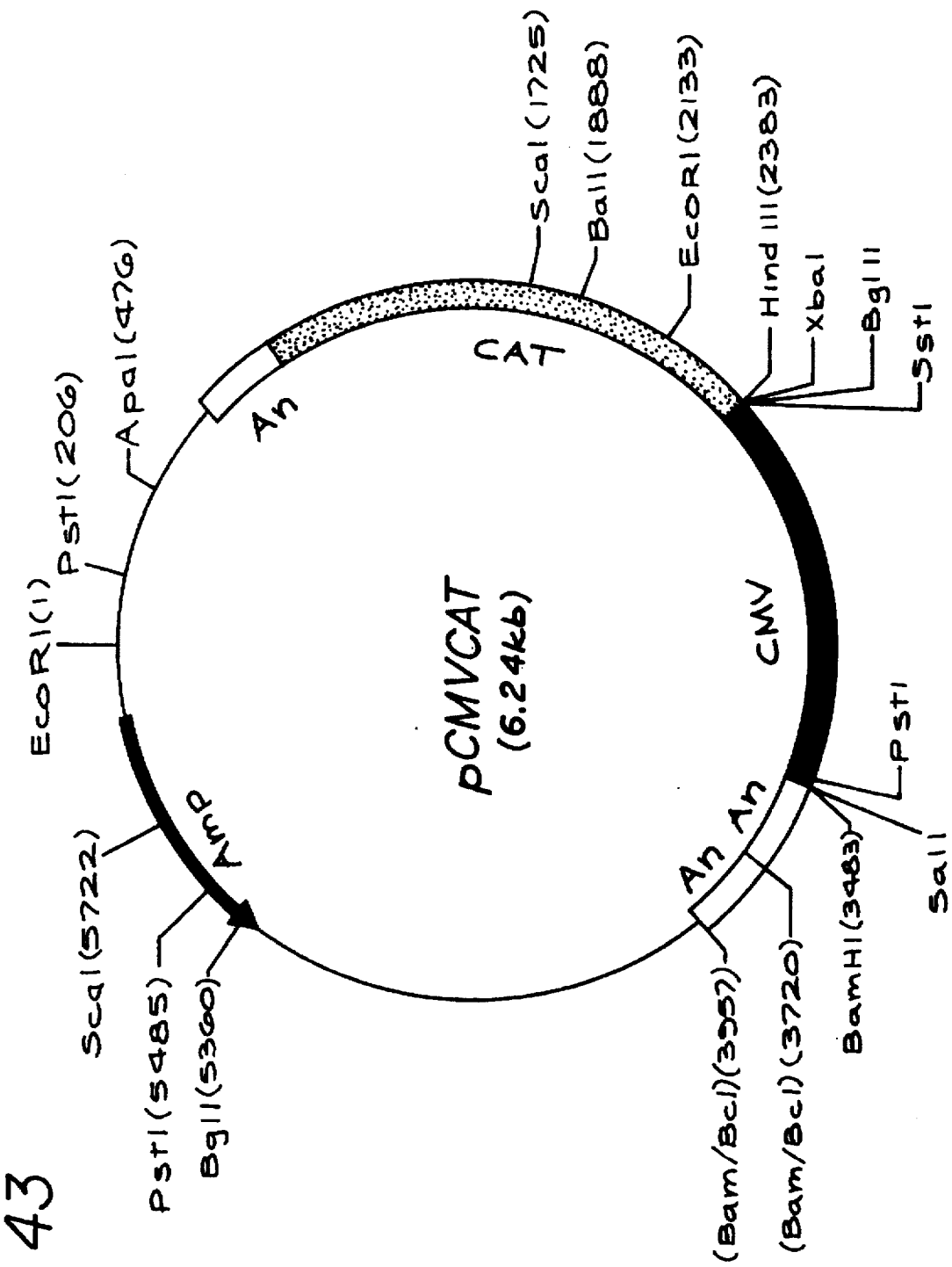
FIG. 43 is a depiction of the circular restriction map of vector pCMVCAT, as described in Example VIII, infra.

Expression vectors containing the CAT gene under the control of various promoters for determining transgene expression in proliferating and quiescent primary fibroblasts, were obtained. The plasmids, pSV2CAT (Gorman et al., *Mol. Cell. Biol.* 2:1044–1051 (1982); Subramani and Southern, *Anal. Biochem.* 135:1 (1983); ATCC No. 37155) in which the CAT gene is under the control of the SV40 promoter plus the SV40 enhancer sequence, and pSV232ACAT (FIG. 41, provided by Dr. D. Jolly and Dr. Theodore Friedmann, University of California, San Diego, Calif., constructed from pSV232Agpt described by Fromm and Berg, *J. Mol. Appl. Genet.* 2:127–135 (1983)), were used. Plasmids pRSVCAT (Rous sarcoma virus long terminal repeat promoter and enhancer, Gorman et al., *Proc. Natl. Acad. Sci. USA* 79:6777–6781 (1982); ATCC No. 37152), pMLVCAT (FIG. 42, murine Moloney leukemia virus long terminal repeat promoter and enhancer, constructed from pSV232ACAT, pGEM-3 (Promega Corp., Madison, Wis.) and pN2 (Eglitis et al., *Science* 230:1345–1398 (1985) and provided by Dr. M. Rosenberg, University of California, San Diego, Calif.) and pCMVCAT (FIG. 43, human cytomegalovirus immediate early promoter and enhancer, constructed by Dr. M. Rosenberg from pSV232ACAT and pON249 (from E. S. Mocarski, Stanford University School of Medicine, Palo Alto, Calif.)) were provided by Dr. Friedmann (University of California, San Diego, Calif.). Collagen promoters were supplied by Dr. de Crombrugghe, M.D. Anderson Cancer Center, Houston, Tex. Plasmids pG100 and pAZ1003 (de Crombrugghe and Schmidt, *Methods in Enzymology* 266:61–76 (1987)), were provided by Dr. de Crombrugghe (Houston, Tex.) and contain the CAT gene under the control of mouse α1(I) and α2(I) collagen promoters (de Crombrugghe, supra, α2(I); Thompson et al., *Annals New York Acad. Sci.* 580:454–458 (1990)) α1(I)).

Because CAT is a bacterial gene with no mammalian equivalent, any CAT activity detected in transfected cells is due to the presence of the transfected plasmid. The level of CAT enzyme in transfected cells is proportional to the strength of the promoters (Gorman et al., *Proc. Natl. Acad. Sci. USA* 79:6772 (1982)).

Establishment of Fibroblast Cultures

To obtain rat primary skin fibroblasts, the abdomens of twenty young (200–250 g) anesthetized Fischer 344 rats were soaked with 70% ethanol. 25×25 mm biopsies were removed from the abdomen of each rat and immediately dipped in 70% alcohol for 2–3 min. The tissue was then transferred to phosphate-buffered saline (PBS, pH 7.4) to remove the alcohol. The biopsy material was then placed into a solution containing 10 mg/ml of collagenase in PBS and incubated for 15 min. at 37° C. The dermal layer was removed from the epidermal layer with the aid of fine tweezers and subject to further enzyme digestion for 0.5 hr. The cells were then pelleted and plated into 35 $mm^2$ tissue culture dishes and maintained in Dulbecco's minimal essential medium (DMEM, Gibco, Grand Island, N.Y.) supplemented with 10% fetal bovine serum (FBS). All cultures were maintained in a 10% $CO_2$ atmosphere at 37° C. and were passaged at a split ratio of 1:2 upon reaching >80% to 90% confluency. Transfected fibroblasts were grown to 70% to 80% confluency for assay of CAT activity during log phase. For assay of CAT activity in confluency, cells were grown to 100% confluency and then maintained for an additional 7 days before assay.

Transfection of Fibroblasts

Fibroblasts were transfected with the selected plasmid in a ratio of 10:1 plasmid DNA to pRSVneo$^R$ plasmid using Lipofectin reagent (BRL, Inc., Gaithersburg, Md.) as described by Felgner et al., *Proc. Natl. Acad. Sci. USA* 84:7413–7417 (1987) and Felgner and Holm, *Focus* 11:21–25 (1988), both incorporated by reference herein. For each 60 mm dish (5×10$^5$ cells/dish) different amounts of DNA and 30 µg Lipofectin reagent/3 ml Opti-MEM media (BRL, Inc.) were used.

For selection of stable transformants plasmid DNA containing the neo$^R$ gene under the control of RSV/LTR was mixed with vector DNA containing the reporter gene (CAT) under the control of various promoters at a ratio of 1:10. After washing once with Opti-MEM, fibroblasts were incubated in the presence of the DNA/Lipofectin mixture for 5 h at 37° C. After that time, the media were changed with DMEM, 10% FCS and incubated for 24–36 h before selection.

The stable transformants were selected in the presence of 200 µg/ml G418. The transfected cells were passaged when the plate was at least 50% confluent. Transfected fibroblasts were split at a 1:2 ratio upon reaching >80% confluency.

Transfected cells expressing CAT were assayed as described below at both log phase and after confluency. Results were compared to determine whether the expression of the CAT transgene remained stable, decreased or increased after the cells became confluent.

Assay for CAT Activity

CAT activity was assayed using a modification of the method of Sleigh, *Anal. Biochem.* 162:156–159 (1987), incorporated by reference herein. The dish containing the transfected fibroblasts was washed in PBS and the cells were collected by scraping. The cells were resuspended in 0.25M Tris-HCl, pH 7.8 buffer (100 µl/plate), lysed by sonication and centrifuged to remove the cell debris. The protein concentration of the soluble fraction was determined using Coomassie protein reagent (Pierce Chemical Co., Rockford, Ill.). An equal amount of protein from each transfection was used for assay. In addition to cell extracts, 100 µl of reaction mixture contained 20 µl of 8 mM chloramphenicol and 5 µl of 0.5 mM cold and [$^{14}$C] acetyl-CoA. After incubation for 1 h at 37° C., the chloramphenicol and its acetylated form was extracted with 0.12 ml ethyl acetate. About 80 µl of the organic phase was collected after centrifugation (10,000×g) at room temperature. The reaction mixture was then re-extracted with ethyl acetate. About 100 µl of organic phase was collected and mixed with 80 µl of the organic phase collected earlier. After adding 1 ml of Packard Instagel (Packard, Downers Grove, Ill.) to the organic phase the samples were counted in a scintillation counter.

Northern Blot Analysis

To determine whether the variable expressions of the transgene during log or confluent stages of fibroblast growth occur at the transcriptional level, Northern blot analysis was performed to quantitate the amount of RNA synthesized as follows. Cells grown in a 10 cm plate were processed for isolation of total RNA by Northern blot analysis at either 70–80% confluence or after maintenance in a confluent state for 7 days. Total RNA from each culture was isolated by extracting the cells in 0.5 ml of a guanididium isothiocyanate solution as described by Chomczynski and Sacchi, in the *Anal. Biochem.* 162:156–159 (1987), incorporated by reference herein. Protein and DNA were separated from DNA by extracting with phenolchloroform. The amount of total RNA was quantified by measuring absorbance at 260 nm. Ten to 15 µg of total RNA was subsequently loaded onto a 1.2% formaldehyde-agarose gel. Separated RNA was blotted onto a nylon membrane (Hybridization Transfer Membrane, MSI, Inc.) by capillary diffusion using 10×SSC. Prehybridization (50% formamide, 5×Denhardt's solution, 5×SSPE, 0.5% SDS, 100 µg/ml denatured herring sperm DNA) of the blot was performed at 42° C. for 1–2 hr.

For preparation of probes, dChAT cDNA was excised from pCMVCAT using pstI enzymes from pLChRNL and was purified from low melting point agarose gel as described by Maniatis et al., in Molecular Cloning-A Laboratory Manual, Cold Spring Harbor Laboratory, Cold Spring Harbor, N.Y. (1982), incorporated by reference herein. $^{32}$P labelled probe was generated by random priming (Maniatis et al., supra). Denatured radiolabeled probe (boiled for 2 min and cooled on ice) was directly added to the prehybridization solution. Hybridization was conducted at 42° C. for 12–24 hr. The blot was then washed twice with 6×SSC, 0.1% SDS at ambient room temperature, twice with 1×SSC, 0.1% SDS at 42° C., and once with 0.1×SSC, 0.1% SDS at 65° C. All washes were for 10 min. The washed gel was then wrapped in plastic XAR film and autoradiographed (Kodak, Rochester, N.Y.). The intensity of each RNA band was measured by densitometer scanning in LKB Ultrascan XL (LKB, Sweden). Blots were washed to remove all counts and reprobed with a cyclophilin probe for use as an internal standard. The probe was removed for subsequent hybridizations by washing the blot in 50% formamide, 6×SSPE at >65° C. for >30 min. The blot was rinsed in 2×SSPE before successive prehybridizations.

Figure 44:
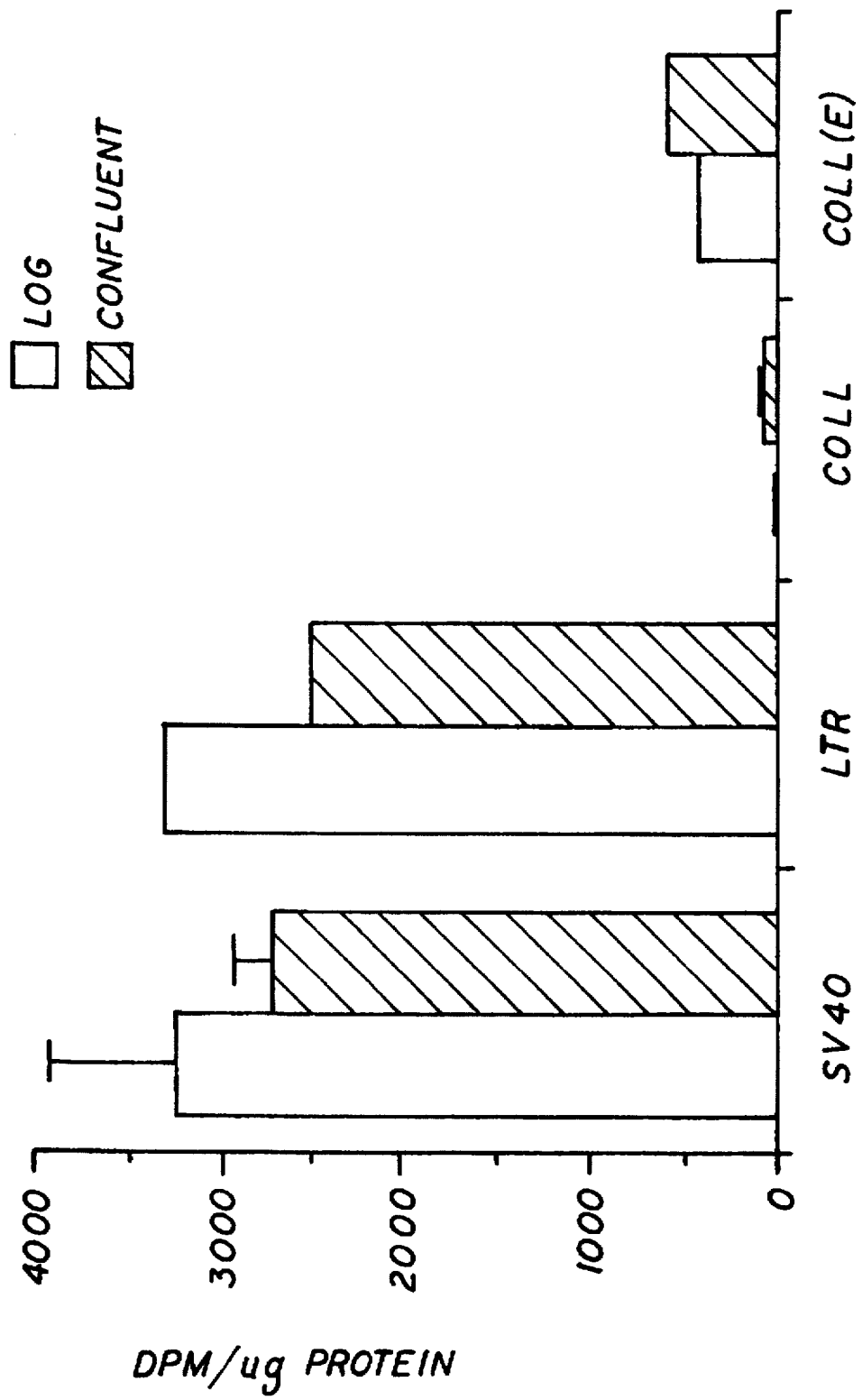
FIG. 44 is a bar graph depicting the relative CAT expression of the SV 40, LTR and Collagen promoters (Coll and Coll(E) promoter-enhancer) as described in Example VIII, infra.

In this example, the SV40 and LTR promoters and the α2(I) collagen promoter, both with and without the collagen enhancer were tested in log and quiescent fibroblasts. The results are summarized in FIG. 44.

The level of CAT activity in fibroblasts containing the SV40 promoter (SV40) was approximately 3247 and approximately 2712 DPM/µg protein for growing and quiescent cells, respectively. This is a decline of approximately 17%. Similarly, CAT activity in fibroblasts containing the LTR decreased by approximately 24% at confluence (3291 DPM/µg protein for log and 2494 DPM/µg protein for quiescent cells). In contrast, the levels of CAT measured in fibroblasts containing the α2(I) collagen promoter increased with quiescence, although the overall expression from these cells was lower. CAT activity in fibroblasts containing the enhancerless α2(I) collagen promoter (CoII) was approximately 13 DPM/μg and approximately 75 DPM/μg protein for log and quiescent cells, respectively. This is an increase of approximately 576%. Fibroblasts containing the α2(I) collagen promoter with the collagen enhancer (CoII(E); described by Rossi and de Crombrugghe, *Proc. Natl. Acad. Sci.* (*USA*) 84:5590–5594 (1981)) exhibited CAT levels of 405 DPM/μg protein for log and 606 DPM/μg protein for quiescent fibroblasts. This is an increase of approximately 149%.

These results indicate that transgene expression from viral promoters may decline in quiescent fibroblasts. In contrast, transgene expression from the α2(I) collagen promoter increases with quiescence. Because fibroblasts grafted into the brain are nondividing, one way to maximize stable transgene expression is by using a promoter that is normally active in quiescent fibroblasts. The α2(I) collagen promoter is such a promoter. Moreover, the CoII(E) promoter-enhancer is as efficient as the α2(I) promoter in driving transgene expression under appropriate culture conditions.

These results demonstrate a method for increasing transgene expression in cells that have ceased dividing when implanted into the body to promote long term stable expression of therapeutic transgenes.

EXAMPLE IX

Regulation of Promoters by Cytokines and Anti-inflammatory Agents

Many mononuclear phagocytes and lymphocytes invade the CNS after the blood-brain barrier is compromised; for example after the implantation of cells into the brain. These cells are known to secrete cytokines into the surrounding extracellular environment. The infiltration and accumulation of these cells around grafted material is observed within a week after grafting. Because fibroblasts have been shown to respond to a variety of cytokines this example was performed to assess the role of cytokines in regulating LTR-driven transgene expression in primary rat fibroblasts.

This Example describes the use of 1) an anti-inflammatory agent, dexamethasone, to eliminate the effects of cytokines on the steady state levels of LTR-driven proviral mRNA; and 2) the use of the α2(I) collagen (CoII) promoter with the collagen enhancer (CoII(E)) to take advantage of the high levels of cytokines present in the brain after implantation. The transgenes used in this example were *Drosophila* choline acetyltransferase (dChAT) and chloramphenicol acetyltransferase (CAT).

Methods

The methods used in this Example were as described above for example VIII with the following exceptions:

Lipofection

The method of lipofection was as described above in Example VIII. The plasmids used to transfect fibroblasts in this example were pMLVCAT (LTR promoter supplied by Dr. Friedmann, University of California, San Diego, Calif.) and pR40 (CoII(E) promoter and enhancer (described in Rossi and de Crombrugghe, *Proc. Natl. Acad. Sci. USA* 84:5590–5594 (1987), and supplied by Dr. de Crombrugghe, MD Anderson Cancer Center, Houston, Tex.). The dChAT-fibroblasts were transduced by infection with retroviruses-as described above for Example VII.

Fibroblast cultures

Primary skin fibroblast cultures were established from rat skin as described above in Example VIII with the following differences. dChAT-fibroblasts were grown to confluence in a 35 mm tissue culture dish using DMEM supplemented with 10% FBS and 200 μg/ml of G418. Upon reaching confluence, the cells were switched to medium containing 2% serum and maintained for an additional 7 days. Fibroblasts that were lipofected with the pMLVCAT or pR40 plasmids were grown to confluence as described for the dChAT-fibroblasts. However, after reaching confluence, these cells were maintained in 10% serum for 4 days. They were subsequently switched to 2% serum-containing medium for the final 3 days (for a total of 7 days post-confluency).

Treatment of Transfected Fibroblasts with Cytokines or Anti-Inflammatory Agent

Cytokines were added on the 7th day of post-confluency. TGFβ1 (10 ng/ml), IL-1β (30 μ/ml), and TNFα (150 ng/ml) were incubated with the cultures for 24 hrs. In addition, the anti-inflammatory agent dexamethasone (25 μM) was added to fibroblasts alone and in the presence of TGFβ and IL-1β1. The cells were then taken for Northern blot analysis (dChAT-fibroblasts) or CAT assay (cells containing the LTR or CoII(E) promoters). Infγ was incubated as described for the other cytokines; however, for some experiments the medium containing Infγ was aspirated and replaced with fresh 2% serum-containing medium. The cells were maintained in this way for an additional 48 hours before they were processed for Northern blot or CAT assay. This procedure was used because it was determined that Infγ required this amount of time to function.

Figure 45B:
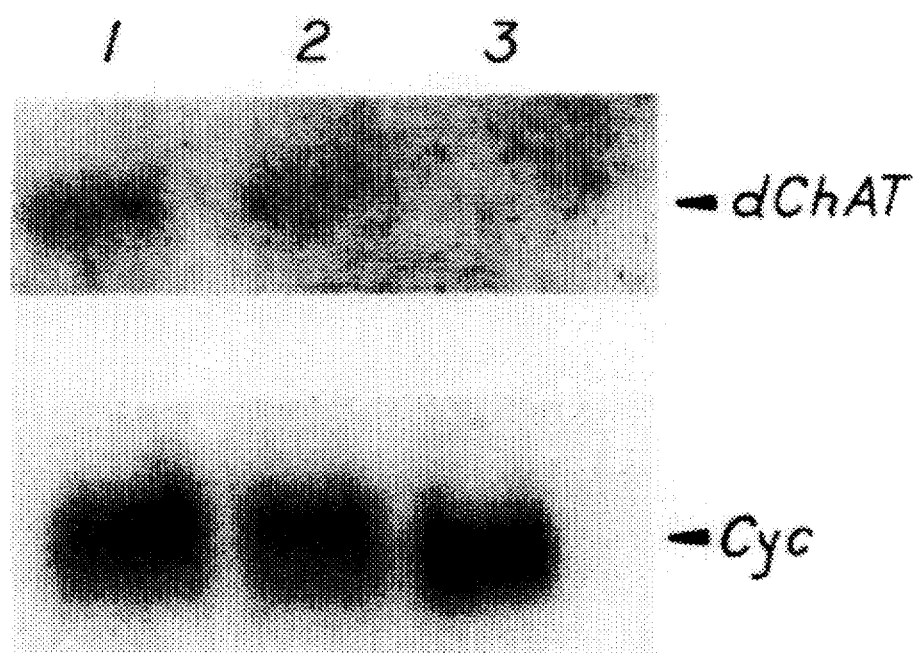

Confluent, dChAT-expressing fibroblasts were incubated with TGFβ1, TNFα, IL-1β or Infγ as described. Total mRNA from these cultures was isolated and probed with a cDNA fragment that specifically recognizes proviral mRNA for the Northern blot. FIG. 45a demonstrates that both TGFβ1 (lane 2) and IL-1β (lane 3) significantly decreased the steady state level of proviral mRNA. TNFα (lane 4), on the other hand, did not significantly affect the levels of proviral mRNA. FIG. 45b illustrates the effects of Infγ on dChAT mRNA content. After 24 hrs there was no change in the steady state level of proviral MRNA; however, mRNA levels were markedly reduced 48 hrs after Infγ was removed and replaced with fresh medium.

These results demonstrate that cytokines affect LTR-driven dChAT expression in vitro.

Figure 46:
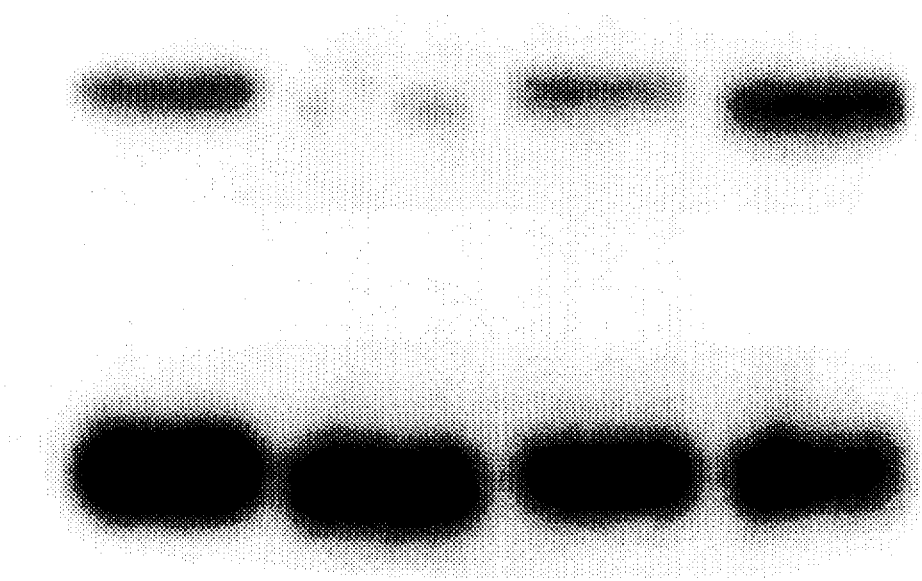
FIG. 46 is a photograph of a Northern blot showing the effects of coadministration of TGFβ and IL-1β, and dexamethasone, on confluent dChAT-producing fibroblasts, as described in Example IX, infra (lane 1=control; lane 2=TGFβ/IL-1β; lane 3=dexamethasone alone; lane 4=TGFβ/IL-1β and dexamethasone; top signals=dChAT mRNA; lower signals=cyclophilin mRNA).

FIG. 46 is a Northern blot illustrating that the co-administration of TGFβ1 and IL-1β to confluent LTR-driven dChAT-producing fibroblasts significantly decreased the amount of proviral mRNA contained within the fibroblasts. In contrast, dexamethasone increased the amount of dChAT mRNA detected by Northern blot analysis. If dChAT-fibroblasts were simultaneously exposed to dexamethasone, TGFβ1, and IL-1β for 24 hrs, the level of proviral mRNA was similar to that detected in control cultures. These results suggest that anti-inflammatory agents, including steroids such as dexamethasone, can mitigate the combined negative effects of TGFβ1 and IL-1β on the steady state level of proviral mRNA in vitro.

As described above, several cytokines downregulate the expression of transgenes from the LTR. One way to minimize the effects of these cytokines after grafting fibroblasts into the brain would be to reduce the inflammatory response using an anti-inflammatory agent such as dexamethasone. An alternative approach that would not require the administration of anti-inflammatory drugs is the use of a promoter or promoters that are not affected, or are possibly enhanced, by the presence of cytokines. One such promoter is the α2(I) collagen promoter. In these experiments, the CAT gene was used as the reporter.

Figure 47A:
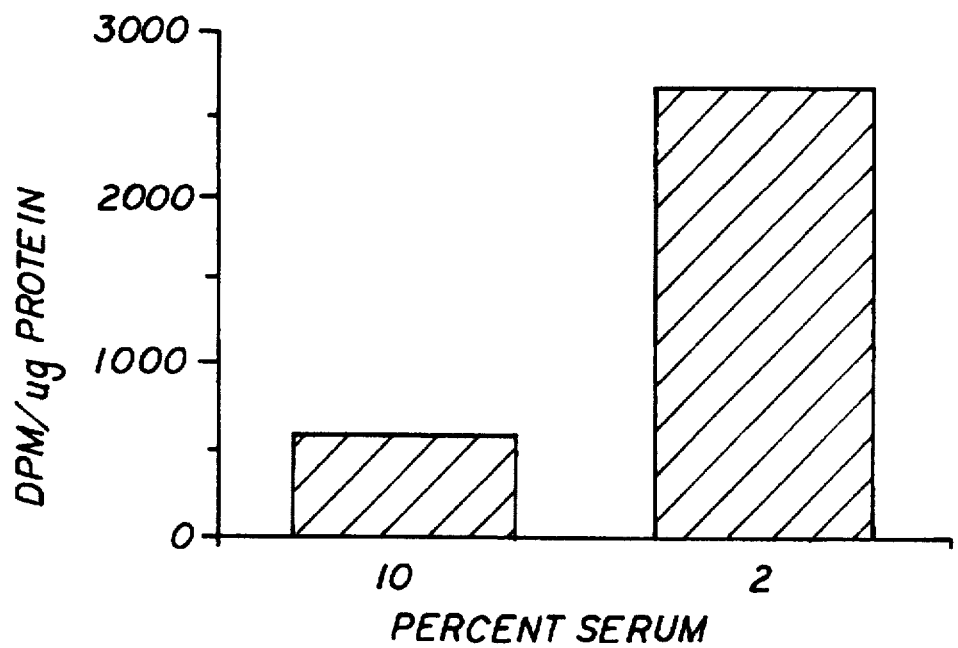
FIG. 47a–FIG. 47b are bar graphs showing the activity of the collagen promoter in 10% versus 2% serum (FIG. 47a) and the effect of various cytokines on the collagen promoter (FIG. 47b) as described in Example IX, infra.

FIG. 47 depicts the effects of TGFβ1, TNFα, IL-1β and Infγ on the expression of CAT in cultures of quiescent fibroblasts in which the Coll(E) promoter-enhancer was used to drive transgene expression (Coll(E)-fibroblasts). For these experiments the cultures were maintained in 2% serum containing medium for the final three days of a seven day post-confluent culture state. Surprisingly, the activity of CAT in Coll(E)-fibroblast cultures maintained in 2% serum was 440% greater than comparable cultures maintained in 10% serum-containing medium (FIG. 47a). This activity approached that measured for LTR (compare with FIGS. 44 (Example VIII) and 47a).

Figure 47B:
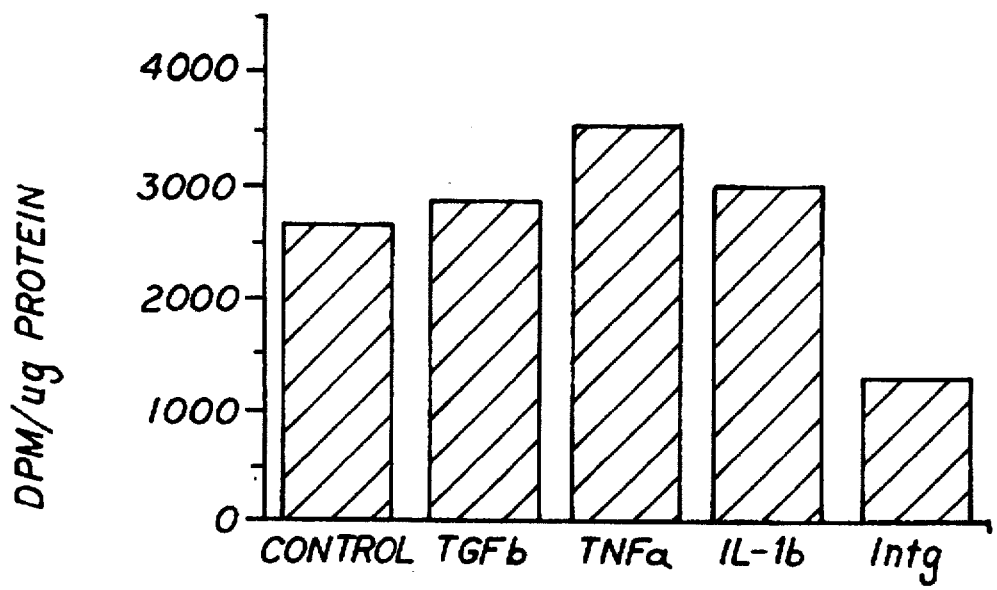

Of the cytokines tested, TGFβ and IL-1β did not appear to significantly affect CAT activity (FIG. 47b). Exposure to TNFα, on the other hand, resulted in an approximately 32% increase in CAT activity. In contrast, Coll(E)-fibroblasts incubated with INFγ displayed an approximately 53% decrease in CAT activity. This measurement was made 48 hrs after Infγ was removed and replaced with fresh 2% serum-containing medium.

In vivo Expression Using Coll(E)

LTR-CAT cells (fibroblasts in which the CAT gene is driven by the LTR) and Coll(E)-CAT cells (fibroblasts in which the CAT gene is driven by the α2(I) collagen promoter-collagen enhancer) were transplanted into the striatum of adult Fischer 344 rats as described in Example VIII above. Three (3) μl of LTR-CAT or Coll(E)-CAT cells (200,000 cells/μl; a total of 600,000 cells) was injected. LTR-CAT fibroblasts were injected into the right side, Coll (E)-CAT cells were injected into the left. At 1 and 4 weeks after implantation, the rats were perfused, the brains sectioned, and processed for CAT immunohistochemistry. The antibody, anti-chloramphenicol, was used at a dilution of 1:2000 and was purchased from 5 prime-3-prime, Boulder, Colo.

Figure 48A:
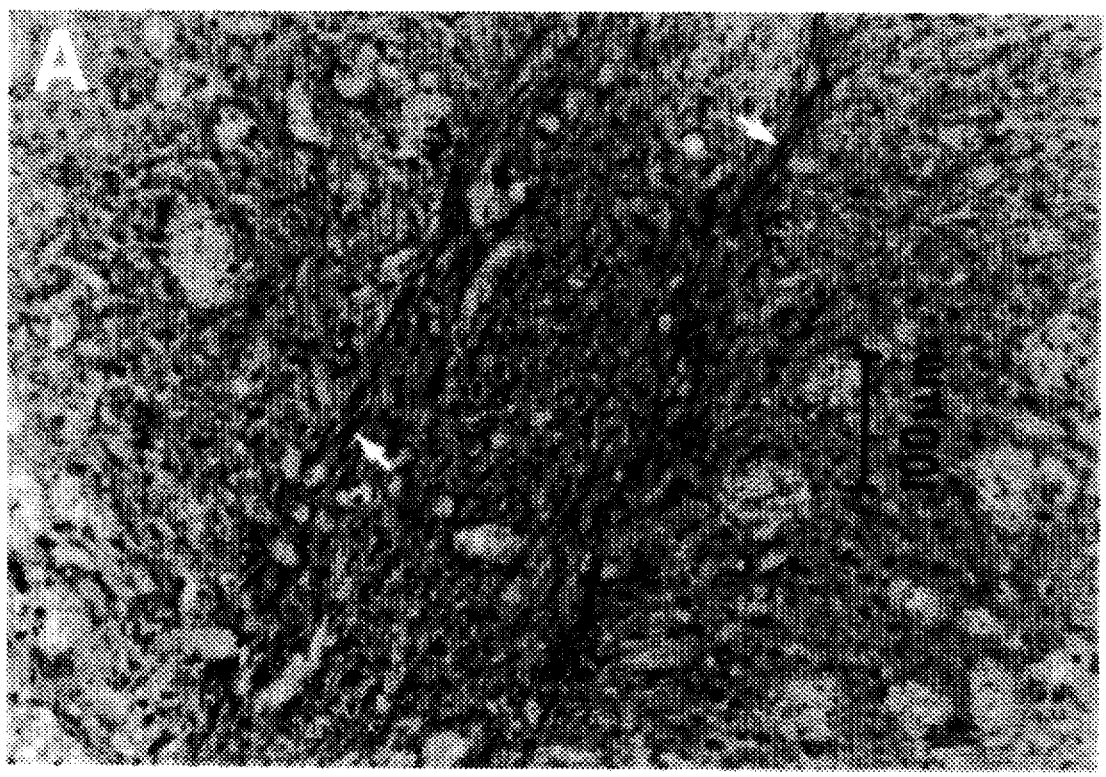
FIG. 48a–FIG. 48d are photomicrographs showing grafts of LTR-CAT (FIG. 48a, FIG. 48b) or Coll(E)-CAT (FIG. 48c, FIG. 48d) cells grafted into the striatum of adult Fischer rats as described in Example IX, infra (white arrows=fibroblasts).
Figure 48B:
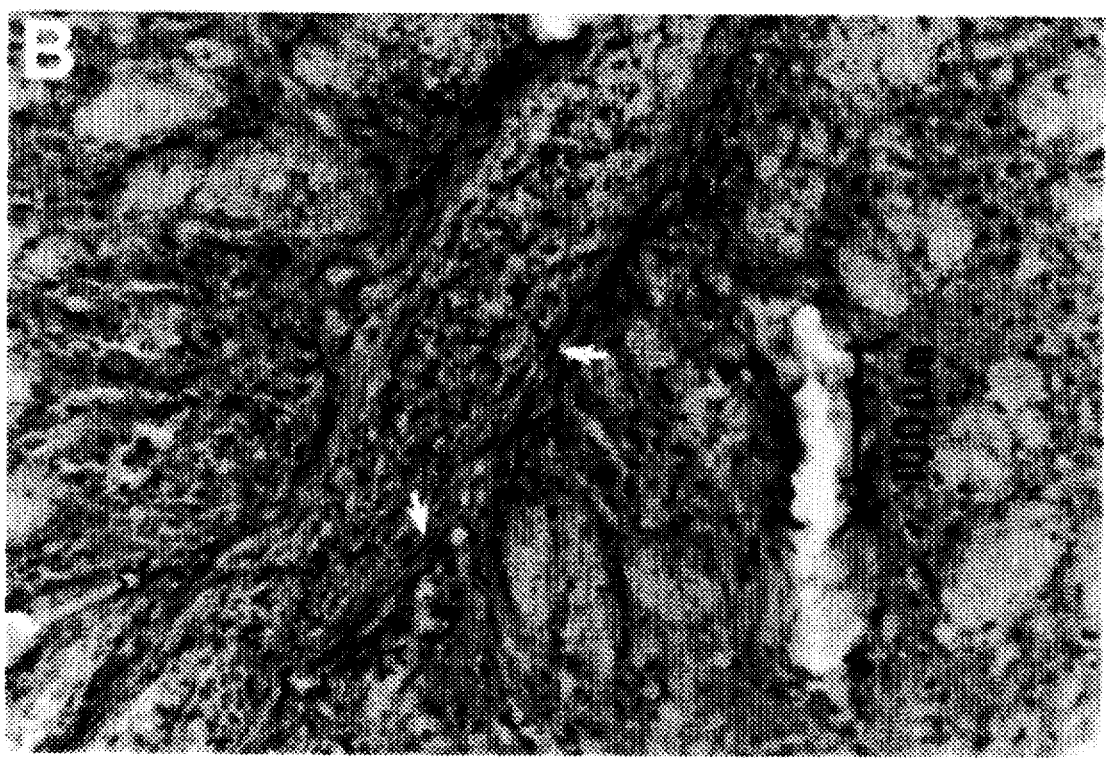
Figure 48C:
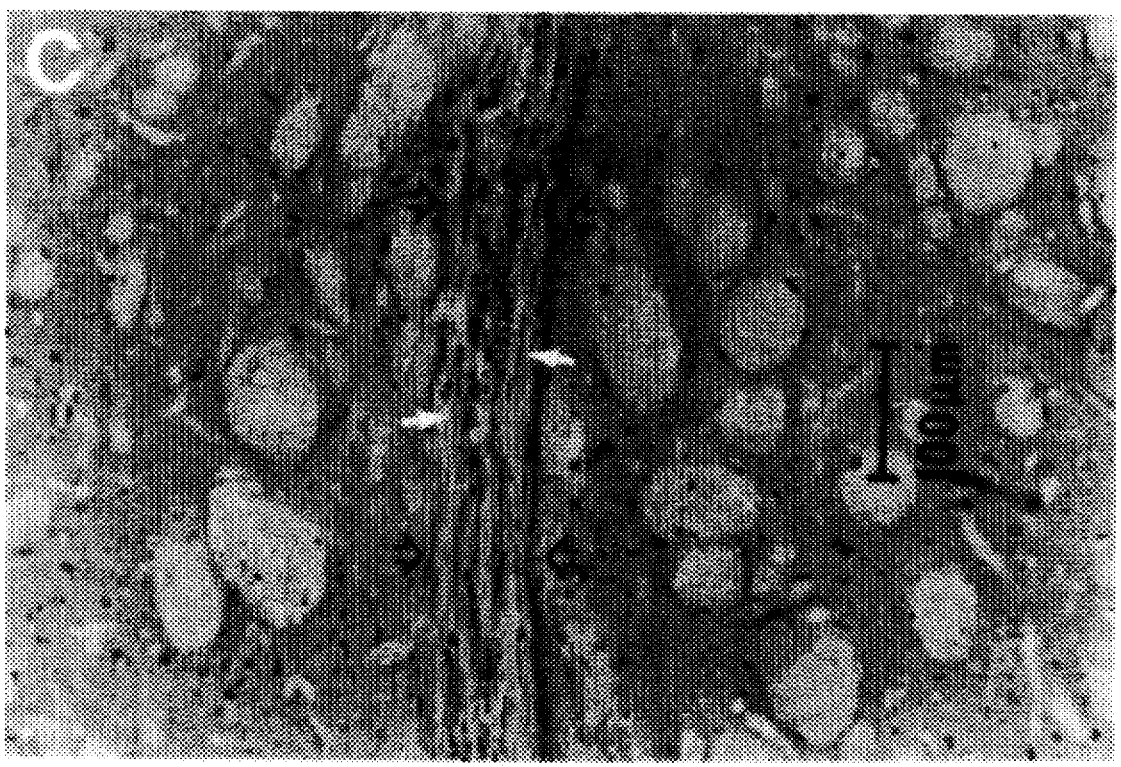
Figure 48D:
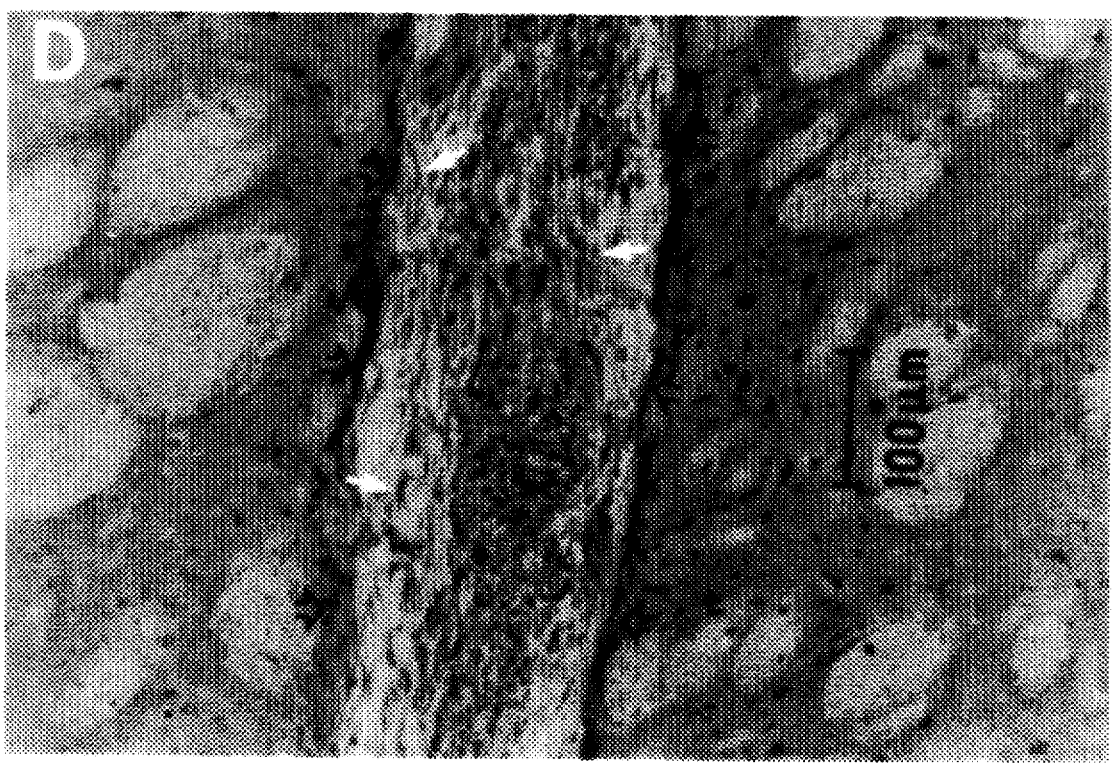

As shown in FIG. 48, many strongly stained CAT-positive fibroblasts were observed in grafts containing either LTR- or Coll(E)-CAT fibroblasts at 1 week post-transplantation (FIG. 48a, FIG. 48b, white arrows). The intensity of staining was comparable between the two graft types. At 4 weeks, (FIG. 48c and 48d, white arrows), the staining for CAT was more robust in Coll(E)-CAT fibroblasts grafts. There were still many phagocytic cells associated with all grafts at this time point (Arrowheads indicate the graft-host brain interface).

These results suggest that the Coll(E) promoter-enhancer may provide more stable and stronger expression of transgene after donor cell implantation into the brain. The presence of phagocytic cells within the center of the grafts at 4 weeks indicates that cytokines may still be present at high levels. Thus, one reason for the stronger expression from the Coll(E) promoter-enhancer as compared to the LTR may be that the cytokines are acting to increase expression.

The data obtained in this example demonstrate that 1) some cytokines (for example, TGFβ1, IL-162 and Infγ) negatively affect the level of proviral mRNA, and that 2) dexamethasone can counteract the negative effect of TGFβ and IL-1β on the steady state level of proviral mRNA and that 3) the Coll(E) promoter-enhancer may be useful to take advantage of the levels of cytokines found in the brain after grafting.

The observation that cytokines can downregulate the expression from the LTR suggests that fibroblasts implanted into the brain may be affected by cytokines that are produced by blood-borne mononuclear phagocytes and lymphocytes that have penetrated into the brain after grafting. Microglial and endothelial cells, another source of cytokines in the brain, may contribute to this scenario. Thus, expression of LTR-driven transgenes in grafted fibroblasts may eventually be compromised with time post-transplantation. One way to counteract the detrimental actions of cytokines on the LTR is to use molecules such as anti-inflammatory agents that curtail the production of cytokines. This treatment may not only increase the stability of transgene expression in implanted fibroblasts, but may contribute to the survival of the cells by reducing the immune response.

An alternative approach takes advantage of cytokines by using a promoter that is up-regulated, or at least not affected, by cytokines. This example demonstrates that TGFβ1 and TNFα do not negatively affect transgene expression (as assessed by CAT activity) in Coll(E)-fibroblasts. In comparison, TNFα increases expression. Infγ had a similar effect on the Coll(E) promoter-enhancer as it did on the LTR (i.e. reduction of transgene expression). Therefore, it may still be necessary to control the release of cytokines such as Infγ from T-lymphocytes, with immunosuppression drugs such as cyclosporin.

The data also indicates that expression from the Coll(E) promoter-enhancer is significantly increased in cells maintained in 2% as compared to 10% serum-containing medium. The level of expression is comparable to that observed in fibroblasts containing the LTR. Fibroblasts implanted into the body would be exposed to less serum elements than in culture. Therefore, expression from the Coll(E) promoter-enhancer under certain conditions may be equal to the strongest viral promoters currently used to drive transgene expression.

EXAMPLE X

Regeneration of Adult Axotomized Neurons

In this Example, a new in vivo model is presented to assess the substrate that supports aberrant axon growth in response to trophic factors in the adult rat CNS. In addition, the importance of NGF on the regenerative capacities of rat septal neurons after axotomy is assessed.

This Example demonstrates that adult reactive astrocytes can serve as permissive substrates for axon growth when supplied by NGF from intrastriatal grafts of genetically modified primary fibroblasts. In addition, the effects of grafts of modified primary fibroblasts secreting NGF on the regenerative capacities of rat septal neurons after axotomy are assessed.

Grafts consisting of primary skin fibroblasts genetically modified to express and secrete NGF prepared as described above in Example II were implanted into the striatum of adult rats. Primary fibroblasts were obtained from a skin biopsy of a female Fischer 344 rat. The cells were maintained under standard culture conditions and fed DMEM containing 10% fetal calf serum three times a week. Primary cells were infected with a murine retroviral vector containing the cDNA for mouse β-NGF, pLN.8RNL, as described above in Example II; infected cells were selected with the neomyocin analogue G418. Prior to isolating the cells for grafting, samples of culture media were taken from control and infected cells. Employing a sensitive two-site immunoassay (Boerhinger-Mannheim), it was determined that the infected cells produced and secreted 154–173 pg NGF/hr/$10^5$ cells; levels of NGF could not be detected in control media. Female Fischer rats (weighing approximately 175–200 g) were anesthesized with a mixture of ketamine-xylazine (ketamine, 25 mg/ml; rompun, 1.3 mg/ml; and acepromazine, 0.25 mg/ml). The heads were shaved and placed in a stereotaxic frame; antiseptic was applied to the head before surgery commenced. Each animal received $3\times10^5$ cells in 3 μl of grafting solution (phosphate buffered saline supplemented with 1 μg/ml of $MgCl_2$ and $CaCl_2$, and 0.1% glucose) into the striatum: NGF-producing cells into the right, and non-infected cells into the left. After survival periods of one, three and eight weeks, the animals were anesthetized and perfused transcardially with 4% paraformaldehyde and 0.1% glutaraldehyde in 0.1M phosphate buffer. Horizontal or sagittal sections through grafts were cut on freezing microtome and processed for NGF receptor immunoreactivity, or were cut on a vibratome and processed for electron microscopic examination.

Genetically modified cells were injected into the right striatum and non-infected control cells into the left striatum. One week after implantation, a plexus of NGF receptor-immunoreactive axons was evident at the caudal pole of striatal grafts composed of NGF-producing fibroblasts, whereas only a small number of enlarged and swollen immunoreactive axonic profiles were observed adjacent to grafts of non-infected control cells (FIG. 49a and 49b). At three weeks, the density of immunoreactive axons surrounding the NGF-producing grafts increased dramatically; a few NGF receptor-immunoreactive profiles completely filled the grafts composed of NGF-producing cells, and the plexus of axonic profiles surrounding the grafts was no longer present (FIG. 49d). These immunoreactive profiles appeared larger than a single axon and usually extended in a vertical fashion. Although grafts of non-infected primary fibroblasts lacked such patterns of immunostained axonic profiles at three and eight weeks after implantation, NGF receptor immunoreactivity was confined to a few blood vessels (FIG. 49c).

Figure 50:
FIG. 50 is an electron photomicrograph of a graft composed of NGF-producing cells eight weeks post-implantation as described in Example X, infra (F=fibroblasts; E=endothelial cells; arrow=astrocytic processes; scale bar=1.0 μm).
Figure 51:
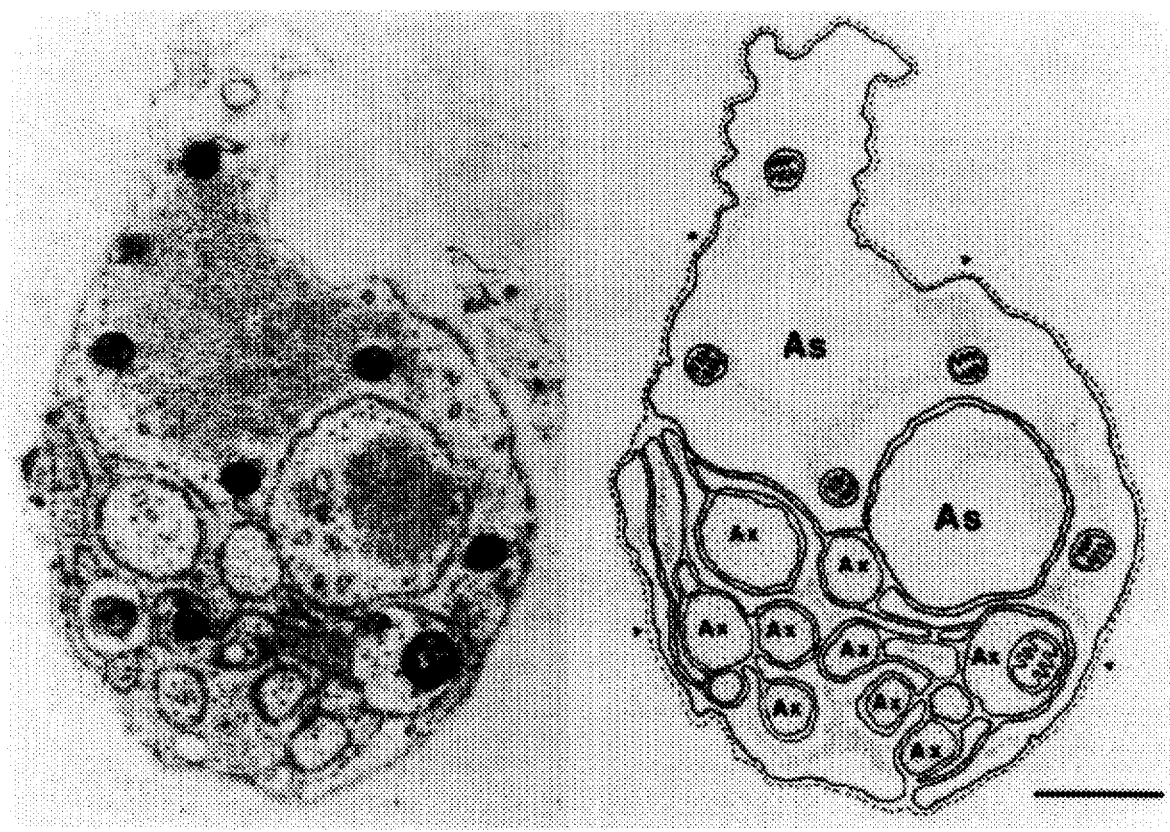
FIG. 51 is a photomicrograph and schematic illustration of an axo-glial arrangement within a graft of NGF-producing cells at eight weeks as described in Example X, infra (Ax=unmyelinated axons; As=reactive astrocytic processes; arrowheads=basal lamina; scale bar=1.0 μm).

Ultrastructural examination revealed that all intrastriatal grafts were composed of primary fibroblasts with extensive rough endoplasmic reticulum and an extracellular matrix filled with collagen. (FIG. 50). Capillaries composed of nonfenestrated endothelial cells contributed to the extensive vascular plexus within these grafts (FIG. 50). At three and eight weeks after implantation, reactive astrocytes completely enveloped the grafts; these astrocytic profiles possessed a distinct basal lamina on those surfaces apposing the graft environment. This barrier between the CNS neuropil and non-CNS graft was characteristic of a "glial scar" usually found following penetrating wounds of the neuropil. Also, many processes of reactive astrocytes extended into the substance of the grafts and were often closely associated with capillaries. Within the extracellular matrix of the NGF-producing grafts only, bundles of unmyelinated axons were interspersed throughout the grafts; terminals containing clear, spherical vesicles were occasionally observed as well. Reactive astrocytic processes laden with filaments were found to envelope these axonic profiles in a convoluted fashion (FIG. 51a and 51b). Basal lamina surrounded the entire axoglial complex and was not evident on opposing plasma membranes between axons and astrocytes. The incidence of these axoglial arrangements was greater at eight weeks than at three weeks following implantation. Axonic profiles were not found within grafts of non-infected control cells.

These data reveal that NGF receptor-positive axons grow toward grafts of NGF-producing primary skin fibroblasts. Grafts of non-infected cells, on the other hand, do not elicit a similar neuronal response. Implants of both types of cells did, however, induce reactive astrocytes to surround and encapsulate the grafts before three weeks. Despite the presence of this glial barrier, unmyelinated axons migrating along elaborate arrangements of reactive astrocytic processes were found within the NGF-producing grafts only; these axons were confined exclusively to astrocytic surfaces that lacked a distinct basal lamina. Although the extracellular matrix of primary fibroblast implants consists of other conducive substrates for axon growth, e.g. collagen, laminin and fibronectin, growing axons within the grafts were not associated with these components, all of which have been previously demonstrated as conducive substrates for axon growth in vitro. Thus, for NGF-sensitive axons penetrating grafts of genetically modified primary skin fibroblasts, reactive astrocytes are the preferred substrate for axon elongation.

These results show that mature reactive astrocytes in the adult CNS can act as substrates which promote rather than inhibit axon growth. Employing intrastriatal grafts of genetically modified cells that produce NGF, these data show that successful axon elongation requires the necessary tropic and trophic support. Thus, it appears that the availability of growth-promoting factors, and not the substrates for growth, is a critical influence during regeneration.

To examine the effects of grafts on regeneration of axons, primary cells genetically modified to express NGF in vivo were established and shown to provide trophic support of axotomized cholinergic septal neurons. To provide a cellular source of NGF in vivo, primary skin fibroblasts genetically modified to express NGF prepared as described in Example II, were suspended in a collagen matrix and placed in the cavity formed by a unilateral ablation of the fimbria-fornix (FF) pathway, a major route for septal axons projecting to the rostral hippocampus.

Under anesthesia, primary skin fibroblasts were obtained from biopsies of the ventral abdominal wall of a female Fischer 344 rat and these cells were maintained under standard culture conditions. Using a retroviral vector containing the cDNA for mouse β-NGF, pLN.8RNL, primary cells were infected in culture, and NGF production by these cells was later assessed using a two-site immunoassay (also as described in Example II). To suspend the cells in a collagen matrix, cultures of NGF-producing and control non-infected primary cells were rinsed in phosphate-buffered saline, trypsinized and suspended in DMEM. The cells were then counted and a total of $10^6$ cells were aliquoted in medium. Type I collagen from rat tail (Sigma) was dissolved with 0.1% acetic acid for a final concentration of 3% collagen. Sodium hydroxide (0.1N) was added to the cell suspension to make the medium more alkaline, and the collagen was then added (final concentration of 1%), mixed and aliquoted into centrifuge tubes. The collagen/fibroblast matrices were then incubated at 37° C. for 48 h. Forty female Fischer 344 rats (weighing approximately 175 g) were anesthetized for surgery using a mixture of ketamine (75 mg/kg), Rompun (4.0 mg/kg) and acepromazine (5.6 mg/kg). Their heads were shaved, and the animals were placed in a Kopf stereotaxic frame. Surgery was a two-step procedure as described in Example II. First, unilateral aspiration lesions through the cingulate cortex and the FF pathway were performed under stereoscopic vision. Then, pieces of the collagen/fibroblast matrices were cut into small pieces (approximately 2–3 $mm^3$) and placed into the wound cavity; other animals received only FF lesions. The animals recovered from surgery and survived for three, four or eight weeks. After these survival periods, the animals were deeply anesthetized, as described above, and were perfused transcardially with 4% paraformaldehyde in phosphate buffer (0.1% glutaraldehyde was added for ultrastructural cases). The brains were removed, post-fixed, cut on either a freezing microtome or vibratome, and the sections (40 to 50 μm in thickness) were processed for acetylcholinesterase histochemistry, immunohistochemistry and ultramicrotomy.

Only those animals that received a complete unilateral FF lesion and possessed a graft within the cavity were assessed for: 1) septal neuronal savings following axotomy; 2) acetylcholinesterase (AChE) histochemical and NGF receptor immunohistochemical staining in the grafts and hippocampus; 3) Nissl staining and tyrosine hydroxylase (TH), glial fibrillary acidic protein (GFAP), and laminin immunohistochemical staining in the grafts; 4) retrograde transport of fluorescent markers from the hippocampus ipsilateral to the lesion and grafts of either NGF-producing or control non-infected fibroblasts; 5) ultrastructural organization of the grafts; and 6) ultrastructural distribution of AChE staining in the deafferented dentate gyrus ipsilateral to grafts of NGF-producing grafts.

Histochemistry and immunohistochemical detection were performed as follows. Alternate sections through collagen/fibroblast grafts were stained for Nissl substance using aqueous 0.5% thionin, stained histochemically for AChE using a modified method of Hedreen et al., *J. Histochem. Cytochem.* 33:134-140 (1985), and stained immunohistochemically for laminin, glial fibrillary acidic protein (GFAP) and tyrosine hydroxylase (TH). Sections through the septum were stained immunohistochemically for NGF receptor, and sections through the hippocampus were stained histochemically for AChE and immunohistochemically for NGF receptor and TH.

Immunohistochemical detection of NGF receptor, TH and GFAP used the same protocol. Sections were initially treated in a solution of 0.6% aqueous hydrogen peroxide for thirty minutes, briefly rinsed in TBS and incubated in a solution containing TBS, 3% normal horse serum and 0.25% Triton-X for one hour (this solution was used to dilute all antibodies). The sections were then incubated for 48 hours at 4° C. in a solution containing one of the following antibodies: monoclonal 192 IgG to NGF receptor, (Chandler et al., *J. Biol. Chem.* 259:6882-6889 (1984, 1:100 dilution), monoclonal IgG to TH (Boehringer-Mannheim; 1:250) and monoclonal IgG to GFAP (Amersham, 1:100). Control-sections were incubated in solutions lacking primary antisera. All sections were then rinsed in buffer, incubated in biotinylated horse anti-mouse IgG (1:167) for one hour at room temperature. After another rinse, the sections were incubated in avidin-biotin complex (ABC; Vector Laboratories) for one hour. They were then rinsed again and reacted in a solution containing 0.025% diaminobenzidine tetrahydrochloride, 0.5% nickel chloride, and 0.18% hydrogen peroxide in TBS for five minutes. The reaction was stopped by rinsing the sections in buffer.

The sections through the grafts were also stained immunohistochemically for laminin. Again, the sections were initially treated with 0.6% aqueous hydrogen peroxide, rinsed, and incubated in a solution of TBS, 3% normal goat serum and 0.25% Triton-X. The sections were then incubated in the same solution as above with the addition of rabbit anti-human laminin IgG (1:800 dilution) for 48 hours at 4° C.; control sections were incubated in a solution lacking the primary antiserum. They were then rinsed and incubated in biotinylated goat anti-rabbit (1:220) for one hour at room temperature. After another rinse, the sections were incubated in ABC and reacted as above.

Figure 52:
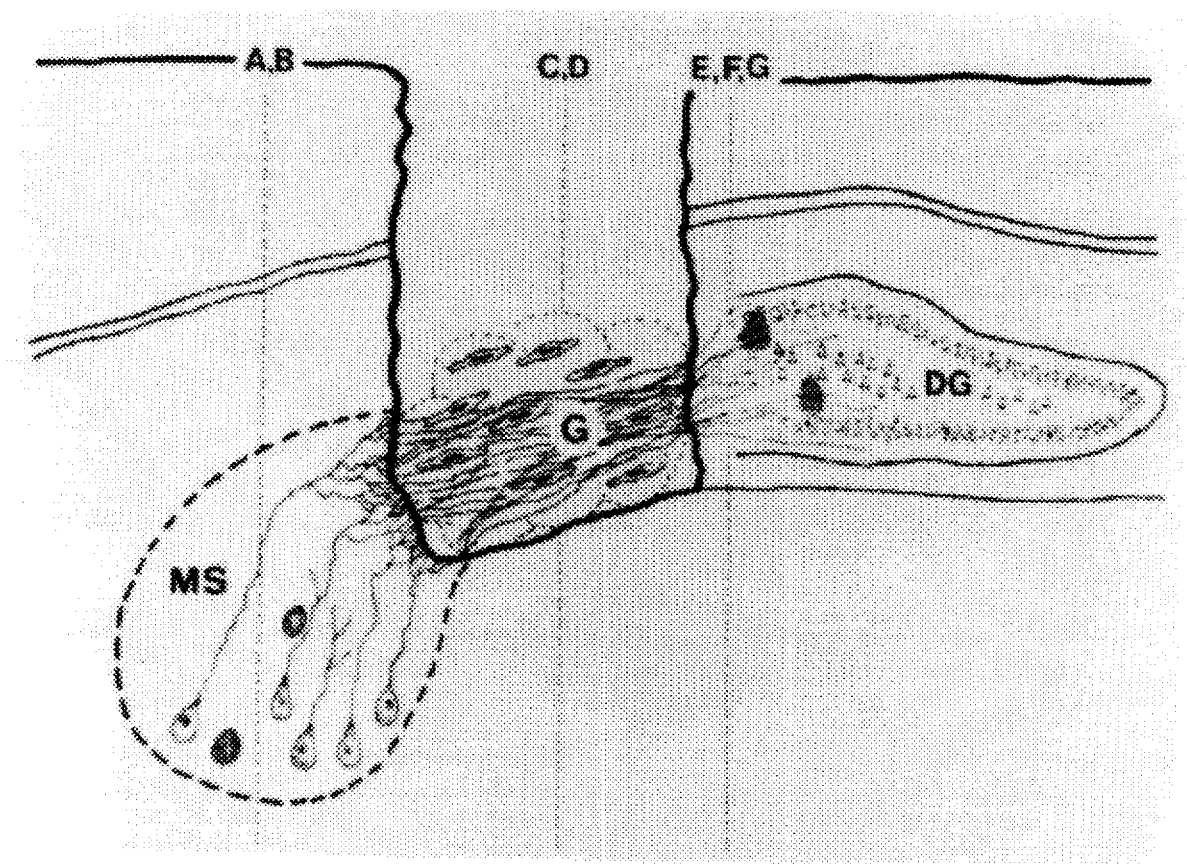
FIG. 52a–FIG. 52g are schematic illustrations of a sagittal view of the adult rat forebrain after unilateral fimbria-fornix (FF) ablation and placement of a graft consisting of collagen with either NGF-producing or control, non-infected primary fibroblasts, as described in Example X, infra (MS=media septum, G=graft, and DG=hippocampal dentate gyrus, FIG. 52a, FIG. 52b=coronal sections at comparable levels through the medial septum stained immunohistochemically for NGF receptor after unilateral FF aspirative lesion and placement of either NGF-producing (FIG. 52a) or control (FIG. 52b) grafts (arrowheads indicate septal midline)
Figures 52A, 52B, 52C, 52D:
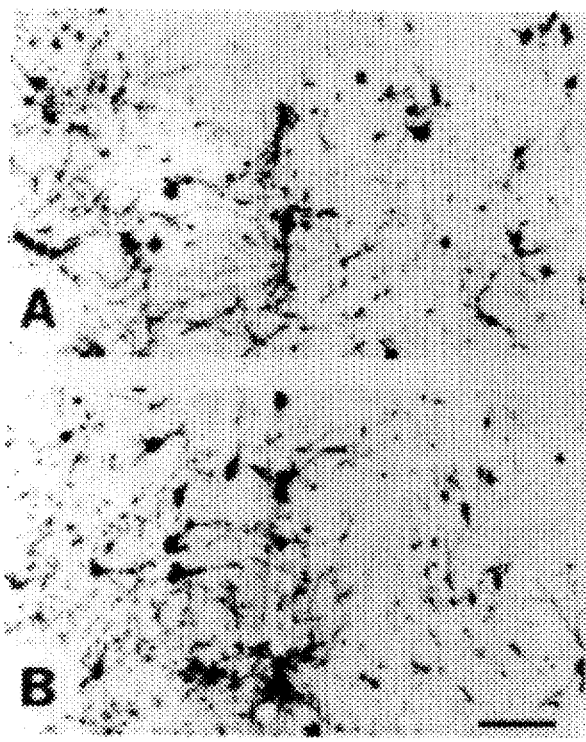

Three (3) and eight (8) weeks after unilateral ablation of the FF and placement of grafts composed of collagen and primary fibroblasts, a marked decrease in the population of NGF receptor-immunoreactive neurons was evident in the ipsilateral medial septum (FIG. 52a and 52b). The lines drawn through the medial septum (MS) and graft (G) and hippocampal dentate gyrus (DG) represent the level of coronal sections of photomicrographs in this illustration. Injection sites for the fluorescent microspheres within the hippocampus are also shown. A modest savings of NGF receptor-positive neurons in the ipsilateral (right) septum is evident with NGF-producing grafts (arrowheads indicate septal midline).

For determination of NGF receptor-immunoreactive septal neurons saved with grafts of NGF-producing fibroblasts, five sections, 120 μm apart, through the septal area stained immunohistochemically for NGF receptor were selected for neuronal cell counting. A counting grid (0.5×0.5 mm) was used to count all immunoreactive neurons in the silateral and contralateral medial septum. Differences between the percentage of NGF receptor-positive surviving cells per animal for each group of animals were assessed by a one-way ANOVA. The results are summarized in Table 4, showing percentages of septal neurons saved (contralateral vs. ipsilateral) with grafts of NGF-producing fibroblasts or control non-infected fibroblasts in the lesion cavity, or without grafts, three (or four) and eight weeks following unilateral FF ablation. Coronal sections through the septum were stained immunohistochemically for NGF receptor to evaluate the survival of septal neurons. Sections through the fibroblast grafts were stained immunohistochemically for TH to assess sympathetic axon ingrowth, for GFAP to assess astrocytic responses to the grafts, and for laminin to reveal neovascularization. Sections through the grafts and ipsilateral hippocampus were stained histochemically for AChE and NGF receptor to examine the regrowth of septal axons.

TABLE 4

|  | Post-operative survival periods | |
| --- | --- | --- |
|  | 3 (or 4) weeks | 8 weeks |
| NGF-producing grafts | 68 ± 4* (n = 3) | 62 ± 7* (n = 7) |
| Control grafts | 47 ± 4 (n = 4) | 47 ± 5 (n = 8) |
| No grafts | 44 ± 8 (n = 3) | — |

*Significance at the $P < 0.01$ level

Table 4 shows that grafts of NGF-producing primary fibroblasts sustained significantly higher percentages of NGF receptor-positive septal neurons at three (or four) and eight weeks than did grafts of collagen with control non-infected primary fibroblasts at the same time periods. The percentages of NGF receptor-immunoreactive neurons are comparable with control non-infected grafts and without grafts. Thus, while the degree of savings with NGF-producing cells was modest, these results provide indirect evidence for the in vivo expression of the transgene for NGF by genetically modified primary fibroblasts. This expression should enable the cells to provide trophic support to axotomized cholinergic septal neurons.

Regeneration of septal axons within the grafts and deafferented hippocampal dentate gyrus was assessed through the detection of AChE and NGF receptor staining. Grafts of NGF-producing fibroblasts usually stained moderately to intensely for AChE (FIG. 52c). Grafts of control, non-infected primary fibroblasts, on the other hand, often lacked AChE reactivity (FIG. 52d). Note that the NGF-producing graft possesses a densely stained perimeter, whereas the control graft lacks AChE reactivity (dotted line represents approximate boundary of the graft).

Figure 52E:
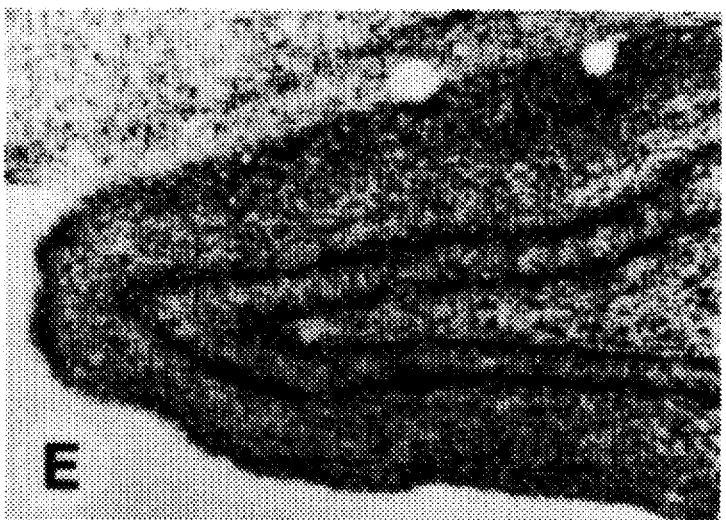
Figure 52F:
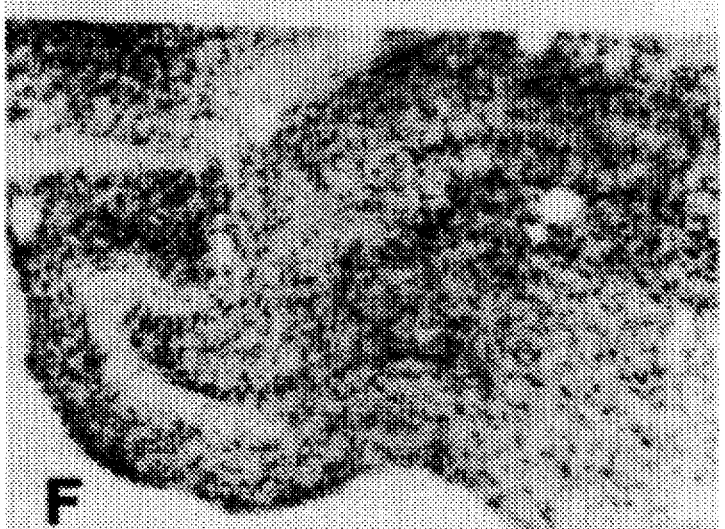
Figure 52G:
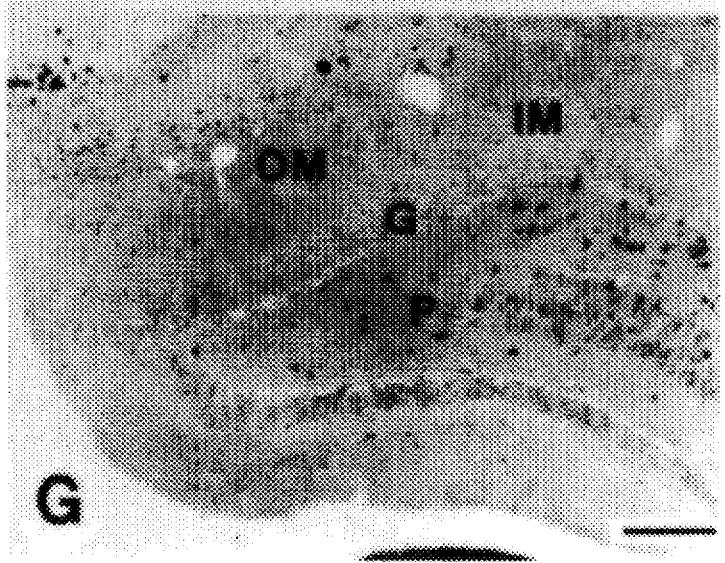
Figure 53A:
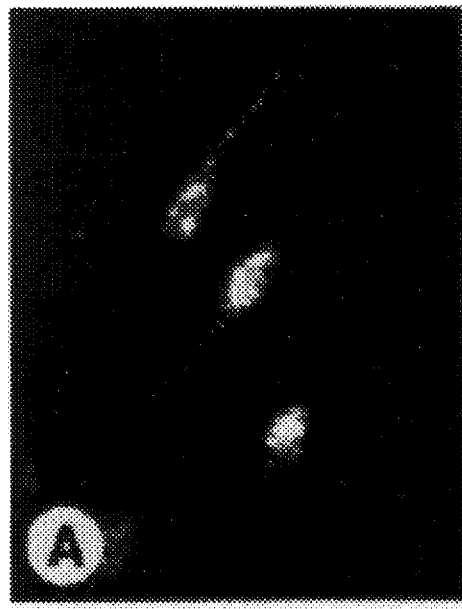
FIG. 53a–FIG. 53d are photomicrographs showing retrogradely fluorescently labeled septal neurons following stereotaxic placement of fluorescent microspheres in the dentate gyrus after surgery in animals that received NGF-producing grafts as described in Example X, infra (FIG. 53a=ipsilateral medial septum.
Figure 53B:
Figure 53C:
Figure 53D:

Three weeks after the transection of the FF unilaterally and placement of control, non-infected fibroblasts/collagen grafts within the cavity, the deafferented dentate gyrus was devoid of axons stained for AChE and NGF receptor. This was in stark contrast to the prominent staining for AChE (FIG. 52e) and NGF receptor seen in the normal dentate gyrus. The normal pattern of AChE staining reveals a robust input to all layers of the dentate gyrus. By eight weeks after lesion/implantation, the deafferented dentate gyrus still lacked AChE-positive axons (FIG. 52g) but now possessed large-diameter axons stained immunohistochemically for NGF receptor, particularly in the polymorphic layer of the dentate gyrus; these axons are reminiscent of sympathetic axons that sprout into the hippocampus following FF lesions (see Batchelor et al., *J. Comp. Neurol.* 284:187 (1989)). In two cases, AChE-positive axons were observed traversing beneath the control grafts from the contralateral to the deafferented hippocampus. Three weeks after the unilateral transection of the FF and placement of NGF-producing fibroblasts in collagen, a moderate plexus of AChE-positive axons was evident in the medial and rostral aspects of the deafferented dentate gyrus. By eight weeks, the density of AChE-positive fibers increased markedly, yet most axons were still confined to the rostromedial dentate gyrus. In certain cases, however, a robust plexus of topographically organized AChE-positive axons was observed within the dentate gyrus and CA2-3 fields (FIG. 52f). Although the pattern of reinnervation was comparable to the distribution of AChE-positive septal axons in the normal undamaged hippocampus (FIG. 52e), the density of axons was usually less. In those cases with NGF-producing grafts, large-diameter axons stained for NGF receptor were also observed in the polymorphic layer of the deafferented dentate gyrus, usually in the caudal portions of the hippocampus.

Although the pattern of AChE staining within the NGF-producing and control grafts was strikingly different, both types of grafts possessed similar cellular populations and immunostaining for TH, GFAP and laminin. Nissl staining showed that all grafts were composed of dense bundles of collagen with a variety of different cell types within and surrounding the grafts, including fibroblasts, lymphocytes, mast cells, plasma cells, astrocytes and endothelial cells of capillaries. Also, both types of grafts possessed a small number of TH-immunoreactive axons, particularly within the dense collagen bundles. Astrocytic processes stained immunohistochemically for GFAP were seen extending from the damaged neural tissue around the wound cavity and penetrating into the outer aspects of the grafts; occasionally, GFAP-positive cells were seen within the grafts as well. Laminin immunostaining of grafts of NGF-producing and non-infected primary fibroblasts revealed an extensive host-derived vascular network. Also, elongated laminin-immunoreactive cell bodies, perhaps Schwann cells, were found within and around the dense collagen bundles of both types of grafts.

To determine the origin of those septal neurons that regenerate new axons following FF ablation and reinnervate the deafferented hippocampus, stereotaxic placements of fluorescent microspheres were made into the ipsilateral dentate gyrus and CA2-3 fields. Nine (9) deeply anesthetized animals with grafts of either NGF-producing (n=5) or control, non-infected (n=4) fibroblasts received two stereotaxic placements of rhodamine-fluorescent microspheres (200 nl/site) into the dentate gyrus and CA2-3 fields in the hippocampus ipsilateral to the lesion and graft eight weeks after surgery. Following a 48h recovery, the animals were again anesthetized and perfused transcardially with 4% paraformaldehyde. The brains were sectioned coronally on a freezing microtome, and retrogradely labeled neurons within the septal areas were viewed with a fluorescence microscope. The schematic illustration in FIG. 52 shows the injection sites.

Most retrogradely fluorescently labeled elongated neurons were found within the ipsilateral medial septum and diagonal band areas, while a smaller number were observed in the septal midline and in the contralateral septal nuclei (FIG. 53). Cases with grafts of control, non-infected fibroblasts did not possess retrogradely labeled neurons in any area of septal region.

At the ultrastructural level, the grafts consisted of dense collagen bundles with a loose outer reticular arrangement eight weeks after implantation. Fibroblasts were observed both within the dense and reticular collagenous formations, and attenuated processes of these cells enveloped dense accumulations of collagen in both areas. Capillaries composed of non-fenestrated endothelial cells surrounded by basal lamina were found throughout the grafts. Several types of cells were also observed within the grafts, including lymphocytes, plasma cells, mast cells, and phagocytes. Astrocytes and their processes were found predominantly within the loose reticulum around the dense collagen center. The most prominent difference between grafts of NGF-producing and non-infected fibroblasts was the number of unmyelinated axons, i.e. within an area of 960 $\mu m^2$, 1625 axons were found in the NGF-producing grafts compared with 329 axons in the control grafts. Ultrathin sections of either NGF-producing (n=3 different cases) or control, non-infected (n=3 different cases) fibroblast/collagen grafts were examined and the total number of axons were counted in 10 grid squares (2 parallel columns of 5 grid squares, a total area of 960 $\mu m^2$, with graft tissue of the dense and loose collagen areas). Among the three cases of NGF-producing grafts, 1625 axons were found in comparison to 329 axons among the three cases of control, non-infected grafts.

Figure 54A:
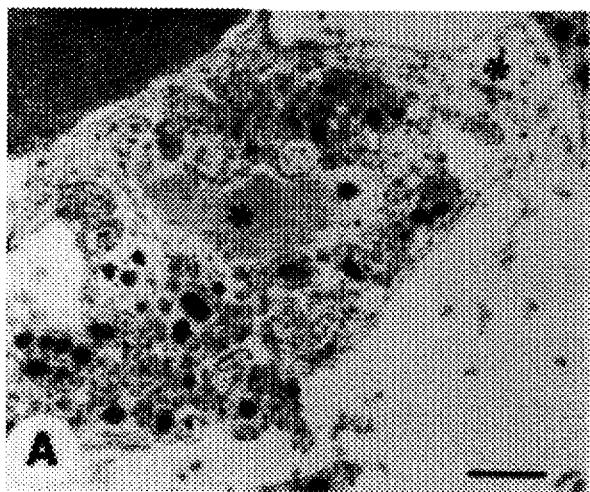
FIG. 54a–FIG. 54f are electron photomicrographs showing the ultrastructural distribution of unmyelinated axons within grafts of collagen and NGF-producing fibroblasts after surgery as described in Example X, infra (*=astrocytic processes; S=Schwann cells; L=lumen of the capillary; scale bars=1.0 μμm).
Figure 54B:
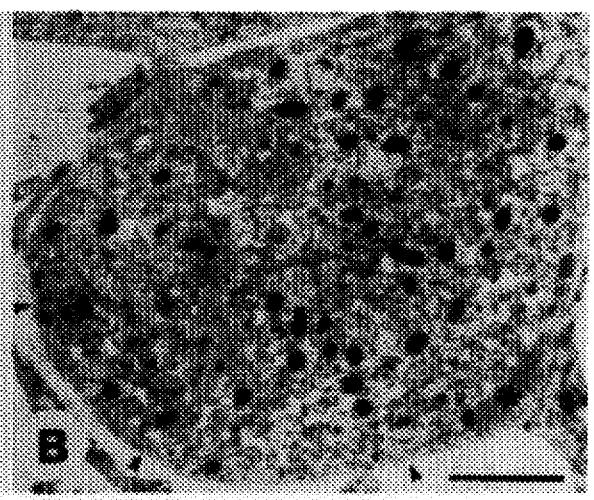
Figure 54C:
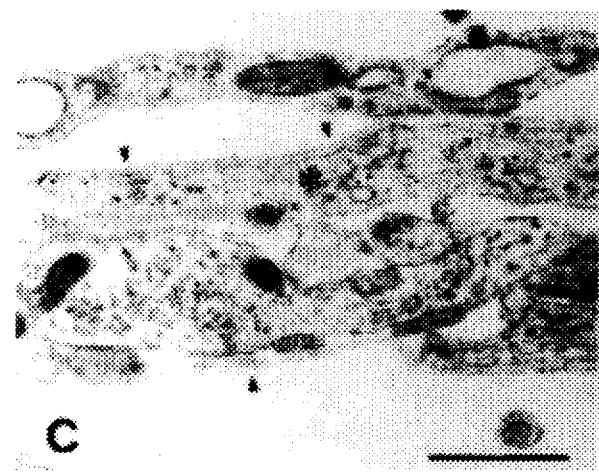
Figure 54D:
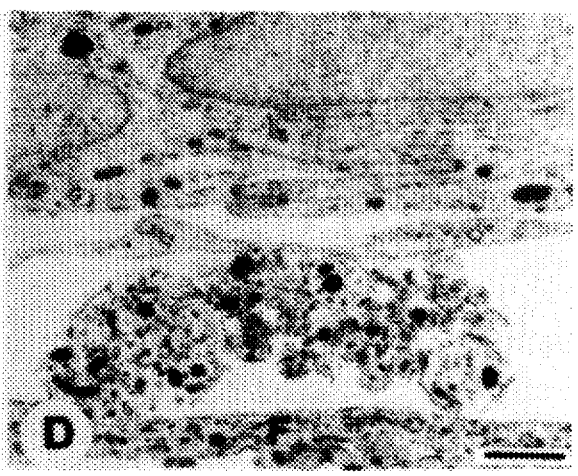
Figures 54E, 54F:
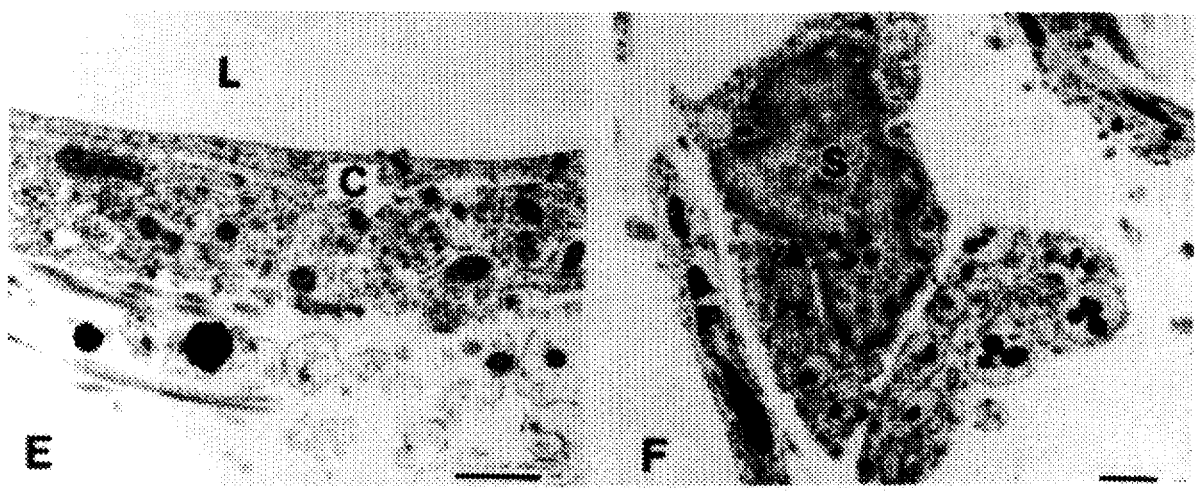
Figures 55A, 55B, 55C:
FIG. 55a–FIG. 55f depicts topographical (FIG. 55a) and synaptic (FIG. 55b–f) distribution of AChE activity within the dentate gyrus after FF ablation and implants of NGF-producing fibroblasts in a collagen matrix as described in Example X, infra (FIG. 55a=coronal section (40 μm) of the dentate gyrus stained for AChE, taken immediately adjacent to that tissue examined at the ultrastructural level. IM=inner molecular layer, OM=outer molecular layer; G=granular layer; P=polymorphic layer.
Figure 55D:
Figure 55E:
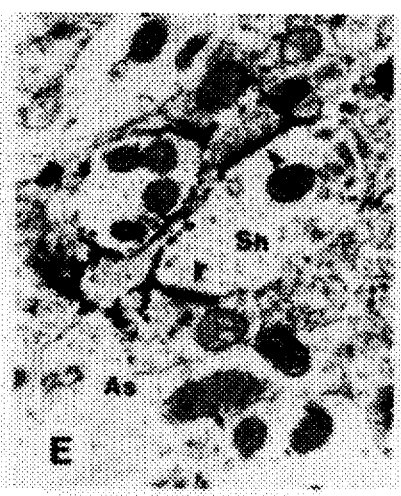
Figure 55F:
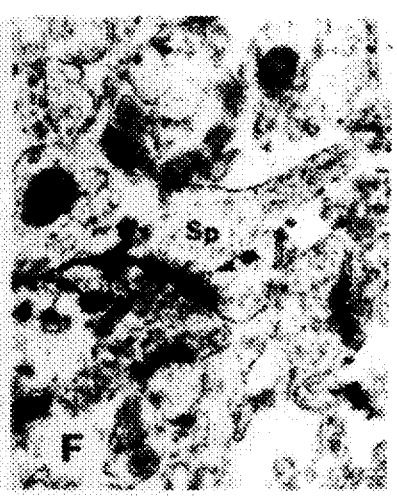

As shown in FIGS. 54a–FIG. 54c large numbers of axons were surrounded by or passed along narrow processes of astrocytes (*) that contain intermediate filaments. These astrocytic profiles possess basal lamina (arrowheads) on those cell surfaces facing the graft extracellular matrix. The axons are usually found apposing those astrocytic surfaces lacking a basal lamina. Such axons were also found near the cell bodies of the astrocytes and other cells, including fibroblasts (F) (FIG. 54d) and other astrocyte-like cells and their processes. Still other unmyelinated axons were closely associated with the basal lamina of the endothelial cells of capillaries (C) or found within the extracellular matrix of the NGF-producing grafts; collagen fibrils are distributed among the axons (FIG. 54e). Within grafts of either NGF-producing or control fibroblasts, small numbers of unmyelinated axons enveloped by Schwann cells (S) and their processes were observed within the reticular areas (L=lumen of capillary) (FIG. 54f). Axons observed within the dense collagen area of both types of grafts were usually ensheathed within attenuated glial profiles. Occasionally, control grafts also possessed a very small population of axons within the extracellular matrix.

Ultrastructural examination of the deafferented hippocampus following the placement of NGF-producing grafts revealed a sparse distribution of AChE reactivity within the dentate neuropil. The electron-dense reaction production was localized to the plasma membranes of small-diameter, unmyelinated axons and terminal containing clear spherical vesicles; these stained axonic profiles were found predominantly in the molecular layers of the dentate gyrus (FIG. 55). Dispersed throughout the dentate neuropil were clusters of AChE-positive unmyelinated axons, and these axonal aggregates were usually found near astrocytic processes. Occasionally, axon terminals possessing reactivity for AChE formed synaptic contacts with dendritic shafts and spines. The symmetry of contacts between AChE-positive terminals and dendritic profiles of granular neurons, however, was usually obscured by the localization of reaction product at the site of apposition. Since sections of the deafferented dentate gyrus of those animals with control non-infected cells lacked AChE reactivity, further analysis was not conducted at the ultrastructural level.

In particular, FIG. 55 shows a coronal section (40 μm) of the dentate gyrus stained for AChE, taken immediately adjacent to that tissue examined at the ultrastructural level. AChE-positive fibers are evident in the inner (IM) and outer (OM) molecular layers and the granular layer (G). AChE-positive somata and fibers are also found in the polymorphic layer (P). FIG. 55b and 55c show that clusters of AChE-positive unmyelinated axons are found throughout the granular (B) and molecular (C) layers. FIG. 55d, 55e and 55f show that AChE-positive terminals form synaptic contacts (arrowheads) with dendritic shafts (Sh) and spines (Sp) in the molecular layers. Astrocytic processes (As) are usually observed near clusters of AChE-positive axons and terminals in the dentate gyrus.

These results demonstrate the importance of trophic/tropic substances such as NGF in the regenerative capacity of septal cholinergic neurons, as assessed by the percentage of NGF receptor-positive neurons saved within the medial septum and the reinnervation of the hippocampal dentate gyrus following a unilateral FF lesion and placement of grafts composed of a collagen matrix with NGF-producing primary fibroblasts. Intracerebral grafts of NGF-producing primary fibroblasts are thus capable of preventing the retrograde degeneration of cholinergic septal neurons after axotomy like grafts of NGF-producing immortalized fibroblasts as shown in Example II herein, and infusions of exogenous NGF into the lateral ventricle (Hefti, *J. Neurosci.* 6:2155 (1986); Kromer, *Science* 235:214 (1987) and Williams et al., *Proc. Natl. Acad. Sci. USA* 83:9231 (1986)). The percentages of cells saved with NGF-producing primary fibroblasts in a collagen matrix, however, is much lower than that achieved with intraventricular infusions of NGF or implants of NGF-producing immortalized fibroblasts. This may be due to 1) a small number of cells actually implanted within the collagen matrix resulting in a lower level of NGF production; and 2) a possible down-regulation of the transgene following implantation.

These results show that, like other different types of tissues which support new axon growth from septal neurons, grafts of NGF-producing fibroblasts within a collagen matrix also support the growth of septal fibers, such that a sparse reinnervation of the hippocampus is evident at three weeks. By eight weeks, however, the density of axons within the hippocampus is clearly greater than that seen at three weeks. Implants of control cells in collagen offer little or no support, since the ingrowth of septal AChE-positive fibers to the hippocampus is negligible and no labeled cells are found in the septal area ipsilateral to the dentate gyrus following placements of retrograde tracer. Likewise, grafts of acellular peripheral nerve (i.e., those lacking Schwann cells) cannot support the growth of septal axons (Hagg et al., *Exp. Neurol.* 112:79 (1991)). Together, these data reveal that septal axons are able to use many different graft environments, consisting of both cellular and extracellular substrates for growth.

These data also show that collagen grafts containing primary skin fibroblasts induce a similar ingrowth of capillaries with basal lamina, astrocytes and Schwann cells, regardless of whether the primary cells are genetically modified to produce NGF or not. Moreover, the extracellular matrices of both types of grafts are similar, such that the patterns of laminin immunostaining and collagen distribution are comparable. The real differences between NGF-producing grafts and control grafts lie in the robust staining for AChE and abundance of unmyelinated axons within the NGF-producing grafts. First, prominent AChE reactivity is only evident in NGF-producing grafts; control grafts usually lack AChE staining. Both types of grafts, however, possess a sparse population of TH-immunoreactive fibers, as well as axons enveloped within Schwann cells and their processes; most axons associated with these glial elements may represent TH-positive sympathetic ingrowth. Second, NGF-producing grafts possess numerous axons that are ensheathed by astrocytic processes, pass along the basal lamina of capillaries and astrocytes, or extend within the loose arrangements of collagen. Control grafts, on the other hand, only possess a very small population of axons within the extracellular environment. From these collective data, it appears that NGF-sensitive axons arising from perturbed septal neurons require the availability of NGF and a permissive graft environment for new growth. Using grafts of genetically modified cells that produce NGF in vivo regenerating septal axons have been shown herein to grow on a variety of different substrates only in its presence. Without elevated levels of NGF, axons do not regenerate in response to grafts consisting of collagen and control non-infected fibroblasts, even though the same cellular and extracellular substrates are available.

Previous studies examining the regenerative capacity of septal cholinergic neurons in the rat following axotomy and grafting have referred to the "reinnervation" of the deafferented hippocampus with certain bridging environments (Hagg et al., *Exp. Neurol.* 112:79 (1991)). To date, however, no investigation has provided direct morphological evidence that AChE-positive septal axons within the hippocampus actually innervate postsynaptic targets. Ultrastructural data presented herein reveal that axons stained for AChE activity are sparsely distributed within the deafferented dentate gyrus eight weeks after FF lesion and grafting of NGF-producing fibroblasts. These axons are often seen in clusters of two or more. The ultrastructural organization of AChE-positive septal axons is similar to recent observations that septal axons stained immunohistochemically for NGF receptor also form small aggregates within the normal rat dentate gyrus (Kawaja and Gage, *J. Comp. Neurol.* 307:517 (1991)). In addition, these newly-formed AChE-positive axons give rise to terminals that form synaptic contacts with dendritic shafts and spines in the deafferented dentate gyrus. The pattern of synaptic contacts between septal cholinergic axons and granular dendritic profiles is comparable to that normally found in the rat dentate gyrus; axosomatic contacts between cholinergic axons and granular neurons are rare (Shute and Lewis, *Zellforsch. Mikrosk.* 69:334 (1966); and Clarke, *Brain Res.* 360:349 (1985)). It is worth noting that when grafts of fetal septum are implanted within the adult rat dentate gyrus after FF ablation, cholinergic axons from the grafts innervate the somata of granular neurons at higher frequency than normal (Clarke et al., *Brain Res.* 369:151 (1986)). Further, the number of graft-derived cholinergic axons contacting dendritic profiles decreases dramatically (Id). From these data, it appears that while the cholinergic axons from fetal septal grafts within the deafferented dentate gyrus form unique synaptic arrangements with granular neurons, septal axons that regenerate across NGF-rich grafts of collagen and fibroblasts recapitulate a normal synaptic organization within the dentate gyrus (i.e., AChE-positive septal axons terminate predominantly on dendritic shafts and spines).

The results presented in this example demonstrate that grafts of NGF-producing fibroblasts in a collagen matrix sustain damaged cholinergic neurons of the rat medial septum, provide a conducive environment for regrowing NGF-sensitive axons arising from these neurons and influence the reinnervation of the deafferented granular neurons of the dentate gyrus by septal axons. In particular, these grafts induce axonal elongation and synaptic connectivity. Regenerating NGF-sensitive septal axons use both cellular and matrix substrates for growth within grafts consisting of NGF-producing primary fibroblasts and collagen. Without elevated levels of NGF (i.e. using control fibroblast/collagen grafts), a higher proportion of septal neurons undergo degeneration and axons fail to grow, despite the presence of conducive substrates.

In addition to NGF, other neurotrophic factors, such as brain-derived growth factor (BDNF), neurotrophin (NT)-3, NT-4, and ciliary neuronal trophic factor (CNTF), may be used to sustain axotomized neurons and promote axon regrowth of other neuronal populations in the CNS.

It is apparent that many modifications and variations of this invention as set forth above may be made without departing from the spirit and scope of the present invention. The specific embodiments described are given by way of example only and the invention is limited only by the terms of the appended claims.

We claim:

1. A method for treating defective, diseased or damaged cells in the mammalian central nervous system comprising grafting donor cells into the central nervous system of a subject, said subject or donor cells treated so as to minimize or reduce graft rejection, said donor cells genetically modified by insertion of at least one transgene encoding a product or products which directly or indirectly affect the cells into said cells to produce functional molecules in a sufficient amount to ameliorate said defective, diseased or damaged cells in the central nervous system, the transgene being selected from the group consisting of genes coding for tryptophan hydroxylase, GABA-decarboxylase, enkephalin, dopa decarboxylase (AADC), ciliary neuronal trophic factor (CNTF), brain derived neurotrophic factor (BDNF), neurotrophin (NT)-3, NT-4, and basic fibroblast growth factor (bFGF).

2. The method of claim 1, wherein the step of grafting said donor cells comprises introducing said donor cells into the brain of a subject.

3. The method of claim 1, wherein the step of grafting said donor cells comprises introducing said donor cells into the spinal cord of a subject.

4. The method of claim 2, wherein said introducing comprises intracerebral, intraventricular, subdural space, putamen, nucleus basalis, hippocampus, cortex, striatal, caudate and intravenous introduction.

5. The method of claim 1, wherein said transgene is carried by a viral vector.

6. The method of claim 5, wherein said vector is a herpes virus vector.

7. The method of claim 5, wherein said vector is a neurotropic viral vector.

8. The method of claim 5, wherein said vector is a retroviral vector.

9. The method of claim 8, wherein said retroviral vector is the retroviral vector pLN.8PNL having a final construction as shown in FIG. 12.

10. The method of claim 8, wherein said retroviral vector is the retroviral vector pLThRNL having a final construction as shown in FIG. 16.

11. The method of claim 1, wherein the transgene is insert into donor cells by nonviral physical transfection.

12. The method of claim 11, wherein said nonviral physical transfection comprises microinjection of DNA encoding a transgene.

13. The method of claim 1, wherein the transgene is insert into donor cells by electroporation.

14. The method of claim 1, wherein the transgene is insert into donor cells by chemically mediated transfection.

15. The method of claim 14, wherein said chemically mediated transfection comprises calcium phosphate transfection.

16. The method of claim 1, wherein the transgene is insert into donor cells by liposomal mediated transfection.

17. The method of claim 1, wherein the transgene is insert into donor cells by lipofection.

18. The method of claim 1, wherein said molecules are selected from the group consisting of growth factors, enzymes, gangliosides, antibiotics, neurotransmitters, neurohormones, toxins, neurite promoting molecules, antimetabolites and precursors of said molecules.

19. The method of claim 1, further comprising co-administration of a therapeutic agent for treating said disease or damage to the central nervous system.

20. The method of claim 19, wherein said therapeutic agent is selected from the group consisting of growth factors, gangliosides, antibiotics, neurotransmitters, neurohormones, toxins, antimetabolites, neurite promoting molecules and precursors of these agents.

21. The method of claim 19, wherein said therapeutic agent is cellular matter.

22. The method of claim 21, wherein said cellular matter is selected from the group consisting of adrenal chromaffin cells, fetal brain tissue cells and placental cells.

23. The method of claim 1, further comprising implanting material to the site of said damage or disease, said material to facilitate reconnection or ameliorative interactions of injured neurons.

24. The method of claim 23, wherein said material is selected from the group consisting of homogenate of brain, homogenate of placenta, collagen, whole cells, synthetic material, neurite promoting extracellular matrix, and genetically modified donor cells.

25. The method of claim 1, wherein said donor cells are selected from the group consisting of fibroblasts, neurons, glial cells, keratinocytes, hepatocytes, ependymal cells, bone marrow cells, hippocampal cells, olfactory mucosa cells, stem cells, adrenal cells, connective cells, leukocytes and chromaffin cells.

26. The method of claim 1, wherein said donor cells comprise a mixture of cell types from different anatomical regions.

27. The method of claim 1, wherein said cells are primary cells.

28. The method of claim 1, wherein said cells are immortalized cells.

29. The method of claim 1, wherein the step of grafting said donor cells comprises grafting from approximately $10^4$ to approximately $10^8$ cells per graft.

30. The method of claim 1, wherein said donor cells consist of cells that have been passaged from approximately 2 to approximately 20 times.

31. The method of claim 1, wherein the step of grafting comprises multiple grafting of genetically modified donor cells in several different sites.

32. The method of claim 31, wherein said donor cells comprise a mixture of transgenes inserted into said cells.

33. The method of claim 31, wherein said donor cells comprise a mixture of cell types.

34. The method of claim 1, wherein the step of grafting comprises multiple grafting of genetically modified donor cells into a single site.

35. The method of claim 34, wherein said donor cells comprise a mixture of cell types.

36. The method of claim 5, wherein said vector carries a promoter to enhance expression of said transgene when said donor cells are quiescent.

37. The method of claim 36, wherein said promoter is a collagen promoter.

38. The method of claim 37, wherein said collagen promoter is selected from the group consisting of $\alpha 1(I)$ and $\alpha 2(I)$.

39. The method of claim 36, wherein said vector further carries an enhancer sequence to increase the activity of said promoter.

40. The method of claim 39, wherein said enhancer sequence is SV40 enhancer sequence.

41. The method of claim 39, wherein said enhancer sequence is a collagen promoter enhancer sequence.

42. The method of claim 41, wherein said enhancer sequence is a $\alpha 2(I)$ collagen enhancer sequence.

43. The method of claim 36, further comprising the administration of cytokines to regulate the expression of said molecules.

44. The method of claim 43, wherein said cytokines are selected from the group consisting of interleukin-1$\beta$, interferon-$\alpha$, tumor necrosis factor-$\alpha$, tumor growth factors-$\beta$, basic fibroblast growth factor (bFGF) and epidermal growth factor (EGF).

45. The method of claim 1, further comprising the use of growth factors to maintain survival of the donor cells in the mammalian CNS.

46. The method of claim 45, wherein said growth factors are bFGF or EGF.

47. The method of claim 1, further comprising regulation of the secretion of said functional molecules by administration of a precursor for said molecules.

48. The method of claim 47, wherein said functional molecules are acetylcholine, and said precursor is choline.

49. The method of claim 1, wherein said donor cells are primary fibroblasts.

50. The method of claim 49, wherein said donor cells are primate fibroblasts.

51. The method of claim 49, wherein said donor cells are human fibroblasts.

* * * * *